US009115378B2

(12) United States Patent
Beuzelin-Ollivier et al.

(10) Patent No.: US 9,115,378 B2

(45) Date of Patent: Aug. 25, 2015

(54) FERMENTATIVE VITAMIN C PRODUCTION

(71) Applicant: DSM IP Assets B.V., Heerlen (NL)

(72) Inventors: Marie-Gabrielle Beuzelin-Ollivier, Tolochenaz (CH); Bastien Chevreux, Rheinfelden (DE); Manuela Dalluege, Rheinfelden (DE); Marina Van Gelder, Spijkenisse (NL); Markus G. Goese, Basel (CH); Corina Hauk, Weil am Rhein (DE); Bertus P. Koekman, Schipluiden (NL); Connie Lee, Reykjavik (IS); Anne F. Mayer, Basel (CH); Anja Meury, Basel (CH); Nigel J. Mouncey, Binningen (CH); Dick Schipper, Delft (NL); Masako Shinjoh, Kanagawa (JP); Christine Toepfer, Murg (DE); Adrianus W. H. Vollebregt, Naaldwijk (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 13/654,105

(22) Filed: Oct. 17, 2012

(65) Prior Publication Data

US 2013/0143280 A1 Jun. 6, 2013

Related U.S. Application Data

(63) Continuation of application No. 11/882,456, filed on Aug. 1, 2007, now Pat. No. 8,318,462, which is a continuation of application No. PCT/EP2006/001214, filed on Feb. 10, 2006.

(30) Foreign Application Priority Data

| | | |
|---|---|---|
| Feb. 11, 2005 | (EP) | 05405066 |
| Feb. 11, 2005 | (EP) | 05405067 |
| Feb. 11, 2005 | (EP) | 05405072 |
| Feb. 11, 2005 | (EP) | 05405073 |
| Feb. 11, 2005 | (EP) | 05405081 |
| Feb. 11, 2005 | (EP) | 05405082 |
| Feb. 11, 2005 | (EP) | 05405083 |
| Feb. 11, 2005 | (EP) | 05405084 |
| Feb. 11, 2005 | (EP) | 05405087 |
| Feb. 11, 2005 | (EP) | 05405088 |
| Feb. 11, 2005 | (EP) | 05405089 |
| Feb. 11, 2005 | (EP) | 05405090 |
| Feb. 11, 2005 | (EP) | 05405091 |
| Feb. 11, 2005 | (EP) | 05405093 |
| Feb. 11, 2005 | (EP) | 05405094 |
| Feb. 11, 2005 | (EP) | 05405109 |
| Feb. 11, 2005 | (EP) | 05405110 |
| Feb. 11, 2005 | (EP) | 05405111 |
| Feb. 11, 2005 | (EP) | 05405112 |
| Feb. 11, 2005 | (EP) | 05405119 |
| Feb. 11, 2005 | (EP) | 05405120 |
| Feb. 11, 2005 | (EP) | 05405121 |
| Feb. 11, 2005 | (EP) | 05405139 |
| Feb. 11, 2005 | (EP) | 05405140 |
| Feb. 11, 2005 | (EP) | 05405146 |
| Feb. 11, 2005 | (EP) | 05405147 |
| Feb. 11, 2005 | (EP) | 05405148 |
| Feb. 11, 2005 | (EP) | 05405149 |
| Feb. 11, 2005 | (EP) | 05405150 |
| Feb. 11, 2005 | (EP) | 05405151 |
| Feb. 11, 2005 | (EP) | 05405152 |
| Feb. 11, 2005 | (EP) | 05405153 |
| Feb. 11, 2005 | (EP) | 05405166 |
| Feb. 11, 2005 | (EP) | 05405167 |
| Feb. 11, 2005 | (EP) | 05405168 |
| Feb. 11, 2005 | (EP) | 05405169 |
| Feb. 11, 2005 | (EP) | 05405170 |

(51) Int. Cl.
*C12P 17/04* (2006.01)
*C12N 9/02* (2006.01)

(52) U.S. Cl.
CPC ............... *C12P 17/04* (2013.01); *C12N 9/0008* (2013.01)

(58) Field of Classification Search
None
See application file for complete search history.

(56) References Cited

U.S. PATENT DOCUMENTS 5,376,544 A 12/1994 Lazarus et al.
7,700,723 B2 4/2010 Berry et al.

(Continued)

FOREIGN PATENT DOCUMENTS

WO 2004/029268 A1 4/2004
WO 2005/017159 A2 2/2005

OTHER PUBLICATIONS

Seffernick et al. (J. Bacteriology, vol. 183, pp. 2405-2410, 2001).*

(Continued)

*Primary Examiner* — Hope Robinson
(74) *Attorney, Agent, or Firm* — Nixon & Vanderhye P.C.

(57) ABSTRACT

The present invention relates to newly identified microorganisms capable of direct production of L-ascorbic acid (hereinafter also referred to as Vitamin C). The invention also relates to polynucleotide sequences comprising genes that encode proteins which are involved in the synthesis of Vitamin C. The invention also features polynucleotides comprising the full length polynucleotide sequences of the novel genes and fragments thereof, the novel polypeptides encoded by the polynucleotides and fragments thereof, as well as their functional equivalents. The present invention also relates to the use of said polynucleotides and polypeptides as biotechnological tools in the production of Vitamin C from microorganisms, whereby a modification of said polynucleotides and/or encoded polypeptides has a direct or indirect impact on yield, production, and/or efficiency of production of the fermentation product in said microorganism. Also included are methods/processes of using the polynucleotides and modified polynucleotide sequences to transform host microorganisms. The invention also relates to genetically engineered microorganisms and their use for the direct production of Vitamin C.

13 Claims, No Drawings

(56) References Cited

U.S. PATENT DOCUMENTS

| | | | |
|---|---|---|---|
| 2006/0035349 | A1 | 2/2006 | Hoshino et al. |
| 2006/0121582 | A1 | 6/2006 | Hoshino et al. |
| 2007/0161093 | A1 | 7/2007 | Hoshino et al. |

OTHER PUBLICATIONS

Wells, Biochemistry, vol. 29, pp. 8509-8517, 1990.*

International Search Report for related Appln. No. PCT/EP2006/001214, completed May 2006.

Saito et al. "Cloning of genes coding for L-sorbose and L-sorbosone dehydrogenases from *Gluconobacter oxydans* and microbial production of 2-keto-L-gulonate, a precursor of L-ascorbic acid, in a recombinant *G. oxydans* strain" Applied and Environmental Microbiology, vol. 63, No. 2, pp. 454-460 (Feb. 1997).

Shibata et al. "Metabolic engineering study on the direct fermentation of 2-keto-L-gulonic acid, a key intermediate of L-ascorbic acid in *Pseudomonas putida* IFO3738" Journal of Bioscience and Bioengineering, vol. 90, No. 2, pp. 223-225 (Aug. 2000).

Database UniProt Glucose dehydrogenase, Buell et al., "Q882Q7__PSEM" retrieved from EBI, Database accession No. Q882Q7 (Jun. 2003).

Buell et al. "The complete genome sequence of the *Arabidopsis* and tomato pathogen *Pseudomonas syringae* pv. *tomato* DC3000" Proceedings of the National Academy of Sciences USA, vol. 100, No. 18, pp. 10181-10186 (Sep. 2003).

Seffernick et al, "Melamine Deaminase and Atrazine Chlorohydrolase: 98 Percent Identical but Functionally Different", J. Bacteriology 183:2405-2410 (2001).

Wells, "Additivity of mutational effects in proteins", Biochemistry 29:8509-8517 (1990).

* cited by examiner

FERMENTATIVE VITAMIN C PRODUCTION

This application is a continuation of U.S. application Ser. No. 11/882,456, filed Aug. 1, 2007, now U.S. Pat. No. 8,318,462, which is a continuation of International Patent Application No. PCT/EP2006/001214, filed 10 Feb. 2006, which designated the U.S. and claims priority benefit of EP 05405066.1, 05405067.9, 05405072.9, 05405073.7, 05405081.0, 05405082.8, 05405083.6, 05405084.4, 05405087.7, 05405088.5, 05405089.3, 05405090.1, 05405091.9, 05405093.5, 05405094.3, 05405109.9, 05405110.7, 05405111.5, 05405112.3, 05405119.8, 05405120.6, 05405121.4, 05405139.6, 05405140.4, 05405146.1, 05405147.9, 05405148.7, 05405149.5, 05405150.3, 05405151.1, 05405152.9, 05405153.7, 05405166.9, 05405167.7, 05405168.5, 05405169.3, 05405170.1, all filed 11 Feb. 2005; the entire contents of each of which are hereby incorporated by reference.

The present invention relates to the use of polynucleotides and polypeptides as biotechnological tools in the production of Vitamin C from microorganisms, whereby said polynucleotides and/or encoded polypeptides have a direct or indirect impact on yield, production, and/or efficiency of production of the fermentation product. The invention also relates to genetically engineered microorganisms and their use for the direct production of Vitamin C.

Vitamin C is one of very important and indispensable nutrient factors for human beings. Vitamin C is also used in animal feed even though some farm animals can synthesize it in their own body.

For the past 70 years, Vitamin C has been produced industrially from D-glucose by the well-known Reichstein method. All steps in this process are chemical except for one (the conversion of D-sorbitol to L-sorbose), which is carried out by microbial conversion. Since its initial implementation for industrial production of Vitamin C, several chemical and technical modifications have been used to improve the efficiency of the Reichstein method. Recent developments of Vitamin C production are summarized in Ullmann's Encyclopedia of Industrial Chemistry, 5$^{th}$ Edition, Vol. A27 (1996), pp. 547ff.

Different intermediate steps of Vitamin C production have been performed with the help of microorganisms or enzymes isolated therefrom. Thus, 2-keto-L-gulonic acid (2-KGA), an intermediate compound that can be chemically converted into Vitamin C by means of an alkaline rearrangement reaction, may be produced by a fermentation process starting from L-sorbose, by means of strains belonging e.g. to the *Ketogulonicigenium* or *Gluconobacter* genera, or by an alternative fermentation process starting from D-glucose, by means of recombinant strains belonging to the *Gluconobacter* or *Pantoea* genera.

Current chemical production methods for Vitamin C have some undesirable characteristics such as high-energy consumption and use of large quantities of organic and inorganic solvents. Therefore, over the past decades, other approaches to manufacture Vitamin C using microbial conversions, which would be more economical as well as ecological, have been investigated.

Fermentative Vitamin C production from a number of substrates including D-sorbitol, L-sorbose and L-sorbosone has been reported in several microorganisms, such as algae and yeast, using different cultivation methods. The disadvantage of using these microorganisms, however, is the low yield of Vitamin C produced since then organisms are known to be capable of the production of both 2-keto-L-gulonic acid and Vitamin C, the yield of microbiologically produced Vitamin C is then limited by the relatively high production of 2-KGA which is more readily synthesized by said microorganism, leading, for instance, to ratios between the concentration of Vitamin C and 2-KGA which are less than 0.1.

Therefore it is desirable to develop production systems which have better industrial applicability, e.g. can be manipulated for increased titers and/or which have reduced fermentation times. One particularly useful system employs genes encoding membrane-bound L-sorbosone dehydrogenases or membrane-bound PQQ bound D-sorbitol dehydrogenases. An example of such a system uses a gene from *Gluconobacter oxydans* N44-1 encoding L-sorbosone dehydrogenase (hereafter called SNDHai) which converts L-sorbosone to L-ascorbic acid. This gene and homologous thereof have already been described in WO 2005/017159 which are incorporated herein.

There is a continuing need in even more optimized fermentation systems for the microbial production of Vitamin C to get higher yields as with the systems described above.

Surprisingly, it has now been found that under suitable culture conditions host cells expressing SNDHai can be used for further optimizing the direct production of Vitamin C.

This may be achieved by concurrent manipulation of a specific set of genes as further described herein. Such genes may be selected from the group consisting of RCS or SMS genes. This group of genes/proteins and the manipulation of each set is further described and exemplified herein.

The term "direct fermentation", "direct production", "direct conversion" and the like is intended to mean that a microorganism is capable of the conversion of a certain substrate into the specified product by means of one or more biological conversion steps, without the need of any additional chemical conversion step. For instance, the term "direct conversion of D-sorbitol into Vitamin C" is intended to describe a process wherein a microorganism is producing Vitamin C and wherein D-sorbitol is offered as a carbon source without the need of an intermediate chemical conversion step. A single microorganism capable of directly fermenting Vitamin C is preferred.

As used herein, "improved" or "improved yield of Vitamin C" caused by a genetic alteration means an increase of at least 5%, 10%, 25%, 30%, 40%, 50%, 75%, 100%, 200% or even more than 500%, compared to a cell which is not genetically altered. Such unaltered cells are also often referred to as wild type cells Therefore, it is in the first instance an object of the present invention to provide a process for the direct fermentative production of Vitamin C by cultering under suitable culture conditions a host cell which genome is genetically engineered by DNA sequences comprising the following polynucleotides a) a polynucleotide encoding L-sorbosone dehydrogenase according to SEQ ID NO: 2 or an active fragment or derivative thereof, and
b) at least one polynucleotide encoding a protein selected from the group consisting of
    1) proteins which are involved in the Sorbitol/Sorbose Metabolization System (SMS); and
    2) proteins which are involved in the Respiratory Chain System (RCS); and by isolation of Vitamin C from such cells or the culture medium.

The term "genetically engineered" or "genetically altered" means the scientific alteration of the structure of genetic material in a living organism. It involves the production and use of recombinant DNA. More in particular it is used to delineate the genetically engineered or modified organism from the naturally occurring organism. Genetic engineering may be done by a number of techniques known in the art, such as e.g. gene replacement, gene amplification, gene disruption, transfection, transformation using plasmids, viruses, or other vectors. A genetically modified organism, e.g. genetically modified microorganism, is also often referred to as a recombinant organism, e.g. recombinant microorganism.

SMS proteins are proteins involved in the Sorbitol/Sorbose Metabolization System. Polynucleotides and proteins encoded by these polynucleotides are herein abbreviated by SMS. SMS proteins function in the direct metabolization of D-sorbitol or L-sorbose.

RCS proteins are involved in the Respiratory Chain System. Polynucleotides and proteins encoded by these polynucleotides are herein abbreviated by RCS. RCS proteins function in the well-known respiratory chain of an organism, also known as the electron transport system.

In a preferred embodiment, the activity of the protein selected from RCS or SMS proteins is manipulated in such a way that it leads to an improved yield and/or efficiency of production of Vitamin C produced by said host cell compared to the wild type counterpart of said protein. The term "manipulated" as used herein is intended to encompass the genetic modification or alteration of a gene including the modification of its expression level, preferably by molecular biological techniques. In particular the term is intended to include the upregulation and downregulation of the activity of a protein, such a regulation can be achieved by the upregulation or downregulation of a gene encoding the protein. Further methods for the upregulation or downregulation of the activity of a certain protein as detailed above may also be used in this embodiment of the invention.

It is also an object of the present invention to provide vectors comprising such polynucleotides, preferably in the form of an expression vector.

Furthermore, it is also an object of the present invention to provide a process for producing a host cell which is genetically engineered, for example transformed by such DNA sequences or vectors. This may be accomplished, for example, by transferring polynucleotides es exemplified herein into a recombinant or non-recombinant host cell that may or may not contain an endogenous equivalent of the corresponding gene. Such a transformed cell is also an object of the invention.

Advantageous embodiments of the invention become evident from the dependent claims. These and other aspects and embodiments of the present invention should be apparent to those skilled in the art from the teachings herein.

Any cell that serves as recipient of the foreign nucleotide acid molecules may be used as a host cell, such as for instance a cell carrying a replicable expression vector or cloning vector or a cell being genetically engineered or genetically altered by well known techniques to contain desired gene(s) on its chromosome(s) or genome. The host cell may be of prokaryotic or eukaryotic origin, such as, for instance bacterial cells, animal cells, including human cells, fungal cells, including yeast cells, and plant cells. Preferably the host cell is a microorganism. More preferably the microorganism belongs to bacteria that can express the L-sorbosone dehydrogenase as an active form in vivo.

Examples of known bacteria able to directly produce Vitamin C in good quantities when altered according to the present invention include strains from the genera of *Ketogulonicigenium, Pantoea, Pseudomonas* or *Escherichia* or *Corynebacterium* and acetic acid bacteria.

Microorganisms which can be used in the present invention in order to improve the direct production of Vitamin C may be publicly available from different sources, e.g., Deutsche Sammlung von Mikroorganismen und Zellkulturen (DSMZ), Mascheroder Weg 1B, D-38124 Braunschweig, Germany, American Type Culture Collection (ATCC), P.O. Box 1549, Manassas, Va. 20108 USA or Culture Collection Division, NITE Biological Resource Center, 2-5-8, Kazusakamatari, Kisarazu-shi, Chiba, 292-0818, Japan (formerly: Institute for Fermentation, Osaka (IFO), 17-85, Juso-honmachi 2-chome, Yodogawa-ku, Osaka 532-8686, Japan). Examples of preferred bacteria deposited with IFO are for instance *Gluconobacter oxydans* (formerly known as *G. melanogenus*) IFO 3293, *Gluconobacter oxydans* (formerly known as *G. melanogenus*) IFO 3292, *Gluconobacter oxydans* (formerly known as *G. rubiginosus*) IFO 3244, *Gluconobacter frateurii* (formerly known as *G. industrius*) IFO 3260, *Gluconobacter cerinus* IFO 3266, *Gluconobacter oxydans* IFO 3287, and *Acetobacter aceti* subsp. *orleanus* IFO 3259, which were all deposited on Apr. 5, 1954; *Acetobacter aceti* subsp. *xylinum* IFO 13693 deposited on Oct. 22, 1975, and *Acetobacter aceti* subsp. *xylinum* IFO 13773 deposited on Dec. 8, 1977. Strain *Acetobacter* sp. ATCC 15164, which is also an example of a preferred bacterium, was deposited with ATCC. Strain *Gluconobacter oxydans* (formerly known as *G. melanogenus*) N 44-1 as another example of a preferred bacterium is a derivative of the strain IFO 3293 and is described in Sugisawa et al., Agric. Biol. Chem. 54: 1201-1209, 1990.

Acetic acid bacteria are preferred in the present invention to directly produce Vitamin C in high yields from a number of substrates including D-sorbitol, L-sorbose and L-sorbosone. Strains from the genera of *Gluconobacter, Gluconacetobacter* and *Acetobacter* are further preferred, they were found to be able to directly produce Vitamin C from L-sorbosone, whereas at least *Gluconobacter oxydans* DSM 17078 was found to be able to produce Vitamin C directly from D-sorbitol, L-sorbose or L-sorbosone. *Gluconobacter oxydans* DSM 17078 (formerly known as *Gluconobacter* oxydans N44-1) has been deposited at Deutsche Sammlung von Mikroorganismen und Zellkulturen (DSMZ), Mascheroder Weg 1B, D-38124 Braunschweig, Germany according to the Budapest Treaty on 26. January 2005.

In particular, the present invention is related to a process for the direct production of Vitamin C wherein a combination of polynucleotides as disclosed herein or a combination of modified polynucleotide sequences as described hereinafter are introduced into a suitable microorganism, the recombinant microorganism is cultured under conditions that allow the production of Vitamin C in high productivity, yield, and/or efficiency, the produced fermentation product is isolated from the culture medium and optionally further purified.

Several substrates may be used as a carbon source in the above-mentioned process. Particularly suited carbon sources are those that are obtainable from the D-glucose or D-sorbitol metabolization pathway such as, for example, D-glucose, D-sorbitol, L-sorbose, L-sorbosone, 2-keto-L-gulonate, D-gluconate, 2-keto-D-gluconate or 2,5-diketo-gluconate. Preferably, the substrate is selected from for instance D-glucose, D-sorbitol, L-sorbose or L-sorbosone, more preferably from D-glucose, D-sorbitol or L-sorbose, and most preferably from D-sorbitol or L-sorbose. The term "substrate" and "production substrate" in connection with the above process using a microorganism is used interchangeably herein.

Conversion of the substrate into Vitamin C in connection with the above process using a microorganism means that the conversion of the substrate resulting in Vitamin C is performed by the microorganism, i.e. the substrate may be directly converted into Vitamin C. Said microorganism is cultured under conditions which allow such conversion from the substrate as defined above.

A medium as used herein for the above process using a microorganism may be any suitable medium for the production of Vitamin C. Typically, the medium is an aqueous medium comprising for instance salts, substrate(s), and a certain pH. The medium in which the substrate is converted into Vitamin C is also referred to as the production medium.

"Fermentation" or "production" or "fermentation process" as used herein may be the use of growing cells using media, conditions and procedures known to the skilled person, or the use of non-growing so-called resting cells, after they have been cultivated by using media, conditions and procedures known to the skilled person, under appropriate conditions for the conversion of suitable substrates into desired products such as Vitamin C.

In connection with the above process it is understood that the above-mentioned microorganisms also include synonyms or basonyms of such species having the same physiological properties, as defined by the International Code of Nomenclature of Prokaryotes. The nomenclature of the microorganisms as used herein is the one officially accepted (at the filing date of the priority application) by the International Committee on Systematics of Prokaryotes and the Bacteriology and Applied Microbiology Division of the International Union of Microbiological Societies, and published by its official publication vehicle International Journal of Systematic and Evolutionary Microbiology (IJSEM). A particular reference is made to Urbance et al., IJSEM (2001) vol 51:1059-1070, with a corrective notification on IJSEM (2001) vol 51:1231-1233, describing the taxonomically reclassification of *G. oxydans* DSM 4025 as *Ketogulonicigenium vulgare.*

As used herein, resting cells refer to cells of a microorganism which are for instance viable but not actively growing, or which are growing at low specific growth rates [μ], for instance, growth rates that are lower than 0.02 $h^{-1}$, preferably lower than 0.01 $h^{-1}$. Cells which show the above growth rates are said to be in a "resting cell mode".

The process of the present invention may be performed in different steps or phases: preferably, the microorganism is cultured in a first step (also referred to as step (a) or growth phase) under conditions which enable growth. This phase is terminated by changing of the conditions such that the growth rate of the microorganism is reduced leading to resting cells, also referred to as step (b), followed by the production of Vitamin C from the substrate using the (b), also referred to as production phase.

Growth and production phase as performed in the above process using a microorganism may be performed in the same vessel, i.e., only one vessel, or in two or more different vessels, with an optional cell separation step between the two phases. The produced Vitamin C can be recovered from the cells by any suitable means. Recovering means for instance that the produced Vitamin C may be separated from the production medium. Optionally, the thus produced Vitamin C may be further processed.

For the purpose of the present invention relating to the above process, the terms "growth phase", "growing step", "growth step" and "growth period" are used interchangeably herein. The same applies for the terms "production phase", "production step", "production period".

One way of performing the above process may be a process wherein the microorganism is grown in a first vessel, the so-called growth vessel, as a source for the resting cells, and at least part of the cells are transferred to a second vessel, the so-called production vessel. The conditions in the production vessel may be such that the cells transferred from the growth vessel become resting cells as defined above. Vitamin C is produced in the second vessel and recovered therefrom.

In connection with the above process, the growing step can be performed in an aqueous medium, i.e. the growth medium, supplemented with appropriate nutrients for growth under aerobic conditions. The cultivation may be conducted, for instance, in batch, fed-batch, semi-continuous or continuous mode. The cultivation period may vary depending on the kind of cells, pH, temperature and nutrient medium to be used, and may be for instance about 10 h to about 10 days, preferably about 1 to about 10 days, more preferably about 1 to about 5 days when run in batch or fed-batch mode, depending on the microorganism. If the cells are grown in continuous mode, the residence time may be for instance from about 2 to about 100 h, preferably from about 2 to about 50 h, depending on the microorganism. If the microorganism is selected from bacteria, the cultivation may be conducted for instance at a pH of about 3.0 to about 9.0, preferably about 4.0 to about 9.0, more preferably about 4.0 to about 8.0, even more preferably about 5.0 to about 8.0. If algae or yeast are used, the cultivation may be conducted, for instance, at a pH below about 7.0, preferably below about 6.0, more preferably below about 5.5, and most preferably below about 5.0. A suitable temperature range for carrying out the cultivation using bacteria may be for instance from about 13° C. to about 40° C., preferably from about 18° C. to about 37° C., more preferably from about 13° C. to about 36° C., and most preferably from about 18° C. to about 33° C. If algae or yeast are used, a suitable temperature range for carrying out the cultivation may be for instance from about 15° C. to about 40° C., preferably from about 20° C. to about 45° C., more preferably from about 25° C. to about 40° C., even more preferably from about 25° C. to about 38° C., and most preferably from about 30° C. to about 38° C. The culture medium for growth usually may contain such nutrients as assimilable carbon sources, e.g., glycerol, D-mannitol, D-sorbitol, L-sorbose, erythritol, ribitol, xylitol, arabitol, inositol, dulcitol, D-ribose, D-fructose, D-glucose, and sucrose, preferably L-sorbose, D-glucose, D-sorbitol, D-mannitol, and glycerol; and digestible nitrogen sources such as organic substances, e.g., peptone, yeast extract and amino acids. The media may be with or without urea and/or corn steep liquor and/or baker's yeast. Various inorganic substances may also be used as nitrogen sources, e.g., nitrates and ammonium salts. Furthermore, the growth medium usually may contain inorganic salts, e.g., magnesium sulfate, manganese sulfate, potassium phosphate, and calcium carbonate.

In connection with the above process, the specific growth rates are for instance at least 0.02 $h^{-1}$. For cells growing in batch, fed-batch or semi-continuous mode, the growth rate depends on for instance the composition of the growth medium, pH, temperature, and the like. In general, the growth rates may be for instance in a range from about 0.05 to about 0.2 $h^{-1}$, preferably from about 0.06 to about 0.15 $h^{-1}$, and most preferably from about 0.07 to about 0.13 $h^{-1}$.

In another aspect of the above process, resting cells may be provided by cultivation of the respective microorganism on agar plates thus serving as growth vessel, using essentially the same conditions, e.g., cultivation period, pH, temperature, nutrient medium as described above, with the addition of agar agar.

If the growth and production phase are performed in two separate vessels, then the cells from the growth phase may be harvested or concentrated and transferred to a second vessel, the so-called production vessel. This vessel may contain an aqueous medium supplemented with any applicable production substrate that can be converted to Vitamin C by the cells. Cells from the growth vessel can be harvested or concentrated by any suitable operation, such as for instance centrifugation, membrane crossflow ultrafiltration or microfiltration, filtration, decantation, flocculation. The cells thus obtained may also be transferred to the production vessel in the form of the original broth from the growth vessel, without being harvested, concentrated or washed, i.e. in the form of a cell suspension. In a preferred embodiment, the cells are transferred from the growth vessel to the production vessel in the form of a cell suspension without any washing or isolating step in-between.

If the growth and production phase are performed in the same vessel, cells may be grown under appropriate conditions to the desired cell density followed by a replacement of the growth medium with the production medium containing the production substrate. Such replacement may be, for instance, the feeding of production medium to the vessel at the same time and rate as the withdrawal or harvesting of supernatant from the vessel. To keep the resting cells in the vessel, operations for cell recycling or retention may be used, such as for instance cell recycling steps. Such recycling steps, for instance, include but are not limited to methods using centrifuges, filters, membrane crossflow microfiltration of ultrafiltration steps, membrane reactors, flocculation, or cell immobilization in appropriate porous, non-porous or polymeric matrixes. After a transition phase, the vessel is brought to process conditions under which the cells are in a resting cell mode as defined above, and the production substrate is efficiently converted into Vitamin C.

The aqueous medium in the production vessel as used for the production step in connection with the above process using a microorganism, hereinafter called production medium, may contain only the production substrate(s) to be converted into Vitamin C, or may contain for instance additional inorganic salts, e.g., sodium chloride, calcium chloride, magnesium sulfate, manganese sulfate, potassium phosphate, calcium phosphate, and calcium carbonate. The production medium may also contain digestible nitrogen sources such as for instance organic substances, e.g., peptone, yeast extract, urea, amino acids, and corn steep liquor, and inorganic substances, e.g. ammonia, ammonium sulfate, and sodium nitrate, at such concentrations that the cells are kept in a resting cell mode as defined above. The medium may be with or without urea and/or corn steep liquor and/or baker's yeast. The production step may be conducted for instance in batch, fed-batch, semi-continuous or continuous mode. In case of fed-batch, semi-continuous or continuous mode, both cells from the growth vessel and production medium can be fed continuously or intermittently to the production vessel at appropriate feed rates. Alternatively, only production medium may be fed continuously or intermittently to the production vessel, while the cells coming from the growth vessel are transferred at once to the production vessel. The cells coming from the growth vessel may be used as a cell suspension within the production vessel or may be used as for instance flocculated or immobilized cells in any solid phase such as porous or polymeric matrixes. The production period, defined as the period elapsed between the entrance of the substrate into the production vessel and the harvest of the supernatant containing Vitamin C, the so-called harvest stream, can vary depending for instance on the kind and concentration of cells, pH, temperature and nutrient medium to be used, and is preferably about 2 to about 100 h. The pH and temperature can be different from the pH and temperature of the growth step, but is essentially the same as for the growth step.

In a preferred embodiment, the production step is conducted in continuous mode, meaning that a first feed stream containing the cells from the growth vessel and a second feed stream containing the substrate is fed continuously or intermittently to the production vessel. The first stream may either contain only the cells isolated/separated from the growth medium or a cell suspension, coming directly from the growth step, i.e. cells suspended in growth medium, without any intermediate step of cell separation, washing and/or isolating. The second feed stream as herein defined may include all other feed streams necessary for the operation of the production step, e.g. the production medium comprising the substrate in the form of one or several different streams, water for dilution, and base for pH control.

In connection with the above process, when both streams are fed continuously, the ratio of the feed rate of the first stream to feed rate of the second stream may vary between about 0.01 and about 10, preferably between about 0.01 and about 5, most preferably between about 0.02 and about 2. This ratio is dependent on the concentration of cells and substrate in the first and second stream, respectively.

Another way of performing the process as above using a microorganism of the present invention may be a process using a certain cell density of resting cells in the production vessel. The cell density is measured as absorbance units (optical density) at 600 nm by methods known to the skilled person. In a preferred embodiment, the cell density in the production step is at least about 10, more preferably between about 10 and about 200, even more preferably between about 15 and about 200, even more preferably between about 15 to about 120, and most preferably between about 20 and about 120.

In order to keep the cells in the production vessel at the desired cell density during the production phase as performed, for instance, in continuous or semi-continuous mode, any means known in the art may be used, such as for instance cell recycling by centrifugation, filtration, membrane crossflow ultrafiltration of microfiltration, decantation, flocculation, cell retention in the vessel by membrane devices or cell immobilization. Further, in case the production step is performed in continuous or semi-continuous mode and cells are continuously or intermittently fed from the growth vessel, the cell density in the production vessel may be kept at a constant level by, for instance, harvesting an amount of cells from the production vessel corresponding to the amount of cells being fed from the growth vessel.

In connection with the above process, the produced Vitamin C contained in the so-called harvest stream is recovered/harvested from the production vessel. The harvest stream may include, for instance, cell-free or cell-containing aqueous solution coming from the production vessel, which contains Vitamin C as a result of the conversion of production substrate by the resting cells in the production vessel. Cells still present in the harvest stream may be separated from the Vitamin C by any operations known in the art, such as for instance filtration, centrifugation, decantation, membrane crossflow ultrafiltration or microfiltration, tangential flow ultrafiltration or microfiltration or dead end filtration. After this cell separation operation, the harvest stream is essentially free of cells.

In a further aspect, the process of the present invention may be combined with further steps of separation and/or purification of the produced Vitamin C from other components contained in the harvest stream, i.e., so-called downstream processing steps. These steps may include any means known to a skilled person, such as, for instance, concentration, crystallization, precipitation, adsorption, ion exchange, electrodialysis, bipolar membrane electrodialysis and/or reverse osmosis. Vitamin C may be further purified as the free acid form or any of its known salt forms by means of operations such as for instance treatment with activated carbon, ion exchange, adsorption and elution, concentration, crystallization, filtration and drying. Specifically, a first separation of Vitamin C from other components in the harvest stream might be performed by any suitable combination or repetition of for instance, the following methods: two- or three-compartment electrodialysis, bipolar membrane electrodialysis, reverse osmosis or adsorption on, for instance, ion exchange resins or non-ionic resins. If the resulting form of Vitamin C is a salt of Vitamin C, conversion of the salt form into the free acid form may be performed by for instance bipolar membrane electrodialysis, ion exchange, simulated moving bed chromatographic techniques, and the like. Combination of the mentioned steps, e.g., electrodialysis and bipolar membrane electrodialysis into one step might be also used as well as combination of the mentioned steps e.g. several steps of ion exchange by using simulated moving bed chromatographic methods. Any of these procedures alone or in combination constitute a convenient means for isolating and purifying the product, i.e. Vitamin C. The product thus obtained may further be isolated in a manner such as, e.g. by concentration, crystallization, precipitation, washing and drying of the crystals and/or further purified by, for instance, treatment with activated carbon, ion exchange and/or re-crystallization.

In a preferred embodiment of the process, Vitamin C is purified from the harvest stream by a series of downstream processing steps as described above without having to be transferred to a non-aqueous solution at any time of this processing, i.e. all steps are performed in an aqueous environment. Such preferred downstream processing procedure may include for instance the concentration of the harvest stream coming from the production vessel by means of two- or three-compartment electrodialysis, conversion of Vitamin C in its salt form present in the concentrated solution into its acid form by means of bipolar membrane electrodialysis and/or ion exchange, purification by methods such as for instance treatment with activated carbon, ion exchange or non-ionic resins, followed by a further concentration step and crystallization. These crystals can be separated, washed and dried. If necessary, the crystals may be again re-solubilized in water, treated with activated carbon and/or ion exchange resins and recrystallized. These crystals can then be separated, washed and dried.

According to the invention, host cells (in particular recombinant microorganisms from the genera of *Gluconobacter, Gluconacetobacter* and *Acetobacter*) carrying a SNDHai gene according to the invention and at least one genetically engineered gene selected from SMS or RCS as exemplified herein are able to directly produce Vitamin C from a suitable carbon source in significantly higher yield, productivity, and/or efficiency then other known organsisms, for example in quantities of 300 mg/l or more or 800 mg/l or more from D-sorbitol or L-sorbose, respectively when measured in a resting cell method after an incubation period of 20 hours. The yield of Vitamin C produced from D-sorbitol when measured in a resting cell method after an incubation period of 20 hours may even be as high as 400, 600, 1000 mg/l or even exceed 1.5, 2, 4, 10, 20, 50, 100 g/l. The yield of Vitamin C produced from L-sorbose when measured in a resting cell method after an incubation period of 20 hours may even be as high as 1000 mg/l or even exceed 1.5, 2, 4, 10, 20, 50, 100 g/l.

The SNDHai protein shown in SEQ ID NO:2 and described herein performs an important function in the direct Vitamin C production in microorganisms, in particular in bacteria, such as acetic acid bacteria, such as *Gluconobacter, Acetobacter* and *Gluconacetobacter*, i.e. whose function compared to the wild type counterpart is enhanced or improved. This means that the direct production of Vitamin C is enhanced and/or increased and/or improved when a protein with SNDHai activity is expressed or preferably overexpressed in a particularly suitable host organism.

Production of Vitamin C in such a host organism is even further improved when at least one polynucleotide encoding a protein selected from SMS or RCS systems is altered concurrently.

The SNDHai protein may be encoded by a nucleotide sequence as shown in SEQ ID NO:1, which was isolated from *G. oxydans* DSM 17078 or by a polynucleotide that is substantially identical thereto In this context it should be mentioned that the expression of "a polynucleotide which is substantially identical" refers with respect to the SNDHai encoding sequence to a polynucleotide sequence selected from the group consisting of:

a) polynucleotides comprising the nucleotide sequence according to SEQ ID NO:1 b) polynucleotides comprising a nucleotide sequence obtainable by nucleic acid amplification such as polymerase chain reaction, using genomic DNA from a microorganism as a template and a primer set according to SEQ ID NO:3 and SEQ ID NO:4;

c) polynucleotides comprising a nucleotide sequence encoding a fragment or derivative of a polypeptide comprising the amino acid sequence according to SEQ ID 0:2 or encoding a fragment or derivative of a polypeptide encoded by a polynucleotide of any of (a) or (b) wherein in said derivative or fragment one or more amino acid residues are conservatively substituted compared to said polypeptide, and said fragment or derivative has the activity of a SNDHai polypeptide;

d) polynucleotides the complementary strand of which hybridizes under stringent conditions to a polynucleotide encoding a polypeptide comprising the amino acid sequence according to SEQ ID NO:2 or to a polynucleotide as defined in any one of (a) to (c) and which encode a SNDHai polypeptide; and e) polynucleotides which are at least 70%, such as 85, 90 or 95% identical to a polynucleotide encoding a polypeptide comprising the amino acid sequence according to SEQ ID NO:2 or to a polynucleotide as defined in any one of (a) to (c) and which encode a SNDHai polypeptide or the complementary strand of such a polynucleotide.

The polypeptide according to SEQ ID NO:2 was isolated from several different microorganisms according to the method described in example 22 and its annotated function was confirmed in activity assays as described in examples 23 and 24.

SNDHai activity is defined herein as the enzymatic activity that is able to convert L-Sorbosone directly to Ascorbic acid.

A nucleic acid as defined above may be obtained by nucleic acid amplification using cDNA, mRNA or alternatively, genomic DNA, as a template and appropriate oligonucleotide primers such as the nucleotide primers according to SEQ ID NO:3 and SEQ ID NO:4 according to standard PCR amplification techniques. The nucleic acid thus amplified may be cloned into an appropriate vector and characterized by DNA sequence analysis.

Further included are polynucleotide sequences coding for partial polypeptide sequences of a polypeptide which retains L-sorbosone dehydrogenase activity to produce Vitamin C from L-sorbosone such as, for example, polypeptides represented by SEQ ID NOs: 12, 14, 16, 18, 20, 22, and 27. The polypeptides comprise preferably partial amino acid sequences of at least 25 consecutive amino acids selected from the amino acids sequences of the polypeptides disclosed in the present application. The person skilled in the art is aware of the fact that certain stretches in polypeptides are essential for the biological activity. There are, however, other areas wherein amino acids can be inserted, deleted or substituted by other amino acids preferably such amino acids which are similar to the amino acids to be replaced.

As used herein, “active fragment or derivative” means a polypeptide which retains essentially the same biological function or activity as the polypeptide shown in SEQ ID NO:2. Examples of biological activity may for instance be enzymatic activity, signaling activity or antibody reactivity. The term “same biological function” or “functional equivalent” as used herein means that the protein has essentially the same biological activity, e.g. enzymatic, signaling or antibody reactivity, as a polypeptide shown in SEQ ID NO:2.

Metabolization of D-sorbitol or L-sorbose includes on one side the assimilation of these compounds into the cytosol and further conversion into metabolites useful for assimilation pathways such as the Embden-Meyerhof-Parnas pathway, the pentose phosphate pathway, the Entner-Doudoroff pathway, and the tricarboxyclic acid cycle, all of them involved in all vital energy-forming and anabolic reactions necessary for growth and maintenance of living cells. On the other side, metabolization of D-sorbitol or L-sorbose also includes the conversion of these compounds into further oxidized products such as L-sorbosone, 2-KGA and Vitamin C by so-called incomplete oxidation processes.

SMS proteins are herein defined as proteins involved in the Sorbitol/Sorbose Metabolisation System. Preferably, SMS proteins are selected from the group consisting of membrane-bound PQQ-dependent D-sorbitol dehydrogenase, membrane-bound L-sorbose dehydrogenase, membrane-bound L-sorbosone dehydrogenase, membrane-bound FAD-dependent D-sorbitol dehydrogenase, cytosolic NAD-dependent D-sorbitol dehydrogenase, NAD(P)-dependent D-sorbitol dehydrogenase (also called as NADPH-dependent sorbose reductase), NAD-dependent xylitol dehydrogenase, NAD-dependent alcohol dehydrogenase, membrane-bound L-sorbose dehydrogenase, NAD(P)H-dependent L-sorbose reductase, cytosolic NADP-dependent sorbosone dehydrogenase, cytosolic NAD(P)H-dependent L-sorbosone reductase, membrane-bound aldehyde dehydrogenase, cytosolic aldehyde dehydrogenase, glycerol-3-phophate dehydrogenase, glyceraldehyde-3-phosphate dehydrogenase. Even more preferred SMS proteins are selected from the family of oxidoreductases, more preferably oxidoreductases [EC 1] as recommended by the Nomenclature Committee of the International Union of Biochemistry and Molecular Biology (NC-IUBMB). Particularly preferred are oxidoreductases acting on the CH—OH group of donors [EC 1.1], in particular oxidoreductases with $NAD^+$ or $NADP^+$ as acceptor [EC 1.1.1] and oxidoreductases with other acceptors [EC 1.1.99], or oxidoreductases acting on the aldehyde or oxo group of donors [EC 1.2], in particular oxidoreductases with $NAD^+$ or NADP as acceptor [EC 1.2.1]. Even more preferably, they are selected from dehydrogenases belonging to enzyme classes [EC 1.1.1.1], [EC 1.1.1.15] or [EC 1.2.1.-].

The biological, enzymatic or other activity of SMS proteins can be measured by methods well known to a skilled person, such as, for example, by incubating a cell fraction containing the SMS protein in the presence of its substrate, electron acceptor(s) or donor(s) including phenazine methosulfate (PMS), dichlorophenol-indophenol (DCIP), NAD, NADH, NADP, NADPH, which consumption can be directly or indirectly measured by photometric, colorimetric or fluorimetric methods, and other inorganic components which might be relevant for the development of the activity. Thus, for example, the activity of membrane-bound D-sorbitol dehydrogenase can be measured in an assay where membrane fractions containing this enzyme are incubated in the presence of phosphate buffer at pH 6, D-sorbitol and the artificial electron acceptors DCIP and PMS. The rate of consumption of DCIP can be measured at 600 nm, and is directly proportional to the D-sorbitol dehydrogenase activity present in the membrane fraction.

Thus, for example, by increasing the activity of SMS proteins involved in incomplete oxidations of the D-sorbitol metabolization pathway, one can achieve increased conversion yields of D-sorbitol into products such as Vitamin C. In another example, by decreasing the activity of SMS proteins involved in the assimilation of D-sorbitol into the central metabolism, one can achieve increased conversion yields of D-sorbitol into products such as Vitamin C as well.

RCS proteins are known to be important in the mechanism through which electrons generated by any oxidoreduction reaction in the cell are further transported, in general by means of a series of oxidoreduction reactions involving cofactors and oxidases, and a final electron acceptor.

The main mechanism that living organisms use for producing energy necessary for vital activities is respiration. In higher organisms, carbohydrates, proteins, aliphatic acids are metabolised into acetyl-CoA by means of the glycolysis catabolic pathway and oxidation in cytoplasm. Acetyl-CoA is further metabolised through a series of reactions known as the citric acid cycle, which happens at the mitochondria. Energy resulting from these reactions is used for the production of reducing power, saved in the form of compounds such as $FADH_2$ and NADH. These compounds are then used in the so-called electron transport chain, a series of oxido-reduction chain reactions involving different components localized in the mitochondrial inner membranes. The final electron acceptor is oxygen, which then reacts with the protons resulting from the reaction chain and forms water. The proton concentration gradient resulting from this process is the driving force of the ATP synthesis.

In bacteria, this basic respiration process follows the same physiologic principle, but can occur in different ways, involving different components, intermediates, enzymatic complexes and final products. The efficiency of bacterial respiration processes can greatly vary, depending on the functional biological components expressed by each species, which in its turn depends on the genetic machinery available and on given growing conditions.

As an example, acetic acid bacteria, which are obligate aerobe, gram-negative microorganisms belonging to the genus *Acetobacter, Gluconobacter*, and *Gluconacetobacter*, present peculiar characteristics in terms of energy generating processes. These bacteria are well known for their ability to incompletely oxidize different substrates such as alcohols, sugars, sugar alcohols and aldehydes. These processes are generally known as oxidative fermentations, and they have been well established for a long time in the food and chemical industry, especially in vinegar and in L-sorbose production. Useful products known to be obtained from incomplete oxidations using strains belonging to the *Gluconobacter* genus are 2-keto-L-gulonic acid (2-KGA) starting from D-sorbitol and L-sorbose, and 5-keto-D-gluconic acid, a precursor for the biosynthesis of D-tartaric acid, starting from D-glucose. Incomplete oxidations are the main mechanism of generation of energy for acetic acid bacteria. They accomplish these reactions by means of different dehydrogenases located either in the periplasmic space, on the periplasmic membrane as well as in the cytoplasm. Different co-factors are employed by the different dehydrogenases, the most common being PQQ and FAD for membrane-bound or periplasmic enzymes, and NAD/NADP for cytoplasmic enzymes. The electron transport chain of *Gluconobacter/Gluconacetobacter* and *Acetobacter* strains is known to include co-enzyme Q10 (CoQ10) and CoQ9, respectively, as universal electron transport compound for all processes, as well as in some cases several kinds of cytochrome c elements. *Gluconobacter* strains are reported not to contain cytochrome c oxidase, but have other kinds of terminal oxidases, such as the bo type.

In one preferred embodiment, the RCS proteins or subunits of proteins which are involved in the transport of electrons are selected from respiratory chain proteins, more preferably, they are selected from those functioning in the biosynthesis of cofactors, prosthetic groups or which function as carrier proteins, in particular proteins involved in the biosynthesis or maturation of cofactors and/or their precursors such as FAD, NAD, NADP, PQQ, ubiquinone including CoQ10, cytochromes a, b, c, d, and heme. Most preferably, they are selected from PQQ biosynthetic proteins such as PQQ biosynthetic proteins A, B, C, D, E or from heme exporters such as CcmA or CcmB.

The biological, enzymatic or other activity of RCS proteins can be measured by methods well known to a skilled person, such as, for example, by incubating a membrane fraction or cell-free extract containing the RCS protein in the presence of coenzyme Q2 (CoQ2), an artificial electron acceptor, and by measuring the consumption of oxygen by methods such as the Clark-type oxygen electrode (Rank Brothers, Cambridge, United Kingdom). Thus, for example, the activity of ubiquinol oxidase bd, a cyanide-resistant terminal oxidase, can be measured in an assay where membrane fractions or cell-free extracts containing this enzyme are incubated in the presence of 50 mM phosphate buffer at pH 6.5, 0.02% of the detergent Tween20 and 100 μM cyanide in order to inactivate other cyanide-sensitive oxidases. The enzyme reaction can then be started by addition of 30 mM of the reduced artificial electron acceptor, $CoQ_{2red}$, and followed by measuring the increase in absorbance at 275 nm. The rate of consumption of oxygen can be measured with help of the Clark-type electrode, and is directly proportional to the ubiquinol oxidase bd activity present in the membrane fraction or in the cell-free extract.

Thus, for example, by modifying the RCS polynucleotide/proteins involved in the biosynthesis of terminal oxidases in such a form that they have enhanced activity, the overall efficiency of production of fermentation products depending on a series of dehydrogenation reactions, such as Vitamin C or 2-KGA, might be enhanced. In another example, by modifying the RCS polynucleotide/proteins involved in the biosynthesis of cofactors such as, for example, CoQ10 or cytochrome c, so that these cofactors are synthesized at a higher level, the overall capacity of the electron transfer system in bacteria which depend on those compounds as important elements of the respiratory chain can be enhanced, and have a positive impact on growth and production of fermentation compounds depending on oxidoreduction reactions, such as Vitamin C or 2-KGA. In still another example, the modification of the RCS polynucleotides/proteins involved in the biosynthesis of the cyanide-insensitive bypass oxidase (non-energy forming type) in such a way that its activity is enhanced, might have a positive impact on the overall capacity of production of fermentation products by bacteria even at non-growing or at low overall metabolic activity state.

The Vitamin C production by direct fermentation can greatly be improved when a protein selected from RCS or SMS as disclosed herein is expressed or modified as described hereinafter in a microorganism that also expresses SNDHai. Such is herein also referred to as concurrent expression. If the concurrent expression is the result of a genetic manipulation event, this is also referred to as concurrent manipulation. This may be accomplished for instance in a microorganism that expresses SNDHai, such as recombinant SNDHai, the latter microorganisms are then referred to as recombinant microorganisms.

Exemplified herein are also 7 novel SMS genes that may have an impact on the improvement of the production of Vitamin C in a microorganism that expresses SNDHai: Each of these genetically engineered genes may be used alone or in combination with at least one additional gene selected from the same group or from RCS.

The 7 different genes encoding a SMS polypeptide comprising the amino acid sequence according to SEQ ID NO: 125, SEQ ID NO: 129, SEQ ID NO: 133, SEQ ID NO: 45, SEQ ID NO: 137, SEQ ID NO: 141, SEQ ID NO: 145 respectively.

Corresponding nucleotide sequences are shown in SEQ ID NO: 124, SEQ ID NO: 128, SEQ ID NO: 132, SEQ ID NO: 44, SEQ ID NO: 136, SEQ ID NO: 140, SEQ ID NO: 144 respectively, which were isolated from *G. oxydans* DSM 17078. The invention also encompasses polynucleotides which are substantially homologous to one of these sequences.

In this context it should be mentioned that the expression of "a polynucleotide which is substantially homologous" with respect to the SMS encoding sequence refers to a polynucleotide sequence selected from the group consisting of:

a) polynucleotides comprising the nucleotide sequence according to SEQ ID NO: 124, SEQ ID NO: 128, SEQ ID NO: 132, SEQ ID NO: 44, SEQ ID NO: 136, SEQ ID NO: 140, SEQ ID NO: 144 respectively
b) polynucleotides comprising a nucleotide sequence obtainable by nucleic acid amplification such as polymerase chain reaction, using genomic DNA from a microorganism as a template and a primer set according to SEQ ID NO: 126 and SEQ ID NO: 127 or SEQ ID NO: 130 and SEQ ID NO: 131 or SEQ ID NO: 134 and SEQ ID NO: 135 or SEQ ID NO: 46 and SEQ ID NO: 47 or SEQ ID NO: 138 and SEQ ID NO: 139 or SEQ ID NO: 142 and SEQ ID NO: 143 or SEQ ID NO: 146 and SEQ ID NO: 147 respectively
c) polynucleotides comprising a nucleotide sequence encoding a fragment or derivative of a polypeptide comprising the amino acid sequence according to SEQ ID NO: 125, SEQ ID NO: 129, SEQ ID NO: 133, SEQ ID NO: 45, SEQ ID NO: 137, SEQ ID NO: 141, SEQ ID NO: 145 respectively or encoding a fragment or derivative of a polypeptide encoded by a polynucleotide of any of (a) or (b) wherein in said derivative one or more amino acid residues are conservatively substituted compared to said polypeptide, and said fragment or derivative has the activity of a SMS Protein;
d) polynucleotides the complementary strand of which hybridizes under stringent conditions to a polynucleotide encoding a polypeptide comprising the amino acid sequence according to SEQ ID NO: 125, SEQ ID NO: 129, SEQ ID NO: 133, SEQ ID NO: 45, SEQ ID NO: 137, SEQ ID NO: 141, SEQ ID NO: 145 respectively or to a polynucleotide as defined in any one of (a) to (c) and which encode a SMS Protein; and
e) polynucleotides which are at least 70%, such as 85, 90 or 95% homologous to a polynucleotide encoding a polypeptide comprising the amino acid sequence according to SEQ ID NO: 125, SEQ ID NO: 129, SEQ ID NO: 133, SEQ ID NO: 45, SEQ ID NO: 137, SEQ ID NO: 141, SEQ ID NO:

145 respectively or to a polynucleotide as defined in any one of (a) to (c) and which encode a SMS Protein;

or the complementary strand of such a polynucleotide.

The nucleotide and amino acid sequences determined above were used as a "query sequence" to perform a search with Blast2 program (version 2 or BLAST from National Center for Biotechnology [NCBI] against the database PRO SW-SwissProt (full release plus incremental updates). Gene SMS 02 (SEQ ID NO: 124) was annotated as encoding a protein showing similarity to NAD(P)-dependent D-sorbitol dehydrogenase of *Bacillus subtilis* (SEQ ID NO: 125). Gene SMS 03 (SEQ ID NO: 128) was annotated as encoding a protein showing similarity to NAD(P)-dependent sorbitol dehydrogenase of *Bacillus subtilis* (SEQ ID NO: 129). Gene SMS 04 (SEQ ID NO: 132) was annotated as encoding NAD (P)H-dependent L-sorbose reductase (SEQ ID NO: 133). Gene SMS 05 (SEQ ID NO: 44) was annotated as encoding NAD(P)-dependent sorbosone dehydrogenase (SEQ ID NO: 45). Gene SMS 12 (SEQ ID NO: 136) was annotated as encoding membrane-bound L-sorbose dehydrogenase (SDH) (SEQ ID NO: 137). Gene SMS 13 (SEQ ID NO: 140) was annotated as encoding subunit A of membrane-bound PQQ-dependent D-sorbitol dehydrogenase (SEQ ID NO: 141). Gene SMS 14 (SEQ ID NO: 144) was annotated as encoding subunit B of membrane-bound PQQ-dependent D-sorbitol dehydrogenase (SEQ ID NO: 145).

A nucleic acid encoding an SMS protein according to the invention may be obtained from any suitable organism by nucleic acid amplification using cDNA, mRNA or alternatively, genomic DNA, as a template and appropriate oligonucleotide primers such as the nucleotide primer pairs according to SEQ ID NO: 126 and SEQ ID NO: 127 or SEQ ID NO: 130 and SEQ ID NO: 131 or SEQ ID NO: 134 and SEQ ID NO: 135 or SEQ ID NO: 46 and SEQ ID NO: 47 or SEQ ID NO: 138 and SEQ ID NO: 139 or SEQ ID NO: 142 and SEQ ID NO: 143 or SEQ ID NO: 146 and SEQ ID NO: 147 respectively according to standard PCR amplification techniques. The nucleic acid thus amplified may be cloned into an appropriate vector and characterized by DNA sequence analysis.

The different SEQ ID NO's related to the SMS proteins/genes are summarized below:

| Protein/Gene | SEQ ID NO's Polynucleotide Seq. | SEQ ID NO's of Amino Acid Seq. | SEQ ID NO's of Primers |
|---|---|---|---|
| SMS 02 | 124 | 125 | 126/127 |
| SMS 03 | 128 | 129 | 130/131 |
| SMS 04 | 132 | 133 | 134/135 |
| SMS 05 | 44 | 45 | 46/47 |
| SMS 12 | 136 | 137 | 138/139 |
| SMS 13 | 140 | 141 | 142/143 |
| SMS 14 | 144 | 145 | 146/147 |

Exemplified herein are also 5 novel RCS genes that may have an impact on the improvement of the production of Vitamin C in a microorganism that expresses SNDHai: Each of these genetically engineered genes may be used alone or in combination with at least one additional gene selected from the same group or from SMS.

The 5 different genes encoding a RCS polypeptide comprising the amino acid sequence according to SEQ ID NO: 181, SEQ ID NO: 185, SEQ ID NO: 189, SEQ ID NO: 193, SEQ ID NO: 197, respectively.

Corresponding nucleotide sequences are shown in SEQ ID NO: 180, SEQ ID NO: 184, SEQ ID NO: 188, SEQ ID NO: 192, SEQ ID NO: 196, respectively, which were isolated from *G. oxydans* DSM 17078. The invention also encompasses polynucleotides which are substantially homologous to one of these sequences.

In this context it should be mentioned that the expression of "a polynucleotide which is substantially homologous" with respect to the RCS encoding sequence refers to a polynucleotide sequence selected from the group consisting of:

a) polynucleotides comprising the nucleotide sequence according to SEQ ID NO: 180, SEQ ID NO: 184, SEQ ID NO: 188, SEQ ID NO: 192, SEQ ID NO: 196, respectively b) polynucleotides comprising a nucleotide sequence obtainable by nucleic acid amplification such as polymerase chain reaction, using genomic DNA from a microorganism as a template and a primer set according to SEQ ID NO: 182 and SEQ ID NO: 183 or SEQ ID NO: 186 and SEQ ID NO: 187 or SEQ ID NO: 190 and SEQ ID NO: 191 or SEQ ID NO: 194 and SEQ ID NO: 195 or SEQ ID NO: 198 and SEQ ID NO: 199 respectively c) polynucleotides comprising a nucleotide sequence encoding a fragment or derivative of a polypeptide comprising the amino acid sequence according to SEQ ID NO: 181, SEQ ID NO: 185, SEQ ID NO: 189, SEQ ID NO: 193, SEQ ID NO: 197, respectively or encoding a fragment or derivative of a polypeptide encoded by a polynucleotide of any of (a) or (b) wherein in said derivative one or more amino acid residues are conservatively substituted compared to said polypeptide, and said fragment or derivative has the activity of a RCS Protein;

d) polynucleotides the complementary strand of which hybridizes under stringent conditions to a polynucleotide encoding a polypeptide comprising the amino acid sequence according to SEQ ID NO: 181, SEQ ID NO: 185, SEQ ID NO: 189, SEQ ID NO: 193, SEQ ID NO: 197, respectively or to a polynucleotide as defined in any one of (a) to (c) and which encode a RCS Protein; and e) polynucleotides which are at least 70%, such as 85, 90 or 95% homologous to a polynucleotide encoding a polypeptide comprising the amino acid sequence according to SEQ ID NO: 181, SEQ ID NO: 185, SEQ ID NO: 189, SEQ ID NO: 193, SEQ ID NO: 197, respectively or to a polynucleotide as defined in any one of (a) to (c) and which encode a RCS Protein;

or the complementary strand of such a polynucleotide.

The nucleotide and amino acid sequences determined above were used as a "query sequence" to perform a search with Blast2 program (version 2 or BLAST from National Center for Biotechnology [NCBI] against the database PRO SW-SwissProt (full release plus incremental updates). Gene RCS 21 (SEQ ID NO: 180) was annotated as encoding coenzyme PQQ biosynthesis protein A (SEQ ID NO: 181). Gene RCS 22 (SEQ ID NO: 184) was annotated as encoding coenzyme PQQ biosynthesis protein B (SEQ ID NO: 185). Gene RCS 23 (SEQ ID NO: 188) was annotated as encoding coenzyme PQQ biosynthesis protein C (SEQ ID NO: 189). Gene RCS 24 (SEQ ID NO: 192) was annotated as encoding coenzyme PQQ biosynthesis protein D (SEQ ID NO: 193). Gene RCS 25 (SEQ ID NO: 196) was annotated as encoding coenzyme PQQ biosynthesis protein E (SEQ ID NO: 197).

A nucleic acid encoding an RCS protein according to the invention may be obtained from any suitable organism by nucleic acid amplification using cDNA, mRNA or alternatively, genomic DNA, as a template and appropriate oligonucleotide primers such as the nucleotide primer pairs according to SEQ ID NO: 182 and SEQ ID NO: 183 or SEQ ID NO: 186 and SEQ ID NO: 187 or SEQ ID NO: 190 and SEQ ID NO: 191 or SEQ ID NO: 194 and SEQ ID NO: 195 or SEQ ID NO: 198 and SEQ ID NO: 199 respectively according to standard PCR amplification techniques. The nucleic acid thus amplified may be cloned into an appropriate vector and characterized by DNA sequence analysis.

The different SEQ ID NO's related to the RCS proteins/genes are summarized below:

| Protein/Gene | SEQ ID NO's Polynucleotide Seq. | SEQ ID NO's of Amino Acid Seq. | SEQ ID NO's of Primers |
|---|---|---|---|
| RCS 21 | 180 | 181 | 182/183 |
| RCS 22 | 184 | 185 | 186/187 |
| RCS 23 | 188 | 189 | 190/191 |
| RCS 24 | 192 | 193 | 194/195 |
| RCS 25 | 196 | 197 | 198/199 |

Before the concurrent expression will be illustrated further the construction and expression of a single gene/polynucleotide and the alteration in the genome of the host cell as exemplified above will be described in more detail on the basis of SNDHai. Unless otherwise indicated, the description is also applicable for the construction and expression of RCS and SMS genes disclosed herein.

A wide variety of host/cloning vector combinations may be employed in cloning the double stranded DNA. Preferred vectors for the expression of the genes of the present invention, i.e. the SNDHai gene, in *E. coli* may be selected from any vectors usually used in *E. coli*, such as for instance pQE vectors which can express His-tagged recombinant proteins (QIAGEN AG Switzerland), pBR322 or its derivatives including for instance pUC18 and pBluescript II (Stratagene Cloning Systems, Calif., USA), pACYC177 and pACYC184 and their derivatives, and a vector derived from a broad host range plasmid such as RK2 and RSF1010. A preferred vector for the expression of the nucleotide sequence of the present invention in bacteria including *Gluconobacter, Gluconacetobacter, Acetobacter*, and *Pseudomonas* is selected from any vectors which can replicate in *Gluconobacter, Acetobacter*, or *Pseudomonas* as well as in a preferred cloning organism such as *E. coli*. The preferred vector is a broad-host-range vector such as for instance a cosmid vector like pVK100 and its derivatives and RSF 1010. Copy number and stability of the vector should be carefully considered for stable and efficient expression of the cloned gene and also for efficient cultivation of the host cell carrying the cloned gene. Nucleic acid molecules containing for instance transposable elements such as Tn5 may also be used as a vector to introduce the desired gene into the preferred host, especially on a chromosome. Nucleic acid molecules containing any DNAs isolated from the preferred host together with a the SNDHai gene of the present invention may be also useful to introduce this gene into the preferred host cell, especially on a chromosome. Such nucleic acid molecules may be transferred to the preferred host by applying any of conventional methods, e.g., transformation, transduction, conjugal mating or electroporation, which are well known in the art, considering the nature of the host cell and the nucleic acid molecule.

The L-sorbosone dehydrogenase gene/nucleotide sequences may be ligated into a suitable vector containing a regulatory region such as for instance a promoter, a ribosomal binding site, and a transcriptional terminator operable in the host cell described above with a well-known method in the art to produce an expression vector.

The polypeptides and polynucleotides as exemplified herein are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living microorganism is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment.

An isolated polynucleotide or nucleic acid as used herein may be a DNA or RNA that is not immediately contiguous with both of the coding sequences with which it is immediately contiguous (one on the 5'-end and one on the 3'-end) in the naturally occurring genome of the organism from which it is derived. Thus, in one embodiment, a nucleic acid includes some or all of the 51-non-coding (e.g., promoter) sequences that are immediately contiguous to the coding sequence. The term "isolated polynucleotide" therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide", "gene" and "recombinant gene" refer to nucleic acid molecules which may be isolated from chromosomal DNA, which include an open reading frame encoding a protein, e.g. *G. oxydans* DSM 17078 SNDHai proteins. A polynucleotide may include a polynucleotide sequence as shown in SEQ ID NO:1 or fragments thereof and regions upstream and downstream of the gene sequences which may include, for example, promoter regions, regulator regions and terminator regions important for the appropriate expression and stabilization of the polypeptide derived thereof.

A gene may include coding sequences, non-coding sequences such as for instance untranslated sequences located at the 3'- and 5'-ends of the coding region of a gene, and regulatory sequences. Moreover, a gene refers to an isolated nucleic acid molecule as defined herein. It is furthermore appreciated by the skilled person that DNA sequence polymorphisms that lead to changes in the amino acid sequences of SNDHai proteins may exist within a population, e.g., the *Gluconobacter oxydans* population. Such genetic polymorphism in the SNDHai gene may exist among individuals within a population due to natural variation or in cells from different populations. Such natural variations can typically result in 1-5% variance in the nucleotide sequence of the SNDHai gene. Any and all such nucleotide variations and the resulting amino acid polymorphism in SNDHai are the result of natural variation and that do not alter the functional activity of SNDHai proteins are intended to be within the scope of the invention.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule may be single-stranded or double-stranded, but preferably is double-stranded DNA. The nucleic acid may be synthesized using oligonucleotide analogs or derivatives (e.g., inosine or phosphorothioate nucleotides). Such oligonucleotides may be used, for example, to prepare nucleic acids that have altered base-pairing abilities or increased resistance to nucleases.

The sequence information as provided herein should not be so narrowly construed as to require inclusion of erroneously identified bases. The specific sequences disclosed herein may be readily used to isolate the complete gene from a recombinant or non-recombinant microorganism capable of converting a given carbon source directly into Vitamin C, in particular *Gluconobacter oxydans*, preferably *Gluconobacter oxydans* DSM 17078 which in turn may easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence may be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

A nucleic acid molecule according to the invention may comprise only a portion or a fragment of the nucleic acid sequence provided by the present invention, such as for instance the sequence shown in SEQ ID NO:1, for example a fragment which may be used as a probe or primer such as for instance SEQ ID NO:3 or SEQ ID NO:4 or a fragment encoding a portion of a protein according to the invention. The nucleotide sequence determined from the cloning of the SNDHai gene allows for the generation of probes and primers designed for use in identifying and/or cloning other SNDHai family members, as well as SNDHai homologues from other species. The probe/primer typically comprises substantially purified oligonucleotides which typically comprises a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequence shown in SEQ ID NO:1 or a fragment or derivative thereof.

A nucleic acid molecule encompassing all or a portion of the nucleic acid sequence of SEQ ID NO:1 may be isolated by the polymerase chain reaction (PCR) using synthetic oligonucleotide primers designed based upon the sequence information contained herein.

A nucleic acid of the invention may be amplified using cDNA, mRNA or alternatively, genomic DNA, as a template and appropriate oligonucleotide primers according to standard PCR amplification techniques. The nucleic acid thus amplified may be cloned into an appropriate vector and characterized by DNA sequence analysis.

Fragments of a polynucleotide may also comprise polynucleotides not encoding functional polypeptides. Such polynucleotides may function as probes or primers for a PCR reaction.

Nucleic acids irrespective of whether they encode functional or non-functional polypeptides, may be used as hybridization probes or polymerase chain reaction (PCR) primers. Uses of the nucleic acid molecules of the present invention that do not encode a polypeptide having a SNDHai activity include, inter alia, (1) isolating the gene encoding the protein of the present invention, or allelic variants thereof from a cDNA library, e.g., from other organisms than *Gluconobacter oxydans* and (2) Northern blot analysis for detecting expression of mRNA of said protein in specific cells or (3) use in enhancing and/or improving the function or activity of homologous SNDHai genes in said other organisms.

Probes based on the nucleotide sequences provided herein may be used to detect transcripts or genomic sequences encoding the same or homologous proteins for instance in other organisms. Nucleic acid molecules corresponding to natural variants and non-*G. oxydans* homologues of the *G. oxydans* SNDHai DNA of the invention which are also embraced by the present invention may be isolated based on their homology to the *G. oxydans* SNDHai nucleic acid disclosed herein using the *G. oxydans* DNA, or a portion thereof, as a hybridization probe according to standard hybridization techniques, preferably under highly stringent hybridization conditions.

In preferred embodiments, the probe further comprises a label group attached thereto, e.g., the label group can be a radioisotope, a fluorescent compound, an enzyme, or an enzyme cofactor.

Homologous or substantially identical gene sequences may be isolated, for example, by performing PCR using two degenerate oligonucleotide primer pools designed on the basis of nucleotide sequences as taught herein.

The template for the reaction may be cDNA obtained by reverse transcription of mRNA prepared from strains known or suspected to express a polynucleotide according to the invention. The PCR product may be subcloned and sequenced to ensure that the amplified sequences represent the sequences of a new nucleic acid sequence as described herein, or a functional equivalent thereof.

The PCR fragment may then be used to isolate a full length cDNA clone by a variety of known methods. For example, the amplified fragment may be labeled and used to screen a bacteriophage or cosmid cDNA library. Alternatively, the labeled fragment may be used to screen a genomic library.

PCR technology can also be used to isolate full-length cDNA sequences from other organisms. For example, RNA may be isolated, following standard procedures, from an appropriate cellular or tissue source. A reverse transcription reaction may be performed on the RNA using an oligonucleotide primer specific for the most 5'-end of the amplified fragment for the priming of first strand synthesis.

The resulting RNA/DNA hybrid may then be "tailed" (e.g., with guanines) using a standard terminal transferase reaction, the hybrid may be digested with RNaseH, and second strand synthesis may then be primed (e.g., with a poly-C primer). Thus, cDNA sequences upstream of the amplified fragment may easily be isolated. For a review of useful cloning strategies, see e.g., Sambrook et al., supra; and Ausubel et al., supra.

Homologues, substantially identical sequences, functional equivalents, and orthologs of the genes exemplified herein, such as the SNDHai gene according to SEQ ID NO:1 may be obtained from a number of different microorganisms. The procedures for the isolation of specific genes and/or fragments thereof are exemplified herein. Following these procedures, SNDHai genes have successfully been isolated from *Gluconobacter* oxydans IFO 3292, *Gluconobacter oxydans* IFO 3287, *Acetobacter* sp. ATCC 15164 and *Gluconobacter oxydans* IFO 3244. Accordingly, nucleic acids encoding other SNDHai family members, which thus have a nucleotide sequence that differs from a nucleotide sequence according to SEQ ID NO:1, are within the scope of the invention. Moreover, nucleic acids encoding SNDHai proteins from different species which thus have a nucleotide sequence which differs from a nucleotide sequence shown in SEQ ID NO:1 are within the scope of the invention.

The invention also discloses an isolated polynucleotide hybridisable under stringent conditions, preferably under highly stringent conditions, to a polynucleotide according to the present invention, such as for instance a polynucleotide shown in SEQ ID NO:1. Advantageously, such polynucleotide may be obtained from a microorganism capable of converting a given carbon source directly into Vitamin C, in particular *Gluconobacter oxydans*, preferably *Gluconobacter oxydans* DSM 17078.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

In one embodiment, a nucleic acid of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence shown in SEQ ID NO:1 or the complement thereof.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include, for example, 2 h to 4 days incubation at 42° C. using a digoxigenin (DIG)-labeled DNA probe (prepared by using a DIG labeling system; Roche Diagnostics GmbH, 68298 Mannheim, Germany) in a solution such as DigEasyHyb solution (Roche Diagnostics GmbH) with or without 100 μg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

Preferably, an isolated nucleic acid molecule of the invention that hybridizes under preferably highly stringent conditions to a nucleotide sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *G. oxydans* SNDHai protein.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.). Of course, a polynucleotide which hybridizes only to a poly (A) sequence (such as the 3'-terminal poly (A) tract of mRNAs), or to a complementary stretch of T (or U) residues, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

In a typical approach, genomic DNA or cDNA libraries constructed from other organisms, e.g. microorganisms capable of converting a given carbon source such as D-Sorbitol, L-Sorbose or L-Sorbosone, directly into Vitamin C, in particular other *Gluconobacter* species may be screened.

For example, *Gluconobacter* strains may be screened for homologous polynucleotides by Northern blot analysis. Upon detection of transcripts homologous to polynucleotides according to the invention, DNA libraries may be constructed from RNA isolated from the appropriate strain, utilizing standard techniques well known to those of skill in the art. Alternatively, a total genomic DNA library may be screened using a probe hybridisable to a polynucleotide according to the invention.

A nucleic acid molecule of the present invention, such as for instance a nucleic acid molecule shown in SEQ ID NO:1 or a fragment or derivative thereof, may be isolated using standard molecular biology techniques and the sequence information provided herein. For example, using all or portion of the nucleic acid sequence shown in SEQ ID NO:1 as a hybridization probe, nucleic acid molecules according to the invention may be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Furthermore, oligonucleotides corresponding to or hybridisable to nucleotide sequences according to the invention may be prepared by standard synthetic techniques, e.g., using an automated DNA synthesizer.

The terms "homology", "identically" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). Preferably, the two sequences are the same length.

The skilled person will be aware of the fact that several different computer programs are available to determine the homology between two sequences. For instance, a comparison of sequences and determination of percent identity between two sequences may be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at dotaccelrysdotcom), using either a Blossom 62 matrix or a PAM250 matrix, and a gap weight of 16, 14, 12, 10, 8, 6 or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at wwwdotaccelrysdotcom), using a NWSgapdna.CMP matrix and a gap weight of 40, 50, 60, 70 or 80 and a length weight of 1, 2, 3, 4, 5 or 6. In another embodiment, the percent identity between two amino acid or nucleotide sequences is determined using the algorithm of E. Meyers and W. Miller (CABIOS, 4:11-17 (1989) which has been incorporated into the ALIGN program (version 2.0) (available at vegadotighdotcnrsdotfrslashbinlalign-guessdotcgi) using a PAM120 weight residue table, a gap length penalty of 12 and a gap penalty of 4.

The nucleic acid and protein sequences of the present invention may further be used as a "query sequence" to perform a search against public databases to, for example, identify other family members or related sequences. Such searches may be performed using the BLASTN and BLASTX programs (version 2.0) of Altschul, et al. (1990) J. Mol. Biol. 215:403-10. BLAST nucleotide searches may be performed with the BLASTN program, score=100, word length=12 to obtain nucleotide sequences homologous to the nucleic acid molecules of the present invention. BLAST protein searches may be performed with the BLASTX program, score=50, word length=3 to obtain amino acid sequences homologous to the protein molecules of the present invention. To obtain gapped alignments for comparison purposes, Gapped BLAST may be utilized as described in Altschul et al., (1997) Nucleic Acids Res. 25 (17): 3389-3402. When utilizing BLAST and Gapped BLAST programs, the default parameters of the respective programs (e.g., BLASTX and BLASTN) may be used. See wwwdotncbidotnimdotnihdotgov.

In another embodiment, an isolated nucleic acid molecule of the invention comprises a nucleic acid molecule which is the complement of a nucleotide sequence as of the present invention, such as for instance the sequence shown in SEQ ID NO:1. A nucleic acid molecule, which is complementary to a nucleotide sequence disclosed herein, is one that is sufficiently complementary to a nucleotide sequence shown in SEQ ID NO:1 such that it may hybridize to said nucleotide sequence thereby forming a stable duplex.

In a further embodiment, a nucleic acid of the invention as shown in SEQ ID NO:1 or the complement thereof contains at least one mutation leading to a gene product with modified function/activity. The at least one mutation may be introduced by methods known in the art or described herein. In regard to SNDHai, the at least one mutation leads to a SNDHai protein whose function compared to the wild type counterpart is enhanced or improved. The activity of the SNDHai protein is thereby increased. Methods for introducing such mutations are well known in the art.

Cells with an increased SNDHai activity are preferred, since such cells will produce more Vitamin C particularly when any of the other genes selected from SMS or RCS genes is genetically altered as described herein.

Another aspect pertains to vectors, containing a nucleic acid encoding a protein according to the invention or a functional equivalent or portion thereof. As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome.

Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions The recombinant vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., attenuator). Such regulatory sequences are described, for example, in Goeddel; Gene Expression Technology: Methods in Enzymology 185, Academic Press, San Diego, Calif. (1990). Regulatory sequences include those which direct constitutive or inducible expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention may be introduced into host cells to thereby produce proteins or peptides, encoded by nucleic acids as described herein, including, but not limited to, mutant proteins, fragments thereof, variants or functional equivalents thereof, and fusion proteins, encoded by a nucleic acid as described herein, e.g., SNDHai proteins, mutant forms of SNDHai proteins, fusion proteins and the like.

Functional equivalents of polypeptides as exemplified herein may be also part of the present invention and are defined on the basis of the amino acid sequences of the present invention by addition, insertion, deletion and/or substitution of one or more amino acid residues of such sequences wherein such derivatives preferably still have the L-sorbosone dehydrogenase activity measured by an assay known in the art or specifically described herein. Such functional derivatives may be made either by chemical peptide synthesis known in the art or by recombinant techniques on the basis of the DNA sequences as disclosed herein by methods known in the state of the art. Amino acid exchanges in proteins and peptides which do not generally alter the activity of such molecules are known.

The recombinant expression vectors of the invention may be designed for expression of SNDHai proteins in a suitable microorganism. For example, a protein according to the invention may be expressed in bacterial cells such as strains belonging to the genera *Gluconobacter*, Gluconacetobacter or *Acetobacter*. Expression vectors useful in the present invention include chromosomal-, episomal- and virus-derived vectors e.g., vectors derived from bacterial plasmids, bacteriophage, and vectors derived from combinations thereof, such as those derived from plasmid and bacteriophage genetic elements, such as cosmids and phagemids.

The DNA insert may be operatively linked to an appropriate promoter, which may be either a constitutive or inducible promoter. The skilled person will know how to select suitable promoters. The expression constructs may contain sites for transcription initiation, termination, and, in the transcribed region, a ribosome binding site for translation. The coding portion of the mature transcripts expressed by the constructs may preferably include an initiation codon at the beginning and a termination codon appropriately positioned at the end of the polypeptide to be translated.

Vector DNA may be introduced into suitable host cells via conventional transformation or transfection techniques. As used herein, the terms "transformation", "transconjugation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipidmediated transfection or electroporation. Suitable methods for transforming or transfecting host cells may be found in Sambrook, et al. (supra), Davis et al., Basic Methods in Molecular Biology (1986) and other laboratory manuals.

In order to identify and select cells which have integrated the foreign DNA into their genome, a gene that encodes a selectable marker (e.g., resistance to antibiotics) is generally introduced into the host cells along with the gene of interest. Preferred selectable markers include those that confer resistance to drugs, such as kanamycin, tetracycline, ampicillin and streptomycin. A nucleic acid encoding a selectable marker is preferably introduced into a host cell on the same vector as that encoding a protein according to the invention or can be introduced on a separate vector such as, for example, a suicide vector, which cannot replicate in the host cells. Cells stably transfected with the introduced nucleic acid can be identified by drug selection (e.g., cells that have incorporated the selectable marker gene will survive, while the other cells die).

The invention provides also an isolated polypeptide having the amino acid sequence shown in SEQ ID NO:2 or an amino acid sequence obtainable by expressing a polynucleotide of the present invention, such as for instance a polynucleotide sequence shown in SEQ ID NO:1 in an appropriate host.

Polypeptides according to the invention may contain only conservative substitutions of one or more amino acids in the amino acid sequence represented by SEQ ID NO:2 or substitutions, insertions or deletions of non-essential amino acids. Accordingly, a non-essential amino acid is a residue that may be altered in the amino acid sequences shown in SEQ ID NO:2 without substantially altering the biological function. For example, amino acid residues that are conserved among the proteins of the present invention, are predicted to be particularly unamenable to alteration. Furthermore, amino acids conserved among the proteins according to the present invention and other SNDHai proteins are not likely to be amenable to alteration.

The term "conservative substitution" is intended to mean that a substitution in which the amino acid residue is replaced with an amino acid residue having a similar side chain. These families are known in the art and include amino acids with basic side chains (e.g., lysine, arginine and histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, praline, phenylalanine, methionine, tryptophan), beta-branched side chains (e.g., threonine, valine, isoleucine) and aromatic side chains (e.g., tyrosine, phenylalanine, tryptophan, histidine).

As mentioned above, the polynucleotides of the present invention may be utilized in the genetic engineering of a suitable host cell to make it better and more efficient in the fermentation, for example in a direct fermentation process for Vitamin C.

Therefore, the invention also relates to the concurrent use of a gene encoding a SNDHai polypeptide or an active fragment or derivative thereof and a gene encoding a polypeptide having SMS or RCS activity or an active fragment or derivative thereof for the preparation of a recombinant host cell. Such a host cell will then show an improved capability to directly produce Vitamin. C.

The alteration in the genome of the microorganism may be obtained e.g. by replacing through a single or double cross-over recombination a wild type DNA sequence by a DNA sequence containing the alteration. For convenient selection of transformants of the microorganism with the alteration in its genome the alteration may, e.g. be a DNA sequence encoding an antibiotic resistance marker or a gene complementing a possible auxotrophy of the microorganism. Mutations include, but are not limited to, deletion-insertion mutations.

An alteration in the genome of the microorganism leading to a more functional polypeptide may also be obtained by randomly mutagenizing the genome of the microorganism using e.g. chemical mutagens, radiation or transposons and selecting or screening for mutants which are better or more efficient producers of one or more fermentation products. Standard methods for screening and selection are known to the skilled person.

In a specific embodiment, it is desired to knockout or suppress a repressor of the SNDHai gene of the present invention, i.e., wherein its repressor gene expression is artificially suppressed in order to improve the yield, production, and/or efficiency of production of the fermentation product when introduced into a suitable host cell. Methods of providing knockouts as well as microorganisms carrying such suppressed genes are well known in the art. As used herein, "suppression of the gene expression" includes complete and partial suppression, as well as suppression under specific conditions and also suppression of the expression of either one of the two alleles.

The aforementioned mutagenesis strategies for SNDHai proteins may result in increased yields of a desired compound in particular Vitamin C. This list is not meant to be limiting; variations on these mutagenesis strategies will be readily apparent to one of ordinary skill in the art. By these mechanisms, the nucleic acid and protein molecules of the invention may be utilized to generate microorganisms such as *Gluconobacter oxydans* or related strains of bacteria expressing mutated SNDHai nucleic acid and protein molecules such that the yield, production, and/or efficiency of production of a desired compound such as Vitamin C is improved.

The nucleic acid molecules, polypeptides, vectors, primers, and recombinant microorganisms described herein may be used in one or more of the following methods: identification of *Gluconobacter oxydans* and related organisms; mapping of genomes of organisms related to *Gluconobacter oxydans*; identification and localization of *Gluconobacter oxydans* sequences of interest; evolutionary studies; determination of SNDHai protein regions required for function; modulation of a SNDHai protein activity or function; modulation of the activity of a SNDHai pathway; and modulation of cellular production of a desired compound, such as Vitamin C.

The activity of an SNDHai peptide may be determined by methods known in the art and further exemplified herein.

In order to illustrate the invention in more detail, several examples are provided herein, wherein the manipulation of genes selected from RCS or SMS genes is exemplified in great detail. It will be evident for the skilled person now to select other genes encoding proteins selected from RCS or SMS proteins and manipulate them according to the teachings provided herein in order to obtain a microorganism that produces improved yields of Vitamin C.

In order to provide additional guidance in the above process, the following table is provided wherein it is further detailed how to manipulate specific genes selected from RCS or SMS genes. Herein the expressions "Up" and"Down" refer to the preferably overexpression and underexpression of the proteins, respectively, such as may be achieved by the up-regulation and down-regulation of the corresponding genes respectively. Equivalent results may be obtained when the activity of the corresponding proteins is enhanced or reduced by any other means than genetic manipulation.

| Name; polypeptide/ gene SEQ ID NO: | Similarity to | Up | Down |
|---|---|---|---|
| SMS 02; 124/125 | NAD(P)-dependent D-sorbitol dehydrogenase | | X |
| SMS 03; 128/129 | NAD(P)-dependent D-sorbitol dehydrogenase | | X |
| SMS 04; 132/133 | NAD(P)H-dependent L-sorbose reductase | | X |
| SMS 05; 44/45 | NAD(P)-dependent L-sorbosone dehydrogenase | | X |
| SMS 12; 136/137 | Membrane-bound L-sorbose dehydrogenase | X | |
| SMS 13; 140/141 | Membrane-bound PQQ-dependent D-sorbitol dehydrogenase subunit A | X | |
| SMS 14; 144/145 | Membrane-bound PQQ-dependent D-sorbitol dehydrogenase subunit B | X | |
| RCS 21; 180/181<br>RCS 22; 184/185<br>RCS 23; 188/189<br>RCS 24; 192/193<br>RCS 25; 196/197 | Proteins involved in biosynthesis of PQQ | X | |

The skilled person will know how to enhance and/or improve the activity of a protein, as for example SNDHai or alcohol dehydrogenase. Such may be accomplished by either genetically modifying the host organism in such a way that it produces more or more stable copies of the said protein than the wild type organism. It may also be accomplished by increasing the specific activity of the protein.

In the following paragraphs procedures are described how to achieve this goal, i.e. the increase in the yield and/or production of Vitamin C which is directly produced from D-sorbitol or L-sorbose by increasing (up-regulation) the activity of a specific protein, as for example SNDHai. These procedures apply mutatis mutandis for the similar RCS and SMS proteins whose functions compared to the wild type counterpart have to be enhanced or improved.

Modifications in order to have the organism produce more copies of the SNDHai gene, i.e. overexpressing the gene, and/or protein may include the use of a strong promoter, or the mutation (e.g. insertion, deletion or point mutation) of (parts of) the SNDHai gene or its regulatory elements. It may also involve the insertion of multiple copies of the gene into a suitable microorganism. An increase in the specific activity of an SNDHai protein may also be accomplished by methods known in the art. Such methods may include the mutation (e.g. insertion, deletion or point mutation) of (parts of) the SNDHai gene.

A mutation as used herein may be any mutation leading to a more functional or more stable polypeptide, e.g. more functional or more stable SNDHai gene products. This may include for instance an alteration in the genome of a microorganism, which improves the synthesis of SNDHai or leads to the expression of a SNDHai protein with an altered amino acid sequence whose function compared with the wild type counterpart having a non-altered amino acid sequence is improved and/or enhanced. The interference may occur at the transcriptional, translational or post-translational level.

Also known in the art are methods of increasing the activity of a given protein by contacting the SNDHai protein with a specific enhancer or other substances that specifically interact with the SNDHai protein. In order to identify such specific enhancers, the SNDHai protein may be expressed and tested for activity in the presence of compounds suspected to enhance the activity of the SNDHai protein. The activity of the SNDHai protein may also be increased by stabilizing the messenger RNA encoding SNDHai. Such methods are also known in the art, see for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

The term "increase" of activity as used herein encompasses increasing activity of one or more polypeptides in the producing organism, which in turn are encoded by the corresponding polynucleotides described herein. There are a number of methods available in the art to accomplish the increase of activity of a given protein, in this case the SNDHai protein. In general, the specific activity of a protein may be increased or the copy number of the protein may be increased. The term "increase of activity" or equivalent expressions also encompasses the situation wherein SNDHai protein activity is introduced in a cell that did not contain this activity before, e.g. by introducing a gene encoding SNDHai in a cell that did not contain an equivalent of this gene before, or that could not express an active form of the corresponding protein before.

To facilitate such an increase, the copy number of the genes corresponding to the polynucleotides described herein may be increased. Alternatively, a strong promoter may be used to direct the expression of the polynucleotide. In another embodiment, the promoter, regulatory region and/or the ribosome binding site upstream of the gene can be altered to increase the expression. The expression may also be enhanced or increased by increasing the relative half-life of the messenger RNA. In another embodiment, the activity of the polypeptide itself may be increased by employing one or more mutations in the polypeptide amino acid sequence, which increase the activity. For example, altering the relative Km of the polypeptide with its corresponding substrate will result in improved activity. Likewise, the relative half-life of the polypeptide may be increased. In either scenario, that being enhanced gene expression or increased specific activity, the improvement may be achieved by altering the composition of the cell culture media and/or methods used for culturing. "Enhanced expression" or "improved activity" as used herein means an increase of at least 5%, 10%, 25%, 50%, 75%, 100%, 200% or even more than 500%, compared to a wild-type protein, polynucleotide, gene; or the activity and/or the concentration of the protein present before the polynucleotides or polypeptides are enhanced and/or improved. The activity of the SNDHai protein may also be enhanced by contacting the protein with a specific or general enhancer of its activity.

In other cases disclosed herein the activity of an SMS or RCS polypeptide is to be reduced or abolished so that the yield of Vitamin C which is directly produced from D-sorbitol or L-sorbose is additionally increased.

The following procedures relating to the decrease (down-regulation) of SMS 05 protein activity apply mutatis mutandis for the RCS and SMS proteins, in particular those exemplified herein whose functions compared to the wild type counterpart have to be decreased.

To facilitate such a decrease, the copy number of the genes corresponding to the polynucleotides described herein may be decreased, such as for instance by underexpression or disruption of a gene. A gene is said to be "underexpressed" if the level of transcription of said gene is reduced in comparison to the wild type gene. This may be measured by for instance Northern blot analysis quantifying the amount of mRNA as an indication for gene expression. As used herein, a gene is underexpressed if the amount of generated mRNA is decreased by at least 1%, 2%, 5% 10%, 25%, 50%, 75% or 100% compared to the amount of mRNA generated from a wild-type gene. Alternatively, a weak promoter may be used to direct the expression of the polynucleotide. In another embodiment, the promoter, regulatory region and/or the ribosome binding site upstream of the gene can be altered to achieve the down-expression. The expression may also be reduced by decreasing the relative half-life of the messenger RNA.

In another embodiment, the activity of the polypeptide itself may be decreased by employing one or more mutations in the gene encoding the polypeptide, resulting in at least one mutation in the polypeptide amino acid sequence, which decreases the activity. For example, altering the affinity of the polypeptide for its corresponding substrate may result in reduced activity. Likewise, the relative half-life of the polypeptide may be decreased.

In either scenario, that being reduced gene expression or reduced activity, the reduction may be achieved by altering the composition of the cell culture media and/or methods used for culturing. "Reduced expression" or "reduced activity" as used herein means a decrease of at least 5%, 10%, 25%, 50%, 75% or 100% compared to a wild-type protein, polynucleotide or gene. The activity of a given protein may also be reduced by contacting the protein with a specific or general inhibitor of its activity. The terms "reduced activity", "decreased or abolished activity" are used interchangeably herein.

To improve the Vitamin C production of a certain recombinant host cell, SMS 05 gene expression may be inhibited in that organism for instance by targeting nucleotide sequences complementary to the regulatory region of a SMS 05 nucleotide sequence (e.g., a SMS 05 promoter and/or enhancers) to form triple helical structures that prevent transcription of a SMS 05 gene in target cells. See generally, Helene, C. (1991) AnticancerDrugDes. 6 (6): 569-84; Helene, C. et al. (1992) Ann. N.Y. Acad. Sci. 660: 27-36; and Maher, L. J. (1992) Bioassays 14 (12): 807-15.

Inhibition or prevention of gene expression may also be achieved by modifying the SMS 05 gene, e.g., by introducing one or more mutations into the SMS 05gene wherein said modification leads to a SMS 05 protein with a function which is significantly decreased in comparison to the wild-type protein.

A mutation as used herein may be any mutation leading to a less functional or unstable polypeptide, e.g. less functional or unstable SMS 05 gene products. This may include for instance an alteration in the genome of a microorganism, which interferes with the synthesis of SMS 05 or leads to the expression of a SMS 05 protein with an altered amino acid sequence whose function compared with the wild type counterpart having a non-altered amino acid sequence is completely or partially destroyed. The interference may occur at the transcriptional, translational or post-translational level.

The alteration in the genome of the microorganism may be obtained e.g. by replacing through a single or double crossover recombination a wild type DNA sequence by a DNA sequence containing the alteration. For convenient selection of transformants of the microorganism with the alteration in its genome the alteration may, e.g. be a DNA sequence encoding an antibiotic resistance marker or a gene complementing a possible auxotrophy of the microorganism. Mutations include, but are not limited to, deletion-insertion mutations. An example of such an alteration includes a gene disruption, i.e. a perturbation of a gene such that the product that is normally produced from this gene is not produced in a functional form. This could be due to a complete deletion, a deletion and insertion of a selective marker, an insertion of a selective marker, a frameshift mutation, an in-frame deletion, or a point mutation that leads to premature termination. In some of these cases the entire mRNA for the gene is absent, in others the amount of mRNA produced varies. In all cases the polypeptide encoded by said gene is not produced in a functional form, either absent or in a mutated form, such as e.g. a protein having reduced activity as defined herein.

An alteration in the genome of the microorganism leading to a less functional or non-functional polypeptide may also be obtained by randomly mutagenizing the genome of the microorganism using e.g. chemical mutagens, radiation or transposons and selecting or screening for mutants which are better or more efficient producers of one or more fermentation products. Standard methods for screening and selection are known to the skilled person.

In a specific embodiment, it is desired to knockout the SMS 05 gene of the present invention, i.e., wherein its gene expression is artificially suppressed in order to improve the yield, productivity, and/or efficiency of production of the fermentation product Vitamin C when introduced into a suitable host cell. Methods of providing knockouts as well as microorganisms carrying such suppressed genes are well known in the art. The suppression of the endogenous SMS 05 gene may be induced by deleting at least a part of the gene or the regulatory region thereof. As used herein, "suppression of the gene expression" includes complete and partial suppression, as well as suppression under specific conditions and also suppression of the expression of either one of the two alleles.

In order to create a knockout microorganism in which the expression of the SMS 05 gene is artificially suppressed, first the SMS 05 gene may be cloned and then a vector for homologous recombination may be constructed by using the gene to inactivate the endogenous SMS 05 gene in the target microorganism. The vector for homologous recombination then contains a nucleic acid sequence designed to inactivate the endogenous SMS 05 gene in the target microorganism. Such a nucleic acid may be for instance a nucleic acid sequence of the SMS 05 gene or the regulatory region thereof, such as the existing flanking region of the gene to be inactivated (in cis), or existing separately (in trans), containing at least a partial deletion, or alternatively it may be a nucleic acid sequence of the SMS 05 gene or the regulatory region thereof containing other genes. A gene which can also function as a marker is preferably selected as the gene to be inserted into the SMS 05 gene or the regulatory region thereof. The insert genes to be used include for instance drug-resistance genes as defined above. There is no particular limitation on the position where the genes may be inserted in the SMS 05 gene, as long as the insertion at that position results in the suppression of the expression of the endogenous SMS 05 gene in the target. To avoid polar effects of the insertion, in-frame silent deletions can be introduced by using, for example, the sacB system or long-flanking homology PCR. These techniques are well known to the person skilled in the art.

The aforementioned mutagenesis strategies for SMS 05 proteins may result in increased yields of a desired compound in particular Vitamin C. This list is not meant to be limiting; variations on these mutagenesis strategies will be readily apparent to one of ordinary skill in the art. By these mechanisms, the nucleic acid and protein molecules of the invention may be utilized to generate microorganisms such as *Gluconobacter oxydans* or related strains of bacteria expressing mutated SMS 05 nucleic acid and protein molecules such that the yield, productivity, and/or efficiency of production of a desired compound such as Vitamin C is improved.

In other cases disclosed herein the activity of an SMS or RCS polypeptide is to be increased so that the yield of Vitamin C which is directly produced from D-sorbitol or L-sorbose is additionally increased.

Also, particularly good results were obtained when a recombinant microorganism overexpressing SNDHai was transformed in such a way that an endogenous gene SMS 05 (SEQ ID NO: 44) encoding a NAD(P)-dependent sorbosone dehydrogenase (SEQ ID NO: 45) was knocked out according to examples 15-19.

Also, particularly good results were obtained when a recombinant microorganism overexpressing SNDHai was transformed in such a way that a gene RCS 21 (SEQ ID NO: 180) encoding a protein (pqqA) involved in the PQQ biosynthesis (SEQ ID NO: 181) is overexpressed according to examples 20 and 21.

This invention is further illustrated by the following examples which should not be construed as limiting. The contents of all references, patent applications, patents and published patent applications, cited throughout this application are hereby incorporated by reference.

EXAMPLES

Example 1

Preparation of Chromosomal DNA and Amplification of DNA Fragment by PCR

Chromosomal DNA of *Gluconobacter oxydans* DSM 17078 were prepared from the cells cultivated at 30° C. for 1 day in mannitol broth (MB) liquid medium consisting of 25 g/l mannitol, 5 g/l of yeast extract (Difco), and 3 g/l of Bactopeptone (Difco) by the method described by Sambrook et al (1989) "Molecular Cloning: A Laboratory Manual/Second Edition", Cold Spring Harbor Laboratory Press).

A DNA fragment was prepared by PCR with the chromosomal DNA prepared above and a set of primers, Pf (SEQ ID NO:3) and Pr (SEQ ID NO:4). For the reaction, the Expand High Fidelity PCR kit (Roche Diagnostics) and 10 ng of the chromosomal DNA was used in total volume of 100 μl according to the supplier's instruction to have the PCR product containing SNDHai DNA sequence (SEQ ID NO:1). The PCR product was recovered from the reaction and its correct sequence confirmed.

Example 2

Production of Vitamin C from L-Sorbosone Using Resting Cells Grown on Mannitol Broth Agar Medium IFO strains 3293, 3292, 3244, 3260, 3266, 3287, 3259, 13693, and 13773 as well as *Acetobacter* sp. ATCC 15164 and *Gluconobacter oxydans* DSM 17078, a derivative of the strain IFO 3293, were used for the production of Vitamin C from L-sorbosone.

Strains IFO 13693 and IFO 13773 were grown at 27° C. for 3 days on No. 350 medium containing 5 g/l Bactopeptone (Difco), 5 g/l yeast extract (Difco), 5 g/l glucose, 5 g/l mannitol, 1 g/l $MgSO_4.7H_2O$, 5 ml/l ethanol, and 15 g/l agar. All other *Acetobacter* strains and all *Gluconobacter* strains were grown at 27° C. for 3 days on mannitol broth (MB) agar medium containing 25 g/1 mannitol, 5 g/l yeast extract (Difco Laboratories, Detroit, Mich., USA), 3 g/l Bactopeptone (Difco), and 18 g/l of agar (Difco).

Cells were scraped from the agar plates, suspended in distilled water and used for resting cell reactions conducted at 30° C. for 20 h in 5 ml tubes with shaking at 230 rpm. The reaction mixtures (0.5 ml) contained 1% L-sorbosone, 0.3% NaCl, 1% $CaCO_3$ and cells at a final concentration of 10 absorbance units at 600 nanometers ($OD_{600}$). At the conclusion of the incubation period, the reaction mixtures were analyzed by high performance liquid chromatography (HPLC) using an Agilent 1100 HPLC system (Agilent Technologies, Wilmington, USA) with a LiChrospher-100-RP18 (125×4.6 mm) column (Merck, Darmstadt, Germany) attached to an Aminex-HPX-78H (300×7.8 mm) column (Biorad, Reinach, Switzerland). The mobile phase was 0.004 M sulfuric acid, and the flow rate was 0.6 ml/min. Two signals were recorded using an UV detector (wavelength 254 nm) in combination with a refractive index detector. In addition, the identification of the Vitamin C was done using an amino-column (YMC-Pack Polyamine-II, YMC, Inc., Kyoto, Japan) with UV detection at 254 nm. The mobile phase was 50 mM $NH_4H_2PO_4$ and acetonitrile (40:60).

An Agilent Series 1100 HPLC-mass spectrometry (MS) system was used to identify Vitamin C. The MS was operated in positive ion mode using the electrospray interface. The separation was carried out using a LUNA-C8(2) column (100×4.6 mm) (Phenomenex, Torrance, USA). The mobile phase was a mixture of 0.1% formic acid and methanol (96:4). Vitamin C eluted with a retention time of 3.1 minutes. The identity of the Vitamin C was confirmed by retention time and the molecular mass of the compound.

To exclude the presence of D-isoascorbic acid, the identification of Vitamin C was additionally done by retention time using an amino-column (YMC-Pack Polyamine-II, YMC, Inc., Kyoto, Japan) with UV detection at 254 nm. The mobile phase was 50 mM $NH_4H_2PO_4$ and acetonitrile (40:60).

The *Gluconobacter* and *Acetobacter* strains produced Vitamin C from L-sorbosone as shown in Table 1.

TABLE 1

Production of Vitamin C from L-sorbosone

| Strain | Vitamin C (mg/L) |
|---|---|
| *G. oxydans* IFO 3293 | 1740 |
| *G. oxydans* DSM 17078 | 570 |
| *G. oxydans* IFO 3292 | 410 |
| *G. oxydans* IFO 3244 | 1280 |
| *G. frateurii* IFO 3260 | 50 |
| *G. cerinus* IFO 3266 | 140 |
| *G. oxydans* IFO 3287 | 60 |
| *A. aceti* subsp. *Orleanus* IFO 3259 | 30 |
| *A. aceti* subsp. *Xylinum* IFO 13693 | 40 |
| *A. aceti* subsp. *Xylinum* IFO 13693 | 120 |
| *Acetobacter* sp. ATCC 15164 | 310 |
| Blank | Not detected |

Blank; reaction was done in the reaction mixture without cells.

Example 3

Vitamin C Production from L-Sorbose and D-Sorbitol in Tube and Flask Fermentations Cells of *G. oxydans* DSM 17078 were used to inoculate 4 ml of No. 3BD liquid medium and cultivated in a tube (18 mm diameter) at 30° C. for 3 days with shaking at 220 rpm. 20 mg/l of Vitamin C had accumulated at the end of the incubation period.

Cells of strain DSM 17078 were cultivated (in triplicate) in 50 ml of No. 5 medium containing 100 g/l D-sorbitol, 0.5 g/l glycerol, 15 g/l yeast extract (Difco), 2.5 g/l of $MgSO_4.7H_2O$, and 15 g/L of $CaCO_3$ in a 500 ml baffled shake flask at 30° C. with shaking at 200 rpm. After 72 h of cultivation, the amounts of Vitamin C measured by HPLC in the three flasks were 400, 500 and 680 mg/1

Example 4

Vitamin C Production from D-Sorbitol in Fed-Batch Fermentation

Cells of *G. oxydans* DSM 17078 were grown in 200 ml No. 5 medium containing 100 g/l D-sorbitol, 0.5 g/l glycerol, 15 g/l yeast extract (Fluka BioChemika, Buchs, Switzerland), 2.5 g/l $MgSO_4.7H_2O$ and 15 g/l $CaCO_3$ in a 2-1 baffled shake flask at 30° C. with shaking at 180 rpm. After 48 h, 150 ml of this culture was used to inoculate a $10^{-1}$ bioreactor (B. Braun ED 10, Melsungen, Germany) previously prepared with 5.3 1 medium containing 20 g/l D-sorbitol, 0.5 g/l glycerol, 15 g/l yeast extract (Fluka BioChemika, Buchs, Switzerland) and 2.5 g/l$MgSO_4.7H_2O$ and equipped with temperature, pH and dissolved oxygen sensors and control loops. Temperature was controlled at 30° C., pH was controlled at 6.0 by adding a 28% ammonia solution, airflow was 4.5 l/min and dissolved oxygen was controlled at 30% by a cascade with stirring speed (minimum 300 rpm). After 6 h process time, a 500 g/l sorbitol solution was fed at a rate of 25 g/h for a period of 44 h. After 96 h process time, about 1% substrate was left in the supernatant, and 950 mg/l Vitamin C had been produced.

Example 5

Vitamin C Production from L-Sorbosone or L-Sorbose with a Cell Membrane Fraction Cells of *G. oxydans* DSM 17078 were cultivated in 100 ml of No. 3BD liquid medium in a 500 ml baffled shake flask at 30° C. with shaking at 220 rpm for 3 days. The resulting culture was centrifuged at 500 rpm to remove $CaCO_3$. The supernatant from this step was then centrifuged at 5,000 rpm to pellet the cells. The collected cells were suspended in 3 ml of 50 mM potassium phosphate buffer (pH 7.0) and the cells were disrupted by two passages through a French Pressure cell (SIM-AMINCO Spetronic Instruments, USA) at 900 psi, The resulting homogenate was first centrifuged at 5,000 rpm to remove cell debris. Then the supernatant was diluted to a final protein concentration of 3 mg of protein/ml. This diluted sample is designated as cell-free extract (CFE). The CFE was centrifuged at 100,000×g for 60 min. The supernatant was discarded and the pellet was collected as the membrane fraction.

The reaction (200 μl) with the membrane fraction (100 μl) was carried out in 50 mM potassium phosphate buffer (pH7.0), 30° C. with shaking at 220 rpm for 15 h. The substrates tested were L-sorbosone (1% final concentration) and L-sorbose (2% final concentration). The final protein concentration used in the reaction was 1.5 mg/ml. At the end of the incubation period, 680 mg/l and 10 mg/l of Vitamin C had been produced from 1% L-sorbosone and 2% L-sorbose, respectively.

Example 6

Production of Vitamin C from D-Sorbitol, L-Sorbose or L-Sorbosone Using Resting Cells Grown on 3BD Agar Medium Cells of *G. oxydans* DSM 17078 were grown at 27° C. for 3 days on No. 3BD agar medium containing 70 g/l L-sorbose, 0.5 g/l glycerol, 7.5 g/l yeast extract (Difco), 2.5 g/l $MgSO_4.7H_2O$, 10 g/l $CaCO_3$ and 18 g/l agar (Difco). The resting cell reactions (1 ml reaction mixture in 10 ml tube) were carried out with 2% D-sorbitol, 2% L-sorbose, or 1% L-sorbosone at 30° C. for 24 h as described in Example 2. Strain DSM 17078 produced 280, 400 and 1780 mg/l of Vitamin C from D-sorbitol, L-sorbose, and L-sorbosone, respectively.

Other reactions (0.5 ml reaction mixture in 10 ml tube) were carried out with DSM 17078 cells grown on No. 3BD agar medium in reaction mixtures containing 2% D-sorbitol, 2% L-sorbose or 2% L-sorbosone for 2 days as described in Example 2. Strain DSM 17078 produced 1.8, 2.0 and 5.1 g/l of Vitamin C from D-sorbitol, L-sorbose, and L-sorbosone, respectively.

A reaction using cells of *G. oxydans* IFO 3293 was carried out with 2% L-sorbosone as described above. Strain IFO 3293 produced 5.7 g/l of Vitamin C in 2 days.

Example 7

Production of Vitamin C from D-Sorbitol Using Resting Cells Grown In Liquid Medium Cells of *G. oxydans* DSM 17078 were grown in 200 ml of No. 5 medium containing 100 g/l D-sorbitol, 0.5 g/l glycerol, 15 g/l yeast extract (Fluka BioChemika, Buchs, Switzerland), 2.5 g/l $MgSO_4.7H_2O$ and 15 g/l $CaCO_3$ in a 2-1 baffled shake flask at 30° C. with shaking at 1.80 rpm. After 24 h, the culture was centrifuged at 3220 g (Eppendorf 5810R, Hamburg, Germany), and the cells were resuspended in 0.9% NaCl solution, centrifuged again at 3220 g and the cell pellet was used to inoculate one baffled 500 ml shake flask containing 50 ml of full growth medium (100 g/l D-sorbitol, 0.5 g/l glycerol, 15 g/l yeast extract, 2.5 g/l $MgSO_4.7H_2O$, 15 g/l $CaCO_3$) and another baffled 500 ml shake flask containing 50 ml production medium (100 g/l D-sorbitol, 3 g/l NaCl, 10 g/l $CaCO_3$). The initial cell density, measured as optical density at 600 nm ($OD_{600}$), in both flasks was 10. Both flasks were incubated at 30° C. with shaking at 180 rpm. After 48 h, the cell suspension in growth medium and production medium had accumulated 1.06 and 1.18 g/l Vitamin C, respectively. No additional growth was observed in full medium during the incubation period time.

Example 8

Southern Blot Analysis of the Bacteria Producing Vitamin C from L-Sorbosone

Chromosomal DNA was prepared from cells of *Gluconobacter oxydans* IFO 3293, IFO 3292, IFO 3244, IFO 3287, *Gluconobacter frateurii* IFO 3260 and IFO 3265, *Gluconobacter cerinus* IFO 3266 and IFO 3269, *Acetobacter aceti* subsp. *orleanus* IFO 3259, *Acetobacter aceti* subsp. *xylinum* IFO 13693 and IFO 13773, *Acetobacter* sp. ATCC 15164, and *Escherichia coli* K-12. Strains IFO 13693 and IFO 13773 were grown at 27° C. for 3 days on No. 350 medium containing 5 g/l Bactopeptone (Difco), 5 g/L yeast extract (Difco), 5 g/L glucose, 5 g/L mannitol, 1 g/L $MgSO_4.7H_2O$, 5 ml/L ethanol, and 15 g/L agar. All other *Acetobacter* strains and all *Gluconobacter* strains were grown at 27° C. for 3 days on mannitol broth (MB) agar medium containing 25 g/l mannitol, 5 g/l yeast extract (Difco Laboratories, Detroit, Mich., USA), 3 g/l Bactopeptone (Difco), and 18 g/l of agar (Difco). *E. coli* K-12 was grown on Luria Broth agar medium. The chromosomal DNA preparations were used for Southern blot hybridization under stringent conditions. The chromosomal DNA preparations were digested with ClaI (when analyzing the N-domain region) or EcoRI (when analyzing the C-domain region), and 1 μg of the DNA fragments were separated by agarose gel electrophoresis (1% agarose). The gel was treated with 0.25 N HCl for 15 min and then 0.5 N NaOH for 30 min, and then was blotted onto a nylon membrane with Vacuum Blotter Model 785 (BIO-RAD Laboratories AG, Switzerland) according to the instruction of the supplier. The probes were prepared with PCR-DIG labeling kit (Roche Diagnostics) by using the primer sets as described in Table 2. The PCR product P1 corresponds to the region of SNDHai designated the N-domain (possible transmembrane region) while PCR product P2 corresponds to the region of SNDHai designated as the C-domain (possible primary dehydrogenase region).

TABLE 2

Primers used for PCR to generate labeled probes for Southern hybridizations

| Primer set | SEQ ID NOs. of primers | PCR product | Expected size of PCR product (bp) |
|---|---|---|---|
| SNDH1F and SNDH420R | 5 and 6 | P1 | 420 |
| SNDH501F and SNDH2364R | 7 and 8 | P2 | 1864 |
| SNDH501F and SNDH1530R | 7 and 9 | P3 | 1030 |
| SNDH1391F and SNDH2364R | 10 and 8 | P4 | 974 |

Table 2 shows the results of the Southern blot hybridization experiments. In the hybridization with the P1 (N-domain) probe, clear positive bands were observed for *G. oxydans* IFO 3293, IFO 3292, IFO 3244, IFO 3287 and A. sp. ATCC 15164. In the hybridization with the P2 (C-domain) probe, clear positive bands were observed for strains IFO 3293, IFO 3292, IFO 3244, IFO 3287 and A. sp. ATCC 15164, while a faint band was observed for stains IFO 3260, IFO 3265, IFO 3266, IFO 3269 and IFO 13773. The control strain, *E. coli* K-12, showed no detectable signals for either domain.

TABLE 3

Detection of hybridization signals in different strains obtained by Southern blot hybridization with probes for N- and C-domains of SNDHai (probes P1 and P2)

| Strain | P1 | P2 |
|---|---|---|
| *G. oxydans* IFO 3293 | + | + |
| *G. oxydans* IFO 3292 | + | + |
| *G. oxydans* IFO 3244 | + | + |
| *G. frateurii* IFO 3260 | nd | Tr |
| *G. frateurii* IFO 3265 | nd | Tr |
| *G. cerinus* IFO 3266 | nd | Tr |
| *G. oxydans* IFO 3269 | nd | Tr |
| *G. oxydans* IFO 3287 | + | + |
| *A. aceti* subsp. *orleanus* IFO 3259 | nd | nd |
| *A. aceti* subsp. *xylinum* IFO 13693 | nd | nd |
| *A. aceti* subsp. *xylinum* IFO 13773 | nd | Tr |
| *Acetobacter* sp. ATCC 15164 | + | + |
| *E. coli* K-12 | nd | nd |

Tr, trace; nd, not detected. Probes P1 and P2 were synthesized (as DIG-labeled PCR products) with the primer sets specified in Table 2.

Example 9

PCR Amplification and Sequencing of Orthologs of the *Gluconobacter oxydans* DSM 17078 SNDHai Gene Chromosomal DNA preparations (prepared as described in Example 8) were used as templates for PCR with the four primer sets shown in Table 2. Five to 100 ng of chromosomal DNA was used per reaction (total volume, 50 μl). Unless specified otherwise, the Expand High Fidelity PCR system was used (Roche Diagnostics). The PCR conditions were as follows:

Incubation at 94° C. for 2 min; 30 cycles of (i) denaturation step at 94° C. for 15 sec, (ii) annealing step at 60° C. for 30 sec, (iii) synthesis step at 72° C. for 45 to 120 sec (time for the synthesis step for primer sets P1, P2, P3 and P4 were 45 sec, 120 sec, 90 sec, and 90 sec, respectively); extension at 72° C. for 7 min.

Samples of the PCR reactions were separated by agarose gel electrophoresis and the bands were visualized with a transilluminator after staining with ethidium bromide. The results of the PCR reactions are summarized in Table 4.

TABLE 4

Detection of PCR products P1, P2, P3 and P4 in different strains obtained with the primer sets of Table 2 (products visualized via agarose gel electrophoresis)

| Strain | P1 | P2 | P3 | P4 |
|---|---|---|---|---|
| *G. oxydans* IFO 3293 | + | +* | nt | + |
| *G. oxydans* IFO 3292 | + | nd | nd | + |
| *G. oxydans* IFO 3244 | + | + | + | + |
| *G. frateurii* IFO 3260 | nd | nd | nd | nd |

TABLE 4-continued

| Detection of PCR products P1, P2, P3 and P4 in different strains obtained with the primer sets of Table 2 (products visualized via agarose gel electrophoresis) | | | | |
|---|---|---|---|---|
| Strain | P1 | P2 | P3 | P4 |
| *G. cerinus* IFO 3266 | nd | nd | nd | nd |
| *G. oxydans* IFO 3287 | + | + | nd | + |
| *A. aceti* subsp. *orleanus* IFO 3259 | nd | nd | nd | nd |
| *A. aceti* subsp. *xylinum* IFO 13693 | nd | nd | nd | nd |
| *A. aceti* subsp. *xylinum* IFO 13773 | nd | nd | nd | nd |
| *Acetobacter* sp. ATCC 15164 | + | + | nd | nd |
| *E. coli* K-12 | nd | nd | nt | nd |

+, detected; nd, not detected; nt, not tested.

*This PCR was done with GC-rich PCR system (Roche Diagnostics) with the same reaction cycle as was used for Expand High Fidelity PCR system.

When clear PCR bands were observed on the agarose gel (Table 4), the PCR products were used directly for nucleotide sequencing using standard methods. The nucleotide sequences obtained for the different PCR products, and the corresponding amino acid sequences of the encoded peptides, were compared with the full length sequence of the SNDHai gene and protein from *G. oxydans* DSM 17078.

*Gluconobacter Oxydans* IFO 3292 SNDHai Ortholog

The PCR product (about 1 kb) obtained upon amplification with primers SNDH1391F (SEQ ID NO:10) and SNDH2364R (SEQ ID NO:8) and chromosomal DNA from *G. oxydans* IFO 3292 as the template, was used for sequencing with primer SNDH1391F (SEQ ID NO:10). The determined nucleotide sequence of 771 by (SEQ ID NO:11) showed 98.7% (761/771) homology with nucleotides 1431-2201 of the sequence of SNDHai from *G. oxydans* DSM 17078 (SEQ ID NO:1). The deduced amino acid sequence of 256 amino acids (SEQ ID NO:12) showed 100% identity to amino acids 478-733 of the amino acid sequence of SNDH from *G. oxydans* DSM 17078 (SEQ ID NO:2).

*Gluconobacter Oxydans* IFO 3287 SNDHai Ortholog

The PCR product (about 0.4 kb) obtained upon amplification with primers SNDH1F (SEQ ID NO:5) and SNDH420R (SEQ ID NO:6) and chromosomal DNA from *G. oxydans* IFO 3287 as the template, was used for sequencing with primer SNDH420R (SEQ ID NO:6). The determined nucleotide sequence of 350 by (SEQ ID NO:13) showed 97.4% (341/350) homology with nucleotides 31-380 of SEQ ID NO:1. The deduced amino acid sequence of 116 residues (SEQ ID NO:14) showed 100% identity with amino acids 11-126 of SEQ ID NO:2.

The PCR product (about 1.9 kb) obtained upon amplification with primers SNDH501F (SEQ ID NO:7) and SNDH2364R (SEQ ID NO:8) was used for sequencing with primer SNDH501F (SEQ ID NO:7). The determined nucleotide sequence of 808 by (SEQ ID NO:15) showed 98.0% (745/808) homology with nucleotides 578-1385 of SEQ ID NO:1). The deduced amino acid sequence of 268 residues (SEQ ID NO:16) showed 100% identity to amino acids 194-461 of SEQ ID NO:2.

The PCR product (about 1 kb) obtained upon amplification with primers SNDH1391F (SEQ ID NO:10) and SNDH2364R (SEQ ID NO:8) was used for sequencing with primer SNDH1391F (SEQ ID NO:10). The determined nucleotide sequence of 800 by (SEQ ID NO:17) showed 98.8% (790/800) homology with nucleotides 1469-2268 of SEQ ID NO:1. The deduced amino acid sequence of 266 residues (SEQ ID NO:18) showed 100% identity with amino acids 491-756 of SEQ ID NO:2.

*Acetobacter* Sp. ATCC 15164 SNDHai Ortholog

The PCR product (about 0.4 kb) obtained upon amplification with primers SNDH1F (SEQ ID NO:5) and SNDH420R (SEQ ID NO:6) and chromosomal DNA from A. sp. ATCC 15164 as the template, was used for sequencing with primer SNDH420R (SEQ ID NO:6). The determined nucleotide sequence of 360 by (SEQ ID NO:19) showed 97.8% (352/360) homology with nucleotides 31-390 of SEQ ID NO:1. The deduced amino acid sequence of 120 residues (SEQ ID NO:20) showed 100% identity with amino acids 11-130 of SEQ ID NO:2.

The PCR product (about 1.9 kb) obtained upon amplification with primers SNDH501F (SEQ ID NO:7) and SNDH2364R (SEQ ID NO:8) was used for sequencing with primer SNDH501F (SEQ ID NO:7). The determined nucleotide sequence of 760 by (SEQ ID NO:21) showed 98.0% (745/760) homology with nucleotides 563-1322 of SEQ ID NO:1. The deduced amino acid sequence of 252 residues (SEQ ID NO:22) showed 100% identity with amino acids 189-440 of SEQ ID NO:2.

*Gluconobacter Oxydans* IFO 3244 SNDHai Ortholog

Complete nucleotide sequence of the SNDHai ortholog gene of *G. oxydans* IFO 3244 was determined by using the PCR products obtained with the chromosomal DNA of *G. oxydans* IFO 3244 as the template and the following primer sets: SNDH1F (SEQ ID NO:5) and SNDH420R (SEQ ID NO:6); SNDH501F (SEQ ID NO:7) and SNDH1530R (SEQ ID NO:9); SNDH1391F (SEQ ID NO:10) and SNDH2364R (SEQ ID NO:8); SNDH382 (SEQ ID NO:23) and SNDH1530R (SEQ ID NO:9); SNDH1F (SEQ ID NO:5) and SNDH689R (SEQ ID NO:24). Chromosomal DNA digested with BgIII and BamHI and ligated was used for two more PCRs with following primer sets: SNDH420R (SEQ ID NO:6) and SNDH501F (SEQ ID NO:7) and SNDH1530R (SEQ ID NO:9) and IS-50.3 (SEQ ID NO:25). The complete nucleotide sequence (SEQ ID NO:26) showed 98.4% homology to the nucleotide sequence of SNDHai from *G. oxydans* DSM 17078 (SEQ ID NO:1). The deduced amino acid sequence (SEQ ID NO:27) showed 100% identity to the amino acid sequence of SEQ ID NO:2.

Example 10

Increased Vitamin C Production from L-Sorbosone by Increasing the SNDHai Gene Dosage The SNDHai gene with upstream and downstream flanking regions was amplified by PCR with chromosomal DNA of strain DSM 17078 as template and the primer set N1 (SEQ ID NO:28) and N2 (SEQ ID NO:29).

The PCR was done with the GC-rich PCR system (Roche Diagnostics) according to the instructions of the supplier. The amplified DNA fragment was inserted into vector pCR2.1-TOPO (Invitrogen, Carlsbad, Calif., USA). The resulting plasmid was then digested with HindIII and XhoI. The HindIII-XhoI fragment including the SNDHai gene was ligated to vector pVK100 (available from the American Type Culture Collection, catalog no. ATCC 37156) previously treated with HindIII and XhoI. The ligation mixture was used to transform *E. coli* TG1. The desired plasmid, designated pVK-P—SNDHai-T, was isolated from *E. coli*, and introduced into *G. oxydans* strain DSM 17078 by electroporation using standard methods (Electrocell manipulator ECM600, BTX Inc., San Diego, Calif., USA).

Cells of *G. oxydans* strains DSM 17078 and DSM 17078 carrying the plasmid pVK-P—SNDHai-T were cultivated in 50 ml of No. 5 medium containing 100 g/l D-sorbitol, 0.5 g/l glycerol, 15 g/l yeast extract (Difco), 2.5 g/l of $MgSO_4.7H_2O$, and 15 g/L of $CaCO_3$ in a 500 ml baffled shake flask at 30° C. with shaking at 200 rpm. After 48 h of cultivation, the amounts of Vitamin C measured in the supernatant by HPLC in the two flasks were 110 mg/l and 200 mg/l, respectively.

Example 11

Production of Vitamin C from L-Sorbosone or D-Sorbitol by Resting Cells of Recombinant Microorganisms with Increased SNDHai Gene Dosage The SNDHai gene of *G. oxydans* DSM 17078 (SEQ ID NO:1) with upstream and downstream flanking regions was amplified by PCR with chromosomal DNA of strain DSM 17078 as template and the primer set N1 (SEQ ID NO:28) and N2 (SEQ ID NO:29).

The PCR was done with the GC-rich PCR system (Roche Diagnostics GmbH) according to the instructions of the supplier. The amplified DNA fragment was inserted into vector pCR2.1-TOPO (Invitrogen, Carlsbad, Calif., USA). The resulting plasmid was then digested with HindIII and XhoI. The HindIII-XhoI fragment including the SNDHai gene was ligated to vector pVK100 (available from the American Type Culture Collection, catalog no. ATCC 37156) previously treated with HindIII and XhoI. The ligation mixture was used to transform *E. coli* TG 1. The desired plasmid, designated pVK-P—SNDHai-T, was isolated from *E. coli*, and introduced into *G. oxydans* strain DSM 17078 by electroporation using standard methods (Electrocell manipulator ECM600, BTX Inc., San Diego, Calif., USA).

Three independent transformants, designated DSM 17078 (pVK-P—SNDHai-T) clone number 1, 2, and 3, together with the parental strain *G. oxydans* DSM 17078, were each grown on No. 3BD agar and MB agar media. The cells were scraped from the plates and used for resting cell reactions (1% L-sorbosone as the substrate) as described in Example 9. After growth on No. 3BD agar, in the resting cell assay strain DSM 17078 produced 2.5 g/l Vitamin C, while strains DSM 17078(pVK-P—SNDHai-T) clones 1, 2 and 3 produced 4.2, 4.1 and 4.2 g/l Vitamin C, respectively.

After growth on MB agar, in the resting cell assay strain DSM 17078 produced 0.12 g/l Vitamin C, while strains DSM 17078(pVK-P—SNDHai-T) clones 1, 2 and 3 produced 1.8, 2.5 and 0.94 g/l Vitamin C, respectively.

Another reaction was carried out using cells of *G. oxydans* DSM 17078 and clone 2 (see above) cultivated in 50 ml of No. 5 medium (100 g/l D-sorbitol, 0.5 g/l glycerol, 15 g/l yeast extract, 2.5 g/l $MgSO_4.7H_2O$, 15 g/l $CaCO_3$) in duplicate 500 ml baffled shake flasks at 30° C. with shaking at 220 rpm for 3 days. From one flask for each strain, the resulting broth was centrifuged at 500 rpm to remove $CaCO_3$. The supernatant from this step was then centrifuged at 5,000 rpm to pellet the cells. The collected cells were re-suspended in 10 ml of 0.9% NaCl solution, and again centrifuged at 5,000 rpm to pellet the cells. The collected cells were re-suspended in water and used to inoculate 1 ml of production medium (20 g/l D-sorbitol, 3 g/l NaCl, 10 g/l $CaCO_3$) in 10 ml reaction tube at a final resting cell density corresponding to 5 OD units at 600 nm. After 20 h reaction time at 30° C. and 220 rpm, the supernatant harvested from the production flask contained 360 and 760 mg/l Vitamin C, respectively for strains DSM 17078 and DSM 17078 overexpressing SNDHai. In contrast, after 72 h the supernatant harvested from the remaining growth medium contained 0 and 440 mg/l Vitamin C, respectively.

Example 12

Production of Vitamin C from L-Sorbosone in Resting Cells of *E. Coli*

The SNDHai gene without stop codon named SNDHai-1, corresponding to nucleotides 1-2364 of SEQ ID NO:1, was amplified from strain DSM 17078 chromosomal DNA by PCR (Roche High Fidelity kit) using the primer pair SNDHai-Nde (SEQ ID NO:30) and SNDHaiHis-X (SEQ ID NO:31).

The amplified DNA was cloned into pCR2.1-TOPO (Invitrogen, Carlsbad, Calif., USA) to obtain pCR2.1-TOPO-SNDHai-1, whose SNDHai sequence was confirmed to be correct by nucleotide sequencing. Then the SNDHai-1 gene was cut out with NdeI and XhoI and ligated between NdeI and XhoI sites of pET-21b(+) (Novagen, Madison, Wis., USA) to produce pET21b-SNDHaiHis; 6×His was added at the C-terminus of SNDHai. The pET21b-SNDHaiHis was introduced into *E. coli* BL21 (DE3).

Five ml of one overnight culture of *E. coli* BL21 (DE3)/pET21b-SNDHaiHis in LB with carbenicillin 50 μg/ml was inoculated into 200 ml of the same medium. The cells were cultivated at 230 rpm at 37° C. for 2 h, then induced with 1 mM IPTG and continued to be cultivated at 230 rpm at 25° C. for 3 h. The resulting culture was centrifuged and washed twice with saline and the cell pellet was resuspended in 2 ml of water. The cells were used for resting cell reaction with the reaction mixture (500 in 5 ml tube) containing cells at OD600=10, 1% sorbosone monohydrate, 5 μM PQQ, 5 mM $MgCl_2$, 0.3% NaCl, and 1% $CaCO_3$ conducted at 30° C. for 15 h. 0.14 g/L of Vitamin C was produced after incubation for 15 h. When the resting cell reaction was done with 1 μM PQQ (the other conditions were the same as those described above), 0.05 g/L of Vitamin C was produced after incubation for 3 h.

Example 13

Production of Vitamin C from D-Sorbitol by Resting Cells of Recombinant Microorganisms with Increased SNDHai Gene Dosage Cells of *G. oxydans* DSM 17078 overexpressing SNDHai are grown in 50 ml of No. 5 medium containing 100 g/l D-sorbitol, 0.5 g/l glycerol, 15 g/l yeast extract (Fluka BioChemika, Buchs, Switzerland), 2.5 g/l $MgSO_4.7H_2O$ and 15 g/l $CaCO_3$ in a 500-ml baffled shake flask at 30° C. with shaking at 180 rpm for 48 h. The resulting cell suspension is used to inoculate a 2-L bioreactor, called growth vessel (Biostat-MD, B. Braun Melsungen, Melsungen, Germany) containing 1.25 l of medium composed of 100 g/l D-sorbitol, 15 g/l yeast extract (Fluka BioChemika, Buchs, Switzerland), 2.5 g/l $MgSO_4.7H_2O$, 0.3 g/l $KH_2PO_4$ and 0.12 g/l $CaSO_4$. Cells are cultivated at 30° C., 1 l/min aeration rate, the pH is controlled to 5.7 with a 25% solution of $Na_2CO_3$, dissolved oxygen is controlled to 10% saturation by varying the stirring speed. After 24 h, the cell density measured as absorption units at 600 nm is 20. At this time point, a feed solution containing 100 g/l D-sorbitol, 15 g/l yeast extract (Fluka BioChemika, Buchs, Switzerland), 2.5 g/l $MgSO_4.7H_2O$, 0.3 g/l $KH_2PO_4$ and 0.12 g/l $CaSO_4$ is fed into the growth vessel at a feed rate of 125 ml/h, and broth is continuously harvested at a harvest rate of 125 ml/h. By this means, the volume in the growth vessel is kept constant at 1.25 l. Other process parameters continue to be controlled as mentioned above.

This broth is continuously fed at a rate of 125 ml/h into a second reactor, called production vessel, filled with 5 l production medium containing 100 g/l D-sorbitol, 0.3 g/l NaCl and 0.12 g/l $CaSO_4$, and the temperature is kept at 30° C., pH at 7.0 by controlling with a 20% solution of NaOH. The aeration rate is kept constant at 10 l/min, and dissolved oxygen is controlled at 20% by varying the stirrer speed. Production medium with the same composition is also continuously fed to the production vessel at a feed rate of 375 ml/h. The vessel volume is kept constant at 5 l by continuously harvesting supernatant at 500 ml/h rate, resulting as a filtrate stream from a crossflow ultrafiltration module with 500 kDa pore size (UFP-500-E-9A, Amersham Biosciences), through which the cell suspension harvested from the production vessel is pumped at 50 l/h using a Masterflex pump. The retentate flow is pumped back into the vessel. Once the cell density in the production vessel reaches 100 absorption units at 600 nm, cells start to be harvested from the concentrated cell stream flowing back into the production vessel at a rate of 25 ml/h, in order to keep the cell density in the production vessel constant.

The harvest stream of cell-free supernatant contains 4 g/l Vitamin C and is continuously fed at a rate of 500 ml/h into a collecting vessel with a double jacket at 30° C. (Ecoline Rel 12, Lauda, Lauda-Koenigshofen, Germany). This vessel feeds continuously supernatant to the diluate compartment of a two-compartment electrodialysis unit (stack containing 10 cell pairs with cation exchange membranes CMX-S and anion exchange membranes ASM, total membrane area 0.2 $m^2$, from Eurodia Industries, Wissous, France) at a rate of 180 l/h, and a constant stream is pumped out of the vessel to keep its volume constant at 2 l. Another vessel with double jacket containing initially deionized water at 30° C. is continuously fed with fresh deionized water at a rate of 62.5 ml/h, pumps constantly aqueous solution into the concentrate compartment of the electrodialysis unit at a rate of 2001/h, and a constant harvest stream is pumped out of the vessel. Feed solutions are pumped to the electrodialysis stack using peristaltic pumps (7518-00, Masterflex, USA), and recirculation of solutions through each electrodialysis compartment is done with help of rotary pumps (MD-20, IWAK, Tokyo, Japan). During the whole process, 14 V are applied to the electrodialysis stack (power source FuMATech TS001/5, St. Ingbert, Germany). The concentration of Vitamin C in the harvest stream is 16 g/l.

Example 14

Purification of Vitamin C Produced by a Resting Cell Reaction Via Downstream Processing Steps The harvest stream of Example 14 containing 16 g/l Vitamin C is fed to a chelating resin (Amberlite IRC 748, Rohm and Haas, Philadelphia, Pa., USA) to eliminate divalent cations from the stream. It is then collected in a cooled vessel (feed vessel), and when 10 l have been collected, they are processed in batch mode through a bipolar membrane electrodialysis unit (stack containing 7 Neosepta BP 1/CMB membranes, total membrane area 0.14 $m^2$, from Eurodia Industries, Wissous, France). This solution is pumped at 200 l/h through the feed compartment of the electrodialysis unit, and recycled into the feed vessel. Another cooled vessel (concentrate vessel) containing initially 5 l of a 2 g/l NaOH solution is pumped at 100 l/h through the concentrate compartment of the bipolar membrane electrodialysis unit. By applying a maximal voltage of 25 V and maximal electric current of 20 A, sodium cations from the feed compartment are transferred to the concentrate compartment, and thus the sodium form of Vitamin C present in the feed stream is converted into the corresponding free acid form. After reaching 90% conversion yield, the process is stopped. In the concentrate vessel, 61 of solution containing 7.5 g/l NaOH are collected in the diluate vessel, 9 l solution containing about 16 g/l Vitamin C in its free acid form and 1.6 g/l Vitamin C in its sodium salt form are further processed through a cation exchange resin (Amberlite FPC 21 H, Rohm and Haas, Philadelphia, Pa., USA), in order to increase conversion yield of the sodium salt into the free acid form to about 99%. Alternatively, the 10 l solution containing 16 g/l Vitamin C in its sodium salt form coming from the electrodialysis step is directly treated by cation exchange resin, being converted to the free acid form at 99% yield. The stream of Vitamin C in the form of the free acid, obtained by either of the methods described above, is then further processed by a sequence of the following steps: anion exchange, activated carbon treatment, concentration, crystallization, filtration of the crystals, and drying. The final purity of the obtained crystals is 98%, and the yield obtained with the combined downstream processing steps is 80%.

Example 15

Preparation of Chromosomal DNA and Amplification of SMS 05 DNA Fragment by PCR

Chromosomal DNA of *Gluconobacter oxydans* DSM 17078 were prepared from the cells cultivated at 30° C. for 1 day in mannitol broth (MB) liquid medium consisting of 25 g/l mannitol, 5 g/l of yeast extract (Difco), and 3 g/l of Bactopeptone (Difco) by the method described by Sambrook et al (1989) "Molecular Cloning: A Laboratory Manual/Second Edition", Cold Spring Harbor Laboratory Press).

A DNA fragment was prepared by PCR with the chromosomal DNA prepared above and a set of primers, Pf (SEQ ID NO:46) and Pr (SEQ ID NO:47). For the reaction, the Expand High Fidelity PCR kit (Roche Diagnostics) and 10 ng of the chromosomal DNA was used in total volume of 100 μl according to the supplier's instruction to have the PCR product containing SMS 05 DNA sequence (SEQ ID NO:44). The PCR product was recovered from the reaction and its correct sequence confirmed.

Example 16

Disruption of SMS 05 Gene in *G. Oxydans* DSM 17078

The PCR product obtained in Example 15 was cloned in an *E. coli* vector pCR2.1-TOPO and transform *E. coli* TG1 to have a $Ap^r$ transformant carrying pCR2.1-SMS 05. Then, the pCR2.1-SMS 05 was subjected to two PCR reactions: (i) PCR1 with a set of primers Psms5No (SEQ ID NO:78) and Psms5Ni (SEQ ID NO:79) to have a fragment SMS5No-Ni. and (ii) PCR2 with a set of primers Psms5Ci (SEQ ID NO: 76) and Psms5Co (SEQ ID NO:77). The resulting two PCR products were used for the $3^{rd}$ PCR reaction, PCR3, with a set of primers Psms5No and Psms5Co to yield SMS5dNo-Co. Then, the fragment was digested with PstI and HindIII and ligated with pK19mobsacB (A. Pühler et al. Gene 145, 69-73, 1994) digested with PstI and HindIII and used to transform *E. coli* TG to have $Km^r$ colonies carrying pK19mobsacB-dSMS 05. The plasmid was used for transformation of *G. oxydans* DSM 17078 by electroporation.

One of the $Km^r$ colony was streaked on MB+Km 50 μg/ml (MK) plates and then checked for Km resistance and sucrose sensitivity on MK and MB+sucrose 10% (MSuc) plates, respectively to confirm $Km^r$ and $sucrose^s$. Then, one $Km^r$ and $sucrose^s$ colony was grown on MB agar plate and resulting grown cells were scraped, diluted appropriately and spread on MB agar. The resulting 100 colonies were streaked on MB, MK, and Msuc agar plates to isolate $Km^s$ $sucrose^r$ colonies. One of the resulting strains was designated as *G. oxydans* DSM 17078-dSMS 05.

Example 17

Production of Vitamin C from D-Sorbitol, L-Sorbose or L-Sorbosone Using Resting Cells Grown on 3BD Agar Medium Containing 7% L-Sorbose Cells of *G. oxydans* DSM 17078 and *G. oxydans* DSM 17078-dSMS 05 were grown at 27° C. for 3 days on No. 3BD agar medium containing 70 g/l L-sorbose, 0.5 g/l glycerol, 7.5 g/l yeast extract (Difco), 2.5 g/l MgSO4.7$H_2O$, 10 g/l CaCO3 and 18 g/l agar (Difco).

Cells were scraped from the agar plates, suspended in distilled water and used for resting cell reactions conducted at 30° C. with shaking at 220 rpm. At the conclusion of the incubation period, the reaction mixtures were analyzed by high performance liquid chromatography (HPLC) using the method described in Example 2.

A series of resting cell reactions (0.5 ml reaction mixture in 5 ml reaction tube) was carried out with 2% D-sorbitol or with 2% L-sorbose, and all reaction mixtures further contained 0.3% NaCl, 1% CaCO3 and cells at a final concentration of 5 absorbance units at 600 nanometers ($OD_{600}$). After 20 h incubation time, *G. oxydans* DSM 17078 produced 270 mg/l or 670 mg/l of Vitamin C, respectively from 2% D-sorbitol or 2% L-sorbose, respectively. In comparison, strain *G. oxydans* DSM 17078-dSMS 05 produced 1540 mg/l or 1990 mg/l of Vitamin C, respectively.

Example 18

Concurrent Mutagenesis of Genes Encoding SNDHai and SMS 05 Results in Improved Production of Vitamin C from L-Sorbosone The pVK-P—SNDHai-T plasmid was introduced into *G. oxydans* DSM 17078-dSMS 05 by electroporation. Cells of *G. oxydans* DSM 17078, *G. oxydans* DSM 17078-dSMS 05 and *G. oxydans* DSM 17078-dSMS 05/pVK-P—SNDHai-T were grown at 27° C. for 3 days on No. 3BD agar medium containing 70 g/l L-sorbose, 0.5 g/l glycerol, 7.5 g/l yeast extract (Difco), 2.5 g/l MgSO4.7$H_2O$, 10 g/l $CaCO_3$ and 18 g/l agar (Difco).

Cells were scraped from the agar plates, suspended in distilled water and used for resting cell reactions conducted at 30° C. with shaking at 220 rpm. A series of reactions (0.5 ml reaction mixture in 5 ml reaction tubes) was carried out in 2% L-sorbosone in reaction mixtures further containing 0.3% NaCl, 1% $CaCO_3$ was incubated with cells at a final concentration of $OD_{600}$=5. After incubation periods of 5 h, 20 h, and 30 h, samples of the reaction mixtures were analyzed by high performance liquid chromatography according to the method described in Example 2. The following concentrations of Vitamin C were measured in the supernatants:

| | Vitamin C (mg/l) | | |
|---|---|---|---|
| Strain | 5 h | 20 h | 30 h |
| *G. oxydans* DSM 17078 | 230 | 1100 | 1300 |
| *G. oxydans* DSM 17078-dSMS 05 | 580 | 1800 | 3100 |
| *G. oxydans* DSM 17078-dSMS 05/ pVK-P-SNDHai-T | 2800 | 6100 | 6800 |

Example 19

Concurrent Mutagenesis of Genes Encoding SNDHai and SMS 05 Results in Improved Production of Vitamin C from D-Sorbitol in Liquid Cultures Cells of *G. oxydans* DSM 17078, *G. oxydans* DSM 17078/pVK-P—SNDHai-T, *G. oxydans* DSM 17078-dSMS 05, and *G. oxydans* DSM 17078-dSMS 05/pVK-P—SNDHai-T were grown in 50 ml of No. 5 medium containing 100 g/l D-sorbitol, 0.5 g/l glycerol, 15 g/l yeast extract (Fluka BioChemika, Buchs, Switzerland), 2.5 g/l MgSO4.7$H_2O$ and 15 g/l $CaCO_3$ in a 2-1 baffled shake flask at 30° C. with shaking at 180 rpm. After 48 h, the optical density $OD_{600}$ of the two cultures was measured, and the value obtained was used to calculate the volume of inoculum into two other shake flasks for each strain (duplicate experiments) containing 50 ml of medium No. 5, in order to obtain standardized inoculum density in the second cultures corresponding to $OD_{600}$=0.12. The flasks were incubated at 30° C. with shaking at 180 rpm. After 48 h and 96 h, samples were taken for analysis using the high performance liquid chromatography method described above. The following concentrations of Vitamin C were measured in supernatants:

| | Vitamin C (mg/l) | |
|---|---|---|
| Strain | 48 h | 96 h |
| *G. oxydans* DSM 17078 | 60 | 0 |
| *G. oxydans* DSM 17078/pVK-P-SNDHai-T | 120 | 0 |
| *G. oxydans* DSM 17078-dSMS 05 | 260 | 350 |
| *G. oxydans* DSM 17078-dSMS 05/ pVK-P-SNDHai-T | 320 | 630 |

Example 20

Overexpression of RCS 21 in *G. Oxydans* DSM 17078 Using an Integrative System For the overexpression of RCS 21, the promoter of RCS 21 may be replaced by the strong constitutive modified Psndh promoter [SEQ ID NO: 204]. In order to achieve this, a DNA fragment is built up by Long Flanking Homology (LFH)—PCR consisting of 500-bp of the upstream region of RCS 21, a kanamycin-resistance cassette, the Psndh-promoter fused to a modified ribosome binding site and the first 500-bp of RCS 21. In order to construct the DNA fragment, firstly the single parts are amplified by PCR using the GC-rich PCR kit (Roche Molecular Biochemicals). The upstream region of RCS 21 is amplified using primer pair RCS 21 US+1 [SEQ ID NO: 213] and Km RCS 21 US-1 [SEQ ID NO: 214 containing complementary kanamycin-resistance cassette overhang sequence at 5'-end]. The Psndh promoter fragment is amplified using primer pair Km Psndh+1 [SEQ ID NO: 207 containing complementary kanamycin-resistance cassette overhang sequence at 5'-end] and RCS 21 Psndh-1 [SEQ ID NO: 217 containing complementary RCS 01 overhang sequence at 5'-end]. The first 500-bp of RCS 21 is amplified using primer pair Psndh RCS 21+1 [SEQ ID NO: 215 containing complementary Psndh promoter overhang sequence at 5'-end] and RCS 21-1 [SEQ ID NO: 216]. In these cases *G. oxydans* DSM17078 genomic DNA may be used as a template. The kanamycin-resistance cassette is amplified using plasmid pUC4K as a template and primer pair Km+1 [SEQ ID NO: 211] and Km-1 [SEQ ID NO: 212]. The PCR reaction conditions consist of 35 cycles of denaturation at 94° C. for 30 sec., annealing at 50° C. for 30 sec. and extension at 72° C. for 1 min. The individual PCR fragments are gel-purified, mixed and re-amplified using the primer pair RCS 21 US+1/RCS 21-1 to amplify a full length product whereby the Psndh promoter is inserted upstream of RCS 21. The PCR reaction conditions for the second round reaction consist of 94° C., 2 min., then 10 cycles of [94° C., 30 sec., 63° C., 30 sec., 68° C., 6 min.], followed by 20 cycles of [94° C., 30 sec., 63° C., 30 sec., 68° C., 6 min. with an additional 20 sec. per cycle] and a final extension at 68° C. for 10 min.

The PCR product is transformed directly into competent *G. oxydans* DSM17078 cells and transformants are selected on mannitol broth agar medium containing kanamycin to a final concentration of 50 μg/ml. Several putative transformants may be observed of which several then can be analysed by PCR using primer pair RCS 21 US+1/RCS 21-1 to verify that the DNA fragment has inserted into the genome via a double crossover. Strains showing the correct size PCR product have the PCR product sequenced. Strains with the correct sequence are named DSM17078-RCS 21 up1 and DSM17078-RCS 21 up2.

Example 21

Concurrent Mutagenesis of Genes Encoding SNDHai and RCS 21 Results in Improved Production of Vitamin C from D-Sorbitol The pVK-P—SNDHai-T plasmid is introduced into *G. oxydans* DSM 17078 and *G. oxydans* DSM 17078-RCS 21 up1 by electroporation. Cells of *G. oxydans* DSM 17078/pVK-P—SNDHai-T and *G. oxydans* DSM 17078-RCS 21 up1/pVK-P—SNDHai-T are grown at 27° C. for 3 days on No. 3BD agar medium containing 70 g/l L-sorbose, 0.5 g/l glycerol, 7.5 g/l yeast extract (Difco), 2.5 g/l $MgSO4.7H_2O$, 10 g/l $CaCO_3$ and 18 g/l agar (Difco).

Cells are scraped from the agar plates, suspended in distilled water and used for resting cell reactions conducted at 30° C. with shaking at 220 rpm. A series of reactions (0.5 ml reaction mixture in 5 ml reaction tubes) is carried out in 2% L-sorbitol in reaction mixtures further containing 0.3% NaCl, 1% $CaCO_3$ is incubated with cells at a final concentration of $OD_{600}$=5. After an incubation period of 24 h, samples of the reaction mixtures are analyzed by high performance liquid chromatography according to the method described in Example 2.

The supernatant of the reaction mixture incubated with cells of *G. oxydans* DSM 17078-RCS 21 up1/pVK-P—SNDHai-T contains at least 20% more Vitamin C than the supernatant of the reaction mixture incubated with cells of *G. oxydans* DSM 17078/pVK-P—SNDHai-T.

Example 22

Purification of SNDHai

Cells of a microorganism capable of producing SNDHai cultivated by fed-batch fermentation (for cultivation see Example 3) were suspended in 25 ml of phosphate buffer (20 mM, pH 7.0) containing $MgCl_2$, 2 mM, dithiothreitol (DTT), 1 mM, and 2-3 EDTA-free protease inhibitor tablets (Roche Diagnostics GmbH). The cell suspension was treated three times with a French Pressure cell. Subsequently, 25 ml of phosphate buffer (20 mM, pH 7.0) containing 2 mM $MgCl_2$ and 1 M NaCl were added and the suspension was ultracentrifuged (30.000 rpm, 60 min, 4° C.). The pellet containing the membrane fraction was washed with phosphate buffer (20 mM, pH 7.0) containing 2 mM $MgCl_2$ and 500 mM NaCl and then suspended in an appropriate amount of phosphate buffer (20 mM, pH 7.0) containing 2 mM $MgCl_2$. N-Octylglucoside (Fluka) was then added at a final concentration of 2% (w/v) and the suspension was incubated for 90 min with gentle stirring on ice. After centrifugation (20.000 rpm, 60 min, 4° C.) the clear reddish supernatant was collected and polyethylene glycol 6000 (Fluka) at a final concentration of 15% (w/v) was added. After incubation for 60 mM at 4° C. with gentle shaking followed by centrifugation (10.000 rpm, 30 min, 4° C.), the pellet was dissolved in Tris-HCl buffer (20 mM, pH 7.6) containing 2 mM $MgCl_2$ and 0.5% (w/v) lauryl sulfobetaine (Fluka). After gentle shaking at 4° C. overnight the solution was centrifuged (20.000 rpm, 30 min, 4° C.). The supernatant was collected and further purified as follows.

The following purification steps were done at 4° C. on an ÄKTA Explorer 10 S-system (Amersham Biosciences) with software UNICORN 3.1. Typical flow rates for ion exchange chromatography were in the range of 1-2 ml/min. Protein elution was monitored at 280 nm and SNDHai-active fractions were determined using the standard photometric assay at all stages of the purification (s. below) or the product assay with purified fractions.

The clear supernatant IV was desalted in 2.5 ml-portions on a Sephadex G 25-gel filtration column (void volume: 2.5 ml) using 20 mM Tris-HCl buffer (pH 7.6) containing 2 mM $MgCl_2$ and 0.5% (w/v) lauryl sulfobetaine.

SNDHai-positive fractions were pooled and an aliquot (approximately 10 ml) was put on a strong anion exchange column (e.g. Mono-Q HR, Amersham Biosciences, column volume: 8 ml) which had been equilibrated prior to use with buffer A1 (10 mM Tris, 10 mM BisTris, 10 mM MES, 2 mM $MgCl_2$, 0.5% lauryl sulfobetaine, pH 7.6). Non-binding proteins were eluted with 100% buffer A1 and after 4 column volumes a linear pH-gradient in 6 column volumes to 100% buffer B1 (Tris, 10 mM; BisTris, 10 mM; MES, 10 mM; $MgCl_2$, 2 mM, and lauryl sulfobetaine, 0.5%, pH 4.7) was applied followed by 8 column volumes of 100% buffer B1. SNDHai eluted at a pH-value of approximately 6.5, which is very close to the pI-value of 6.52 calculated from the amino acid sequence. Active fractions were pooled, diluted with the same amount of HEPES-buffer (50 mM, pH 8.0) containing 2 mM $MgCl_2$ and 0.5% lauryl sulfobetaine (final volume: 15-20 ml), and applied to another strong anion exchange column (e.g. Mono-Q HR, Amersham Biosciences, column volume: 1 ml) which had been equilibrated with buffer A2 (15 mM HEPES, 2 mM $MgCl_2$, 0.5% lauryl sulfobetaine, pH 7.6). Non-binding proteins were eluted with 100% buffer A2 and after 4 column volumes a linear salt-gradient in 20 column volumes to 40% buffer B2 (HEPES, 15 mM; $MgCl_2$, 2 mM, LiCl, 1 M, and lauryl sulfobetaine, 0.5%, pH 7.6) was applied followed by a step gradient to 100% buffer B2. SNDHai eluted around 150 mM LiCl. Active fractions showed one single band at approximately 85 kDa in SDS gel electrophoresis.

Example 23

Photometric Assay for SNDHai

The reaction mixture for the photometric SNDHai-activity measurement consisted of 0.196 mM nitroblue tetrazolium chloride (NBT), 0.137 mM phenazine methosulfate (PMS), 20.4 mM L-sorbosone, and enzyme solution in a final volume of 1.0 ml of 0.1 M sodium phosphate buffer, pH 7.5. The reaction was started with the addition of enzyme, and the enzyme activity was measured in a cuvette with 1-cm light path as the initial reduction rate of NBT at 570 nm (T=25° C.). One unit of the enzyme activity was defined as the amount of enzyme catalyzing the reduction of 1 μM NBT per minute. The extinction coefficient of NBT at pH 7.5 was taken as 100 $mM^{-1}$ $cm^{-1}$. Two kinds of reference cuvettes were used for the activity determination: one contained the above-mentioned components except for L-sorbosone and another one contained all components except for the enzyme solution.

Example 24

Product Assay for SNDHai

Pure SNDHai-containing fractions (see above) were analyzed directly for L-ascorbic acid production from L-sorbosone with an assay of the following composition (0.5 ml total volume): 0.14 mg/ml of purified and desalted SNDHai, 50 mM phosphate buffer (pH 6.5), 8 mg/ml bovine serum albumin (BSA), 100 mM L-sorbosone, 1 mM PMS, 5 mM $CaCl_2$, 50 μM PQQ-$K_2$. The assay was conducted in appropriate reaction tubes at 25° C. with sufficient shaking (900 rpm on a benchtop shaker) under exclusion of light.

Samples were analyzed by high performance liquid chromatography (HPLC) using an Agilent 1100 HPLC system (Agilent Technologies, Wilmington, USA) with a LiChrospher-100-RP18 (125×4.6 mm) column (Merck, Darmstadt, Germany) attached to an Aminex-HPX-78H (300×7.8 mm) column (Biorad, Reinach, Switzerland). The mobile phase was 0.004 M sulfuric acid, and the flow rate was 0.6 ml/min. Two signals were recorded using a UV detector (wavelength 254 nm) in combination with a refractive index detector. In addition, the identification of the L-ascorbic acid was done using an amino-column (YMC-Pack Polyamine-II, YMC, Inc., Kyoto, Japan) with UV detection at 254 nm. The mobile phase was 50 mM $NH_4H_2PO_4$ and acetonitrile (40:60).

Example 25

Presence of the SMS and RCS Genes and Equivalents Thereof in Other Organisms

The presence of the SMS and RCS polynucleotide sequences and/or equivalents showing similarity/identity to these sequences as described in other organisms than the ones disclosed herein before may be determined by a simple DNA hybridization experiment. Genomic DNA is extracted from an organism belonging to e.g. *Gluconobacter, Acetobacter, Pseudomonas, Paracoccus, Rhodopseudomonas, Pantoea, Escherichia, Saccharomyces, Aspergillus* or mouse, in particular the organisms mentioned in the tables B and C.

Strains of *Acetobacter aceti* subsp. *xylinum* IFO 13693 and IFO 13773 are grown at 27° C. for 3 days on No. 350 medium containing 5 g/l Bactopeptone (Difco), 5 g/l yeast extract (Difco), 5 g/l glucose, 5 g/l mannitol, 1 g/l $MgSO_4.7H_2O$, 5 ml/l ethanol, and 15 g/l agar. All other *Acetobacter, Gluconacetobacter* and all *Gluconobacter* strains are grown at 27° C. for 3 days on mannitol broth (MB) agar medium containing 25 g/l mannitol, 5 g/l yeast extract (Difco), 3 g/l Bactopeptone (Difco), and 18 g/l agar (Difco). *E. coli* K-12 is grown on Luria Broth agar medium. The other strains are grown on medium recommended by the suppliers or according to methods known in the art. Genomic DNA is extracted as described by e.g. Sambrook et al., 1989, "Molecular Cloning: A Laboratory Manual/Second Edition", Cold Spring Harbor Laboratory Press) from a suitable organism as, e.g. mentioned in Table B and C.

Genomic DNA preparations are digested with restriction enzymes such as EcoRI or HindIII, and 1 μg of the DNA fragments are separated by agarose gel electrophoresis (1% agarose). The gel is treated with 0.25 N HCl for 15 min and then 0.5 N NaOH for 30 min, and then blotted onto nitrocellulose or a nylon membrane with Vacuum Blotter Model 785 (BIO-RAD Laboratories AG, Switzerland) according to the instruction of the supplier. The resulting blot is then brought into contact/hybridized with a solution containing DNA probes of SMS, STS, RCS or VCS, which may be prepared by using the PCR-DIG labeling kit (Roche Diagnostics) and for each gene a specific set of primers as disclosed in table A. A result of such a blot is depicted in the first column of Table B and C respectively.

TABLE A

| SEQ ID NO's of Primer pairs | |
|---|---|
| SMS 02 | 126/127 |
| SMS 03 | 130/131 |
| SMS 04 | 134/135 |
| SMS 05 | 46/47 |
| SMS 12 | 138/139 |
| SMS 13 | 142/143 |
| SMS 14 | 146/147 |
| RCS 21 | 182/183 |
| RCS 22 | 186/187 |
| RCS 23 | 190/191 |
| RCS 24 | 194/195 |
| RCS 25 | 198/199 |

The hybridization may be performed under stringent or highly stringent conditions. A preferred, non-limiting example of such conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C. Highly stringent conditions include, for example, 2 h to 4 days incubation at 42° C. in a solution such as DigEasyHyb solution (Roche Diagnostics GmbH) with or without 100 μg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 min in 2×SSC and 0.1% SDS at room temperature and then washing twice for 15-30 min in 0.5×SSC and 0.1% SDS or 0.1×SSC and 0.1% SDS at 65-68° C. To detect DNA fragments with lower identity to the probe DNA, final washing steps can be done at lower temperatures such as 50-65° C. and for shorter washing time such as 1-15 min.

The genes corresponding to the positive signals within the respective organisms shown in Table B or C can be cloned by a PCR method well known in the art using genomic DNA of such an organism together with a suitable primer set under the following conditions: 5 to 100 ng of genomic DNA is used per reaction (total volume 50 μl). Expand High Fidelity PCR system (Roche Diagnostics) can be used with reaction conditions consisting of 94° C. for 2 min; 30 cycles of (i) denaturation step at 94° C. for 15 sec, (ii) annealing step at 60° C. for 30 sec, (iii) synthesis step at 72° C. for 0.5 to 5 min depending to the target DNA length (1 min/1 kb); extension at 72° C. for 7 min. Alternatively, one can perform a PCR with degenerate primers, which can be synthesized based on the amino acid sequence of the corresponding SMS or RCS protein disclosed herein or amino acid sequences as consensus sequences selected by aligning several amino acid sequences obtained by a sequence search program such as BLASTP (or BLASTX when nucleotide sequence is used as a "query sequence") to find proteins having a similarity to the specific protein sequence. For PCR using degenerate primers, temperature of the second annealing step (see above) can be lowered to 55° C., or even to 50-45° C. Results of these experiments are shown in column 2 and 3 of the Table B and C respectively.

Samples of the PCR reactions are separated by agarose gel electrophoresis and the bands are visualized with a transilluminator after staining with e.g. ethidium bromide, isolated from the gel and the correct sequence is confirmed.

Consensus sequences mentioned above might be amino acid sequences belonging to certain categories of several protein domain/family databases such as PROSITE (database of protein families and domains), COGs (Cluster of Ortholog Groups), CDD (Conserved Domain Databases), pfam (large collection of multiple sequence alignments and hidden Markov models covering many common protein domains and families). Once one can select certain protein with identical/similar function to the protein of this invention from proteins containing domain or family of such databases, corresponding DNA encoding the protein can be amplified by PCR using the protein sequence or its nucleotide sequence when it is available in public databases.

Disruption of Genes and Equivalents in Other Organisms for Production of Vitamin C In order to improve Vitamin C production in a suitable microorganism which is capable to directly produce Vitamin C from a given substrate, the selected gene and equivalents as e.g. a PCR product obtained as described in the above paragraphs can be disrupted in accordance to examples 15-19 to generate a knockout mutant carrying equivalent gene::Km. Suitable host strains for generation of such knockout mutants may be selected from e.g. *Gluconobacter* strains listed in Table B, in particular e.g. *G. oxydans* IFO 3293, *G. oxydans* IFO 3292, *G. oxydans* ATCC 621H, *G. oxydans* IFO 12528, *G. oxydans* IFO 3291, *G. oxydans* IFO 3255, *G. oxydans* IFO 3244, *G. cerinus* IFO 3266, *G. frateurii* IFO 3260, *G. oxydans* IFO 3287, *Acetobacter* aceti subsp. *orleanus* IFO 3259, *Acetobacter aceti* subsp. *xylinum* IFO 13693, *Acetobacter aceti* subsp. *xylinum* IFO 13773 and *Acetobacter* sp. ATCC 15164.

The knockout mutant can be generated as follows: The PCR product obtained as described above is cloned in an *E. coli* vector pCR2.1-TOPO and used to transform *E. coli* TG1 to have a Apr transformant carrying pCR2.1-gene X. Then, Kmr cassette isolated from pUC-4K (Amersham Bioscience, accession No. X06404) is inserted into one of the restriction site of the target gene with ligase and the resulting ligation product is used to transform *E. coli* TG1 to have Apr Kmr transformant carrying pCR2.1-gene X::Km. The pCR2.1-gene X::Km plasmid prepared from the transformant is digested by two restriction enzymes selected from the multi-cloning site of the vector part to isolate a DNA fragment containing gene X::Km. The resulting DNA fragment is used to transform the host strain carrying the equivalent gene by electroporation to have the gene disruptant.

Further modifications including SNDHai and other genes involved in the conversion of D-sorbitol, L-sorbose and/or L-sorbosone into Vitamin C within said strains may be generated to improve Vitamin C production by such strains according to the invention.

In the resting cell reaction with 1% L-sorbosone as the substrate, the mutant strain can produce at least more than 20% Vitamin C compared to the wild-type strain.

Production of Vitamin C using equivalents to genes which may be up regulated

A PCR product obtained as described above can be used in an SNDHai overexpression system in accordance to examples 20-21 or in accordance with the following procedure exemplified with RCS 21. This procedure apply mutates mutandis for the similar RCS and SMS genes.

In order to improve Vitamin C production in a suitable microorganism which is capable to directly produce Vitamin C from a given substrate, the RCS 21 gene and equivalents as, e.g. a PCR product obtained as described in the above paragraphs, referred to herein as gene X, can be used in an overexpression system as described herein or can be cloned into pCR2.1-TOPO (Invitrogen, Carlsbad, Calif., USA) and used to transform *E. coli* TG1 to have a Apr transformant carrying pCR2.1-TOPO-gene X, i.e. carrying a PCR product. The insert is amplified with a set of primers, PfNdeI [SEQ ID NO:182 with CCCAT at the 5'-end] and PrHindIII [SEQ ID NO:183 with CCAAGCTT at the 5'-end], by PCR. Resulting PCR product is digested with NdeI and HindIII and the fragment is inserted together with PcrtE-SD (Shine-Dalgarno) fragment (WO 02/099095) digested with XhoI and NdeI into pVK100 (ATCC 37156) between the sites of XhoI and HindIII. *E. coli* TG1 is transformed with the ligation product to have $Tc^r$ transformant carrying plasmid pVK-PcrtE-SD-gene X, which is then used to transform a suitable host, e.g. *G. oxydans* DSM 17078 by electroporation to have e.g. $Tc^r$ *G. oxydans* DSM 17078/pVK-PcrtE-SD-gene X.

Production of Vitamin C using the recombinant cells of e.g. *G. oxydans* strains DSM 17078 and the corresponding wild-type strain may be additionally transformed with SNDHai as described herein above.

Further modifications including SNDHai and other genes involved in the conversion of D-sorbitol, L-sorbose and/or L-sorbosone into Vitamin C within said strains may be generated to improve Vitamin C production within such strains according to the invention.

In the resting cell reaction with 1% L-sorbosone as the substrate, the recombinant cells can produce at least more than 20% Vitamin C compared to the wild-type strain.

To the following tables B and C:

Signal 1: Detection of DNA on a blot with genomic DNA of different strains. Signal 2: Detection of DNA of different strains in a PCR reaction using primer pairs. Signal 3: Detection of DNA of different strains in a PCR reaction using degenerate primers.

TABLE B

| Strain | Signal 1 | Signal 2 | Signal 3 |
|---|---|---|---|
| Equivalents of the SMS 02 gene in other organisms. | | | |
| *G. oxydans* DSM 17078 | + | + | + |
| *G. oxydans* IFO 3293 | + | + | + |
| *G. oxydans* IFO 3292 | + | + | + |
| *G. oxydans* ATCC 621H | + | + | + |
| *G. oxydans* IFO 12528 | + | + | + |
| *G. oxydans* G 624 | + | + | + |

TABLE B-continued

| Strain | Signal 1 | Signal 2 | Signal 3 |
|---|---|---|---|
| *G. oxydans* T-100 | + | + | + |
| *G. oxydans* IFO 3291 | + | + | + |
| *G. oxydans* IFO 3255 | + | + | + |
| *G. oxydans* ATCC 9937 | + | + | + |
| *G. oxydans* IFO 3244 | + | + | + |
| *G. cerinus* IFO 3266 | + | + | + |
| *G. frateurii* IFO 3260 | + | + | + |
| *G. oxydans* IFO 3287 | + | + | + |
| *Acetobacter aceti* subsp. *orleanus* IFO 3259 | + | + | + |
| *Acetobacter aceti* subsp. *xylinum* IFO 13693 | + | + | + |
| *Acetobacter aceti* subsp. *xylinum* IFO 13773 | + | + | + |
| *Acetobacter* sp. ATCC 15164 | + | + | + |
| *G. thailandicus* NBRC 100600 | + | + | + |
| *Gluconacetobacter liquefaciens* ATCC 14835 | + | + | + |
| *Gluconacetobacter polyoxogenes* NBI 1028 | + | + | + |
| *Gluconacetobacter diazotrophicus* ATCC 49037 | + | + | + |
| *Gluconacetobacter europaeus* DSM 6160 | + | + | + |
| *Acetobacter aceti* 1023 | + | − | + |
| *Acetobacter pasteurianus* NCI 1193 | + | − | + |
| *Bacillus cereus* ATCC 14579 | − | − | + |
| *Bacillus subtilis* 168 | − | − | + |
| *Bacillus thuringiensis* serovar *konkukian* 97-27 | − | − | + |
| *Brucella suis* 1330 | + | − | + |
| *Brucella melitensis* 16M | + | − | + |
| *Azotobacter vinelandii* AvOP | − | − | + |
| *Azotobacter chroococcum* MCD1 | − | − | + |
| *E. coli* | − | − | − |
| *Saccharomyces cerevisiae* | − | − | − |
| *Aspergillus niger* | − | − | − |
| Mouse | − | − | − |
| Equivalents of the SMS 03 gene in other organisms. | | | |
| *G. oxydans* DSM 17078 | + | + | + |
| *G. oxydans* IFO 3293 | + | + | + |
| *G. oxydans* IFO 3292 | + | + | + |
| *G. oxydans* ATCC 621H | + | + | + |
| *G. oxydans* IFO 12528 | + | + | + |
| *G. oxydans* G 624 | + | + | + |
| *G. oxydans* T-100 | + | + | + |
| *G. oxydans* IFO 3291 | + | + | + |
| *G. oxydans* IFO 3255 | + | + | + |
| *G. oxydans* ATCC 9937 | + | + | + |
| *G. oxydans* IFO 3244 | + | + | + |
| *G. cerinus* IFO 3266 | + | + | + |
| *G. frateurii* IFO 3260 | + | + | + |
| *G. cerinus* IFO 3287 | + | + | + |
| *Acetobacter aceti* subsp. *orleanus* IFO 3259 | + | + | + |
| *Acetobacter aceti* subsp. *xylinum* IFO 13693 | + | + | + |
| *Acetobacter aceti* subsp. *xylinum* IFO 13773 | + | + | + |
| *Acetobacter* sp. ATCC 15164 | + | + | + |
| *G. thailandicus* NBRC 100600 | + | + | + |
| *Gluconacetobacter liquefaciens* ATCC 14835 | + | + | + |
| *Gluconacetobacter polyoxogenes* NBI 1028 | + | + | + |
| *Gluconacetobacter diazotrophicus* ATCC 49037 | + | + | + |
| *Gluconacetobacter europaeus* DSM 6160 | + | + | + |
| *Acetobacter aceti* 1023 | + | − | + |
| *Acetobacter pasteurianus* NCI 1193 | + | − | + |
| *Bacillus cereus* ATCC 14579 | − | − | + |
| *Bacillus subtilis* 168 | − | − | + |
| *Bacillus thuringiensis* serovar *konkukian* 97-27 | − | − | + |

TABLE B-continued

| Strain | Signal 1 | Signal 2 | Signal 3 |
|---|---|---|---|
| *Brucella suis* 1330 | + | − | + |
| *Brucella melitensis* 16M | + | − | + |
| *Azotobacter vinelandii* AvOP | − | − | + |
| *Azotobacter chroococcum* MCD1 | − | − | + |
| *E. coli* | − | − | − |
| *Saccharomyces cerevisiae* | − | − | − |
| *Aspergillus niger* | − | − | − |
| Mouse | − | − | − |
| Equivalents of the SMS 04 gene in other organisms. | | | |
| *G. oxydans* DSM 17078 | + | + | + |
| *G. oxydans* IFO 3293 | + | + | + |
| *G. oxydans* IFO 3292 | + | + | + |
| *G. oxydans* ATCC 621H | + | + | + |
| *G. oxydans* IFO 12528 | + | + | + |
| *G. oxydans* G 624 | + | + | + |
| *G. oxydans* T-100 | + | + | + |
| *G. oxydans* IFO 3291 | + | + | + |
| *G. oxydans* IFO 3255 | + | + | + |
| *G. oxydans* ATCC 9937 | + | + | + |
| *G. oxydans* IFO 3244 | + | + | + |
| *G. cerinus* IFO 3266 | + | + | + |
| *G. frateurii* IFO 3260 | + | + | + |
| *G. oxydans* IFO 3287 | + | + | + |
| *Acetobacter aceti* subsp. *orleanus* IFO 3259 | + | + | + |
| *Acetobacter aceti* subsp. *xylinum* IFO 13693 | + | + | + |
| *Acetobacter aceti* subsp. *xylinum* IFO 13773 | + | + | + |
| *Acetobacter* sp. ATCC 15164 | + | + | + |
| *G. thailandicus* NBRC 100600 | + | + | + |
| *Gluconacetobacter liquefaciens* ATCC 14835 | + | + | + |
| *Gluconacetobacter polyoxogenes* NBI 1028 | + | − | + |
| *Gluconacetobacter diazotrophicus* ATCC 49037 | + | − | + |
| *Gluconacetobacter europaeus* DSM 6160 | + | − | + |
| *Acetobacter aceti* 1023 | + | − | + |
| *Acetobacter pasteurianus* NCI 1193 | + | − | + |
| *Zymomonas mobilis* ATCC 31821 | − | − | + |
| *E. coli* | − | − | − |
| *Saccharomyces cerevisiae* | − | − | − |
| *Aspergillus niger* | − | − | − |
| Mouse | − | − | − |
| Equivalents of the SMS 05 gene in other organisms. | | | |
| *G. oxydans* DSM 17078 | + | + | + |
| *G. oxydans* IFO 3293 | + | + | + |
| *G. oxydans* IFO 3292 | + | + | + |
| *G. oxydans* ATCC 621H | + | + | + |
| *G. oxydans* IFO 12528 | + | + | + |
| *G. oxydans* G 624 | + | + | + |
| *G. oxydans* T-100 | + | + | + |
| *G. oxydans* IFO 3291 | + | + | + |
| *G. oxydans* IFO 3255 | + | + | + |
| *G. oxydans* ATCC 9937 | + | + | + |
| *G. oxydans* IFO 3244 | + | + | + |
| *G. cerinus* IFO 3266 | + | + | + |
| *G. frateurii* IFO 3260 | + | + | + |
| *G. oxydans* IFO 3287 | + | + | + |
| *Acetobacter aceti* subsp. *orleanus* IFO 3259 | + | + | + |
| *Acetobacter aceti* subsp. *xylinum* IFO 13693 | + | + | + |
| *Acetobacter aceti* subsp. *xylinum* IFO 13773 | + | + | + |
| *Acetobacter* sp. ATCC 15164 | + | + | + |
| *G. thailandicus* NBRC 100600 | + | + | + |
| *Gluconacetobacter liquefaciens* ATCC 14835 | + | + | + |
| *Sinorhizobium meloloti* 1021 | − | − | + |
| *Brucella suis* 1330 | − | − | + |
| *Brucella melitensis* 16M | − | − | + |
| *E. coli* | − | − | − |

TABLE B-continued

| Strain | Signal 1 | Signal 2 | Signal 3 |
|---|---|---|---|
| *Saccharomyces cerevisiae* | − | − | − |
| *Aspergillus niger* | − | − | − |
| Mouse | − | − | − |

TABLE C

| Strain | Signal 1 | Signal 2 | Signal 3 |
|---|---|---|---|
| Equivalents of the RCS 21 gene in other organisms. | | | |
| *G. oxydans* DSM 17078 | ++++ | + | + |
| *G. oxydans* IFO 3293 | ++++ | + | + |
| *G. oxydans* IFO 3292 | ++++ | + | + |
| *G. oxydans* ATCC 621H | ++++ | + | + |
| *G. oxydans* IFO 12528 | ++++ | + | + |
| *G. oxydans* G 624 | ++++ | + | + |
| *G. oxydans* T-100 | ++++ | + | + |
| *G. oxydans* IFO 3291 | ++++ | + | + |
| *G. oxydans* IFO 3255 | ++++ | + | + |
| *G. oxydans* ATCC 9937 | ++++ | + | + |
| *G. oxydans* IFO 3244 | ++++ | + | + |
| *G. cerinus* IFO 3266 | +++ | + | + |
| *G. frateurii* IFO 3260 | +++ | + | + |
| *G. oxydans* IFO 3287 | ++++ | + | + |
| *Acetobacter aceti* subsp. *orleanus* IFO 3259 | ++ | − | + |
| *Acetobacter aceti* subsp. *xylinum* IFO 13693 | ++ | − | + |
| *Acetobacter aceti* subsp. *xylinum* IFO 13773 | ++ | − | + |
| *Acetobacter* sp. ATCC 15164 | ++ | − | + |
| *G. thailandicus* NBRC 100600 | +++ | + | + |
| *Gluconacetobacter liquefaciens* ATCC 14835 | ++ | + | + |
| *Gluconacetobacter polyoxogenes* NBI 1028 | ++ | + | + |
| *Gluconacetobacter diazotrophicus* ATCC 49037 | ++ | + | + |
| *Gluconacetobacter europaeus* DSM 6160 | ++ | + | + |
| *Acetobacter aceti* 1023 | ++ | − | + |
| *Acetobacter pasteurianus* NCI 1193 | ++ | − | + |
| *Pseudomonas putida* ATCC 21812 | + | − | + |
| *Pseudomonas aeruginosa* PAO1 | + | − | + |
| *Pseudomonas fluorescens* DSM 50106 | + | − | + |
| *Pseudomonas syringae* B728a | + | − | + |
| *Paracoccus denitrificans* strain Pd1222 | + | − | + |
| *Rhodopseudomonas palustris* CGA009 | + | − | + |
| *Pantoea citrea* 1056R | − | − | − |
| *E. coli* K-12 | − | − | − |
| *Saccharomyces cerevisiae* | − | − | − |
| *Aspergillus niger* | − | − | − |
| Mouse | − | − | − |
| Equivalents of the RCS 22 gene in other organisms. | | | |
| *G. oxydans* DSM 17078 | ++++ | + | + |
| *G. oxydans* IFO 3293 | ++++ | + | + |
| *G. oxydans* IFO 3292 | ++++ | + | + |
| *G. oxydans* ATCC 621H | ++++ | + | + |
| *G. oxydans* IFO 12528 | ++++ | + | + |
| *G. oxydans* G 624 | ++++ | + | + |
| *G. oxydans* T- 100 | ++++ | + | + |
| *G. oxydans* IFO 3291 | ++++ | + | + |
| *G. oxydans* IFO 3255 | ++++ | + | + |
| *G. oxydans* ATCC 9937 | ++++ | + | + |
| *G. oxydans* IFO 3244 | ++++ | + | + |
| *G. cerinus* IFO 3266 | +++ | + | + |
| *G. frateurii* IFO 3260 | +++ | + | + |
| *G. oxydans* IFO 3287 | ++++ | + | + |
| *Acetobacter aceti* subsp. *orleanus* IFO 3259 | ++ | − | + |
| *Acetobacter aceti* subsp. *xylinum* IFO 13693 | ++ | − | + |
| *Acetobacter aceti* subsp. *xylinum* IFO 13773 | ++ | − | + |

TABLE C-continued

| Strain | Signal 1 | Signal 2 | Signal 3 |
|---|---|---|---|
| *Acetobacter* sp. ATCC 15164 | ++ | − | + |
| *G. thailandicus* NBRC 100600 | +++ | + | + |
| *Gluconacetobacter liquefaciens* ATCC 14835 | ++ | + | + |
| *Gluconacetobacter polyoxogenes* NBI 1028 | ++ | + | + |
| *Gluconacetobacter diazotrophicus* ATCC 49037 | ++ | + | + |
| *Gluconacetobacter europaeus* DSM 6160 | ++ | + | + |
| *Acetobacter aceti* 1023 | ++ | − | + |
| *Acetobacter pasteurianus* NCI 1193 | ++ | − | + |
| *Pseudomonas putida* ATCC 21812 | + | − | + |
| *Pseudomonas aeruginosa* PAO1 | + | − | + |
| *Pseudomonas fluorescens* DSM 50106 | + | − | + |
| *Pseudomonas syringae* B728a | + | − | + |
| *Paracoccus denitrificans* strain Pd1222 | + | − | + |
| *Rhodopseudomonas palustris* CGA009 | + | − | + |
| *Pantoea citrea* 1056R | − | − | − |
| *E. coli* K-12 | − | − | − |
| *Saccharomyces cerevisiae* | − | − | − |
| *Aspergillus niger* | − | − | − |
| Mouse | − | − | − |
| Equivalents of the RCS 23 gene in other organisms. | | | |
| *G. oxydans* DSM 17078 | ++++ | + | + |
| *G. oxydans* IFO 3293 | ++++ | + | + |
| *G. oxydans* IFO 3292 | ++++ | + | + |
| *G. oxydans* ATCC 621H | ++++ | + | + |
| *G. oxydans* IFO 12528 | ++++ | + | + |
| *G. oxydans* G 624 | ++++ | + | + |
| *G. oxydans* T-100 | ++++ | + | + |
| *G. oxydans* IFO 3291 | ++++ | + | + |
| *G. oxydans* IFO 3255 | ++++ | + | + |
| *G. oxydans* ATCC 9937 | ++++ | + | + |
| *G. oxydans* IFO 3244 | ++++ | + | + |
| *G. cerinus* IFO 3266 | +++ | + | + |
| *G. frateurii* IFO 3260 | +++ | + | + |
| *G. cerinus* IFO 3287 | ++++ | + | + |
| *Acetobacter aceti* subsp. *orleanus* IFO 3259 | ++ | − | + |
| *Acetobacter aceti* subsp. *xylinum* IFO 13693 | ++ | − | + |
| *Acetobacter aceti* subsp. *xylinum* IFO 13773 | ++ | − | + |
| *Acetobacter* sp. ATCC 15164 | ++ | − | + |
| *G. thailandicus* NBRC 100600 | +++ | + | + |
| *Gluconacetobacter liquefaciens* ATCC 14835 | ++ | + | + |
| *Gluconacetobacter polyoxogenes* NBI 1028 | ++ | + | + |
| *Gluconacetobacter diazotrophicus* ATCC 49037 | ++ | + | + |
| *Gluconacetobacter europaeus* DSM 6160 | ++ | + | + |
| *Acetobacter aceti* 1023 | ++ | − | + |
| *Acetobacter pasteurianus* NCI 1193 | ++ | − | + |
| *Pseudomonas putida* ATCC 21812 | + | − | + |
| *Pseudomonas aeruginosa* PAO1 | + | − | + |
| *Pseudomonas fluorescens* DSM 50106 | + | − | + |
| *Pseudomonas syringae* B728a | + | − | + |
| *Paracoccus denitrificans* strain Pd1222 | + | − | + |
| *Rhodopseudomonas palustris* CGA009 | + | − | + |
| *Pantoea citrea* 1056R | − | − | − |
| *E. coli* K-12 | − | − | − |
| *Saccharomyces cerevisiae* | − | − | − |
| *Aspergillus niger* | − | − | − |
| Mouse | − | − | − |
| Equivalents of the RCS 24 gene in other organisms. | | | |
| *G. oxydans* DSM 17078 | ++++ | + | + |
| *G. oxydans* IFO 3293 | ++++ | + | + |
| *G. oxydans* IFO 3292 | ++++ | + | + |
| *G. oxydans* ATCC 621H | ++++ | + | + |
| *G. oxydans* IFO 12528 | ++++ | + | + |
| *G. oxydans* G 624 | ++++ | + | + |
| *G. oxydans* T- 100 | ++++ | + | + |
| *G. oxydans* IFO 3291 | ++++ | + | + |
| *G. oxydans* IFO 3255 | ++++ | + | + |

TABLE C-continued

| Strain | Signal 1 | Signal 2 | Signal 3 |
|---|---|---|---|
| *G. oxydans* ATCC 9937 | ++++ | + | + |
| *G. oxydans* IFO 3244 | ++++ | + | + |
| *G. cerinus* IFO 3266 | +++ | + | + |
| *G. frateurii* IFO 3260 | +++ | + | + |
| *G. oxydans* IFO 3287 | ++++ | + | + |
| *Acetobacter aceti* subsp. *orleanus* IFO 3259 | ++ | − | + |
| *Acetobacter aceti* subsp. *xylinum* IFO 13693 | ++ | − | + |
| *Acetobacter aceti* subsp. *xylinum* IFO 13773 | ++ | − | + |
| *Acetobacter* sp. ATCC 15164 | ++ | − | + |
| *G. thailandicus* NBRC 100600 | +++ | + | + |
| *Gluconacetobacter liquefaciens* ATCC 14835 | ++ | + | + |
| *Gluconacetobacter polyoxogenes* NBI 1028 | ++ | + | + |
| *Gluconacetobacter diazotrophicus* ATCC 49037 | ++ | + | + |
| *Gluconacetobacter europaeus* DSM 6160 | ++ | + | + |
| *Acetobacter aceti* 1023 | ++ | − | + |
| *Acetobacter pasteurianus* NCI 1193 | ++ | − | + |
| *Pseudomonas putida* ATCC 21812 | + | − | + |
| *Pseudomonas aeruginosa* PAO1 | + | − | + |
| *Pseudomonas fluorescens* DSM 50106 | + | − | + |
| *Pseudomonas syringae* B728a | + | − | + |
| *Paracoccus denitrificans* strain Pd1222 | + | − | + |
| *Rhodopseudomonas palustris* CGA009 | + | − | + |
| *Pantoea citrea* 1056R | − | − | − |
| *E. coli* K-12 | − | − | − |
| *Saccharomyces cerevisiae* | − | − | − |
| *Aspergillus niger* | − | − | − |
| Mouse | − | − | − |
| Equivalents of the RCS 25 gene in other organisms. | | | |
| *G. oxydans* DSM 17078 | ++++ | + | + |
| *G. oxydans* IFO 3293 | ++++ | + | + |
| *G. oxydans* IFO 3292 | ++++ | + | + |
| *G. oxydans* ATCC 621H | ++++ | + | + |
| *G. oxydans* IFO 12528 | ++++ | + | + |
| *G. oxydans* G 624 | ++++ | + | + |
| *G. oxydans* T-100 | ++++ | + | + |
| *G. oxydans* IFO 3291 | ++++ | + | + |
| *G. oxydans* IFO 3255 | ++++ | + | + |
| *G. oxydans* ATCC 9937 | ++++ | + | + |
| *G. oxydans* IFO 3244 | ++++ | + | + |
| *G. cerinus* IFO 3266 | +++ | + | + |
| *G. frateurii* IFO 3260 | +++ | + | + |
| *G. oxydans* IFO 3287 | ++++ | + | + |
| *Acetobacter aceti* subsp. *orleanus* IFO 3259 | ++ | − | + |
| *Acetobacter aceti* subsp. *xylinum* IFO 13693 | ++ | − | + |
| *Acetobacter aceti* subsp. *xylinum* IFO 13773 | ++ | − | + |
| *Acetobacter* sp. ATCC 15164 | ++ | − | + |
| *G. thailandicus* NBRC 100600 | +++ | + | + |
| *Gluconacetobacter liquefaciens* ATCC 14835 | ++ | + | + |
| *Gluconacetobacter polyoxogenes* NBI 1028 | ++ | + | + |
| *Gluconacetobacter diazotrophicus* ATCC 49037 | ++ | + | + |
| *Gluconacetobacter europaeus* DSM 6160 | ++ | + | + |
| *Acetobacter aceti* 1023 | ++ | − | + |
| *Acetobacter pasteurianus* NCI 1193 | ++ | − | + |
| *Pseudomonas putida* ATCC 21812 | + | − | + |
| *Pseudomonas aeruginosa* PAO1 | + | − | + |
| *Pseudomonas fluorescens* DSM 50106 | + | − | + |
| *Pseudomonas syringae* B728a | + | − | + |
| *Paracoccus denitrificans* strain Pd1222 | + | − | + |
| *Rhodopseudomonas palustris* CGA009 | + | − | + |
| *Pantoea citrea* 1056R | − | − | − |
| *E. coli* K-12 | − | − | − |
| *Saccharomyces cerevisiae* | − | − | − |
| *Aspergillus niger* | − | − | − |

TABLE C-continued

| Strain | Signal 1 | Signal 2 | Signal 3 |
|---|---|---|---|
| Mouse | − | − | − |
| Equivalents of the SMS 12 gene in other organisms. | | | |
| *G. oxydans* DSM 17078 | ++++ | + | + |
| *G. oxydans* IFO 3293 | ++++ | + | + |
| *G. oxydans* IFO 3292 | ++++ | − | + |
| *G. oxydans* ATCC 621H | − | − | − |
| *G. oxydans* IFO 12528 | − | − | − |
| *G. oxydans* G 624 | + | + | + |
| *G. oxydans* T-100 | ++++ | + | + |
| *G. oxydans* IFO 3291 | + | + | + |
| *G. oxydans* IFO 3255 | + | + | + |
| *G. oxydans* ATCC 9937 | + | + | + |
| *G. oxydans* IFO 3244 | + | + | + |
| *G. cerinus* IFO 3266 | + | + | + |
| *G. frateurii* IFO 3260 | + | + | + |
| *G. oxydans* IFO 3287 | + | + | + |
| *Acetobacter aceti* subsp. *orleanus* IFO 3259 | − | − | − |
| *Acetobacter aceti* subsp. *xylinum* IFO 13693 | − | − | − |
| *Acetobacter aceti* subsp. *xylinum* IFO 13773 | − | − | − |
| *Acetobacter* sp. ATCC 15164 | − | − | − |
| *G. thailandicus* NBRC 100600 | + | + | + |
| *Gluconacetobacter liquefaciens* ATCC 14835 | ++ | + | + |
| *Gluconacetobacter polyoxogenes* NBI 1028 | − | − | + |
| *Gluconacetobacter diazotrophicus* ATCC 49037 | − | − | + |
| *Gluconacetobacter europaeus* DSM 6160 | − | − | + |
| *Acetobacter aceti* 1023 | − | − | − |
| *Acetobacter pasteurianus* NCI 1193 | − | − | − |
| *Pseudomonas putida* ATCC 21812 | − | − | − |
| *Pseudomonas aeruginosa* PAO1 | − | − | − |
| *Pseudomonas fluorescens* DSM 50106 | − | − | − |
| *Pseudomonas syringae* B728a | − | − | − |
| *Azotobacter vinelandii* AvOP | − | − | − |
| *Azotobacter chroococcum* MCD1 | − | − | − |
| *Paracoccus denitrificans* strain Pd1222 | − | − | − |
| *Rhodopseudomonas palustris* CGA009 | − | − | − |
| *Pantoea citrea* 1056R | − | − | − |
| *E. coli* K-12 | − | − | − |
| *Saccharomyces cerevisiae* | − | − | − |
| *Aspergillus niger* | − | − | − |
| Mouse | − | − | − |
| Equivalents of the SMS 13 gene in other organisms. | | | |
| *G. oxydans* DSM 17078 | ++++ | + | + |
| *G. oxydans* IFO 3293 | ++++ | + | + |
| *G. oxydans* IFO 3292 | ++++ | + | + |
| *G. oxydans* ATCC 621H | ++++ | + | + |
| *G. oxydans* IFO 12528 | ++++ | + | + |
| *G. oxydans* G 624 | ++++ | + | + |
| *G. oxydans* T-100 | ++++ | + | + |
| *G. oxydans* IFO 3291 | ++++ | + | + |
| *G. oxydans* IFO 3255 | ++++ | + | + |
| *G. oxydans* ATCC 9937 | ++++ | + | + |
| *G. oxydans* IFO 3244 | ++++ | + | + |
| *G. oxydans* IFO 3266 | +++ | + | + |
| *G. frateurii* IFO 3260 | +++ | + | + |
| *G. oxydans* IFO 3287 | +++ | + | + |
| *Acetobacter aceti* subsp. *orleanus* IFO 3259 | − | − | − |
| *Acetobacter aceti* subsp. *xylinum* IFO 13693 | − | − | − |
| *Acetobacter aceti* subsp. *xylinum* IFO 13773 | − | − | − |
| *Acetobacter* sp. ATCC 15164 | − | − | − |
| *G. thailandicus* NBRC 100600 | +++ | + | + |
| *Gluconacetobacter liquefaciens* ATCC 14835 | ++ | + | + |
| *Gluconacetobacter polyoxogenes* NBI 1028 | − | − | + |
| *Gluconacetobacter diazotrophicus* ATCC 49037 | − | − | + |

TABLE C-continued

| Strain | Signal 1 | Signal 2 | Signal 3 |
|---|---|---|---|
| *Gluconacetobacter europaeus* DSM 6160 | − | − | + |
| *Acetobacter aceti* 1023 | − | − | − |
| *Acetobacter pasteurianus* NCI 1193 | − | − | − |
| *Pseudomonas putida* ATCC 21812 | − | − | − |
| *Pseudomonas aeruginosa* PAO1 | − | − | − |
| *Pseudomonas fluorescens* DSM 50106 | − | − | − |
| *Pseudomonas syringae* B728a | − | − | − |
| *Azotobacter vinelandii* AvOP | − | − | − |
| *Azotobacter chroococcum* MCD1 | − | − | − |
| *Paracoccus denitrificans* strain Pd1222 | − | − | − |
| *Rhodopseudomonas palustris* CGA009 | − | − | − |
| *Pantoea citrea* 1056R | − | − | − |
| *E. coli* | − | − | − |
| *Saccharomyces cerevisiae* | − | − | − |
| *Aspergillus niger* | − | − | − |
| Mouse | − | − | − |
| Equivalents of the SMS 14 gene in other organisms. | | | |
| *G. oxydans* DSM 17078 | ++++ | + | + |
| *G. oxydans* IFO 3293 | ++++ | + | + |
| *G. oxydans* IFO 3292 | ++++ | + | + |
| *G. oxydans* ATCC 621H | ++++ | + | + |
| *G. oxydans* IFO 12528 | ++++ | + | + |
| *G. oxydans* G 624 | ++++ | + | + |
| *G. oxydans* T-100 | ++++ | + | + |
| *G. oxydans* IFO 3291 | ++++ | + | + |
| *G. oxydans* IFO 3255 | ++++ | + | + |
| *G. oxydans* ATCC 9937 | ++++ | + | + |
| *G. oxydans* IFO 3244 | ++++ | + | + |
| *G. cerinus* IFO 3266 | +++ | + | + |
| *G. frateurii* IFO 3260 | +++ | + | + |

TABLE C-continued

| Strain | Signal 1 | Signal 2 | Signal 3 |
|---|---|---|---|
| *G. oxydans* IFO 3287 | +++ | + | + |
| *Acetobacter aceti* subsp. *orleanus* IFO 3259 | − | − | − |
| *Acetobacter aceti* subsp. *xylinum* IFO 13693 | − | − | − |
| *Acetobacter aceti* subsp. *xylinum* IFO 13773 | − | − | − |
| *Acetobacter* sp ATCC 15164 | − | − | − |
| *G. thailandicus* NBRC 100600 | +++ | + | + |
| *Gluconacetobacter liquefaciens* ATCC 14835 | ++ | + | + |
| *Gluconacetobacter polyoxogenes* NBI 1028 | − | − | + |
| *Gluconacetobacter diazotrophicus* ATCC 49037 | − | − | + |
| *Gluconacetobacter europaeus* DSM 6160 | − | − | + |
| *Acetobacter aceti* 1023 | − | − | − |
| *Acetobacter pasteurianus* NCI 1193 | − | − | − |
| *Pseudomonas putida* ATCC 21812 | − | − | − |
| *Pseudomonas aeruginosa* PAO1 | − | − | − |
| *Pseudomonas fluorescens* DSM 50106 | − | − | − |
| *Pseudomonas syringae* B728a | − | − | − |
| *Azotobacter vinelandii* AvOP | − | − | − |
| *Azotobacter chroococcum* MCD1 | − | − | − |
| *Paracoccus denitrificans* strain Pd1222 | − | − | − |
| *Rhodopseudomonas palustris* CGA009 | − | − | − |
| *Pantoea citrea* 1056R | − | − | − |
| *E. coli* | − | − | − |
| *Saccharomyces cerevisiae* | − | − | − |
| *Aspergillus niger* | − | − | − |
| Mouse | − | − | − |

The invention claimed is:

1. A process for the fermentative production of Vitamin C, comprising: cultivating a host cell selected from the group consisting of *Gluconobacter, Gluconacetobacter* and *Acetobacter* to allow the direct production of Vitamin C from a carbon source obtainable from D-glucose or D-sorbitol metabolization pathway, wherein the genome of said host cell is genetically engineered with a polynucleotide encoding L-sorbosone dehydrogenase selected from the group consisting of: (i) a polynucleotide comprising the nucleotide sequence of SEQ ID NO:1; (ii) a polynucleotide encoding L-sorbosone dehydrogenase that has the ability to directly convert L-sorbosone into Vitamin C comprising the amino acid sequence of SEQ ID NO:2; (iii) a polynucleotide that hybridizes under highly stringent conditions to a polynucleotide encoding L-sorbosone dehydrogenase that has the ability to directly convert L-sorbosone into Vitamin C comprising the amino acid sequence of SEQ ID NO:2, and wherein said highly stringent conditions comprise hybridization at 42° C. for 2 to 4 days followed by two washes in 2×SSC, 0.1% SDS at room temperature and two washes in 0.5×SSC, 0.1% SDS or 0.1×SSC, 0.1% SDS at 65° C. to 68° C.; and (iv) a polynucleotide that is at least 95% identical to a polynucleotide encoding L-sorbosone dehydrogenase that has the ability to directly convert L-sorbosone into Vitamin C comprising the amino acid sequence of SEQ ID NO:2, and wherein a polynucleotide that encodes a Sorbitol/Sorbose Metabolization System (SMS) protein having the amino acid sequence of SEQ ID NO:137 is overexpressed, and isolating Vitamin C from the cell or the culture medium.

2. The process of claim 1, wherein said host cell is cultivated in an aqueous nutrient medium under conditions that allow the direct production of Vitamin C from D-sorbitol or L-sorbose.

3. The process of claim 1, wherein the genetically engineered host cell is selected from the group consisting of *Acetobacter* sp., *Acetobacter aceti, Gluconobacter frateurii, Gluconobacter cerinus, Gluconobacter thailandicus*, and *Gluconobacter oxydans*.

4. A genetically engineered host cell selected from the group consisting of *Gluconobacter, Acetobacter* and *Gluconacetobacter* that expresses a polypeptide having L-sorbosone dehydrogenase activity wherein the polypeptide has the amino acid sequence of SEQ ID NO:2, and wherein a polynucleotide of said genetically engineered host cell that encodes a Sorbitol/Sorbose Metabolization System (SMS) protein having the amino acid sequence of SEQ ID NO:137 is overexpressed.

5. The genetically engineered host cell of claim 4, wherein said polynucleotide that encodes the SMS protein having the amino acid sequence of SEQ ID NO:137 has the nucleotide sequence of SEQ ID NO:136.

6. The process of claim 1, wherein said host cell directly produces Vitamin C from D-sorbitol in quantities of 300 mg/l or more when measured in a resting cell method after an incubation period of 20 hours.

7. The process of claim 1, wherein said host cell directly produces Vitamin C from L-sorbose in quantities of 800 mg/l or more when measured in a resting cell method after an incubation period of 20 hours.

8. The genetically engineered host cell of claim 4, wherein said genetically engineered host cell is selected from the group consisting of *Acetobacter* sp., *Acetobacter aceti, Gluconobacter frateurii, Gluconobacter cerinus, Gluconobacter thailandicus*, and *Gluconobacter oxydans*.

9. A process for producing a genetically engineered cell comprising introducing into a host cell a polynucleotide that encodes a polypeptide having L-sorbosone dehydrogenase activity having the amino acid sequence of SEQ ID NO:2, wherein a polynucleotide of said host cell that encodes a Sorbitol/Sorbose Metabolization System (SMS) protein having the amino acid sequence of SEQ ID NO:137 is overexpressed.

10. The process of claim 3, wherein said host cell is *Gluconobacter oxydans.*

11. The process of claim 10, wherein said host cell is *Gluconobacter oxydans* DSM 17078.

12. The genetically engineered host cell of claim 8, wherein said genetically engineered host cell is *Gluconobacter oxydans.*

13. The genetically engineered host cell of claim 12, wherein said genetically engineered host cell is *Gluconobacter oxydans* DSM 17078.

* * * * *

SEQUENCE LISTING

```
<160> NUMBER OF SEQ ID NOS: 217

<210> SEQ ID NO 1
<211> LENGTH: 2367
<212> TYPE: DNA
<213> ORGANISM: Gluconobacter oxydans DSM 17078

<400> SEQUENCE: 1

atgaacagcg gcccccgcac gctctccatg atcatcggga ttctgggcgc cctcatggcc      60

gccttcctga tcatcgaagg cctccacctc atcatcctcg gcggctcgtg gttctacacc     120

ctcgccggca tcgcgctggc ggccagcagc gtctacatga tccgtcgcaa catcctctcg     180

acatggatcg ccctgggcct gcttgtggca acagccctgt ggtcgctcgc cgaagtcggc     240

accagcttct ggcccagctt ctcccgcctg atcgtgttcc tgtgcgtcgc cctgatcgcg     300

actctcatgg cgccctggct cagcggcccc ggccggcgct acttcacccg ccccgtcaca     360

ggcgccacat ccggcgccct cggcgcgatc atcgtggctt tcctcgccgg catgttccgg     420

gtccacccga ccatcgcccc gcaggacacc acccacccgc aggaaaccgc gtccaccgcc     480

gactccgacc agccaggcca tgactggccc gcctatggcc gcacggcttc cggcacgcgc     540

tacgccagct tcacgcagat caaccgcgac aatgtcagca agctccgcgt cgcctggacc     600

taccgcaccg gcgacatggc gctgaacggc gccgagttcc agggcacccc catcaagatc     660

ggcgacacgg tctatatctg ctcaccgcac aacatcgtct cggcccttga cccggacacc     720

ggcacggaaa agtggaagtt cgacccccac gcccagacga aagtctggca gcgctgccgc     780

ggcgtcggct actggcatga cagcacggcc acggacgcca acgcgccctg cgcctcgcgc     840

atcgtcctca ccacgatcga cgcccgcctc atcaccatcg acgcccgtac cggccaggcc     900
```

-continued

```
tgcacggatt tcggaacgaa cggcaacgtc aatctcctga ccggcctcgg cccgacagct    960
cccggctcgt actacccgac cgccgccccc ctcgtggcgg gtgacatcgt ggtcgtcggc   1020
ggccgcatcg ccgataacga gcgcaccggc gagccctccg gcgtcgtccg cggctatgat   1080
gtccgcaccg gcgcacaggt ctgggcctgg gacgccacca acccgcatcg cggcaccaca   1140
cctctggccg aaggcgagat ctaccccgcc gaaacccccca acatgtgggg caccgccagc  1200
tacgacccga aactcaacct cgtcttcttc ccgctcggca accagacccc cgatttctgg   1260
ggcggcgacc gcagcaaggc ctcagacgaa tacaacgacg ccttcgtcgc cgtggacgcc   1320
aagaccggcg acgaacgctg gcacttccgc accgccaacc acgacctcgt ggactacgat   1380
gccacggccc agcccatcct ctatgacatt ccggacggcc atggcggcac ccgcccggcg   1440
atcatcgcca tgaccaagcg cggccagatc ttcgtgctcg accgccgcga cggcaccccg   1500
atcgtccctg tggaaatgcg caaagtcccg caggacggcg caccggaaca ccagtacctc   1560
gcccccgaac agccctattc cgccctctcc atcggaacag agcgcctgaa acccagcgac   1620
atgtggggtg gtacgatctt cgaccagctc ctgtgccgca tccagttcgc ctcctaccgc   1680
tatgaaggcg agttcacccc cgtcaacgag aaacaggcca ccatcatcta tccgggctat   1740
tacggcggca tcaactgggg cggcggcgcc gtggatgaaa gcaccggaac gctgctggtc   1800
aacgacatcc gcatggccca gtggggcaag ttcatgaagc aggaagaagc ccgtcgcagc   1860
ggcttcaaac ccagctcgga aggcgaatat tccgaacaga aaggcacccc ctggggcgtc   1920
gtccgctcga tgttcttctc ccccgccggt ctcccctgcg tgaaaccgcc ctatggcacg   1980
atgaacgcca tcgacctgcg cagcggcaag gtcaaatgga gcatgccgct tggcacgatc   2040
caggacatgc cggtccacgg catggtccca ggcctcgcca tcccgctcgg aatgccgacc   2100
atgagcggcc cgctggccac ccataccggc ctggtgttct tctccggcac gctcgacaac   2160
tatgtccgcg cgctcaacac cgacaccggc gaagtcgtct ggaaagcccg tctccccgtc   2220
gcctcacagg ccgctccgat gagctacatg tccgacaaga ccggcaaaca gtacatcgtc   2280
gtcaccgcag gcggcctgac ccgctccggc gtcgacaaaa accgcggcga ctacgtcatc   2340
gcctacgccc tgccctccga agaataa                                       2367

<210> SEQ ID NO 2
<211> LENGTH: 788
<212> TYPE: PRT
<213> ORGANISM: Gluconobacter oxydans DSM 17078

<400> SEQUENCE: 2

Met Asn Ser Gly Pro Arg Thr Leu Ser Met Ile Ile Gly Ile Leu Gly
1               5                   10                  15

Ala Leu Met Ala Ala Phe Leu Ile Ile Glu Gly Leu His Leu Ile Ile
            20                  25                  30

Leu Gly Gly Ser Trp Phe Tyr Thr Leu Ala Gly Ile Ala Leu Ala Ala
        35                  40                  45

Ser Ser Val Tyr Met Ile Arg Arg Asn Ile Leu Ser Thr Trp Ile Ala
    50                  55                  60

Leu Gly Leu Leu Val Ala Thr Ala Leu Trp Ser Leu Ala Glu Val Gly
65                  70                  75                  80

Thr Ser Phe Trp Pro Ser Phe Ser Arg Leu Ile Val Phe Leu Cys Val
                85                  90                  95

Ala Leu Ile Ala Thr Leu Met Ala Pro Trp Leu Ser Gly Pro Gly Arg
            100                 105                 110
```

-continued

```
Arg Tyr Phe Thr Arg Pro Val Thr Gly Ala Thr Ser Gly Ala Leu Gly
        115                 120                 125

Ala Ile Ile Val Ala Phe Leu Ala Gly Met Phe Arg Val His Pro Thr
    130                 135                 140

Ile Ala Pro Gln Asp Thr Thr His Pro Gln Glu Thr Ala Ser Thr Ala
145                 150                 155                 160

Asp Ser Asp Gln Pro Gly His Asp Trp Pro Ala Tyr Gly Arg Thr Ala
                165                 170                 175

Ser Gly Thr Arg Tyr Ala Ser Phe Thr Gln Ile Asn Arg Asp Asn Val
            180                 185                 190

Ser Lys Leu Arg Val Ala Trp Thr Tyr Arg Thr Gly Asp Met Ala Leu
        195                 200                 205

Asn Gly Ala Glu Phe Gln Gly Thr Pro Ile Lys Ile Gly Asp Thr Val
    210                 215                 220

Tyr Ile Cys Ser Pro His Asn Ile Val Ser Ala Leu Asp Pro Asp Thr
225                 230                 235                 240

Gly Thr Glu Lys Trp Lys Phe Asp Pro His Ala Gln Thr Lys Val Trp
                245                 250                 255

Gln Arg Cys Arg Gly Val Gly Tyr Trp His Asp Ser Thr Ala Thr Asp
            260                 265                 270

Ala Asn Ala Pro Cys Ala Ser Arg Ile Val Leu Thr Thr Ile Asp Ala
        275                 280                 285

Arg Leu Ile Thr Ile Asp Ala Arg Thr Gly Gln Ala Cys Thr Asp Phe
    290                 295                 300

Gly Thr Asn Gly Asn Val Asn Leu Leu Thr Gly Leu Gly Pro Thr Ala
305                 310                 315                 320

Pro Gly Ser Tyr Tyr Pro Thr Ala Ala Pro Leu Val Ala Gly Asp Ile
                325                 330                 335

Val Val Val Gly Gly Arg Ile Ala Asp Asn Glu Arg Thr Gly Glu Pro
            340                 345                 350

Ser Gly Val Val Arg Gly Tyr Asp Val Arg Thr Gly Ala Gln Val Trp
        355                 360                 365

Ala Trp Asp Ala Thr Asn Pro His Arg Gly Thr Thr Pro Leu Ala Glu
    370                 375                 380

Gly Glu Ile Tyr Pro Ala Glu Thr Pro Asn Met Trp Gly Thr Ala Ser
385                 390                 395                 400

Tyr Asp Pro Lys Leu Asn Leu Val Phe Phe Pro Leu Gly Asn Gln Thr
                405                 410                 415

Pro Asp Phe Trp Gly Gly Asp Arg Ser Lys Ala Ser Asp Glu Tyr Asn
            420                 425                 430

Asp Ala Phe Val Ala Val Asp Ala Lys Thr Gly Asp Glu Arg Trp His
        435                 440                 445

Phe Arg Thr Ala Asn His Asp Leu Val Asp Tyr Asp Ala Thr Ala Gln
    450                 455                 460

Pro Ile Leu Tyr Asp Ile Pro Asp Gly His Gly Gly Thr Arg Pro Ala
465                 470                 475                 480

Ile Ile Ala Met Thr Lys Arg Gly Gln Ile Phe Val Leu Asp Arg Arg
                485                 490                 495

Asp Gly Thr Pro Ile Val Pro Val Glu Met Arg Lys Val Pro Gln Asp
            500                 505                 510

Gly Ala Pro Glu His Gln Tyr Leu Ala Pro Glu Gln Pro Tyr Ser Ala
        515                 520                 525

Leu Ser Ile Gly Thr Glu Arg Leu Lys Pro Ser Asp Met Trp Gly Gly
```

```
    530                 535                 540

Thr Ile Phe Asp Gln Leu Leu Cys Arg Ile Gln Phe Ala Ser Tyr Arg
545                 550                 555                 560

Tyr Glu Gly Glu Phe Thr Pro Val Asn Glu Lys Gln Ala Thr Ile Ile
                565                 570                 575

Tyr Pro Gly Tyr Tyr Gly Gly Ile Asn Trp Gly Gly Gly Ala Val Asp
            580                 585                 590

Glu Ser Thr Gly Thr Leu Leu Val Asn Asp Ile Arg Met Ala Gln Trp
        595                 600                 605

Gly Lys Phe Met Lys Gln Glu Glu Ala Arg Arg Ser Gly Phe Lys Pro
    610                 615                 620

Ser Ser Glu Gly Glu Tyr Ser Glu Gln Lys Gly Thr Pro Trp Gly Val
625                 630                 635                 640

Val Arg Ser Met Phe Phe Ser Pro Ala Gly Leu Pro Cys Val Lys Pro
                645                 650                 655

Pro Tyr Gly Thr Met Asn Ala Ile Asp Leu Arg Ser Gly Lys Val Lys
            660                 665                 670

Trp Ser Met Pro Leu Gly Thr Ile Gln Asp Met Pro Val His Gly Met
        675                 680                 685

Val Pro Gly Leu Ala Ile Pro Leu Gly Met Pro Thr Met Ser Gly Pro
    690                 695                 700

Leu Ala Thr His Thr Gly Leu Val Phe Phe Ser Gly Thr Leu Asp Asn
705                 710                 715                 720

Tyr Val Arg Ala Leu Asn Thr Asp Thr Gly Glu Val Val Trp Lys Ala
                725                 730                 735

Arg Leu Pro Val Ala Ser Gln Ala Ala Pro Met Ser Tyr Met Ser Asp
            740                 745                 750

Lys Thr Gly Lys Gln Tyr Ile Val Val Thr Ala Gly Gly Leu Thr Arg
        755                 760                 765

Ser Gly Val Asp Lys Asn Arg Gly Asp Tyr Val Ile Ala Tyr Ala Leu
    770                 775                 780

Pro Ser Glu Glu
785
```

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atgaacagcg gcccccgcac 20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ttattcttcg gagggcaggg 20

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
atgaacagcg gcccccgcac gctctccatg 30

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
ccggaacatg ccggcgagga aagccacgat 30

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
tgactggccc gcctatggcc gcacggcttc 30

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
ttcttcggag ggcagggcgt aggcgatgac 30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
cgggactttg cgcatttcca cagggacgat 30

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
agcccatcct ctatgacatt ccggacggcc 30

<210> SEQ ID NO 11
<211> LENGTH: 771
<212> TYPE: DNA
<213> ORGANISM: Gluconobacter oxydans IFO 3292

<400> SEQUENCE: 11
ccgcccggcg atcatcgcca tgaccaagcg cggccagatc ttcgtgctcg accgccgcga 60
cggcaccccg atcgtccccg tggaaatgcg caaagtcccc caggacggcg caccggaaca 120

-continued

```
ccagtacctc gcccccgaac agccctattc cgccctctcc atcggaacag agcgcctgaa    180

acccagcgat atgtggggcg gcacgatctt cgaccagctc ctgtgccgca tccagttcgc    240

ctcctaccgc tatgaaggcg agttcacccc cgtcaacgag aagcaggcca ccatcatcta    300

tccgggctat tacggcggca tcaactgggg cggcggcgcc gtggatgaaa gcaccggaac    360

gctgctggtc aacgacatcc gcatggccca gtggggcaag ttcatgaagc aagaagaagc    420

ccgccgcagc ggcttcaaac ccagctcgga aggcgaatat tccgaacaga aaggcacccc    480

ctggggcgtc gtccgctcga tgttcttctc ccccgccggt ctcccctgcg tgaaaccgcc    540

ctatggcacg atgaacgcca tcgacctgcg cagcggcaag gtcaaatgga gcatgccgct    600

tggcacgatc caggacatgc cggtccacgg catggtcccc ggcctcgcca tcccgctcgg    660

aatgccgacc atgagcggcc cgctggccac ccataccggc ctggtcttct tctccggcac    720

gctcgacaac tatgtccgcg cgctcaacac cgacaccggc gaagtcgtct g             771


<210> SEQ ID NO 12
<211> LENGTH: 256
<212> TYPE: PRT
<213> ORGANISM: Gluconobacter oxydans IFO 3292

<400> SEQUENCE: 12

Arg Pro Ala Ile Ile Ala Met Thr Lys Arg Gly Gln Ile Phe Val Leu
1               5                   10                  15

Asp Arg Arg Asp Gly Thr Pro Ile Val Pro Val Glu Met Arg Lys Val
            20                  25                  30

Pro Gln Asp Gly Ala Pro Glu His Gln Tyr Leu Ala Pro Glu Gln Pro
        35                  40                  45

Tyr Ser Ala Leu Ser Ile Gly Thr Glu Arg Leu Lys Pro Ser Asp Met
    50                  55                  60

Trp Gly Gly Thr Ile Phe Asp Gln Leu Leu Cys Arg Ile Gln Phe Ala
65                  70                  75                  80

Ser Tyr Arg Tyr Glu Gly Glu Phe Thr Pro Val Asn Glu Lys Gln Ala
                85                  90                  95

Thr Ile Ile Tyr Pro Gly Tyr Tyr Gly Gly Ile Asn Trp Gly Gly Gly
            100                 105                 110

Ala Val Asp Glu Ser Thr Gly Thr Leu Leu Val Asn Asp Ile Arg Met
        115                 120                 125

Ala Gln Trp Gly Lys Phe Met Lys Gln Glu Glu Ala Arg Arg Ser Gly
    130                 135                 140

Phe Lys Pro Ser Ser Glu Gly Glu Tyr Ser Glu Gln Lys Gly Thr Pro
145                 150                 155                 160

Trp Gly Val Val Arg Ser Met Phe Phe Ser Pro Ala Gly Leu Pro Cys
                165                 170                 175

Val Lys Pro Pro Tyr Gly Thr Met Asn Ala Ile Asp Leu Arg Ser Gly
            180                 185                 190

Lys Val Lys Trp Ser Met Pro Leu Gly Thr Ile Gln Asp Met Pro Val
        195                 200                 205

His Gly Met Val Pro Gly Leu Ala Ile Pro Leu Gly Met Pro Thr Met
    210                 215                 220

Ser Gly Pro Leu Ala Thr His Thr Gly Leu Val Phe Phe Ser Gly Thr
225                 230                 235                 240

Leu Asp Asn Tyr Val Arg Ala Leu Asn Thr Asp Thr Gly Glu Val Val
                245                 250                 255
```

<210> SEQ ID NO 13
<211> LENGTH: 350
<212> TYPE: DNA
<213> ORGANISM: Gluconobacter oxydans IFO 3287
<220> FEATURE:
<221> NAME/KEY: misc_feature
<222> LOCATION: (123)..(123)
<223> OTHER INFORMATION: n is a or c or g or t

<400> SEQUENCE: 13

```
atcatcggga ttctgggcgc cctcatggcc gccttcctga tcatcgaagg cctccacctc      60

atcatcctcg gcggctcatg gttttacacc ctcgccggca tcgcgctggc agccagcagc     120

gtntacatga tccgtcgcaa catcctctcg acatggatcg ccctcggcct gcttgtggca     180

acagccctgt ggtcgctcgc cgaagtcggc accagcttct ggcccagctt ctcccgcctg     240

atcgtatttc tgtgcgtcgc cctgatcgcg accctcatgg cgccctggct cagcggcccc     300

ggccggcgct acttcacccg ccccgtcaca ggcgccacct ccggcgccct                350
```

<210> SEQ ID NO 14
<211> LENGTH: 116
<212> TYPE: PRT
<213> ORGANISM: Gluconobacter oxydans IFO 3287

<400> SEQUENCE: 14

```
Ile Ile Gly Ile Leu Gly Ala Leu Met Ala Ala Phe Leu Ile Ile Glu
1               5                   10                  15

Gly Leu His Leu Ile Ile Leu Gly Gly Ser Trp Phe Tyr Thr Leu Ala
            20                  25                  30

Gly Ile Ala Leu Ala Ala Ser Ser Val Tyr Met Ile Arg Arg Asn Ile
        35                  40                  45

Leu Ser Thr Trp Ile Ala Leu Gly Leu Leu Val Ala Thr Ala Leu Trp
    50                  55                  60

Ser Leu Ala Glu Val Gly Thr Ser Phe Trp Pro Ser Phe Ser Arg Leu
65                  70                  75                  80

Ile Val Phe Leu Cys Val Ala Leu Ile Ala Thr Leu Met Ala Pro Trp
                85                  90                  95

Leu Ser Gly Pro Gly Arg Arg Tyr Phe Thr Arg Pro Val Thr Gly Ala
            100                 105                 110

Thr Ser Gly Ala
        115
```

<210> SEQ ID NO 15
<211> LENGTH: 808
<212> TYPE: DNA
<213> ORGANISM: Gluconobacter oxydans IFO 3287

<400> SEQUENCE: 15

```
gcaagctccg cgtcgcctgg acctaccgca ctggcgacat ggcgctgaac ggggccgagt      60

tccagggcac ccccatcaag atcggcgaca cggtctatat ctgctcgccg cacaacatcg     120

tctcggccct cgaccccgat accggcacgg aaaagtggaa gttcgacccc cacgcccaga     180

cgaaagtctg gcagcgctgc cgcggcgtcg gctactggca tgacagcacg gccacggacg     240

ccaacgcgcc ctgcgcctcg cgcatcgtcc tcaccacgat cgacgcccgc ctcatcacca     300

tcgacgcccg caccggccag gcctgcacgg atttcggaac gaacggcaac gtcaatctcc     360

tgaccggcct cggcccgaca gcccccggtt cctactaccc gaccgccgcc cccctcgtgg     420

ccggtgacat cgtggtcgtc ggcggccgca tcgccgataa cgagcgcacc ggcgaaccct     480
```

| | |
|---|---:|
| ccggcgtcgt ccgcggctat gacgtccgca ccggcgcgca ggtctgggcc tgggacgcca | 540 |
| ccaacccgca tcgcggcacc acaccgctgg ccgaaggcga gatctatccc gccgaaaccc | 600 |
| ccaacatgtg gggcaccgcc agctacgacc cgaagctcaa cctcgtcttc ttcccgctcg | 660 |
| gcaaccagac ccccgatttc tggggcggcg accgcagcaa ggcttctgat gaatacaacg | 720 |
| acgccttcgt cgccgtggac gccaagaccg gcgacgaacg ctggcacttc cgcaccgcca | 780 |
| accacgacct cgtggactac gatgccac | 808 |

<210> SEQ ID NO 16
<211> LENGTH: 268
<212> TYPE: PRT
<213> ORGANISM: Gluconobacter oxydans IFO 3287

<400> SEQUENCE: 16

Lys Leu Arg Val Ala Trp Thr Tyr Arg Thr Gly Asp Met Ala Leu Asn
1               5                   10                  15

Gly Ala Glu Phe Gln Gly Thr Pro Ile Lys Ile Gly Asp Thr Val Tyr
            20                  25                  30

Ile Cys Ser Pro His Asn Ile Val Ser Ala Leu Asp Pro Asp Thr Gly
        35                  40                  45

Thr Glu Lys Trp Lys Phe Asp Pro His Ala Gln Thr Lys Val Trp Gln
    50                  55                  60

Arg Cys Arg Gly Val Gly Tyr Trp His Asp Ser Thr Ala Thr Asp Ala
65                  70                  75                  80

Asn Ala Pro Cys Ala Ser Arg Ile Val Leu Thr Thr Ile Asp Ala Arg
                85                  90                  95

Leu Ile Thr Ile Asp Ala Arg Thr Gly Gln Ala Cys Thr Asp Phe Gly
            100                 105                 110

Thr Asn Gly Asn Val Asn Leu Leu Thr Gly Leu Gly Pro Thr Ala Pro
        115                 120                 125

Gly Ser Tyr Tyr Pro Thr Ala Ala Pro Leu Val Ala Gly Asp Ile Val
    130                 135                 140

Val Val Gly Gly Arg Ile Ala Asp Asn Glu Arg Thr Gly Glu Pro Ser
145                 150                 155                 160

Gly Val Val Arg Gly Tyr Asp Val Arg Thr Gly Ala Gln Val Trp Ala
                165                 170                 175

Trp Asp Ala Thr Asn Pro His Arg Gly Thr Thr Pro Leu Ala Glu Gly
            180                 185                 190

Glu Ile Tyr Pro Ala Glu Thr Pro Asn Met Trp Gly Thr Ala Ser Tyr
        195                 200                 205

Asp Pro Lys Leu Asn Leu Val Phe Phe Pro Leu Gly Asn Gln Thr Pro
    210                 215                 220

Asp Phe Trp Gly Gly Asp Arg Ser Lys Ala Ser Asp Glu Tyr Asn Asp
225                 230                 235                 240

Ala Phe Val Ala Val Asp Ala Lys Thr Gly Asp Glu Arg Trp His Phe
                245                 250                 255

Arg Thr Ala Asn His Asp Leu Val Asp Tyr Asp Ala
            260                 265

<210> SEQ ID NO 17
<211> LENGTH: 800
<212> TYPE: DNA
<213> ORGANISM: Gluconobacter oxydans IFO 3287

<400> SEQUENCE: 17

-continued

```
tcttcgtgct cgaccgccgc gacggcaccc cgatcgtccc cgtggaaatg cgcaaagtcc      60

cgcaggacgg cgcaccggaa caccagtacc tcgcccccga acagccctat tccgccctct     120

ccatcggaac agagcgcctg aaacccagcg atatgtgggg tggtacgatt ttcgaccagc     180

tcctgtgccg catccagttc gcctcctacc gctatgaagg cgagttcacc cccgtcaacg     240

agaaacaggc caccatcatc tatccgggct attacggcgg catcaactgg ggcggcggcg     300

ccgtggatga aagcaccgga acgctgctgg tcaacgacat ccgcatggcc cagtggggca     360

agttcatgaa gcaggaagaa gcccgtcgca gcggcttcaa acccagctcg gaaggcgaat     420

attccgaaca gaaaggcacc ccctggggcg tcgtccgctc gatgttcttc tcccccgccg     480

gtctcccctg cgtaaaaccg ccctatggca cgatgaacgc catcgacctg cgcagcggca     540

aggtgaaatg gagcatgccg cttggcacga tccaggacat gccggtccac ggcatggtcc     600

caggcctcgc catcccgctc ggaatgccaa ccatgagcgg cccgctggcc acccataccg     660

gcttggtctt cttctccggc acgctcgaca actacgtccg cgcgctcaac accgacaccg     720

gcgaggtcgt ctggaaagcc cgtctccccg tcgcctcaca ggccgctccg atgagctaca     780

tgtccgacaa gaccggcaaa                                                 800
```

<210> SEQ ID NO 18
<211> LENGTH: 266
<212> TYPE: PRT
<213> ORGANISM: Gluconobacter oxydans IFO 3287

<400> SEQUENCE: 18

```
Phe Val Leu Asp Arg Arg Asp Gly Thr Pro Ile Val Pro Val Glu Met
1               5                   10                  15

Arg Lys Val Pro Gln Asp Gly Ala Pro Glu His Gln Tyr Leu Ala Pro
            20                  25                  30

Glu Gln Pro Tyr Ser Ala Leu Ser Ile Gly Thr Glu Arg Leu Lys Pro
        35                  40                  45

Ser Asp Met Trp Gly Gly Thr Ile Phe Asp Gln Leu Leu Cys Arg Ile
    50                  55                  60

Gln Phe Ala Ser Tyr Arg Tyr Glu Gly Glu Phe Thr Pro Val Asn Glu
65                  70                  75                  80

Lys Gln Ala Thr Ile Ile Tyr Pro Gly Tyr Tyr Gly Gly Ile Asn Trp
                85                  90                  95

Gly Gly Gly Ala Val Asp Glu Ser Thr Gly Thr Leu Leu Val Asn Asp
            100                 105                 110

Ile Arg Met Ala Gln Trp Gly Lys Phe Met Lys Gln Glu Glu Ala Arg
        115                 120                 125

Arg Ser Gly Phe Lys Pro Ser Ser Glu Gly Glu Tyr Ser Glu Gln Lys
    130                 135                 140

Gly Thr Pro Trp Gly Val Val Arg Ser Met Phe Phe Ser Pro Ala Gly
145                 150                 155                 160

Leu Pro Cys Val Lys Pro Pro Tyr Gly Thr Met Asn Ala Ile Asp Leu
                165                 170                 175

Arg Ser Gly Lys Val Lys Trp Ser Met Pro Leu Gly Thr Ile Gln Asp
            180                 185                 190

Met Pro Val His Gly Met Val Pro Gly Leu Ala Ile Pro Leu Gly Met
        195                 200                 205

Pro Thr Met Ser Gly Pro Leu Ala Thr His Thr Gly Leu Val Phe Phe
    210                 215                 220

Ser Gly Thr Leu Asp Asn Tyr Val Arg Ala Leu Asn Thr Asp Thr Gly
```

-continued 225 230 235 240

Glu Val Val Trp Lys Ala Arg Leu Pro Val Ala Ser Gln Ala Ala Pro
245 250 255

Met Ser Tyr Met Ser Asp Lys Thr Gly Lys
260 265

<210> SEQ ID NO 19
<211> LENGTH: 360
<212> TYPE: DNA
<213> ORGANISM: Acetobacter sp. ATCC 15164
<220> FEATURE:
<221> NAME/KEY: misc_feature
<222> LOCATION: (123)..(123)
<223> OTHER INFORMATION: n is a or c or g or t

<400> SEQUENCE: 19
atcatcggga ttctgggcgc cctcatggcc gccttcctga tcatcgaagg cctccacctc 60
atcatcctcg gcggctcgtg gttttacacc ctcgccggca tcgcgctggc ggccagcagc 120
gtntacatga tccgtcgcaa catcctctcg acatggatcg ccctcggcct gcttgtagca 180
acagccctgt ggtcgctcgc cgaagtcggc accagcttct ggcccagctt ctcccgcctg 240
atcgtgttcc tgtgcgtcgc cctgatcgcg actctcatgg cgccctggct cagcggcccc 300
ggccggcgct acttcacccg ccccgtcaca ggggccacct ccggcgcact cggcgccatc 360

<210> SEQ ID NO 20
<211> LENGTH: 120
<212> TYPE: PRT
<213> ORGANISM: Acetobacter sp. ATCC 15164

<400> SEQUENCE: 20

Ile Ile Gly Ile Leu Gly Ala Leu Met Ala Ala Phe Leu Ile Ile Glu
1 5 10 15

Gly Leu His Leu Ile Ile Leu Gly Gly Ser Trp Phe Tyr Thr Leu Ala
20 25 30

Gly Ile Ala Leu Ala Ala Ser Ser Val Tyr Met Ile Arg Arg Asn Ile
35 40 45

Leu Ser Thr Trp Ile Ala Leu Gly Leu Leu Val Ala Thr Ala Leu Trp
50 55 60

Ser Leu Ala Glu Val Gly Thr Ser Phe Trp Pro Ser Phe Ser Arg Leu
65 70 75 80

Ile Val Phe Leu Cys Val Ala Leu Ile Ala Thr Leu Met Ala Pro Trp
85 90 95

Leu Ser Gly Pro Gly Arg Arg Tyr Phe Thr Arg Pro Val Thr Gly Ala
100 105 110

Thr Ser Gly Ala Leu Gly Ala Ile
115 120

<210> SEQ ID NO 21
<211> LENGTH: 760
<212> TYPE: DNA
<213> ORGANISM: Acetobacter sp. ATCC 15164

<400> SEQUENCE: 21
accgcgacaa tgtcagcaag ctccgcgtcg cctggaccta ccgcaccggc gacatggcgc 60
tgaacggcgc cgaattccag ggcacccccca tcaagatcgg cgatacggtc tatatctgct 120
caccccacaa catcgtctcg gccctcgacc ccgacaccgg cacggaaaag tggaagttcg 180
acccccacgc ccagacgaaa gtctggcagc gctgccgcgg cgtcggctac tggcatgaca 240

-continued

```
gcacagccac ggacgccaac gcgccctgcg cctcgcgcat cgtcctcacc acgatcgacg    300

cccgcctcat caccatcgac gcccgcaccg gccaggcctg cacggatttc ggaacgaacg    360

gcaacgtcaa tctcctgacc ggcctcggcc cgacagcccc cggctcctac tacccgaccg    420

ccgcccccct cgtggcgggt gacatcgtgg tcgtcggcgg ccgcatcgcc gataacgagc    480

gcacaggcga gccttccggc gtcgtccgcg gctacgacgt ccgcaccggc gcacaggtct    540

gggcctggga cgccaccaac ccgcatcgcg gcaccacacc actggccgaa ggcgagatct    600

accccgccga aacccccaac atgtggggca ccgccagcta cgacccgaaa ctcaacctcg    660

tcttcttccc gctcggcaac cagacccccg atttctgggg cggcgaccgc agcaaggcct    720

cggatgaata caacgacgcc ttcgtcgccg tggacgccaa                         760
```

<210> SEQ ID NO 22
<211> LENGTH: 252
<212> TYPE: PRT
<213> ORGANISM: Acetobacter sp. ATCC 15164

<400> SEQUENCE: 22

```
Arg Asp Asn Val Ser Lys Leu Arg Val Ala Trp Thr Tyr Arg Thr Gly
1               5                   10                  15

Asp Met Ala Leu Asn Gly Ala Glu Phe Gln Gly Thr Pro Ile Lys Ile
            20                  25                  30

Gly Asp Thr Val Tyr Ile Cys Ser Pro His Asn Ile Val Ser Ala Leu
        35                  40                  45

Asp Pro Asp Thr Gly Thr Glu Lys Trp Lys Phe Asp Pro His Ala Gln
    50                  55                  60

Thr Lys Val Trp Gln Arg Cys Arg Gly Val Gly Tyr Trp His Asp Ser
65                  70                  75                  80

Thr Ala Thr Asp Ala Asn Ala Pro Cys Ala Ser Arg Ile Val Leu Thr
                85                  90                  95

Thr Ile Asp Ala Arg Leu Ile Thr Ile Asp Ala Arg Thr Gly Gln Ala
            100                 105                 110

Cys Thr Asp Phe Gly Thr Asn Gly Asn Val Asn Leu Leu Thr Gly Leu
        115                 120                 125

Gly Pro Thr Ala Pro Gly Ser Tyr Tyr Pro Thr Ala Ala Pro Leu Val
    130                 135                 140

Ala Gly Asp Ile Val Val Val Gly Gly Arg Ile Ala Asp Asn Glu Arg
145                 150                 155                 160

Thr Gly Glu Pro Ser Gly Val Val Arg Gly Tyr Asp Val Arg Thr Gly
                165                 170                 175

Ala Gln Val Trp Ala Trp Asp Ala Thr Asn Pro His Arg Gly Thr Thr
            180                 185                 190

Pro Leu Ala Glu Gly Glu Ile Tyr Pro Ala Glu Thr Pro Asn Met Trp
        195                 200                 205

Gly Thr Ala Ser Tyr Asp Pro Lys Leu Asn Leu Val Phe Phe Pro Leu
    210                 215                 220

Gly Asn Gln Thr Pro Asp Phe Trp Gly Gly Asp Arg Ser Lys Ala Ser
225                 230                 235                 240

Asp Glu Tyr Asn Asp Ala Phe Val Ala Val Asp Ala
                245                 250
```

<210> SEQ ID NO 23
<211> LENGTH: 20
<212> TYPE: DNA

<213> ORGANISM: Artificial Sequence
<220> FEATURE:
<223> OTHER INFORMATION: primer

<400> SEQUENCE: 23
ggcgcgatca tcgtggcttt 20

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
gggtcaaggg ccgagacgat gtt 23

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
gcacgctcga caactatgtc 20

<210> SEQ ID NO 26
<211> LENGTH: 2367
<212> TYPE: DNA
<213> ORGANISM: Gluconobacter oxydans IFO 3244

<400> SEQUENCE: 26
atgaacagcg gcccccgcac gctctccatg atcatcggga ttctgggcgc cctcatggcc 60
gccttcctga tcatcgaagg cctccacctc atcatcctcg gcggctcgtg gttctacacc 120
ctcgccggca tcgcgctggc ggccagcagc gtctacatga tccgtcgcaa catcctctcg 180
acatggatcg ccctcggcct gcttgtagca acagccctgt ggtcgctcgc cgaagtcggc 240
accagcttct ggcccagctt ctcccgcctg atcgtgttcc tgtgcgtcgc cctgatcgcg 300
actctcatgg cgccctggct cagcggcccc ggccggcgct acttcacccg ccccgtcaca 360
ggggccacct ccggcgcact cggcgccatc atcgtggctt tcctcgccgg catgttccgg 420
gtccacccga ccatcgcccc gcaggacacc acccacccgc aggaaaccgc gtccaccgcc 480
gactccgacc agcccggcca tgactggccc gcctatggcc gcacagcttc cggcacgcgc 540
tacgccagct tcacacagat caaccgcgac aatgtcagca agctccgcgt cgcctggacc 600
taccgcaccg gcgacatggc gctgaacggc gccgaattcc agggcacccc catcaagatc 660
ggcgatacgg tctatatctg ctcaccccac aacatcgtct cggccctcga ccccgacacc 720
ggcacggaaa agtggaagtt cgacccccac gcccagacga aagtctggca gcgctgccgc 780
ggcgtcggct actggcatga cagcacagcc acggacgcca acgcgccctg cgcctcgcgc 840
atcgtcctca ccacgatcga cgcccgcctc atcaccatcg acgcccgcac cggccaggcc 900
tgcacggatt tcggaacgaa cggcaacgtc aatctcctga ccggcctcgg cccgacagcc 960
cccggctcct actacccgac cgccgccccc ctcgtggcgg gtgacatcgt ggtcgtcggc 1020
ggccgcatcg ccgataacga gcgcacaggc gagccttccg gcgtcgtccg cggctacgac 1080
gtccgcaccg gcgcacaggt ctgggcctgg gacgccacca acccgcatcg cggcaccaca 1140
ccactggccg aaggcgagat ctaccccgcc gaaaccccca acatgtgggg caccgccagc 1200

```
tacgacccga aactcaacct cgtcttcttc ccgctcggca accagacccc cgatttctgg    1260

ggcggcgacc gcagcaaggc ctcggatgaa tacaacgacg ccttcgtcgc cgtggacgcc    1320

aaaaccggcg acgaacgctg gcacttccgc accgccaacc acgatctcgt ggactacgat    1380

gccacggccc agcccatcct ctacgacatt ccggacggcc atggcggcac ccgcccggcg    1440

atcatcgcca tgaccaagcg cggccagatc ttcgtgctcg accgccgcga cggcaccccg    1500

atcgtccccg tggaaatgcg caaagtcccc caggacggcg caccggaaca ccagtacctc    1560

gcccccgaac agccctattc cgccctctcc atcggaacag agcgcctgaa acccagcgat    1620

atgtggggcg gcacgatctt cgaccagctc ctgtgccgca tccagttcgc ctcctaccgc    1680

tatgaaggcg agttcacccc cgtcaacgag aagcaggcca ccatcatcta tccgggctat    1740

tacggcggca tcaactgggg cggcggcgcc gtggatgaaa gcaccggaac gctgctggtc    1800

aacgacatcc gcatggccca gtggggcaag ttcatgaagc aagaagaagc ccgccgcagc    1860

ggcttcaaac ccagctcgga aggcgaatat tccgaacaga aaggcacccc ctggggcgtc    1920

gtccgctcga tgttcttctc ccccgccggt ctcccctgcg tgaaaccgcc ctatggcacg    1980

atgaacgcca tcgacctgcg cagcggcaag gtcaaatgga gcatgccgct tggcacgatc    2040

caggacatgc cggtccacgg catggtcccc ggcctcgcca tcccgctcgg aatgccgacc    2100

atgagcggcc cgctggccac ccataccggc ctggtcttct tctccggcac gctcgacaac    2160

tatgtccgcg cgctcaacac cgacaccggc gaagtcgtct ggaaagcccg tctccccgtc    2220

gcctcacagg ccgctccgat gagctacatg tccgacaaga ccggcaaaca gtacatcgtc    2280

gtcaccgcag gcggcctgac ccgctccggc gtcgacaaaa accgcggcga ctacgtcatc    2340

gcctacgccc tgccctccga agaataa                                        2367
```

<210> SEQ ID NO 27
<211> LENGTH: 788
<212> TYPE: PRT
<213> ORGANISM: Gluconobacter oxydans IFO 3244

<400> SEQUENCE: 27

```
Met Asn Ser Gly Pro Arg Thr Leu Ser Met Ile Ile Gly Ile Leu Gly
1               5                   10                  15

Ala Leu Met Ala Ala Phe Leu Ile Ile Glu Gly Leu His Leu Ile Ile
            20                  25                  30

Leu Gly Gly Ser Trp Phe Tyr Thr Leu Ala Gly Ile Ala Leu Ala Ala
        35                  40                  45

Ser Ser Val Tyr Met Ile Arg Arg Asn Ile Leu Ser Thr Trp Ile Ala
    50                  55                  60

Leu Gly Leu Leu Val Ala Thr Ala Leu Trp Ser Leu Ala Glu Val Gly
65                  70                  75                  80

Thr Ser Phe Trp Pro Ser Phe Ser Arg Leu Ile Val Phe Leu Cys Val
                85                  90                  95

Ala Leu Ile Ala Thr Leu Met Ala Pro Trp Leu Ser Gly Pro Gly Arg
            100                 105                 110

Arg Tyr Phe Thr Arg Pro Val Thr Gly Ala Thr Ser Gly Ala Leu Gly
        115                 120                 125

Ala Ile Ile Val Ala Phe Leu Ala Gly Met Phe Arg Val His Pro Thr
    130                 135                 140

Ile Ala Pro Gln Asp Thr Thr His Pro Gln Glu Thr Ala Ser Thr Ala
145                 150                 155                 160
```

-continued

```
Asp Ser Asp Gln Pro Gly His Asp Trp Pro Ala Tyr Gly Arg Thr Ala
                165                 170                 175

Ser Gly Thr Arg Tyr Ala Ser Phe Thr Gln Ile Asn Arg Asp Asn Val
            180                 185                 190

Ser Lys Leu Arg Val Ala Trp Thr Tyr Arg Thr Gly Asp Met Ala Leu
        195                 200                 205

Asn Gly Ala Glu Phe Gln Gly Thr Pro Ile Lys Ile Gly Asp Thr Val
    210                 215                 220

Tyr Ile Cys Ser Pro His Asn Ile Val Ser Ala Leu Asp Pro Asp Thr
225                 230                 235                 240

Gly Thr Glu Lys Trp Lys Phe Asp Pro His Ala Gln Thr Lys Val Trp
                245                 250                 255

Gln Arg Cys Arg Gly Val Gly Tyr Trp His Asp Ser Thr Ala Thr Asp
            260                 265                 270

Ala Asn Ala Pro Cys Ala Ser Arg Ile Val Leu Thr Thr Ile Asp Ala
        275                 280                 285

Arg Leu Ile Thr Ile Asp Ala Arg Thr Gly Gln Ala Cys Thr Asp Phe
    290                 295                 300

Gly Thr Asn Gly Asn Val Asn Leu Leu Thr Gly Leu Gly Pro Thr Ala
305                 310                 315                 320

Pro Gly Ser Tyr Tyr Pro Thr Ala Ala Pro Leu Val Ala Gly Asp Ile
                325                 330                 335

Val Val Val Gly Gly Arg Ile Ala Asp Asn Glu Arg Thr Gly Glu Pro
            340                 345                 350

Ser Gly Val Val Arg Gly Tyr Asp Val Arg Thr Gly Ala Gln Val Trp
        355                 360                 365

Ala Trp Asp Ala Thr Asn Pro His Arg Gly Thr Thr Pro Leu Ala Glu
    370                 375                 380

Gly Glu Ile Tyr Pro Ala Glu Thr Pro Asn Met Trp Gly Thr Ala Ser
385                 390                 395                 400

Tyr Asp Pro Lys Leu Asn Leu Val Phe Phe Pro Leu Gly Asn Gln Thr
                405                 410                 415

Pro Asp Phe Trp Gly Gly Asp Arg Ser Lys Ala Ser Asp Glu Tyr Asn
            420                 425                 430

Asp Ala Phe Val Ala Val Asp Ala Lys Thr Gly Asp Glu Arg Trp His
        435                 440                 445

Phe Arg Thr Ala Asn His Asp Leu Val Asp Tyr Asp Ala Thr Ala Gln
    450                 455                 460

Pro Ile Leu Tyr Asp Ile Pro Asp Gly His Gly Gly Thr Arg Pro Ala
465                 470                 475                 480

Ile Ile Ala Met Thr Lys Arg Gly Gln Ile Phe Val Leu Asp Arg Arg
                485                 490                 495

Asp Gly Thr Pro Ile Val Pro Val Glu Met Arg Lys Val Pro Gln Asp
            500                 505                 510

Gly Ala Pro Glu His Gln Tyr Leu Ala Pro Glu Gln Pro Tyr Ser Ala
        515                 520                 525

Leu Ser Ile Gly Thr Glu Arg Leu Lys Pro Ser Asp Met Trp Gly Gly
    530                 535                 540

Thr Ile Phe Asp Gln Leu Leu Cys Arg Ile Gln Phe Ala Ser Tyr Arg
545                 550                 555                 560

Tyr Glu Gly Glu Phe Thr Pro Val Asn Glu Lys Gln Ala Thr Ile Ile
                565                 570                 575

Tyr Pro Gly Tyr Tyr Gly Gly Ile Asn Trp Gly Gly Gly Ala Val Asp
```

```
            580                 585                 590

Glu Ser Thr Gly Thr Leu Leu Val Asn Asp Ile Arg Met Ala Gln Trp
        595                 600                 605

Gly Lys Phe Met Lys Gln Glu Glu Ala Arg Arg Ser Gly Phe Lys Pro
    610                 615                 620

Ser Ser Glu Gly Glu Tyr Ser Glu Gln Lys Gly Thr Pro Trp Gly Val
625                 630                 635                 640

Val Arg Ser Met Phe Phe Ser Pro Ala Gly Leu Pro Cys Val Lys Pro
                645                 650                 655

Pro Tyr Gly Thr Met Asn Ala Ile Asp Leu Arg Ser Gly Lys Val Lys
            660                 665                 670

Trp Ser Met Pro Leu Gly Thr Ile Gln Asp Met Pro Val His Gly Met
        675                 680                 685

Val Pro Gly Leu Ala Ile Pro Leu Gly Met Pro Thr Met Ser Gly Pro
    690                 695                 700

Leu Ala Thr His Thr Gly Leu Val Phe Phe Ser Gly Thr Leu Asp Asn
705                 710                 715                 720

Tyr Val Arg Ala Leu Asn Thr Asp Thr Gly Glu Val Val Trp Lys Ala
                725                 730                 735

Arg Leu Pro Val Ala Ser Gln Ala Ala Pro Met Ser Tyr Met Ser Asp
            740                 745                 750

Lys Thr Gly Lys Gln Tyr Ile Val Val Thr Ala Gly Gly Leu Thr Arg
        755                 760                 765

Ser Gly Val Asp Lys Asn Arg Gly Asp Tyr Val Ile Ala Tyr Ala Leu
    770                 775                 780

Pro Ser Glu Glu
785
```

<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28
ccgaattcag gccgaacagc agcaggtcac 30

<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
gtgcctgggt acctcggtgg aggtcatgaa 30

<210> SEQ ID NO 30
<211> LENGTH: 30
<212> TYPE: DNA
<213> ORGANISM: Artificial Sequence
<220> FEATURE:
<223> OTHER INFORMATION: primer

<400> SEQUENCE: 30
aagtcatatg aacagcggcc cccgcacgct 30

<210> SEQ ID NO 31

<211> LENGTH: 30
<212> TYPE: DNA
<213> ORGANISM: Artificial Sequence
<220> FEATURE:
<223> OTHER INFORMATION: primer

<400> SEQUENCE: 31
atctcgagtt cttcggaggg cagggcgtag 30

<210> SEQ ID NO 32
<211> LENGTH: 966
<212> TYPE: DNA
<213> ORGANISM: Gluconobacter oxydans DSM 17078

<400> SEQUENCE: 32
atggcatcgg cgaaccatcc cgagtctggc tccatatccg gatatgatca tggttcccgc 60
cggatcctga tcgtgacggg tctgtccggg gcgggaaaat catccatatt gcgggttctg 120
gaagatctgg gtcatgaggt cgtggacaac ccacccctga acctgatcca ggcgctcgcc 180
tcacgggccg ggcagaatct ggctatcggg atcgacgtcc gcagtcgcgg gttcgaggcc 240
tcccgtgtgc tggaagagct cgaacgcctc cgacttctgc cggactgctc ggtccagctc 300
ctttacgcca ccgccgagcc cgaaattctt ctgcgtcgct tcaccgccac gcgccgccgc 360
catcctctgg tcaccagcgg caccattctt cccggaatcg aacaggaaac cgcccttctg 420
gccccgctgc gggccaatgc ggatctcgtc atcgacacgt ccgacctgcc atcgccggaa 480
ctgcgccagc tgatcgagac gcgctttggc agcacgggcg gggaagggct gacggttgca 540
ctgatgtcct ttgcctatcc gtccggtctg ccccgcgagg cggacatggt ttttgatgca 600
cgcttcctgc gcaatcccca ttatgatccc gccctccagc ccatgaccgg actggacgag 660
gcagtggtgc agtatgtgaa gtcggacccg gcctatcccg catttttcgg ccatatccag 720
agccttctgg agcttgtgct tccccgcttc gtcgcggagg gcaagaaata cgcgaccatt 780
gccatcgggt gcagtggcgg ccgccaccgc tcggtgacga tcgttgaaga actcgcccgc 840
attctcccga aaaccgtacc ggtcgggccg atgatggtcc tgcaccggga actcgcccgc 900
aagggtctgg cgtcctggcg ctgggccgtt ccaccccagg atccctcaca ggacacaacg 960
gtatga 966

<210> SEQ ID NO 33
<211> LENGTH: 321
<212> TYPE: PRT
<213> ORGANISM: Gluconobacter oxydans DSM 17078

<400> SEQUENCE: 33

Met Ala Ser Ala Asn His Pro Glu Ser Gly Ser Ile Ser Gly Tyr Asp
1 5 10 15

His Gly Ser Arg Arg Ile Leu Ile Val Thr Gly Leu Ser Gly Ala Gly
20 25 30

Lys Ser Ser Ile Leu Arg Val Leu Glu Asp Leu Gly His Glu Val Val
35 40 45

Asp Asn Pro Pro Leu Asn Leu Ile Gln Ala Leu Ala Ser Arg Ala Gly
50 55 60

Gln Asn Leu Ala Ile Gly Ile Asp Val Arg Ser Arg Gly Phe Glu Ala
65 70 75 80

Ser Arg Val Leu Glu Glu Leu Glu Arg Leu Arg Leu Leu Pro Asp Cys
85 90 95

Ser Val Gln Leu Leu Tyr Ala Thr Ala Glu Pro Glu Ile Leu Leu Arg

-continued

```
            100                 105                 110

Arg Phe Thr Ala Thr Arg Arg Arg His Pro Leu Val Thr Ser Gly Thr
        115                 120                 125

Ile Leu Pro Gly Ile Glu Gln Glu Thr Ala Leu Leu Ala Pro Leu Arg
    130                 135                 140

Ala Asn Ala Asp Leu Val Ile Asp Thr Ser Asp Leu Pro Ser Pro Glu
145                 150                 155                 160

Leu Arg Gln Leu Ile Glu Thr Arg Phe Gly Ser Thr Gly Gly Glu Gly
                165                 170                 175

Leu Thr Val Ala Leu Met Ser Phe Ala Tyr Pro Ser Gly Leu Pro Arg
            180                 185                 190

Glu Ala Asp Met Val Phe Asp Ala Arg Phe Leu Arg Asn Pro His Tyr
        195                 200                 205

Asp Pro Ala Leu Gln Pro Met Thr Gly Leu Asp Glu Ala Val Val Gln
    210                 215                 220

Tyr Val Lys Ser Asp Pro Ala Tyr Pro Ala Phe Phe Gly His Ile Gln
225                 230                 235                 240

Ser Leu Leu Glu Leu Val Leu Pro Arg Phe Val Ala Glu Gly Lys Lys
                245                 250                 255

Tyr Ala Thr Ile Ala Ile Gly Cys Ser Gly Gly Arg His Arg Ser Val
            260                 265                 270

Thr Ile Val Glu Glu Leu Ala Arg Ile Leu Pro Lys Thr Val Pro Val
        275                 280                 285

Gly Pro Met Met Val Leu His Arg Glu Leu Ala Arg Lys Gly Leu Ala
    290                 295                 300

Ser Trp Arg Trp Ala Val Pro Pro Gln Asp Pro Ser Gln Asp Thr Thr
305                 310                 315                 320

Val


<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34

atggcatcgg cgaaccatcc                                                   20


<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35

tcataccgtt gtgtcctgtg                                                   20


<210> SEQ ID NO 36
<211> LENGTH: 1422
<212> TYPE: DNA
<213> ORGANISM: Gluconobacter oxydans DSM 17078

<400> SEQUENCE: 36

atgtcccaga agatcgttcc agtcattctc tccggtggat caggcagccg tctgtggccg      60

gtttcgcgca gcagctaccc caagcagttc tggcctctcc tgtcgaaaca taccctgatc     120
```

```
caggaaacgg cgctgcgtgg cgcgcgggca gggctggcgg atccgatcgt gatctgtaat     180

gccgagcacc gcttcattgt tgcggaacag ctgcgggatg tcggggttga aaacgcccgg     240

atcgtcctcg aacccgtggg ccgtaattcc gccccggcca tcgctgcggc cgcgttcctg     300

gtggccgaaa ccgatccgga cgccgttctg tggatcatgg cagcggatgc ggccattacc     360

gatgaggccg ctctctactc cgcgcttgag catgcggttg ccgcagcagc ccagggacgg     420

atcgtgacgt tcggaatgaa gcccacgcgc gtcgagacgg gctatggcta tatcgagagc     480

ggtgcgcccc tttcaggtct tgaaggcgtt tatgaagtct cgcgttttgt cgagaagccg     540

gatgccgtga cggcggaagc ctttttccgg gatgggcggt atctgtggaa ttccggcatg     600

ttcgtcaccc aggccggcgt tttctttcc gagatccaga ccttcgagcc tgcgatccac      660

gagcatgtcg gacaggccgt ccgggcccgc cggagcgacc tcgatttcga ccgcctggac     720

gatgcgagtt tccgtcaggc accggatatt tccgtggatt atgccgtggc cgagcggacg     780

aaacgggcgg ccgtggtgcc gggaacattc ggctggtcgg atatcggcag ctgggatgcg     840

ctgtgggagc tgacgtccaa ggatgaagcg ggcaacgcca cgttcgggga tgttttcctt     900

gatgacgcgc gaaactgcta tgtccgctcg gacggaatcg tggccacagt cgccggtgtg     960

gaagatctga tcgtcgtcgt gacgcaggac gccgtcatgg tctcgcatcg tgaccgggcg    1020

caggacgtca agcacatggt cagccggctg aagaaagccg ggcgcaagga agcggtggcc    1080

cataaccgca tgtatcgtcc gtggggcttc tatgagagcc tgatccaggc ggaccggttc    1140

caggtcaagc ggatcgtggt tgagccaggc cagaaactct cgctgcagaa gcatttccat    1200

cgcgctgaac actgggttgt cgtgggcggc acggcagtcg tcacccgtga cgccgaccag    1260

atcatggtgc gtgaaaacga gagcatctat ctgccgctgg gctgtgtgca ccgccttgag    1320

aatccggggc ggattccgct gacccttatt gaggtgcagt ccggtcctta cctgggcgaa    1380

gacgatatcg tccggatcga ggacgtctat tcccgaaact ga                       1422
```

<210> SEQ ID NO 37
<211> LENGTH: 473
<212> TYPE: PRT
<213> ORGANISM: Gluconobacter oxydans DSM 17078

<400> SEQUENCE: 37

```
Met Ser Gln Lys Ile Val Pro Val Ile Leu Ser Gly Gly Ser Gly Ser
1               5                   10                  15

Arg Leu Trp Pro Val Ser Arg Ser Ser Tyr Pro Lys Gln Phe Trp Pro
            20                  25                  30

Leu Leu Ser Lys His Thr Leu Ile Gln Glu Thr Ala Leu Arg Gly Ala
        35                  40                  45

Arg Ala Gly Leu Ala Asp Pro Ile Val Ile Cys Asn Ala Glu His Arg
    50                  55                  60

Phe Ile Val Ala Glu Gln Leu Arg Asp Val Gly Val Glu Asn Ala Arg
65                  70                  75                  80

Ile Val Leu Glu Pro Val Gly Arg Asn Ser Ala Pro Ala Ile Ala Ala
                85                  90                  95

Ala Ala Phe Leu Val Ala Glu Thr Asp Pro Asp Ala Val Leu Trp Ile
            100                 105                 110

Met Ala Ala Asp Ala Ala Ile Thr Asp Glu Ala Ala Leu Tyr Ser Ala
        115                 120                 125

Leu Glu His Ala Val Ala Ala Ala Ala Gln Gly Arg Ile Val Thr Phe
    130                 135                 140
```

```
Gly Met Lys Pro Thr Arg Val Glu Thr Gly Tyr Gly Tyr Ile Glu Ser
145                 150                 155                 160

Gly Ala Pro Leu Ser Gly Leu Glu Gly Val Tyr Glu Val Ser Arg Phe
                165                 170                 175

Val Glu Lys Pro Asp Ala Val Thr Ala Glu Ala Phe Phe Arg Asp Gly
            180                 185                 190

Arg Tyr Leu Trp Asn Ser Gly Met Phe Val Thr Gln Ala Gly Val Phe
        195                 200                 205

Leu Ser Glu Ile Gln Thr Phe Glu Pro Ala Ile His Glu His Val Gly
    210                 215                 220

Gln Ala Val Arg Ala Arg Arg Ser Asp Leu Asp Phe Asp Arg Leu Asp
225                 230                 235                 240

Asp Ala Ser Phe Arg Gln Ala Pro Asp Ile Ser Val Asp Tyr Ala Val
                245                 250                 255

Ala Glu Arg Thr Lys Arg Ala Ala Val Val Pro Gly Thr Phe Gly Trp
            260                 265                 270

Ser Asp Ile Gly Ser Trp Asp Ala Leu Trp Glu Leu Thr Ser Lys Asp
        275                 280                 285

Glu Ala Gly Asn Ala Thr Phe Gly Asp Val Phe Leu Asp Asp Ala Arg
    290                 295                 300

Asn Cys Tyr Val Arg Ser Asp Gly Ile Val Ala Thr Val Ala Gly Val
305                 310                 315                 320

Glu Asp Leu Ile Val Val Val Thr Gln Asp Ala Val Met Val Ser His
                325                 330                 335

Arg Asp Arg Ala Gln Asp Val Lys His Met Val Ser Arg Leu Lys Lys
            340                 345                 350

Ala Gly Arg Lys Glu Ala Val Ala His Asn Arg Met Tyr Arg Pro Trp
        355                 360                 365

Gly Phe Tyr Glu Ser Leu Ile Gln Ala Asp Arg Phe Gln Val Lys Arg
    370                 375                 380

Ile Val Val Glu Pro Gly Gln Lys Leu Ser Leu Gln Lys His Phe His
385                 390                 395                 400

Arg Ala Glu His Trp Val Val Val Gly Gly Thr Ala Val Val Thr Arg
                405                 410                 415

Asp Ala Asp Gln Ile Met Val Arg Glu Asn Glu Ser Ile Tyr Leu Pro
            420                 425                 430

Leu Gly Cys Val His Arg Leu Glu Asn Pro Gly Arg Ile Pro Leu Thr
        435                 440                 445

Leu Ile Glu Val Gln Ser Gly Pro Tyr Leu Gly Glu Asp Asp Ile Val
    450                 455                 460

Arg Ile Glu Asp Val Tyr Ser Arg Asn
465                 470
```

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
atgtcccaga agatcgttcc 20

<210> SEQ ID NO 39
<211> LENGTH: 20
<212> TYPE: DNA

<213> ORGANISM: Artificial Sequence
<220> FEATURE:
<223> OTHER INFORMATION: primer

<400> SEQUENCE: 39
tcagtttcgg gaatagacgt 20

<210> SEQ ID NO 40
<211> LENGTH: 1794
<212> TYPE: DNA
<213> ORGANISM: Gluconobacter oxydans DSM 17078

<400> SEQUENCE: 40
atggtcggct tttctggacg gagtgcgggc ctgatgtgtg gaattgcggg tctttcctgc 60
ctgcccgggc atcatccgga tcaggacgcg ctggagcgca tgtctcaggc cattttccat 120
cgcgggccgg atggggaagg gcggctggat ctgggcggtg cggcgttgcg tcatcgcagg 180
ctgtccatcg ttgatatcgc ggggggggcg cagccgttca ggctcggcgc ggcggccctg 240
attgcgaacg gagaaatcta taacgatccg gccattcgca ggcgctttcc caaaacctgt 300
ttccagaccc atagcgactg cgaaccgcct ctacatctgt ggctgcatga tggtgcgggc 360
tacacgcatg aactgcgggg catgtatgcc attgcgatcg ttgagaacga gcatgggcgg 420
cacgaaatgg tgctgtcgcg tgatccgttc ggcatcaagc cgctctatat cgcggcttat 480
gaggggggca ttgcgtttgc gtccgagccg caggcgctgc tggcaggagg gtttggcagg 540
cgcagtgttc gggacggggc gcgcgacgag ttgatgcagc ttcagttcac gacggggcag 600
gacatcattt tcgacgggat ccgtcggctt ctgcctggtg agacgctccg gatcgtggat 660
gggcgaatcg tggaatcgcg ccggcggcat gttctgcatg aagcgcggga tacggttccg 720
gcccgtctga gtgatgagca ggcgctggcg cggctggaca cggcactgct cgacagcgtg 780
tcggcgcatc tgcgggcgga tgtgccgctt gggctgttcc tgtcgggcgg gatcgacagt 840
tcggttattc tggcggcggc gcatcgtttg gggctaccgc atccacgcac ctggacggca 900
cgctttgatg ccgggaaggc agatgaatcc gctgacgctg cggcgctggc tgcgtctgtc 960
ggagcagagc atcatgtcct gaccgtgacg gaagacatgg tctggcgcga tcttccgtcc 1020
atcgtggcgt gcatggatga tccggcagcg gattatgccg tcatcccgac atggtttctg 1080
gcgcgtgagg cgcgaaagga cgtgaccgtc attctcagtg gcgagggggg agacgagctt 1140
tttgccgggt atggtcgcta tcggcgggtc atgaagccct ggtggaaagg gggacgaccg 1200
ccataccgct ccggtacgtt cggcaagcgc tttgcggagc acggacggca gtggcggcgc 1260
ggcatcgcca tgacggaact ggcgctgggg atttccgggc tggaaggggc gcagacgctg 1320
gatattgcgg aatggctgcc taacgatctg ttgctcaagc tggaccgctg cctgatggcg 1380
cattcggtcg aaggacgtac gcccctgctc gatccggttg tggccaaggc gatctggccg 1440
ctgccggagc acttcaaggt gcgggatggt tacggcaagt ggttgctgcg acgctggctt 1500
caggatgcgc tgccgcaggc gcgtcctttt gcgccgaaac agggctttac cgtgccggtc 1560
gggccgtgga tcgagaagca gacgcaccgt ctggggcctc tggtcgcacg gcagccctgc 1620
atccgggcca tgatgcccgc agccgacgta gagcgtcttt ttgcccgcgc cagccagcgc 1680
ggtgtggcgc ggcaggcttg gacgctgctg tttttcgcgc tgtggcatcg tcatcatatc 1740
gaaggggttc ccgtggacgg ggatacgttc gaaactctct cgcgcgcttc atga 1794

<210> SEQ ID NO 41
<211> LENGTH: 597

<212> TYPE: PRT
<213> ORGANISM: Gluconobacter oxydans DSM 17078

<400> SEQUENCE: 41

Met Val Gly Phe Ser Gly Arg Ser Ala Gly Leu Met Cys Gly Ile Ala
1               5                   10                  15

Gly Leu Ser Cys Leu Pro Gly His His Pro Asp Gln Asp Ala Leu Glu
            20                  25                  30

Arg Met Ser Gln Ala Ile Phe His Arg Gly Pro Asp Gly Glu Gly Arg
        35                  40                  45

Leu Asp Leu Gly Gly Ala Ala Leu Arg His Arg Arg Leu Ser Ile Val
    50                  55                  60

Asp Ile Ala Gly Gly Ala Gln Pro Phe Arg Leu Gly Ala Ala Ala Leu
65                  70                  75                  80

Ile Ala Asn Gly Glu Ile Tyr Asn Asp Pro Ala Ile Arg Arg Arg Phe
                85                  90                  95

Pro Lys Thr Cys Phe Gln Thr His Ser Asp Cys Glu Pro Pro Leu His
            100                 105                 110

Leu Trp Leu His Asp Gly Ala Gly Tyr Thr His Glu Leu Arg Gly Met
        115                 120                 125

Tyr Ala Ile Ala Ile Val Glu Asn Glu His Gly Arg His Glu Met Val
    130                 135                 140

Leu Ser Arg Asp Pro Phe Gly Ile Lys Pro Leu Tyr Ile Ala Ala Tyr
145                 150                 155                 160

Glu Gly Gly Ile Ala Phe Ala Ser Glu Pro Gln Ala Leu Leu Ala Gly
                165                 170                 175

Gly Phe Gly Arg Arg Ser Val Arg Asp Gly Ala Arg Asp Glu Leu Met
            180                 185                 190

Gln Leu Gln Phe Thr Thr Gly Gln Asp Ile Ile Phe Asp Gly Ile Arg
        195                 200                 205

Arg Leu Leu Pro Gly Glu Thr Leu Arg Ile Val Asp Gly Arg Ile Val
    210                 215                 220

Glu Ser Arg Arg Arg His Val Leu His Glu Ala Arg Asp Thr Val Pro
225                 230                 235                 240

Ala Arg Leu Ser Asp Glu Gln Ala Leu Ala Arg Leu Asp Thr Ala Leu
                245                 250                 255

Leu Asp Ser Val Ser Ala His Leu Arg Ala Asp Val Pro Leu Gly Leu
            260                 265                 270

Phe Leu Ser Gly Gly Ile Asp Ser Ser Val Ile Leu Ala Ala Ala His
        275                 280                 285

Arg Leu Gly Leu Pro His Pro Arg Thr Trp Thr Ala Arg Phe Asp Ala
    290                 295                 300

Gly Lys Ala Asp Glu Ser Ala Asp Ala Ala Ala Leu Ala Ala Ser Val
305                 310                 315                 320

Gly Ala Glu His His Val Leu Thr Val Thr Glu Asp Met Val Trp Arg
                325                 330                 335

Asp Leu Pro Ser Ile Val Ala Cys Met Asp Asp Pro Ala Ala Asp Tyr
            340                 345                 350

Ala Val Ile Pro Thr Trp Phe Leu Ala Arg Glu Ala Arg Lys Asp Val
        355                 360                 365

Thr Val Ile Leu Ser Gly Glu Gly Gly Asp Glu Leu Phe Ala Gly Tyr
    370                 375                 380

Gly Arg Tyr Arg Arg Val Met Lys Pro Trp Trp Lys Gly Gly Arg Pro
385                 390                 395                 400

```
Pro Tyr Arg Ser Gly Thr Phe Gly Lys Arg Phe Ala Glu His Gly Arg
                405                 410                 415

Gln Trp Arg Arg Gly Ile Ala Met Thr Glu Leu Ala Leu Gly Ile Ser
            420                 425                 430

Gly Leu Glu Gly Ala Gln Thr Leu Asp Ile Ala Glu Trp Leu Pro Asn
        435                 440                 445

Asp Leu Leu Leu Lys Leu Asp Arg Cys Leu Met Ala His Ser Val Glu
    450                 455                 460

Gly Arg Thr Pro Leu Leu Asp Pro Val Val Ala Lys Ala Ile Trp Pro
465                 470                 475                 480

Leu Pro Glu His Phe Lys Val Arg Asp Gly Tyr Gly Lys Trp Leu Leu
                485                 490                 495

Arg Arg Trp Leu Gln Asp Ala Leu Pro Gln Ala Arg Pro Phe Ala Pro
            500                 505                 510

Lys Gln Gly Phe Thr Val Pro Val Gly Pro Trp Ile Glu Lys Gln Thr
        515                 520                 525

His Arg Leu Gly Pro Leu Val Ala Arg Gln Pro Cys Ile Arg Ala Met
    530                 535                 540

Met Pro Ala Ala Asp Val Glu Arg Leu Phe Ala Arg Ala Ser Gln Arg
545                 550                 555                 560

Gly Val Ala Arg Gln Ala Trp Thr Leu Leu Phe Phe Ala Leu Trp His
                565                 570                 575

Arg His His Ile Glu Gly Val Pro Val Asp Gly Asp Thr Phe Glu Thr
            580                 585                 590

Leu Ser Arg Ala Ser
        595


<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42

atggtcggct tttctggacg                                                   20


<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43

tcatgaagcg cgcgagagag                                                   20


<210> SEQ ID NO 44
<211> LENGTH: 1497
<212> TYPE: DNA
<213> ORGANISM: Gluconobacter oxydans DSM 17078

<400> SEQUENCE: 44

atgaatgttg tctcaaagac tgtatcttta ccgttaaagc cgcgtgagtt cggattctat      60

attgatggag aatggcgcgc aggtaaggat ttcttcgatc gttcctcgcc ggctcatgat     120

gttcccgtca cccgtattcc acgctgcacc cgtgaggacc ttgatgaggc agtcgctgct     180

gcacgtcgtg ctttcgagaa cggaagctgg tcgggcctgg cggccgcgga tcgtgcggcg     240
```

gttcttctga aagccgcggg ccttctgcgc gagcgccgcg atgacatcgc ttactgggaa 300
gttctcgaaa acgggaagcc catcagccag gcgaagggcg agatcgatca ctgtatcgcc 360
tgtttcgaga tggcggccgg cgctgcgcgg atgctgcatg gtgatacgtt caacaatctg 420
ggcgaggggc tgttcggcat ggtcctgcgg gagcccatcg gtgtcgtcgg tctgattacg 480
ccgtggaact tcccgttcat gatcctgtgt gagcgcgcgc ctttcattct cgcatccggc 540
tgcacgctgg tcgtcaagcc tgccgaagtc acgagtgcca cgacgcttct tctggcggaa 600
gtgctggcgg atgcggggct gccgaagggt gtcttcaatg ttgtgacggg cacggggcgc 660
acggtcgggc aggccatgac cgagcatcag gacatcgaca tgctgtcctt cacgggctcc 720
acgggcgtcg gcaagtcctg catccatgcg gcggctgaca gcaacctgaa gaaactgggc 780
cttgagcttg gcggcaagaa cccgatcgtc gtgttcgctg acagcaacct tgaggatgcg 840
gccgatgcgg tagctttcgg gattagtttc aacaccgggc agtgctgtgt gtcgtcgagc 900
cgcctgattg tagagcggtc cgtggccgag aagttcgagc gtctcgttgt ggcgaaaatg 960
gagaagatcc gcgtcggcga tccgttcgat cctgagacgc agatcggcgc cattacgacg 1020
gaagcgcaga acaagaccat tctggactat atcgccaagg gcaaggccga gggcgccagg 1080
ctgctctgcg gtggcgggat cgtcgatttc ggcaaagggc agtatatcca gccgacgctt 1140
ttcacggatg tgaagccctc gatgggcatc gcgcgtgacg agatttttgg gccggtcctg 1200
gcgtccttcc acttcgatac cgtcgatgag gcgatcgcga ttgccaatga cacggtttac 1260
ggcctggccg catcggtctg gagcaaggat atcgacaagg cgcttgccgt gacccgtcgt 1320
gttcgcgctg gccgcttctg ggtgaacacc atcatgagcg gtggtcccga gacgccgctg 1380
ggtggtttca agcagtcggg ctggggccgt gaggccggtc tgtacggcgt tgaggaatat 1440
acgcagatca aatctgtcca tatcgaaact ggcaaacgtt cgcactggat ttcgtaa 1497

<210> SEQ ID NO 45
<211> LENGTH: 498
<212> TYPE: PRT
<213> ORGANISM: Gluconobacter oxydans DSM 17078

<400> SEQUENCE: 45

Met Asn Val Val Ser Lys Thr Val Ser Leu Pro Leu Lys Pro Arg Glu
1 5 10 15

Phe Gly Phe Tyr Ile Asp Gly Glu Trp Arg Ala Gly Lys Asp Phe Phe
20 25 30

Asp Arg Ser Ser Pro Ala His Asp Val Pro Val Thr Arg Ile Pro Arg
35 40 45

Cys Thr Arg Glu Asp Leu Asp Glu Ala Val Ala Ala Ala Arg Arg Ala
50 55 60

Phe Glu Asn Gly Ser Trp Ser Gly Leu Ala Ala Ala Asp Arg Ala Ala
65 70 75 80

Val Leu Leu Lys Ala Ala Gly Leu Leu Arg Glu Arg Arg Asp Asp Ile
85 90 95

Ala Tyr Trp Glu Val Leu Glu Asn Gly Lys Pro Ile Ser Gln Ala Lys
100 105 110

Gly Glu Ile Asp His Cys Ile Ala Cys Phe Glu Met Ala Ala Gly Ala
115 120 125

Ala Arg Met Leu His Gly Asp Thr Phe Asn Asn Leu Gly Glu Gly Leu
130 135 140

Phe Gly Met Val Leu Arg Glu Pro Ile Gly Val Val Gly Leu Ile Thr

-continued

```
145                 150                 155                 160

Pro Trp Asn Phe Pro Phe Met Ile Leu Cys Glu Arg Ala Pro Phe Ile
                165                 170                 175

Leu Ala Ser Gly Cys Thr Leu Val Val Lys Pro Ala Glu Val Thr Ser
            180                 185                 190

Ala Thr Thr Leu Leu Leu Ala Glu Val Leu Ala Asp Ala Gly Leu Pro
        195                 200                 205

Lys Gly Val Phe Asn Val Val Thr Gly Thr Gly Arg Thr Val Gly Gln
    210                 215                 220

Ala Met Thr Glu His Gln Asp Ile Asp Met Leu Ser Phe Thr Gly Ser
225                 230                 235                 240

Thr Gly Val Gly Lys Ser Cys Ile His Ala Ala Ala Asp Ser Asn Leu
                245                 250                 255

Lys Lys Leu Gly Leu Glu Leu Gly Gly Lys Asn Pro Ile Val Val Phe
            260                 265                 270

Ala Asp Ser Asn Leu Glu Asp Ala Ala Asp Ala Val Ala Phe Gly Ile
        275                 280                 285

Ser Phe Asn Thr Gly Gln Cys Cys Val Ser Ser Ser Arg Leu Ile Val
    290                 295                 300

Glu Arg Ser Val Ala Glu Lys Phe Glu Arg Leu Val Val Ala Lys Met
305                 310                 315                 320

Glu Lys Ile Arg Val Gly Asp Pro Phe Asp Pro Glu Thr Gln Ile Gly
                325                 330                 335

Ala Ile Thr Thr Glu Ala Gln Asn Lys Thr Ile Leu Asp Tyr Ile Ala
            340                 345                 350

Lys Gly Lys Ala Glu Gly Ala Arg Leu Leu Cys Gly Gly Gly Ile Val
        355                 360                 365

Asp Phe Gly Lys Gly Gln Tyr Ile Gln Pro Thr Leu Phe Thr Asp Val
    370                 375                 380

Lys Pro Ser Met Gly Ile Ala Arg Asp Glu Ile Phe Gly Pro Val Leu
385                 390                 395                 400

Ala Ser Phe His Phe Asp Thr Val Asp Glu Ala Ile Ala Ile Ala Asn
                405                 410                 415

Asp Thr Val Tyr Gly Leu Ala Ala Ser Val Trp Ser Lys Asp Ile Asp
            420                 425                 430

Lys Ala Leu Ala Val Thr Arg Arg Val Arg Ala Gly Arg Phe Trp Val
        435                 440                 445

Asn Thr Ile Met Ser Gly Gly Pro Glu Thr Pro Leu Gly Gly Phe Lys
    450                 455                 460

Gln Ser Gly Trp Gly Arg Glu Ala Gly Leu Tyr Gly Val Glu Glu Tyr
465                 470                 475                 480

Thr Gln Ile Lys Ser Val His Ile Glu Thr Gly Lys Arg Ser His Trp
                485                 490                 495

Ile Ser


<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46

atgaatgttg tctcaaagac                                              20
```

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
ttacgaaatc cagtgcgaac 20

<210> SEQ ID NO 48
<211> LENGTH: 636
<212> TYPE: DNA
<213> ORGANISM: Gluconobacter oxydans DSM 17078

<400> SEQUENCE: 48
atgaccagcc cgtctgactt ccctacgccc cccgtccccg gacgactgct cgatgtcgag 60
gacgtcacag tcttccgcgg agaccggctg gttctcgacg gtgtctccct gacgctggat 120
accggggatg ccatgatcct gacaggcccg aacggggccg ggaaatccac cctcctgcgc 180
acgatttccg gtttgcgccg cgccgattca ggggaagtca ttcgctatgg cgatcttgcc 240
tggctcggcc atcaggacgc gctcaagccc ggactgacgc tggcgcaaaa cctggccctg 300
gctgaaaagc tcggcacgaa cagtctgccc gatgcacttg aggccctgga ccttacccat 360
ctaaccgacc ttccggcgcg cctcctgtct tccgggcaga agcgccgtgc cgcctttgcc 420
cgtgtcatgc tttcaggcgc accgctctgg ctgctcgatg agccgaccgt tgggctggat 480
gttgccagta tcgaacgtct cggcgccgtc atggcggctc atcgcgccaa ggggggggggc 540 atgatcgtca cgacgcatgt tccgcttccc ctcgataaca cccgctcgca cgagctgccc 600
tcgctcgcac atgtagagtc cttctggctg tcatga 636

<210> SEQ ID NO 49
<211> LENGTH: 211
<212> TYPE: PRT
<213> ORGANISM: Gluconobacter oxydans DSM 17078

<400> SEQUENCE: 49

Met Thr Ser Pro Ser Asp Phe Pro Thr Pro Pro Val Pro Gly Arg Leu
1 5 10 15

Leu Asp Val Glu Asp Val Thr Val Phe Arg Gly Asp Arg Leu Val Leu
20 25 30

Asp Gly Val Ser Leu Thr Leu Asp Thr Gly Asp Ala Met Ile Leu Thr
35 40 45

Gly Pro Asn Gly Ala Gly Lys Ser Thr Leu Leu Arg Thr Ile Ser Gly
50 55 60

Leu Arg Arg Ala Asp Ser Gly Glu Val Ile Arg Tyr Gly Asp Leu Ala
65 70 75 80

Trp Leu Gly His Gln Asp Ala Leu Lys Pro Gly Leu Thr Leu Ala Gln
85 90 95

Asn Leu Ala Leu Ala Glu Lys Leu Gly Thr Asn Ser Leu Pro Asp Ala
100 105 110

Leu Glu Ala Leu Asp Leu Thr His Leu Thr Asp Leu Pro Ala Arg Leu
115 120 125

Leu Ser Ser Gly Gln Lys Arg Arg Ala Ala Phe Ala Arg Val Met Leu
130 135 140

Ser Gly Ala Pro Leu Trp Leu Leu Asp Glu Pro Thr Val Gly Leu Asp
145 150 155 160

Val Ala Ser Ile Glu Arg Leu Gly Ala Val Met Ala Ala His Arg Ala
165 170 175

Lys Gly Gly Gly Met Ile Val Thr Thr His Val Pro Leu Pro Leu Asp
180 185 190

Asn Thr Arg Ser His Glu Leu Pro Ser Leu Ala His Val Glu Ser Phe
195 200 205

Trp Leu Ser
210

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
atgaccagcc cgtctgactt 20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
tcatgacagc cagaaggact 20

<210> SEQ ID NO 52
<211> LENGTH: 1422
<212> TYPE: DNA
<213> ORGANISM: Gluconobacter oxydans DSM 17078

<400> SEQUENCE: 52
atgtccagtc ctgatttctc ccccgttacc gtcatcggtg gaggcatcgc cggtgcgaca 60
tccgccatcg cgctcgcccg gcacggcttt cccgtcaccc tgattgacga acagccggct 120
gcgggcggtc agatcttccg cgcgccctca ccctatgccc gccagacggt tccccccaat 180
cacgagtttt ccggcggcga cgccctgcgt cagaaactgg ctgcatcccc ggtggatgtc 240
cggttttcca cccgcgtctg ggcctgtcc cccaccctga ccctcgacct gatcggcccg 300
gacggcatcg atcagcttcc cccgtcgacc gtcgtcgtcg ccaatggtgc caccgagcgt 360
ttcctcccgt tccagggctg gaccacgccg cgcatcaccg ggcttgcggg cgccagcatc 420
ctgatgcgca acggcggcac cctgcccggc cagaccgtcg tagtggcggg gtcggggcca 480
ctcctgttct cggtcgccca tcaggtgctt gaactgggcg gcaaggtcgc cgccatcgtg 540
gatgcgggtc accgctccga ctggctccgt ctcggcgcca tgctgtctct ggatcccgcc 600
cgtctgacgc aggccaccag ctggatgctg cgtctccgga aagctggcat tccgatccac 660
caccgcgccc atatttcggc ggcgcaggaa acggaaaccg gccttctcct gaccgtcagc 720
gagatggacc accctgaacg ccgccacgtc tatgctgccg aggccgcagc ctgcggatat 780
ggactcaagc cttccaccct cattacacgc acggccggtg tccagcaccg tcatgatccc 840
gttggcggtt atctcgaacc cgttacggat gtcgcaggcc gtaccagccg ccccgatctt 900
tacgtcacgg gcgacgcggc aggcatccgg ggcatggccg tggcccgtct gcggggcctg 960
atcacggccc atgccattgc ccaggaccgg ggtgtgatct ccgcccgaac caacgaaacc 1020

-continued

```
ctgacacgtg cgcccctgcg gcagcttcgc cgtctcgaag ccgtctcccg ccggatgctt   1080

cccctgatga acgccggaag cgccctcccg gcccatcttc aggacgaaac catcgtctgc   1140

cgctgcgaac gggtgaaggc cgcgaccctg cgttccgccg tcgaggccgg agccgaagac   1200

ctgaaccaac tcaaggcctg gacacgctgc ggcatggggt cctgtcaggg ccggatgtgc   1260

gaggacagcg cccggggcct gctgacggcg gcctgtggca acactctaga agaagcgggc   1320

agtttcacgg ctcggatgcc tttcttcccc ctccccctca cagccgtgac cgggaccttc   1380

gcctattccg acattcccct tccgaaggca gccccgctat ga                      1422
```

<210> SEQ ID NO 53
<211> LENGTH: 473
<212> TYPE: PRT
<213> ORGANISM: Gluconobacter oxydans DSM 17078

<400> SEQUENCE: 53

```
Met Ser Ser Pro Asp Phe Ser Pro Val Thr Val Ile Gly Gly Gly Ile
1               5                   10                  15

Ala Gly Ala Thr Ser Ala Ile Ala Leu Ala Arg His Gly Phe Pro Val
            20                  25                  30

Thr Leu Ile Asp Glu Gln Pro Ala Ala Gly Gly Gln Ile Phe Arg Ala
        35                  40                  45

Pro Ser Pro Tyr Ala Arg Gln Thr Val Pro Pro Asn His Glu Phe Ser
    50                  55                  60

Gly Gly Asp Ala Leu Arg Gln Lys Leu Ala Ala Ser Pro Val Asp Val
65                  70                  75                  80

Arg Phe Ser Thr Arg Val Trp Gly Leu Ser Pro Thr Leu Thr Leu Asp
                85                  90                  95

Leu Ile Gly Pro Asp Gly Ile Asp Gln Leu Pro Pro Ser Thr Val Val
            100                 105                 110

Val Ala Asn Gly Ala Thr Glu Arg Phe Leu Pro Phe Gln Gly Trp Thr
        115                 120                 125

Thr Pro Arg Ile Thr Gly Leu Ala Gly Ala Ser Ile Leu Met Arg Asn
    130                 135                 140

Gly Gly Thr Leu Pro Gly Gln Thr Val Val Val Ala Gly Ser Gly Pro
145                 150                 155                 160

Leu Leu Phe Ser Val Ala His Gln Val Leu Glu Leu Gly Gly Lys Val
                165                 170                 175

Ala Ala Ile Val Asp Ala Gly His Arg Ser Asp Trp Leu Arg Leu Gly
            180                 185                 190

Ala Met Leu Ser Leu Asp Pro Ala Arg Leu Thr Gln Ala Thr Ser Trp
        195                 200                 205

Met Leu Arg Leu Arg Lys Ala Gly Ile Pro Ile His His Arg Ala His
    210                 215                 220

Ile Ser Ala Ala Gln Glu Thr Glu Thr Gly Leu Leu Leu Thr Val Ser
225                 230                 235                 240

Glu Met Asp His Pro Glu Arg Arg His Val Tyr Ala Ala Glu Ala Ala
                245                 250                 255

Ala Cys Gly Tyr Gly Leu Lys Pro Ser Thr Leu Ile Thr Arg Thr Ala
            260                 265                 270

Gly Val Gln His Arg His Asp Pro Val Gly Gly Tyr Leu Glu Pro Val
        275                 280                 285

Thr Asp Val Ala Gly Arg Thr Ser Arg Pro Asp Leu Tyr Val Thr Gly
    290                 295                 300
```

```
Asp Ala Ala Gly Ile Arg Gly Met Ala Val Ala Arg Leu Arg Gly Leu
305                 310                 315                 320

Ile Thr Ala His Ala Ile Ala Gln Asp Arg Gly Val Ile Ser Ala Arg
                325                 330                 335

Thr Asn Glu Thr Leu Thr Arg Ala Pro Leu Arg Gln Leu Arg Arg Leu
            340                 345                 350

Glu Ala Val Ser Arg Arg Met Leu Pro Leu Met Asn Ala Gly Ser Ala
        355                 360                 365

Leu Pro Ala His Leu Gln Asp Glu Thr Ile Val Cys Arg Cys Glu Arg
    370                 375                 380

Val Lys Ala Ala Thr Leu Arg Ser Ala Val Glu Ala Gly Ala Glu Asp
385                 390                 395                 400

Leu Asn Gln Leu Lys Ala Trp Thr Arg Cys Gly Met Gly Ser Cys Gln
                405                 410                 415

Gly Arg Met Cys Glu Asp Ser Ala Arg Gly Leu Leu Thr Ala Ala Cys
            420                 425                 430

Gly Asn Thr Leu Glu Glu Ala Gly Ser Phe Thr Ala Arg Met Pro Phe
        435                 440                 445

Phe Pro Leu Pro Leu Thr Ala Val Thr Gly Thr Phe Ala Tyr Ser Asp
    450                 455                 460

Ile Pro Leu Pro Lys Ala Ala Pro Leu
465                 470
```

<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54

```
atgtccagtc ctgatttctc                                                 20
```

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55

```
tcatagcggg gctgccttcg                                                 20
```

<210> SEQ ID NO 56
<211> LENGTH: 252
<212> TYPE: DNA
<213> ORGANISM: Gluconobacter oxydans DSM 17078

<400> SEQUENCE: 56

```
atgcaatccg tcaccttcac cttcctgagc caggccatcg aaggcatcga gggagaaccg      60

gttgcagcgg ccctcaggcg cgccggaatc acggaactcg gccagtccgg cgtcgatggc     120

acaccacgcg gcgccttctg cttcatggga agctgccagg aatgccgcgt ccgcatcgac     180

ggcgccgtcg cctatgcctg caaggctccc gtcctcccga acatgaccgt cacgccctat     240

gtccagtcct ga                                                         252
```

<210> SEQ ID NO 57
<211> LENGTH: 83
<212> TYPE: PRT

-continued

<213> ORGANISM: Gluconobacter oxydans DSM 17078

<400> SEQUENCE: 57

Met Gln Ser Val Thr Phe Thr Phe Leu Ser Gln Ala Ile Glu Gly Ile
1 5 10 15

Glu Gly Glu Pro Val Ala Ala Ala Leu Arg Arg Ala Gly Ile Thr Glu
20 25 30

Leu Gly Gln Ser Gly Val Asp Gly Thr Pro Arg Gly Ala Phe Cys Phe
35 40 45

Met Gly Ser Cys Gln Glu Cys Arg Val Arg Ile Asp Gly Ala Val Ala
50 55 60

Tyr Ala Cys Lys Ala Pro Val Leu Pro Asn Met Thr Val Thr Pro Tyr
65 70 75 80

Val Gln Ser

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
atgcaatccg tcaccttcac 20

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
tcaggactgg acatagggcg 20

<210> SEQ ID NO 60
<211> LENGTH: 1392
<212> TYPE: DNA
<213> ORGANISM: Gluconobacter oxydans DSM 17078

<400> SEQUENCE: 60
atgttctcaa gccgggacgc tgagcctgtg ggtgagcggg acgacgcctg gcagaagctg 60
gaccgtccgc tgaggcgtat cctgccgcgt tccctgatgg ggcgatccat gctgatcgtt 120
ctcattccgc tgctggttac acaggccatt gcgctgggcc tgttttatgg cacctacctg 180
aatgtggtct ccaggcgcct ctcggatggt gtcacaggtg aggtctcgct cgttatcgcc 240
atgatcgagc acacctcttc agaggccgag cggacgctcg ttcttcagga tgcatcgtcc 300
cggacccagc tcggattttc attccagccc ggcgaaacgc tttcccggta tggcaccaat 360
cacgttctcg gcccgatgga tgacgatttc gcgcgttcca tccggcagaa tcttggcaga 420
ccctatgatg tggactggtc ggagtctccg cagaccgtcc gggcgtccat ccagcttccg 480
cagggtgtga tggtcgtcat ggtgccggtg aagcgtctga atatcgggcc gatctggctg 540
ttcgtcgtct gggccgtcag cagttcgatc gtgctgttcc tgatcgctgg tctgttcatg 600
cgcaatcagg ttcgggccat tcgcaggctg ggccatgcgg ccgaactgtt tggcatgggg 660
cgggaccagg gaccgatccg tccgcagggc gcgcgggaag tccgtcaggc tgccattgcc 720
ttcaaccgca tgcaggcgcg cgtcaatcgt ttcgtggcgc agaggacggc ggttctcgcc 780

```
ggggtgtcgc acgatctgcg gacgcctctg accaggctgc gtctgaccgt cgccatgatc    840

ccgacctttg gtccgatccg cgccgagacc ctgaagccgg atctcgcgga tatggttgca    900

gatattgagg acatggagcg tctgatcggc agctatctgt catttgcccg gggggaaggt    960

gcggaagagc ccgttctgac tgaactgagg gccatgctgg atgatgtcgc ggcggccacg   1020

gtgagggctg gcgggcaggt tctgggcgtg gaggggcgcg agggcgtgga agctacggtg   1080

cgccccgatg ccctgcggcg tgtgctgaca aatcttgcgg aaaatgcccg ccgtcacggg   1140

ggggcgatgc gcttttccct gcgtgaggga gagcggaacg ttgaaatcac ggttgaggac   1200

aacggtccgg gtctgtcggc cagtcgccgg gcggcaattt cggagcttaa tggcacgacg   1260

gcgagtcagg atgggaacag cgggctgggg ctgacgatcg tgcgggacat cattcatgcc   1320

catggcggat cgatccgtct gctggagagc ccgctgggag gtctgggcgt ggtgctcagc   1380

ctcccgaaat ag                                                       1392
```

<210> SEQ ID NO 61
<211> LENGTH: 463
<212> TYPE: PRT
<213> ORGANISM: Gluconobacter oxydans DSM 17078

<400> SEQUENCE: 61

```
Met Phe Ser Ser Arg Asp Ala Glu Pro Val Gly Glu Arg Asp Asp Ala
1               5                   10                  15

Trp Gln Lys Leu Asp Arg Pro Leu Arg Arg Ile Leu Pro Arg Ser Leu
            20                  25                  30

Met Gly Arg Ser Met Leu Ile Val Leu Ile Pro Leu Leu Val Thr Gln
        35                  40                  45

Ala Ile Ala Leu Gly Leu Phe Tyr Gly Thr Tyr Leu Asn Val Val Ser
    50                  55                  60

Arg Arg Leu Ser Asp Gly Val Thr Gly Glu Val Ser Leu Val Ile Ala
65                  70                  75                  80

Met Ile Glu His Thr Ser Ser Glu Ala Glu Arg Thr Leu Val Leu Gln
                85                  90                  95

Asp Ala Ser Ser Arg Thr Gln Leu Gly Phe Ser Phe Gln Pro Gly Glu
            100                 105                 110

Thr Leu Ser Arg Tyr Gly Thr Asn His Val Leu Gly Pro Met Asp Asp
        115                 120                 125

Asp Phe Ala Arg Ser Ile Arg Gln Asn Leu Gly Arg Pro Tyr Asp Val
    130                 135                 140

Asp Trp Ser Glu Ser Pro Gln Thr Val Arg Ala Ser Ile Gln Leu Pro
145                 150                 155                 160

Gln Gly Val Met Val Val Met Val Pro Val Lys Arg Leu Asn Ile Gly
                165                 170                 175

Pro Ile Trp Leu Phe Val Val Trp Ala Val Ser Ser Ser Ile Val Leu
            180                 185                 190

Phe Leu Ile Ala Gly Leu Phe Met Arg Asn Gln Val Arg Ala Ile Arg
        195                 200                 205

Arg Leu Gly His Ala Ala Glu Leu Phe Gly Met Gly Arg Asp Gln Gly
    210                 215                 220

Pro Ile Arg Pro Gln Gly Ala Arg Glu Val Arg Gln Ala Ala Ile Ala
225                 230                 235                 240

Phe Asn Arg Met Gln Ala Arg Val Asn Arg Phe Val Ala Gln Arg Thr
                245                 250                 255

Ala Val Leu Ala Gly Val Ser His Asp Leu Arg Thr Pro Leu Thr Arg
```

-continued

```
            260                 265                 270

Leu Arg Leu Thr Val Ala Met Ile Pro Thr Phe Gly Pro Ile Arg Ala
        275                 280                 285

Glu Thr Leu Lys Pro Asp Leu Ala Asp Met Val Ala Asp Ile Glu Asp
    290                 295                 300

Met Glu Arg Leu Ile Gly Ser Tyr Leu Ser Phe Ala Arg Gly Glu Gly
305                 310                 315                 320

Ala Glu Glu Pro Val Leu Thr Glu Leu Arg Ala Met Leu Asp Asp Val
                325                 330                 335

Ala Ala Ala Thr Val Arg Ala Gly Gly Gln Val Leu Gly Val Glu Gly
            340                 345                 350

Arg Glu Gly Val Glu Ala Thr Val Arg Pro Asp Ala Leu Arg Arg Val
        355                 360                 365

Leu Thr Asn Leu Ala Glu Asn Ala Arg Arg His Gly Gly Ala Met Arg
    370                 375                 380

Phe Ser Leu Arg Glu Gly Glu Arg Asn Val Glu Ile Thr Val Glu Asp
385                 390                 395                 400

Asn Gly Pro Gly Leu Ser Ala Ser Arg Arg Ala Ala Ile Ser Glu Leu
                405                 410                 415

Asn Gly Thr Thr Ala Ser Gln Asp Gly Asn Ser Gly Leu Gly Leu Thr
            420                 425                 430

Ile Val Arg Asp Ile Ile His Ala His Gly Gly Ser Ile Arg Leu Leu
        435                 440                 445

Glu Ser Pro Leu Gly Gly Leu Gly Val Val Leu Ser Leu Pro Lys
    450                 455                 460
```

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
atgttctcaa gccgggacgc 20

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
ctatttcggg aggctgagca 20

<210> SEQ ID NO 64
<211> LENGTH: 699
<212> TYPE: DNA
<213> ORGANISM: Gluconobacter oxydans DSM 17078

<400> SEQUENCE: 64
atgagcgatg aacatattct ggtggtcgat gacgatccgc gtctgctgcg gctgcttcag 60
cgttacctgt cggaaaacgg ctatcgtgtc agtacggcgc ttgatgcgca gacggcacgg 120
gaagtcctgc agcgcattca gccggatgct cttgtccttg atgtgacgat gccgggcgag 180
gatggcctgt ccctgacgaa cagtctgcgc agggacggtc tgtcgctgcc gatcctgctt 240
ctgacggcgc gtggtgagcc ggcggaccgg attggtgggc tggaagcggg ggcagacgat 300

```
tatctgggca agcccttcga accgcgggag cttctgcttc gtctgcgggc gcatctgcgc    360

aggatggtgc cgtctttgcc ggctgtggat gaggttccgg atgtcctgcg tctgggagag    420

ctggaatttg acgtcaaacg tggcctgctc agcgggccgc agggagcggt ccatctgacg    480

ggcggtgagt ccgctcttct tggggtgctg acccgtcagc ccgggacggt gctctcccgt    540

gaagccatcg cccgtgctct tgaaatggat gaaatcggcg agcgggccgt cgatgtgcag    600

gttacgcgcc tgcgtcgccg gatcgaggcc gatcccaagg agccgcgttt ccttcatacc    660

gtccggggaa agggctatgt tctcaagccg ggacgctga                           699
```

<210> SEQ ID NO 65
<211> LENGTH: 232
<212> TYPE: PRT
<213> ORGANISM: Gluconobacter oxydans DSM 17078

<400> SEQUENCE: 65

```
Met Ser Asp Glu His Ile Leu Val Val Asp Asp Asp Pro Arg Leu Leu
1               5                   10                  15

Arg Leu Leu Gln Arg Tyr Leu Ser Glu Asn Gly Tyr Arg Val Ser Thr
            20                  25                  30

Ala Leu Asp Ala Gln Thr Ala Arg Glu Val Leu Gln Arg Ile Gln Pro
        35                  40                  45

Asp Ala Leu Val Leu Asp Val Thr Met Pro Gly Glu Asp Gly Leu Ser
    50                  55                  60

Leu Thr Asn Ser Leu Arg Arg Asp Gly Leu Ser Leu Pro Ile Leu Leu
65                  70                  75                  80

Leu Thr Ala Arg Gly Glu Pro Ala Asp Arg Ile Gly Gly Leu Glu Ala
                85                  90                  95

Gly Ala Asp Asp Tyr Leu Gly Lys Pro Phe Glu Pro Arg Glu Leu Leu
            100                 105                 110

Leu Arg Leu Arg Ala His Leu Arg Arg Met Val Pro Ser Leu Pro Ala
        115                 120                 125

Val Asp Glu Val Pro Asp Val Leu Arg Leu Gly Glu Leu Glu Phe Asp
    130                 135                 140

Val Lys Arg Gly Leu Leu Ser Gly Pro Gln Gly Ala Val His Leu Thr
145                 150                 155                 160

Gly Gly Glu Ser Ala Leu Leu Gly Val Leu Thr Arg Gln Pro Gly Thr
                165                 170                 175

Val Leu Ser Arg Glu Ala Ile Ala Arg Ala Leu Glu Met Asp Glu Ile
            180                 185                 190

Gly Glu Arg Ala Val Asp Val Gln Val Thr Arg Leu Arg Arg Arg Ile
        195                 200                 205

Glu Ala Asp Pro Lys Glu Pro Arg Phe Leu His Thr Val Arg Gly Lys
    210                 215                 220

Gly Tyr Val Leu Lys Pro Gly Arg
225                 230
```

<210> SEQ ID NO 66
<211> LENGTH: 20
<212> TYPE: DNA
<213> ORGANISM: Artificial Sequence
<220> FEATURE:
<223> OTHER INFORMATION: primer

<400> SEQUENCE: 66

```
atgagcgatg aacatattct                                                 20
```

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
tcagcgtccc ggcttgagaa 20

<210> SEQ ID NO 68
<211> LENGTH: 489
<212> TYPE: DNA
<213> ORGANISM: Gluconobacter oxydans DSM 17078

<400> SEQUENCE: 68
gtgagttccc gtctcatgga cgttccgtca tctgccacgg cgcatcttta tctgcgcgaa 60
gaccgtatcc gtcagtccta cgaagccatg atgctggcct ggcggaccct gaatgccgat 120
tgcgaggcgc ttttgcgtga aaaggggctg gggccggcgc atcatcgcat cctgttcctg 180
acggctgccc atccggggat cacgcccggt gttctgctga acagtctggg cattaccaag 240
cagtctctgg ggcgtgctct gggagatctg cgggagcgca aactgcttat tcaggaagaa 300
gaccgtcatg atcgccgcaa acggcctctg cgactgacga cgagcggaga agcgctggag 360
cgcgaactct ttctcatgat ccgcgaagtt atgacccggg catatcgcga agccggcatg 420
acggctgtcg aggggttccg gcgggttctg gcgccccttc aggttccggc ggaaagtcgt 480
gcacgatga 489

<210> SEQ ID NO 69
<211> LENGTH: 162
<212> TYPE: PRT
<213> ORGANISM: Gluconobacter oxydans DSM 17078

<400> SEQUENCE: 69

Met Ser Ser Arg Leu Met Asp Val Pro Ser Ser Ala Thr Ala His Leu
1 5 10 15

Tyr Leu Arg Glu Asp Arg Ile Arg Gln Ser Tyr Glu Ala Met Met Leu
20 25 30

Ala Trp Arg Thr Leu Asn Ala Asp Cys Glu Ala Leu Leu Arg Glu Lys
35 40 45

Gly Leu Gly Pro Ala His His Arg Ile Leu Phe Leu Thr Ala Ala His
50 55 60

Pro Gly Ile Thr Pro Gly Val Leu Leu Asn Ser Leu Gly Ile Thr Lys
65 70 75 80

Gln Ser Leu Gly Arg Ala Leu Gly Asp Leu Arg Glu Arg Lys Leu Leu
85 90 95

Ile Gln Glu Glu Asp Arg His Asp Arg Arg Lys Arg Pro Leu Arg Leu
100 105 110

Thr Thr Ser Gly Glu Ala Leu Glu Arg Glu Leu Phe Leu Met Ile Arg
115 120 125

Glu Val Met Thr Arg Ala Tyr Arg Glu Ala Gly Met Thr Ala Val Glu
130 135 140

Gly Phe Arg Arg Val Leu Ala Pro Leu Gln Val Pro Ala Glu Ser Arg
145 150 155 160

Ala Arg

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
gtgagttccc gtctcatgga 20

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
tcatcgtgca cgactttccg 20

<210> SEQ ID NO 72
<211> LENGTH: 513
<212> TYPE: DNA
<213> ORGANISM: Gluconobacter oxydans DSM 17078

<400> SEQUENCE: 72
atggccctgc tcaagattgc ccgcatgggc aaccccgttc tgcatcaggt agcacaggcc 60
gtttccgacc cgaaagcccc ggaaatccag tcgctcatcg cagatatgct ggaaacgatg 120
gccgatgccc gtggtgcggg actggccgcg ccgcaggttc atcagcccct gcggattttc 180
gtctatcacg ttcccacgaa ccgcgtggcg aatcccgaag aggcattgct gccccgcgtt 240
ctcatcaacc ccgaaatcac gcctgtcggt gatgagatga tggtctgcag cgagggctgc 300
ctgtcgattc cgggtctgcg ggccgatgtg ccgcgccatg cgaaggtccg gtattcaggg 360
ctggatgaga atggtgcggt gctcgaaggc gaggcgaccg gttttcatgc caatgtcctg 420
caacacgaga acgaccatct gaacggcatt ctctatccgc agcgcattac cgatttcgcg 480
cgattcggat atgtggaaga aattctccgg tga 513

<210> SEQ ID NO 73
<211> LENGTH: 170
<212> TYPE: PRT
<213> ORGANISM: Gluconobacter oxydans DSM 17078

<400> SEQUENCE: 73

Met Ala Leu Leu Lys Ile Ala Arg Met Gly Asn Pro Val Leu His Gln
1 5 10 15

Val Ala Gln Ala Val Ser Asp Pro Lys Ala Pro Glu Ile Gln Ser Leu
20 25 30

Ile Ala Asp Met Leu Glu Thr Met Ala Asp Ala Arg Gly Ala Gly Leu
35 40 45

Ala Ala Pro Gln Val His Gln Pro Leu Arg Ile Phe Val Tyr His Val
50 55 60

Pro Thr Asn Arg Val Ala Asn Pro Glu Glu Ala Leu Leu Pro Arg Val
65 70 75 80

Leu Ile Asn Pro Glu Ile Thr Pro Val Gly Asp Glu Met Met Val Cys
85 90 95

Ser Glu Gly Cys Leu Ser Ile Pro Gly Leu Arg Ala Asp Val Pro Arg
100 105 110

```
His Ala Lys Val Arg Tyr Ser Gly Leu Asp Glu Asn Gly Ala Val Leu
        115                 120                 125

Glu Gly Glu Ala Thr Gly Phe His Ala Asn Val Leu Gln His Glu Asn
    130                 135                 140

Asp His Leu Asn Gly Ile Leu Tyr Pro Gln Arg Ile Thr Asp Phe Ala
145                 150                 155                 160

Arg Phe Gly Tyr Val Glu Glu Ile Leu Arg
                165                 170
```

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
atggccctgc tcaagattgc 20

<210> SEQ ID NO 75
<211> LENGTH: 20
<212> TYPE: DNA
<213> ORGANISM: Artificial Sequence
<220> FEATURE:
<223> OTHER INFORMATION: primer

<400> SEQUENCE: 75
tcaccggaga atttcttcca 20

<210> SEQ ID NO 76
<211> LENGTH: 41
<212> TYPE: DNA
<213> ORGANISM: Artificial Sequence
<220> FEATURE:
<223> OTHER INFORMATION: primer

<400> SEQUENCE: 76
tgtttaagtt tagtggatgg gagcaacctg aagaaactgg g 41

<210> SEQ ID NO 77
<211> LENGTH: 29
<212> TYPE: DNA
<213> ORGANISM: Artificial Sequence
<220> FEATURE:
<223> OTHER INFORMATION: primer

<400> SEQUENCE: 77
cgcaagcttg gtgttcaccc agaagcggc 29

<210> SEQ ID NO 78
<211> LENGTH: 29
<212> TYPE: DNA
<213> ORGANISM: Artificial Sequence
<220> FEATURE:
<223> OTHER INFORMATION: primer

<400> SEQUENCE: 78
cgcctgcagc cgttaaagcc gcgtgagtt 29

<210> SEQ ID NO 79
<211> LENGTH: 41
<212> TYPE: DNA
<213> ORGANISM: Artificial Sequence
<220> FEATURE:
<223> OTHER INFORMATION: primer

<400> SEQUENCE: 79
cccatccact aaacttaaac acgtgcccgt cacaacattg a 41

<210> SEQ ID NO 80
<211> LENGTH: 1311
<212> TYPE: DNA
<213> ORGANISM: Gluconobacter oxydans DSM 17078

<400> SEQUENCE: 80
atgtccgaat cttccccccc caagcacggg cttgcggaag cccttgggat acccagagcc 60
ctgttctggg catttgtggg acagctcctg ttcatggtcg gtgatggcgt ggaggcgggg 120
tatctcgata cctacatgct tcatcacggc catacgcagg gtttcgtgaa cgaaatgttc 180
actttctacg gcatcaccgt gatgatcgcc gcctggttct ccgggccgtt gtcggatctc 240
atggggccga agaaagtcat gtggcttggt cttgtcctgt gggccattct tgaagtgggc 300
ttcctgtccc tgggtcttgg acccaacagc ggaccgatga tcctgctttt ctatacgctt 360
cgcggttttg cctatccgct ctttgcgtat ggtttccttg tctggattgc cgctgccacg 420
ccgaccgcca tgttgggttc ggctgcaggc tggttctggt tttccttctc tgccggcctg 480
ccgacgcttg gctcgcagtt tgcacgtttt gccattcccc agatcggcga gcttcggacc 540
ttctggtgtt ccctcggact ggtgatcatc ggtggtcttg tcgctctgct gtttacgcat 600
gagccgaccg gcaagaagcg ccttctgccg gaccatgttc cgaccaagga cattttcttt 660
ggttccatga gcatcatgtg gcgtgagccc aagacgctga ttgccggtat cgtccgtgtg 720
atcgacacgt cttcggaata tgccttcctg gcgatcatgc cggcgttctt cgtcgaccat 780
ctcggctttt ctcttggtca gtggctgaac ctgctgtcgc tcatcttcct gagcaacatc 840
ctgttcaacc ttgtctcggg tatggttgcc gatagcctgg ggcaccggtt cgttgtcgcc 900
gtgttcggtg gcattggcgg ctttatcgcc attccgctgt tctattatgt gccgctgtgg 960
ttccctggaa acttctgggc cgtggccgcc gcaggcatct tttatggcgc gaccgttgca 1020
gcgtttgttc cgctctccgg cctgatgccg cagatctgcc cgcgtgagaa agctgctgcg 1080
ctgtccattc tgggtctggg tgcaggtgcg tccacctggg ttggtccggc agtcgtggca 1140
ggctgtgaag ccgtcttcgg tccgggcatg cagtatgtga tctggacctt tgccgtgatc 1200
tatctggcct ccgccggcat gacgatggct ctgaccatct cgccggaagc acgtcgctac 1260
agcgaagaag ctgcagcacg gggcgagagc gctccagtgg ttgggcactg a 1311

<210> SEQ ID NO 81
<211> LENGTH: 436
<212> TYPE: PRT
<213> ORGANISM: Gluconobacter oxydans DSM 17078

<400> SEQUENCE: 81

Met Ser Glu Ser Ser Pro Pro Lys His Gly Leu Ala Glu Ala Leu Gly
1 5 10 15

Ile Pro Arg Ala Leu Phe Trp Ala Phe Val Gly Gln Leu Leu Phe Met
20 25 30

Val Gly Asp Gly Val Glu Ala Gly Tyr Leu Asp Thr Tyr Met Leu His
35 40 45

His Gly His Thr Gln Gly Phe Val Asn Glu Met Phe Thr Phe Tyr Gly
50 55 60

Ile Thr Val Met Ile Ala Ala Trp Phe Ser Gly Pro Leu Ser Asp Leu
65 70 75 80

```
Met Gly Pro Lys Lys Val Met Trp Leu Gly Leu Val Leu Trp Ala Ile
                85                  90                  95

Leu Glu Val Gly Phe Leu Ser Leu Gly Leu Gly Pro Asn Ser Gly Pro
            100                 105                 110

Met Ile Leu Leu Phe Tyr Thr Leu Arg Gly Phe Ala Tyr Pro Leu Phe
        115                 120                 125

Ala Tyr Gly Phe Leu Val Trp Ile Ala Ala Ala Thr Pro Thr Ala Met
    130                 135                 140

Leu Gly Ser Ala Ala Gly Trp Phe Trp Phe Ser Phe Ser Ala Gly Leu
145                 150                 155                 160

Pro Thr Leu Gly Ser Gln Phe Ala Arg Phe Ala Ile Pro Gln Ile Gly
                165                 170                 175

Glu Leu Arg Thr Phe Trp Cys Ser Leu Gly Leu Val Ile Ile Gly Gly
            180                 185                 190

Leu Val Ala Leu Leu Phe Thr His Glu Pro Thr Gly Lys Lys Arg Leu
        195                 200                 205

Leu Pro Asp His Val Pro Thr Lys Asp Ile Phe Phe Gly Ser Met Ser
    210                 215                 220

Ile Met Trp Arg Glu Pro Lys Thr Leu Ile Ala Gly Ile Val Arg Val
225                 230                 235                 240

Ile Asp Thr Ser Ser Glu Tyr Ala Phe Leu Ala Ile Met Pro Ala Phe
                245                 250                 255

Phe Val Asp His Leu Gly Phe Ser Leu Gly Gln Trp Leu Asn Leu Leu
            260                 265                 270

Ser Leu Ile Phe Leu Ser Asn Ile Leu Phe Asn Leu Val Ser Gly Met
        275                 280                 285

Val Ala Asp Ser Leu Gly His Arg Phe Val Val Ala Val Phe Gly Gly
    290                 295                 300

Ile Gly Gly Phe Ile Ala Ile Pro Leu Phe Tyr Tyr Val Pro Leu Trp
305                 310                 315                 320

Phe Pro Gly Asn Phe Trp Ala Val Ala Ala Ala Gly Ile Phe Tyr Gly
                325                 330                 335

Ala Thr Val Ala Ala Phe Val Pro Leu Ser Gly Leu Met Pro Gln Ile
            340                 345                 350

Cys Pro Arg Glu Lys Ala Ala Ala Leu Ser Ile Leu Gly Leu Gly Ala
        355                 360                 365

Gly Ala Ser Thr Trp Val Gly Pro Ala Val Val Ala Gly Cys Glu Ala
    370                 375                 380

Val Phe Gly Pro Gly Met Gln Tyr Val Ile Trp Thr Phe Ala Val Ile
385                 390                 395                 400

Tyr Leu Ala Ser Ala Gly Met Thr Met Ala Leu Thr Ile Ser Pro Glu
                405                 410                 415

Ala Arg Arg Tyr Ser Glu Glu Ala Ala Ala Arg Gly Glu Ser Ala Pro
            420                 425                 430

Val Val Gly His
        435
```

<210> SEQ ID NO 82
<211> LENGTH: 20
<212> TYPE: DNA
<213> ORGANISM: Artificial Sequence
<220> FEATURE:
<223> OTHER INFORMATION: primer

<400> SEQUENCE: 82

-continued atgtccgaat cttccccccc 20

<210> SEQ ID NO 83
<211> LENGTH: 20
<212> TYPE: DNA
<213> ORGANISM: Artificial Sequence
<220> FEATURE:
<223> OTHER INFORMATION: primer

<400> SEQUENCE: 83
tcagtgccca accactggag 20

<210> SEQ ID NO 84
<211> LENGTH: 828
<212> TYPE: DNA
<213> ORGANISM: Gluconobacter oxydans DSM 17078

<400> SEQUENCE: 84
gtgagactca caacagagat gctggtcaca ggacgtctgg tcgcgatggc cttcatcatc 60
ctacacacgc tgtttccact ctactgggcg ctcgtcacgt cattccgtca cggaaccaca 120 ctttttttcca cagccctctt cacgttcccc gaccttgaaa actaccgaaa agtcctcggc 180
ggtccagaac tgtggcggga gacgttcaac tcggtcctgt gcgccggttc cgttacgctc 240
ctctcgctcc tcctcggcat tccggcagcc tatgccctcg gtcagatgag ttttcccggg 300
cgccggctgg tgcttggcat cctgctgctc tgctcgatgc tgccccagat cgccatcctg 360
tccggcctgt tcgaactgat ctcggccatg ggctgtatg atcacgttga aagcatcatt 420
ttcgccgacc tgttctttgc ccttcccttc acgatctggt tattgacggg ttttttccgg 480
gacctccccc ccgaactgga cgacgcggca aaactggacg gctgcagcct gatgcgccgg 540
atcttcagca ttcacctgcc cctggtctgg ccgggaattg ccgccacggg actgctgaat 600
atcatgacat gctggaacga gtttcttttt gccctgacct tcacactcaa cgactcagcc 660
cgtacccttc cggtcggtat cggactgatt tccgctccag gccggtttga acttcctttc 720
gggaccatca tggccgcatc ccttctcgca accctccccc cgatcctgct cgtcctgttc 780
ttccagaacc gcattgcctc cggcctgact gcgggggctg tcaaatga 828

<210> SEQ ID NO 85
<211> LENGTH: 275
<212> TYPE: PRT
<213> ORGANISM: Gluconobacter oxydans DSM 17078

<400> SEQUENCE: 85

Val Arg Leu Thr Thr Glu Met Leu Val Thr Gly Arg Leu Val Ala Met
1 5 10 15

Ala Phe Ile Ile Leu His Thr Leu Phe Pro Leu Tyr Trp Ala Leu Val
20 25 30

Thr Ser Phe Arg His Gly Thr Thr Leu Phe Ser Thr Ala Leu Phe Thr
35 40 45

Phe Pro Asp Leu Glu Asn Tyr Arg Lys Val Leu Gly Gly Pro Glu Leu
50 55 60

Trp Arg Glu Thr Phe Asn Ser Val Leu Cys Ala Gly Ser Val Thr Leu
65 70 75 80

Leu Ser Leu Leu Leu Gly Ile Pro Ala Ala Tyr Ala Leu Gly Gln Met
85 90 95

Ser Phe Pro Gly Arg Arg Leu Val Leu Gly Ile Leu Leu Leu Cys Ser
100 105 110

```
Met Leu Pro Gln Ile Ala Ile Leu Ser Gly Leu Phe Glu Leu Ile Ser
        115                 120                 125

Ala Met Gly Leu Tyr Asp His Val Glu Ser Ile Ile Phe Ala Asp Leu
    130                 135                 140

Phe Phe Ala Leu Pro Phe Thr Ile Trp Leu Leu Thr Gly Phe Phe Arg
145                 150                 155                 160

Asp Leu Pro Pro Glu Leu Asp Asp Ala Ala Lys Leu Asp Gly Cys Ser
                165                 170                 175

Leu Met Arg Arg Ile Phe Ser Ile His Leu Pro Leu Val Trp Pro Gly
            180                 185                 190

Ile Ala Ala Thr Gly Leu Leu Asn Ile Met Thr Cys Trp Asn Glu Phe
        195                 200                 205

Leu Phe Ala Leu Thr Phe Thr Leu Asn Asp Ser Ala Arg Thr Leu Pro
    210                 215                 220

Val Gly Ile Gly Leu Ile Ser Ala Pro Gly Arg Phe Glu Leu Pro Phe
225                 230                 235                 240

Gly Thr Ile Met Ala Ala Ser Leu Leu Ala Thr Leu Pro Pro Ile Leu
                245                 250                 255

Leu Val Leu Phe Phe Gln Asn Arg Ile Ala Ser Gly Leu Thr Ala Gly
            260                 265                 270

Ala Val Lys
        275


<210> SEQ ID NO 86
<211> LENGTH: 20
<212> TYPE: DNA
<213> ORGANISM: Artificial Sequence
<220> FEATURE:
<223> OTHER INFORMATION: primer

<400> SEQUENCE: 86

gtgagactca caacagagat                                              20


<210> SEQ ID NO 87
<211> LENGTH: 20
<212> TYPE: DNA
<213> ORGANISM: Artificial Sequence
<220> FEATURE:
<223> OTHER INFORMATION: primer

<400> SEQUENCE: 87

tcatttgaca gcccccgcag                                              20


<210> SEQ ID NO 88
<211> LENGTH: 900
<212> TYPE: DNA
<213> ORGANISM: Gluconobacter oxydans DSM 17078

<400> SEQUENCE: 88

atgctgactg tcccggctcc aaaacggttt gactggcgcc cctgggctct tgtcgcaccg     60

gcactgatcg tgctgatgac agtcaccgca attccgttcg cccgaacgat ctggcttgcc    120

ttccatgatg atccacacgg cttcatgcag gcacagccgg gatggagcct gaccaatttc    180

cgggttctgc ttcaggacag ggcctggtgg accgccgtca gcacgacgct gcttttcgca    240

gccggagccg tcatcagcga aacctgtgcc ggtctggcga ttgccatgct tcttcagggc    300

tacagtctga aactccgggg catcctgctg gccatcatcc ttctgccctg ggccgttccc    360

tccgtcgtgg ccgcccgtct gtggaactgg atgctcaatg accagtacgg catcatcaac    420
```

-continued gcagtgctcg tccggctggg ccttctgcat cagggcgttg catggaccac ccatccgcgc 480
agcatggtcg ccgtcatgat cgccatagat ttctggcagg cgaccccttt catggcgctg 540
ctttccctcg ccggattaca gtccatcccc accgatgttt tcgaagctgc aaaacttgat 600
ggcgcctcac cctggcagcg cttcatctcc atcaccctgc ccctcgtcgc ccccgtcctg 660
tccgtagccg tgctgttccg tctgctggat gccctgcgga tgttcgatct ggccaatgta 720
ctgtacggaa cggatatgag cggcatgacc ctctccgcct tcgtgcagag ccagatcgtc 780
cagttcggag caccaggcta cggcgcggcg tcggcgcttg gaaccctcgg cattatcgct 840
cttgcagctt cgctctatgg tgtgtgcctg aagattccgg ggtggatacg ctcatcgtga 900

<210> SEQ ID NO 89
<211> LENGTH: 299
<212> TYPE: PRT
<213> ORGANISM: Gluconobacter oxydans DSM 17078

<400> SEQUENCE: 89

Met Leu Thr Val Pro Ala Pro Lys Arg Phe Asp Trp Arg Pro Trp Ala
1               5                   10                  15

Leu Val Ala Pro Ala Leu Ile Val Leu Met Thr Val Thr Ala Ile Pro
            20                  25                  30

Phe Ala Arg Thr Ile Trp Leu Ala Phe His Asp Asp Pro His Gly Phe
        35                  40                  45

Met Gln Ala Gln Pro Gly Trp Ser Leu Thr Asn Phe Arg Val Leu Leu
    50                  55                  60

Gln Asp Arg Ala Trp Trp Thr Ala Val Ser Thr Thr Leu Leu Phe Ala
65                  70                  75                  80

Ala Gly Ala Val Ile Ser Glu Thr Cys Ala Gly Leu Ala Ile Ala Met
                85                  90                  95

Leu Leu Gln Gly Tyr Ser Leu Lys Leu Arg Gly Ile Leu Leu Ala Ile
            100                 105                 110

Ile Leu Leu Pro Trp Ala Val Pro Ser Val Val Ala Ala Arg Leu Trp
        115                 120                 125

Asn Trp Met Leu Asn Asp Gln Tyr Gly Ile Ile Asn Ala Val Leu Val
    130                 135                 140

Arg Leu Gly Leu Leu His Gln Gly Val Ala Trp Thr Thr His Pro Arg
145                 150                 155                 160

Ser Met Val Ala Val Met Ile Ala Ile Asp Phe Trp Gln Ala Thr Pro
                165                 170                 175

Phe Met Ala Leu Leu Ser Leu Ala Gly Leu Gln Ser Ile Pro Thr Asp
            180                 185                 190

Val Phe Glu Ala Ala Lys Leu Asp Gly Ala Ser Pro Trp Gln Arg Phe
        195                 200                 205

Ile Ser Ile Thr Leu Pro Leu Val Ala Pro Val Leu Ser Val Ala Val
    210                 215                 220

Leu Phe Arg Leu Leu Asp Ala Leu Arg Met Phe Asp Leu Ala Asn Val
225                 230                 235                 240

Leu Tyr Gly Thr Asp Met Ser Gly Met Thr Leu Ser Ala Phe Val Gln
                245                 250                 255

Ser Gln Ile Val Gln Phe Gly Ala Pro Gly Tyr Gly Ala Ala Ser Ala
            260                 265                 270

Leu Gly Thr Leu Gly Ile Ile Ala Leu Ala Ala Ser Leu Tyr Gly Val
        275                 280                 285

Cys Leu Lys Ile Pro Gly Trp Ile Arg Ser Ser
290 295

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
atgctgactg tcccggctcc 20

<210> SEQ ID NO 91
<211> LENGTH: 20
<212> TYPE: DNA
<213> ORGANISM: Artificial Sequence
<220> FEATURE:
<223> OTHER INFORMATION: primer

<400> SEQUENCE: 91
tcacgatgag cgtatccacc 20

<210> SEQ ID NO 92
<211> LENGTH: 1104
<212> TYPE: DNA
<213> ORGANISM: Gluconobacter oxydans DSM 17078

<400> SEQUENCE: 92
atggcgactg tcgaactcaa gaacctccgc aagacctacc ttacggaaga aatcatcaag 60
gggatttccc tctcgatcga agagcgcgaa tttgtggtct tcgtcggccc gtcaggctgc 120
ggaaaatcca cgctcctgcg catgatcgcg ggccttgagg acatcacatc cggcgatctc 180
ctgatcgacg gacagcgcgt aaatgacgtg gaacccggca agcgcggtct ggcgatggtc 240
tttcagtcct acgcgctcta cccgcacatg gacgtttaca aaaacatgga gttcggcctc 300
aaactggccg gaatgccgga agccgagcgc cgcgagaaaa tcgagcatgt cgcccgcacg 360
cttcagctcg agccctatct gcaccacaag cccggacagc tctccggcgg ccagcgccag 420
cgtgtcgcca tcggtcgcgc catcgtccgc aacccgaaag tctttctgtt cgacgagccg 480
ctctcgaacc tcgatgccgc cctgcgcggc cagatgcgcg tggaactctc cgccctgcac 540
cgcaagcttg gcgccaccac gatctatgtg actcatgatc aggtcgaagc catgaccatg 600
gcggacaaga tcgtcgtcct gcagaaaggc gtggtcgaac agatcggctc cccgctcgaa 660
ctgtaccacc atccccgcaa cctgttcgtg gcccgcttca tcggctcgcc gcccatgaac 720
ttcttcccgg ccattttcca gggcggagat tccgcaggct ccagcgtcca gctccgcgac 780
ggctcgaccc tttacgtgcc cgtcacatcc ccgggcctgc tggccggaac aaaggtgacg 840
gtcggcatcc gtcccgaaca tgtcgaactg gcctcttccg gccccaacag cggcgtcgtg 900
gaagtcatcg aacgcctcgg ggccatcacg ctcgtccatg tccgcatgcc ggacggggaa 960
atcatcgtcg tgcagacgga tggcgcagtc ctgacggagg tcgaaacccg cgtcagcctg 1020
acccttccac caaagaactg ccacctcttt gcacctgacg gcctggcctt cgaagcctgc 1080
caccgccacc cgctcgctgc ctga 1104

<210> SEQ ID NO 93
<211> LENGTH: 367
<212> TYPE: PRT
<213> ORGANISM: Gluconobacter oxydans DSM 17078

<400> SEQUENCE: 93

```
Met Ala Thr Val Glu Leu Lys Asn Leu Arg Lys Thr Tyr Leu Thr Glu
1               5                   10                  15

Glu Ile Ile Lys Gly Ile Ser Leu Ser Ile Glu Glu Arg Glu Phe Val
            20                  25                  30

Val Phe Val Gly Pro Ser Gly Cys Gly Lys Ser Thr Leu Leu Arg Met
        35                  40                  45

Ile Ala Gly Leu Glu Asp Ile Thr Ser Gly Asp Leu Leu Ile Asp Gly
    50                  55                  60

Gln Arg Val Asn Asp Val Glu Pro Gly Lys Arg Gly Leu Ala Met Val
65                  70                  75                  80

Phe Gln Ser Tyr Ala Leu Tyr Pro His Met Asp Val Tyr Lys Asn Met
                85                  90                  95

Glu Phe Gly Leu Lys Leu Ala Gly Met Pro Glu Ala Glu Arg Arg Glu
            100                 105                 110

Lys Ile Glu His Val Ala Arg Thr Leu Gln Leu Glu Pro Tyr Leu His
        115                 120                 125

His Lys Pro Gly Gln Leu Ser Gly Gly Gln Arg Gln Arg Val Ala Ile
    130                 135                 140

Gly Arg Ala Ile Val Arg Asn Pro Lys Val Phe Leu Phe Asp Glu Pro
145                 150                 155                 160

Leu Ser Asn Leu Asp Ala Ala Leu Arg Gly Gln Met Arg Val Glu Leu
                165                 170                 175

Ser Ala Leu His Arg Lys Leu Gly Ala Thr Thr Ile Tyr Val Thr His
            180                 185                 190

Asp Gln Val Glu Ala Met Thr Met Ala Asp Lys Ile Val Val Leu Gln
        195                 200                 205

Lys Gly Val Val Glu Gln Ile Gly Ser Pro Leu Glu Leu Tyr His His
    210                 215                 220

Pro Arg Asn Leu Phe Val Ala Arg Phe Ile Gly Ser Pro Pro Met Asn
225                 230                 235                 240

Phe Phe Pro Ala Ile Phe Gln Gly Gly Asp Ser Ala Gly Ser Ser Val
                245                 250                 255

Gln Leu Arg Asp Gly Ser Thr Leu Tyr Val Pro Val Thr Ser Pro Gly
            260                 265                 270

Leu Leu Ala Gly Thr Lys Val Thr Val Gly Ile Arg Pro Glu His Val
        275                 280                 285

Glu Leu Ala Ser Ser Gly Pro Asn Ser Gly Val Val Glu Val Ile Glu
    290                 295                 300

Arg Leu Gly Ala Ile Thr Leu Val His Val Arg Met Pro Asp Gly Glu
305                 310                 315                 320

Ile Ile Val Val Gln Thr Asp Gly Ala Val Leu Thr Glu Val Glu Thr
                325                 330                 335

Arg Val Ser Leu Thr Leu Pro Pro Lys Asn Cys His Leu Phe Ala Pro
            340                 345                 350

Asp Gly Leu Ala Phe Glu Ala Cys His Arg His Pro Leu Ala Ala
        355                 360                 365
```

<210> SEQ ID NO 94
<211> LENGTH: 20
<212> TYPE: DNA
<213> ORGANISM: Artificial Sequence
<220> FEATURE:
<223> OTHER INFORMATION: primer

<400> SEQUENCE: 94
atggcgactg tcgaactcaa 20

<210> SEQ ID NO 95
<211> LENGTH: 20
<212> TYPE: DNA
<213> ORGANISM: Artificial Sequence
<220> FEATURE:
<223> OTHER INFORMATION: primer

<400> SEQUENCE: 95
tcaggcagcg agcgggtggc 20

<210> SEQ ID NO 96
<211> LENGTH: 828
<212> TYPE: DNA
<213> ORGANISM: Gluconobacter oxydans DSM 17078

<400> SEQUENCE: 96
atggcgctca agaccaaaac cagcacccgg atcggcgtca ccgtcctcgg ctggggcatc 60
gcgctctggc tgttcttccc gatcttctgg atgatcctga caagcttcaa gagcgaggtt 120
caggcgattt ccacgccgcc gaagctgttc ttcatgccaa cgctgagcag ttacggcgaa 180
gtgttcgagc gcgccagtta ctggcatttc gcgctcaata cggtgattgt ctcggtcggc 240
gcgacggcaa ttgccgtcgc tctggccgtc ccggcggcct attcgatggc gttcctgcct 300
tcaaagcgca cacgcggcac cctgctgtgg atgctctcga cccgcatgct gcctcccgtc 360
ggcgtgctgg tcccgatcta tctgctggcc cgcaacacgc atctgctcga cacctgcacc 420
ggcctggccg tcgtggacat gctgacgaac ctgccgatca tcgtctggat gctctacacg 480
ttcttccgcg aagtcccggc ccccattctc gaagcaggcc ggatggacgg cgccacgcgc 540
tggcaggaaa tgacgatggt cctgctgccg ctcgccctgc ccggcatcgc gtccacggcc 600
ctgctgtcgc tcatcctgtg ctggaacgag gccttctggt ccctgaacct gacatcctcg 660
cacgcagccc ccttgacagc cttcatcgcc tccttctcct ctcctgaagg actgtttttc 720
ggcaagctct ctgcggcatc cacccttgcc gtcgccccga tcctcgtttt tggctggatc 780
agccagaagc agctggttcg cggcctgact ttcggagccg tcaagtga 828

<210> SEQ ID NO 97
<211> LENGTH: 275
<212> TYPE: PRT
<213> ORGANISM: Gluconobacter oxydans DSM 17078

<400> SEQUENCE: 97

Met Ala Leu Lys Thr Lys Thr Ser Thr Arg Ile Gly Val Thr Val Leu
1 5 10 15

Gly Trp Gly Ile Ala Leu Trp Leu Phe Phe Pro Ile Phe Trp Met Ile
20 25 30

Leu Thr Ser Phe Lys Ser Glu Val Gln Ala Ile Ser Thr Pro Pro Lys
35 40 45

Leu Phe Phe Met Pro Thr Leu Ser Ser Tyr Gly Glu Val Phe Glu Arg
50 55 60

Ala Ser Tyr Trp His Phe Ala Leu Asn Thr Val Ile Val Ser Val Gly
65 70 75 80

Ala Thr Ala Ile Ala Val Ala Leu Ala Val Pro Ala Ala Tyr Ser Met
85 90 95

Ala Phe Leu Pro Ser Lys Arg Thr Arg Gly Thr Leu Leu Trp Met Leu

```
            100                 105                 110

Ser Thr Arg Met Leu Pro Pro Val Gly Val Leu Val Pro Ile Tyr Leu
        115                 120                 125

Leu Ala Arg Asn Thr His Leu Leu Asp Thr Cys Thr Gly Leu Ala Val
    130                 135                 140

Val Asp Met Leu Thr Asn Leu Pro Ile Ile Val Trp Met Leu Tyr Thr
145                 150                 155                 160

Phe Phe Arg Glu Val Pro Ala Pro Ile Leu Glu Ala Gly Arg Met Asp
                165                 170                 175

Gly Ala Thr Arg Trp Gln Glu Met Thr Met Val Leu Leu Pro Leu Ala
            180                 185                 190

Leu Pro Gly Ile Ala Ser Thr Ala Leu Leu Ser Leu Ile Leu Cys Trp
        195                 200                 205

Asn Glu Ala Phe Trp Ser Leu Asn Leu Thr Ser Ser His Ala Ala Pro
    210                 215                 220

Leu Thr Ala Phe Ile Ala Ser Phe Ser Ser Pro Glu Gly Leu Phe Phe
225                 230                 235                 240

Gly Lys Leu Ser Ala Ala Ser Thr Leu Ala Val Ala Pro Ile Leu Val
                245                 250                 255

Phe Gly Trp Ile Ser Gln Lys Gln Leu Val Arg Gly Leu Thr Phe Gly
            260                 265                 270

Ala Val Lys
        275
```

<210> SEQ ID NO 98
<211> LENGTH: 20
<212> TYPE: DNA
<213> ORGANISM: Artificial Sequence
<220> FEATURE:
<223> OTHER INFORMATION: primer

<400> SEQUENCE: 98
atggcgctca agaccaaaac 20

<210> SEQ ID NO 99
<211> LENGTH: 20
<212> TYPE: DNA
<213> ORGANISM: Artificial Sequence
<220> FEATURE:
<223> OTHER INFORMATION: primer

<400> SEQUENCE: 99
tcacttgacg gctccgaaag 20

<210> SEQ ID NO 100
<211> LENGTH: 924
<212> TYPE: DNA
<213> ORGANISM: Gluconobacter oxydans DSM 17078

<400> SEQUENCE: 100

```
atgcaggccg tactcgaaca cagcccgccc gccggagcga ctgccctgaa ccagacgaar     60

gcacgcggga aaaggacagg tctcctgctc ctttccccgt ccgtcctgct tcttctggtg    120

tggtcgatcg tcccactcgt catgacgctg tggtactcgg tgcagaacta caacctcgtt    180

gaccccacgc tgcacggctt cgcggggatc gacaattact ggtatctgct gaccgatccc    240

gatttcctgc attcgctgct gaacacgttc gtactggttg cgggcgtcct gctcatcagc    300

gtcggcggcg gaacgctgct ggccgtcctg tacgatcagg agttcttcgg ccgcggcatt    360
```

```
gcccgcatca tggtcatctc gccattcttc atcatgccca cggtctcggc gctgctgtgg    420

aagaacctga tgctgcaccc gatctatggc gtctattccg ccatgatgcg ggcagtgggt    480

ctcacgccga tcgactggct ggcacgtttt ccgctcctga ctgtcatgat gatcgtcgcc    540

tgggaatggc tgcctttcgc ggtcctcatc ctgctgacag ccgtgcagtc gctcgacggt    600

gaacagcgcg aagccgcccg gatggacggc gcaggcccga tcgcccgttt ccgctacatc    660

atcctgccac atctgggccg cgccatcagc gtcgtcgtca tgatcgagac gatctacctg    720

ctgacgatct tcgcggaaat ctccgtcacg actgccggcg gtcccggcgt agcctccacc    780

aatctggcct atctgatcta ttcacgcgcc ctgctacaat tcgacgtggg tggcgcctcg    840

gctggtggtg tgattgcaat catcatcgcc aatatcgtcg cgatctttct ggtgcgcgcc    900

gtagcccgca atctggaggc ctga                                           924


<210> SEQ ID NO 101
<211> LENGTH: 307
<212> TYPE: PRT
<213> ORGANISM: Gluconobacter oxydans DSM 17078

<400> SEQUENCE: 101

Met Gln Ala Val Leu Glu His Ser Pro Pro Ala Gly Ala Thr Ala Leu
1               5                   10                  15

Asn Gln Thr Lys Ala Arg Gly Lys Arg Thr Gly Leu Leu Leu Leu Ser
            20                  25                  30

Pro Ser Val Leu Leu Leu Leu Val Trp Ser Ile Val Pro Leu Val Met
        35                  40                  45

Thr Leu Trp Tyr Ser Val Gln Asn Tyr Asn Leu Val Asp Pro Thr Leu
    50                  55                  60

His Gly Phe Ala Gly Ile Asp Asn Tyr Trp Tyr Leu Leu Thr Asp Pro
65                  70                  75                  80

Asp Phe Leu His Ser Leu Leu Asn Thr Phe Val Leu Val Ala Gly Val
                85                  90                  95

Leu Leu Ile Ser Val Gly Gly Gly Thr Leu Leu Ala Val Leu Tyr Asp
            100                 105                 110

Gln Glu Phe Phe Gly Arg Gly Ile Ala Arg Ile Met Val Ile Ser Pro
        115                 120                 125

Phe Phe Ile Met Pro Thr Val Ser Ala Leu Leu Trp Lys Asn Leu Met
    130                 135                 140

Leu His Pro Ile Tyr Gly Val Tyr Ser Ala Met Met Arg Ala Val Gly
145                 150                 155                 160

Leu Thr Pro Ile Asp Trp Leu Ala Arg Phe Pro Leu Leu Thr Val Met
                165                 170                 175

Met Ile Val Ala Trp Glu Trp Leu Pro Phe Ala Val Leu Ile Leu Leu
            180                 185                 190

Thr Ala Val Gln Ser Leu Asp Gly Glu Gln Arg Glu Ala Ala Arg Met
        195                 200                 205

Asp Gly Ala Gly Pro Ile Ala Arg Phe Arg Tyr Ile Ile Leu Pro His
    210                 215                 220

Leu Gly Arg Ala Ile Ser Val Val Val Met Ile Glu Thr Ile Tyr Leu
225                 230                 235                 240

Leu Thr Ile Phe Ala Glu Ile Ser Val Thr Thr Ala Gly Gly Pro Gly
                245                 250                 255

Val Ala Ser Thr Asn Leu Ala Tyr Leu Ile Tyr Ser Arg Ala Leu Leu
            260                 265                 270
```

```
Gln Phe Asp Val Gly Gly Ala Ser Ala Gly Gly Val Ile Ala Ile Ile
        275                 280                 285

Ile Ala Asn Ile Val Ala Ile Phe Leu Val Arg Ala Val Ala Arg Asn
    290                 295                 300

Leu Glu Ala
305


<210> SEQ ID NO 102
<211> LENGTH: 20
<212> TYPE: DNA
<213> ORGANISM: Artificial Sequence
<220> FEATURE:
<223> OTHER INFORMATION: primer

<400> SEQUENCE: 102

atgcaggccg tactcgaaca                                                  20


<210> SEQ ID NO 103
<211> LENGTH: 20
<212> TYPE: DNA
<213> ORGANISM: Artificial Sequence
<220> FEATURE:
<223> OTHER INFORMATION: primer

<400> SEQUENCE: 103

tcaggcctcc agattgcggg                                                  20


<210> SEQ ID NO 104
<211> LENGTH: 1329
<212> TYPE: DNA
<213> ORGANISM: Gluconobacter oxydans DSM 17078

<400> SEQUENCE: 104

atgtcccgtc tcaaagccac acacacagcc atctgcactc tcgcccttct gctcacgggc      60

tccgccctgt ccagcgccga agccgccgga acgctgacga tcgccaccgt caacaacggc     120

gacatgatcg tcatgcggca gctttcccag gagtttgaga aggcccatcc ggacattcac     180

ctgaactggg tcacgctgga agaaaacgtc ctgcgtcagc gcgtcacgac cgatatcgcc     240

atgaaaaccg gtcagttcga tgtcgtgacc atcggcaact acgaagtgcc gatctgggcc     300

aagcagggct ggcttaccga actcaagccg gacgccacct atgacgtgaa cgacatcctg     360

ccctccgtcc gcgacagcct gacaacagat ggcaagctct atgccctgcc gttctacgcc     420

gaaagcgtca tgacctatta tcgcaaggac ctgttccaaa aggccgggct gacgatgccg     480

gacgcgccca cctacgacca gatccgccag ttcgccgaca agatcacgga caagggcaat     540

caggtctatg gtatctgcct gcgcggcaag ccgggctggg gcgagaacat ggcgtatatc     600

tcgtcgctcg ccaacacgtt cggcgctcag tggtttgaca tgtcctggaa gccgaccatg     660

acatccgatg cgtggaaagc gaccctgaac tggtacgtct cggctctgaa ggctgacggt     720

cctccgggtg cgacatccaa tggcttcaac gagaacctgg ccctgttcgc cagcggtcat     780

tgcgggatct ggattgattc caccgtcgca ggcgggctgc tgttcgatcc caaacagtcc     840

caggttgcgg acaaagtcgg tttcgcttcc tcccccaagg gtccttacgg caaaggcccg     900

acctggctgt ggagctggag cctcgccgtc cccgtcagct cccatcagag cgcagatgcc     960

cagaccttca ttacgtgggc aacgtccaag gactacgtga aactggtcgc cgcacagaaa    1020

ggctgggtcg ccgttccggc cggaacccgc gcctccacct atgccgcgcc ggaatacgtc    1080

aaggcagcgc ccttcgcttc cttcgtgctg aacgccatca agacggctga tccgaacggc    1140
```

```
ccgaccgccc agccgcgtcc ctataccggt gcgcagttcg tcggcatccc ggaattccag   1200

gccatcggca cacaggtcgg ccagaccgtt gccgcgaccc tgtccgatca gatgaccgtc   1260

gatcaggccc tgacctccgc ccaggcttcg atcacccgcg cgctccgcca gtccggccgc   1320

gcgcgataa                                                           1329
```

<210> SEQ ID NO 105
<211> LENGTH: 442
<212> TYPE: PRT
<213> ORGANISM: Gluconobacter oxydans DSM 17078

<400> SEQUENCE: 105

```
Met Ser Arg Leu Lys Ala Thr His Thr Ala Ile Cys Thr Leu Ala Leu
1               5                   10                  15

Leu Leu Thr Gly Ser Ala Leu Ser Ser Ala Glu Ala Ala Gly Thr Leu
            20                  25                  30

Thr Ile Ala Thr Val Asn Asn Gly Asp Met Ile Val Met Arg Gln Leu
        35                  40                  45

Ser Gln Glu Phe Glu Lys Ala His Pro Asp Ile His Leu Asn Trp Val
    50                  55                  60

Thr Leu Glu Glu Asn Val Leu Arg Gln Arg Val Thr Thr Asp Ile Ala
65                  70                  75                  80

Met Lys Thr Gly Gln Phe Asp Val Val Thr Ile Gly Asn Tyr Glu Val
                85                  90                  95

Pro Ile Trp Ala Lys Gln Gly Trp Leu Thr Glu Leu Lys Pro Asp Ala
            100                 105                 110

Thr Tyr Asp Val Asn Asp Ile Leu Pro Ser Val Arg Asp Ser Leu Thr
        115                 120                 125

Thr Asp Gly Lys Leu Tyr Ala Leu Pro Phe Tyr Ala Glu Ser Val Met
    130                 135                 140

Thr Tyr Tyr Arg Lys Asp Leu Phe Gln Lys Ala Gly Leu Thr Met Pro
145                 150                 155                 160

Asp Ala Pro Thr Tyr Asp Gln Ile Arg Gln Phe Ala Asp Lys Ile Thr
                165                 170                 175

Asp Lys Gly Asn Gln Val Tyr Gly Ile Cys Leu Arg Gly Lys Pro Gly
            180                 185                 190

Trp Gly Glu Asn Met Ala Tyr Ile Ser Ser Leu Ala Asn Thr Phe Gly
        195                 200                 205

Ala Gln Trp Phe Asp Met Ser Trp Lys Pro Thr Met Thr Ser Asp Ala
    210                 215                 220

Trp Lys Ala Thr Leu Asn Trp Tyr Val Ser Ala Leu Lys Ala Asp Gly
225                 230                 235                 240

Pro Pro Gly Ala Thr Ser Asn Gly Phe Asn Glu Asn Leu Ala Leu Phe
                245                 250                 255

Ala Ser Gly His Cys Gly Ile Trp Ile Asp Ser Thr Val Ala Gly Gly
            260                 265                 270

Leu Leu Phe Asp Pro Lys Gln Ser Gln Val Ala Asp Lys Val Gly Phe
        275                 280                 285

Ala Ser Ser Pro Lys Gly Pro Tyr Gly Lys Gly Pro Thr Trp Leu Trp
    290                 295                 300

Ser Trp Ser Leu Ala Val Pro Val Ser Ser His Gln Ser Ala Asp Ala
305                 310                 315                 320

Gln Thr Phe Ile Thr Trp Ala Thr Ser Lys Asp Tyr Val Lys Leu Val
                325                 330                 335
```

```
Ala Ala Gln Lys Gly Trp Val Ala Val Pro Ala Gly Thr Arg Ala Ser
            340                 345                 350

Thr Tyr Ala Ala Pro Glu Tyr Val Lys Ala Ala Pro Phe Ala Ser Phe
        355                 360                 365

Val Leu Asn Ala Ile Lys Thr Ala Asp Pro Asn Gly Pro Thr Ala Gln
    370                 375                 380

Pro Arg Pro Tyr Thr Gly Ala Gln Phe Val Gly Ile Pro Glu Phe Gln
385                 390                 395                 400

Ala Ile Gly Thr Gln Val Gly Gln Thr Val Ala Ala Thr Leu Ser Asp
                405                 410                 415

Gln Met Thr Val Asp Gln Ala Leu Thr Ser Ala Gln Ala Ser Ile Thr
            420                 425                 430

Arg Ala Leu Arg Gln Ser Gly Arg Ala Arg
        435                 440


<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106

atgtcccgtc tcaaagccac                                                  20


<210> SEQ ID NO 107
<211> LENGTH: 20
<212> TYPE: DNA
<213> ORGANISM: Artificial Sequence
<220> FEATURE:
<223> OTHER INFORMATION: primer

<400> SEQUENCE: 107

ttatcgcgcg cggccggact                                                  20


<210> SEQ ID NO 108
<211> LENGTH: 1767
<212> TYPE: DNA
<213> ORGANISM: Gluconobacter oxydans DSM 17078

<400> SEQUENCE: 108

atggggcttg gccccgcagg gcgtgtcgag gaacttcccc ttcccgacat taccgagcgc      60

tacagcgcga tcggaccgga agccgagggc gtccggctgg atgaagcgat cgcccgcgcg     120

cttcaccaga tcgaaaagat gcgggaccgg ctggtcgggc tgccggaaga gggccgggag     180

gaaattgcct cccttctgat ggtctatgag cggatgctcg gcccgtcgcg gctgctgcgt     240

caggttcgca gccgcatcgc cgatgaggga ctgtgcgccg aggccgccgt ttcggaagtc     300

acgcgggaac tggcgttgca ggtctcgcgc atggccgagg ccgtggcgcg cgagaacaac     360

acgcaggaag ccgatgccaa tctgcgtctg gcgggtgagt tcgaggaaat cggccgccgc     420

ctcgttcgga acctgaccgg catttcctat cgcgcgtttt ccagcctgcc acctggctcc     480

gttctggtgg ccgagcagct ccgtccggcc gatgtcgcca tgatcgaccc ggcccggatt     540

gcggccgtgg tgacgcaggg cggtggtggg gccgatcaca cggccatcct gctgcgcgcg     600

ctcgacattc ccgccatcct cgccgtgccg aacctcatgg cgcaggtgca ggaaggcgag     660

atggtggtcg tggacgggca tctcggcacc gtcacgcttt cccccaatga gaccgaactg     720

cgtctggcgg cggaatccgc acagcgtgaa gtcaaggaaa agcgggcttt cgggcgtctc     780
```

-continued

```
aagcgcctgc cggcccagct tcagagcggc gaggacatcg agctttccgc caatctggag    840

cttccggcgg aactgccgat gctgatgcgc aatggcgcca agggcatcgg cctgctgcgc    900

agcgaattcc tgtttggcga acgtgaagac ctgccggacg aagacggtca gaccgaggcc    960

tatcgcgcta tcgtccaggc catggacggc cgtcccgtga cgatccgcgt gctggactgg   1020

ggcggcgaga agggccgggc ctgcatgcga aggctgggtc tggcggagca ggtcgcggat   1080

ggcgacaatc ccgcgctggg tctgcggggc gtgcggcttc tgctccgcgt gccggaggtg   1140

ctggagacgc agtttgcagc catcctgcgg gccgccgagc ctgcccaggg cgtgcccccc   1200

ggacgggtgc ggatcctgct gccgatggtt acgtcatcgg acgaaatcgt ggacgcccgc   1260

gagatttacg accgcgttgt gcgccgcctc aagcgcaagg gacacacgct ccccgatccg   1320

ctgcccccgc tggggatcat ggtcgaaacg ccggccgcgg ccctcacggt ggacacgctg   1380

gcccgacacg ccgatttcat ggcgctcggc accaatgacc tgacgatgta cacgctcgcc   1440

gtggaccgtg cggattccat ggtggcggac cgctacagcc cgctccatcc cggtgtgctg   1500

aggctgatcg aggcggcggc agattcggcg ctgcgggcgc gccgtccgat ctcggtctgt   1560

ggcgagatgg cgtccgatcc ccgggtggtg gcgctgctga ttggcctggg tctgcggtct   1620

ttttccatga attccgcgtc tctgccacgc gtgaagcggc tgatccgtac cctcacgctc   1680

gaagactgcg accagctccg ccggcaggtc atgctggaaa ccgacccggt cgtgatccgc   1740

gatctggtgc ggcagttcgc gacctga                                       1767


<210> SEQ ID NO 109
<211> LENGTH: 588
<212> TYPE: PRT
<213> ORGANISM: Gluconobacter oxydans DSM 17078

<400> SEQUENCE: 109

Met Gly Leu Gly Pro Ala Gly Arg Val Glu Glu Leu Pro Leu Pro Asp
1               5                   10                  15

Ile Thr Glu Arg Tyr Ser Ala Ile Gly Pro Glu Ala Glu Gly Val Arg
            20                  25                  30

Leu Asp Glu Ala Ile Ala Arg Ala Leu His Gln Ile Glu Lys Met Arg
        35                  40                  45

Asp Arg Leu Val Gly Leu Pro Glu Glu Gly Arg Glu Glu Ile Ala Ser
    50                  55                  60

Leu Leu Met Val Tyr Glu Arg Met Leu Gly Pro Ser Arg Leu Leu Arg
65                  70                  75                  80

Gln Val Arg Ser Arg Ile Ala Asp Glu Gly Leu Cys Ala Glu Ala Ala
                85                  90                  95

Val Ser Glu Val Thr Arg Glu Leu Ala Leu Gln Val Ser Arg Met Ala
            100                 105                 110

Glu Ala Val Ala Arg Glu Asn Asn Thr Gln Glu Ala Asp Ala Asn Leu
        115                 120                 125

Arg Leu Ala Gly Glu Phe Glu Glu Ile Gly Arg Arg Leu Val Arg Asn
    130                 135                 140

Leu Thr Gly Ile Ser Tyr Arg Ala Phe Ser Ser Leu Pro Pro Gly Ser
145                 150                 155                 160

Val Leu Val Ala Glu Gln Leu Arg Pro Ala Asp Val Ala Met Ile Asp
                165                 170                 175

Pro Ala Arg Ile Ala Ala Val Val Thr Gln Gly Gly Gly Gly Ala Asp
            180                 185                 190

His Thr Ala Ile Leu Leu Arg Ala Leu Asp Ile Pro Ala Ile Leu Ala
```

```
        195                 200                 205

Val Pro Asn Leu Met Ala Gln Val Gln Glu Gly Glu Met Val Val Val
    210                 215                 220

Asp Gly His Leu Gly Thr Val Thr Leu Ser Pro Asn Glu Thr Glu Leu
225                 230                 235                 240

Arg Leu Ala Ala Glu Ser Ala Gln Arg Glu Val Lys Glu Lys Arg Ala
                245                 250                 255

Phe Gly Arg Leu Lys Arg Leu Pro Ala Gln Leu Gln Ser Gly Glu Asp
            260                 265                 270

Ile Glu Leu Ser Ala Asn Leu Glu Leu Pro Ala Glu Leu Pro Met Leu
        275                 280                 285

Met Arg Asn Gly Ala Lys Gly Ile Gly Leu Leu Arg Ser Glu Phe Leu
    290                 295                 300

Phe Gly Glu Arg Glu Asp Leu Pro Asp Glu Asp Gly Gln Thr Glu Ala
305                 310                 315                 320

Tyr Arg Ala Ile Val Gln Ala Met Asp Gly Arg Pro Val Thr Ile Arg
                325                 330                 335

Val Leu Asp Trp Gly Gly Glu Lys Gly Arg Ala Cys Met Arg Arg Leu
            340                 345                 350

Gly Leu Ala Glu Gln Val Ala Asp Gly Asp Asn Pro Ala Leu Gly Leu
        355                 360                 365

Arg Gly Val Arg Leu Leu Leu Arg Val Pro Glu Val Leu Glu Thr Gln
    370                 375                 380

Phe Ala Ala Ile Leu Arg Ala Ala Glu Pro Ala Gln Gly Val Pro Pro
385                 390                 395                 400

Gly Arg Val Arg Ile Leu Leu Pro Met Val Thr Ser Ser Asp Glu Ile
                405                 410                 415

Val Asp Ala Arg Glu Ile Tyr Asp Arg Val Val Arg Arg Leu Lys Arg
            420                 425                 430

Lys Gly His Thr Leu Pro Asp Pro Leu Pro Pro Leu Gly Ile Met Val
        435                 440                 445

Glu Thr Pro Ala Ala Ala Leu Thr Val Asp Thr Leu Ala Arg His Ala
    450                 455                 460

Asp Phe Met Ala Leu Gly Thr Asn Asp Leu Thr Met Tyr Thr Leu Ala
465                 470                 475                 480

Val Asp Arg Ala Asp Ser Met Val Ala Asp Arg Tyr Ser Pro Leu His
                485                 490                 495

Pro Gly Val Leu Arg Leu Ile Glu Ala Ala Ala Asp Ser Ala Leu Arg
            500                 505                 510

Ala Arg Arg Pro Ile Ser Val Cys Gly Glu Met Ala Ser Asp Pro Arg
        515                 520                 525

Val Val Ala Leu Leu Ile Gly Leu Gly Leu Arg Ser Phe Ser Met Asn
    530                 535                 540

Ser Ala Ser Leu Pro Arg Val Lys Arg Leu Ile Arg Thr Leu Thr Leu
545                 550                 555                 560

Glu Asp Cys Asp Gln Leu Arg Arg Gln Val Met Leu Glu Thr Asp Pro
                565                 570                 575

Val Val Ile Arg Asp Leu Val Arg Gln Phe Ala Thr
            580                 585
```

<210> SEQ ID NO 110
<211> LENGTH: 20
<212> TYPE: DNA
<213> ORGANISM: Artificial Sequence -continued
<220> FEATURE:
<223> OTHER INFORMATION: primer

<400> SEQUENCE: 110
atggggcttg gccccgcagg 20

<210> SEQ ID NO 111
<211> LENGTH: 20
<212> TYPE: DNA
<213> ORGANISM: Artificial Sequence
<220> FEATURE:
<223> OTHER INFORMATION: primer

<400> SEQUENCE: 111
tcaggtcgcg aactgccgca 20

<210> SEQ ID NO 112
<211> LENGTH: 300
<212> TYPE: DNA
<213> ORGANISM: Gluconobacter oxydans DSM 17078

<400> SEQUENCE: 112
atgagcgaca cgaccctttc tcccggtaca gttgcccccc gcaccgtcac catcgtcaat 60
catctgggcc ttcatgcccg ccccgccgcc aagatcgtca ccacagccga gcgttttgac 120
gccgagacca cgatcgccca tggcaccaat gtcgtctccg ccctgtcgat catggggctg 180
atgatgctgg gcgcgggaga agggcaggac gtcacgctgc gcgcccacgg cccgcaggcc 240
gccgaagcgc tcgatgcact ggcagccctg atcgcggacg ggtttggcga gcgtgactga 300

<210> SEQ ID NO 113
<211> LENGTH: 99
<212> TYPE: PRT
<213> ORGANISM: Gluconobacter oxydans DSM 17078

<400> SEQUENCE: 113

Met Ser Asp Thr Thr Leu Ser Pro Gly Thr Val Ala Pro Arg Thr Val
1 5 10 15

Thr Ile Val Asn His Leu Gly Leu His Ala Arg Pro Ala Ala Lys Ile
20 25 30

Val Thr Thr Ala Glu Arg Phe Asp Ala Glu Thr Thr Ile Ala His Gly
35 40 45

Thr Asn Val Val Ser Ala Leu Ser Ile Met Gly Leu Met Met Leu Gly
50 55 60

Ala Gly Glu Gly Gln Asp Val Thr Leu Arg Ala His Gly Pro Gln Ala
65 70 75 80

Ala Glu Ala Leu Asp Ala Leu Ala Ala Leu Ile Ala Asp Gly Phe Gly
85 90 95

Glu Arg Asp

<210> SEQ ID NO 114
<211> LENGTH: 20
<212> TYPE: DNA
<213> ORGANISM: Artificial Sequence
<220> FEATURE:
<223> OTHER INFORMATION: primer

<400> SEQUENCE: 114
atgagcgaca cgaccctttc 20

<210> SEQ ID NO 115

<211> LENGTH: 20
<212> TYPE: DNA
<213> ORGANISM: Artificial Sequence
<220> FEATURE:
<223> OTHER INFORMATION: primer

<400> SEQUENCE: 115
tcagtcacgc tcgccaaacc 20

<210> SEQ ID NO 116
<211> LENGTH: 441
<212> TYPE: DNA
<213> ORGANISM: Gluconobacter oxydans DSM 17078

<400> SEQUENCE: 116
atgatcggac tgatgctggt aacgcacggg cgccttgggg atgtcctgct ggaaacgctg 60
gttcatgtcg tggggcccca gacccaggtc ggcgtggtgg gcgtggcgga tgatgacgat 120
ccggcgatgc tccgcccggc cgccgagcgt ctgctccagc gcctcgatac cggggacggg 180
gtgcttctgc tgacggacat tttcggcagc tcgccgtcca atctggcgct ctcgctgcgg 240
gagccgggac atgtcgaggt cgtgtcgggc gtgaatgtgc ccatgctggt caagctggcg 300
aaaacgcggc gggatctgga ccttgcaggc tgcgtggaaa aggccacaat ggccgggcgg 360
aagtatatcg ccgtggcgtc acagcttcct gacccctgtc tccatggcgg gccgcgtgcc 420
tgtacgctgc cggttcattg a 441

<210> SEQ ID NO 117
<211> LENGTH: 146
<212> TYPE: PRT
<213> ORGANISM: Gluconobacter oxydans DSM 17078

<400> SEQUENCE: 117

Met Ile Gly Leu Met Leu Val Thr His Gly Arg Leu Gly Asp Val Leu
1 5 10 15

Leu Glu Thr Leu Val His Val Val Gly Pro Gln Thr Gln Val Gly Val
20 25 30

Val Gly Val Ala Asp Asp Asp Asp Pro Ala Met Leu Arg Pro Ala Ala
35 40 45

Glu Arg Leu Leu Gln Arg Leu Asp Thr Gly Asp Gly Val Leu Leu Leu
50 55 60

Thr Asp Ile Phe Gly Ser Ser Pro Ser Asn Leu Ala Leu Ser Leu Arg
65 70 75 80

Glu Pro Gly His Val Glu Val Val Ser Gly Val Asn Val Pro Met Leu
85 90 95

Val Lys Leu Ala Lys Thr Arg Arg Asp Leu Asp Leu Ala Gly Cys Val
100 105 110

Glu Lys Ala Thr Met Ala Gly Arg Lys Tyr Ile Ala Val Ala Ser Gln
115 120 125

Leu Pro Asp Pro Cys Leu His Gly Gly Pro Arg Ala Cys Thr Leu Pro
130 135 140

Val His
145

<210> SEQ ID NO 118
<211> LENGTH: 20
<212> TYPE: DNA
<213> ORGANISM: Artificial Sequence
<220> FEATURE:
<223> OTHER INFORMATION: primer

<400> SEQUENCE: 118
atgatcggac tgatgctggt 20

<210> SEQ ID NO 119
<211> LENGTH: 20
<212> TYPE: DNA
<213> ORGANISM: Artificial Sequence
<220> FEATURE:
<223> OTHER INFORMATION: primer

<400> SEQUENCE: 119
tcaatgaacc ggcagcgtac 20

<210> SEQ ID NO 120
<211> LENGTH: 909
<212> TYPE: DNA
<213> ORGANISM: Gluconobacter oxydans DSM 17078

<400> SEQUENCE: 120
ttgctgttat ttatccggtg tggcggtcag gctgagggcg atgcgctgct cgggcagggg 60
gaaacgctgc acgatccgca gggtcagcgc gggttttgct gccgccaggg cctcgttcag 120
ggcagcctga cactgggcaa aggtctggcc ttcgcgaatc atggcggcga cgtgccgggt 180
gtggcccagg gtcaggccat gatcggccag agcttcggaa atggcggaaa gtgcggcctg 240
acattcatcc gacagtcggc cgggacggtc cccgtccgga ccgaagccac tgaaatcggt 300
gcaggtgact tcgtctccat gtacggtgac ggtctggtga aggaaggatg cgcccatggg 360
ttcgtggtcc tgctccatgt cagggatccg tcatgcccct gtccgaccca aggtcttagt 420
ccgctcctgt ggaggtcgca atccatcatg tccgtcctgt catttctgcc tgaaggctcg 480
gtccacgcct gctgtgtggc gtggaacgga gacggcgtgc tgatttccgg tccccccggc 540
tcggggaaat ccgagctggc cctgcggctg atggatgcgg gtttcgatct cgtggcggat 600
gaccgggtcc tgctggacgg cgccgtggcg tccgcccccg aacgccttgc ggggctgatc 660
gaggtgcgag ggttggaat cctgaggaca tcttttgtca caaacgcgac ggtgcgtctg 720
cgggtctgtc tgggcgaggg gcagccccgt ctgccggagc cctgccggga cccgtggacg 780
ggagcggtca tgctacgtct ggagcccggt tttccgggaa cggtggcgcg gatcagggca 840
gccctgaagg cctgctgcgg cacctatgaa tgggtcgccg gagcaggcga aaatgttgcg 900
gaaacgtga 909

<210> SEQ ID NO 121
<211> LENGTH: 302
<212> TYPE: PRT
<213> ORGANISM: Gluconobacter oxydans DSM 17078

<400> SEQUENCE: 121

Leu Leu Leu Phe Ile Arg Cys Gly Gly Gln Ala Glu Gly Asp Ala Leu
1               5                   10                  15

Leu Gly Gln Gly Glu Thr Leu His Asp Pro Gln Gly Gln Arg Gly Phe
            20                  25                  30

Cys Cys Arg Gln Gly Leu Val Gln Gly Ser Leu Thr Leu Gly Lys Gly
        35                  40                  45

Leu Ala Phe Ala Asn His Gly Gly Asp Val Pro Gly Val Ala Gln Gly
    50                  55                  60

Gln Ala Met Ile Gly Gln Ser Phe Gly Asn Gly Gly Lys Cys Gly Leu
65                  70                  75                  80

```
Thr Phe Ile Arg Gln Ser Ala Gly Thr Val Pro Val Arg Thr Glu Ala
                85                  90                  95

Thr Glu Ile Gly Ala Gly Asp Phe Val Ser Met Tyr Gly Asp Gly Leu
            100                 105                 110

Val Lys Glu Gly Cys Ala His Gly Phe Val Val Leu Leu His Val Arg
        115                 120                 125

Asp Pro Ser Cys Pro Cys Pro Thr Gln Gly Leu Ser Pro Leu Leu Trp
    130                 135                 140

Arg Ser Gln Ser Ile Met Ser Val Leu Ser Phe Leu Pro Glu Gly Ser
145                 150                 155                 160

Val His Ala Cys Cys Val Ala Trp Asn Gly Asp Gly Val Leu Ile Ser
                165                 170                 175

Gly Pro Pro Gly Ser Gly Lys Ser Glu Leu Ala Leu Arg Leu Met Asp
            180                 185                 190

Ala Gly Phe Asp Leu Val Ala Asp Asp Arg Val Leu Leu Asp Gly Ala
        195                 200                 205

Val Ala Ser Ala Pro Glu Arg Leu Ala Gly Leu Ile Glu Val Arg Gly
    210                 215                 220

Val Gly Ile Leu Arg Thr Ser Phe Val Thr Asn Ala Thr Val Arg Leu
225                 230                 235                 240

Arg Val Cys Leu Gly Glu Gly Gln Pro Arg Leu Pro Glu Pro Cys Arg
                245                 250                 255

Asp Pro Trp Thr Gly Ala Val Met Leu Arg Leu Glu Pro Gly Phe Pro
            260                 265                 270

Gly Thr Val Ala Arg Ile Arg Ala Ala Leu Lys Ala Cys Cys Gly Thr
        275                 280                 285

Tyr Glu Trp Val Ala Gly Ala Gly Glu Asn Val Ala Glu Thr
    290                 295                 300


<210> SEQ ID NO 122
<211> LENGTH: 20
<212> TYPE: DNA
<213> ORGANISM: Artificial Sequence
<220> FEATURE:
<223> OTHER INFORMATION: primer

<400> SEQUENCE: 122

ttgctgttat ttatccggtg                                                20


<210> SEQ ID NO 123
<211> LENGTH: 20
<212> TYPE: DNA
<213> ORGANISM: Artificial Sequence
<220> FEATURE:
<223> OTHER INFORMATION: primer

<400> SEQUENCE: 123

tcacgtttcc gcaacatttt                                                20


<210> SEQ ID NO 124
<211> LENGTH: 1032
<212> TYPE: DNA
<213> ORGANISM: Gluconobacter oxydans DSM 17078

<400> SEQUENCE: 124

atggctgata caatgctcgc cgccgtcgtc cgtgaattcg gcaagccgct ctccatcgag     60

cggctaccca tcccggacat caagccccac cagatcctcg tgaaggtcga tacctgtggc    120
```

-continued

```
gtctgccaca ctgacctgca cgccgcgcgc ggggactggc cgtccaagcc caacccgccg    180

ttcattcccg gccatgaagg cgtcggacac atcgtcgccg tcggcagtca ggtcggcgat    240

ttcgtcaaga ccggcgatgt tgtgggcgta ccctggctct actccgcctg cggtcactgc    300

gaacactgtc tgggcggctg ggaaacgctc tgcgaaaagc aggacgacac cggctacacc    360

gtcaatggct gcttcgccga atacgtcgtg gcagacccga actacgtcgc acacctgccc    420

tcgaccatcg acccgcttca ggcctctccc gtcctgtgcg cggggctgac ggtctataag    480

ggcctgaaaa tgaccgaggc ccgcccccggc cagtgggtcg cagtctcggg cgtcggcggt    540

ctcggccaga tggccgtgca gtatgccgtc gccatgggca tgaatgtcgt cgccgtggac    600

atcgacgacg aaaaactcgc cacagccaaa aagctcggcg catccctgac ggtcaacgcc    660

aaggatacgg acccggccaa gttcatccag cagcagatcg gcggcgcgca tggcgccctc    720

gtcaccgctg tcggacggac ggcgttttcg caggccatgg gttatgcccg gcgcggcggc    780

accatcgtcc tgaacggcct gccgcccggc gatttcccgg tctcgatctt cgacatggtc    840

atgaacggca ccaccatccg cggatccatc gtcggaacac gactggacat gatcgaagcc    900

atggatttct tcgcccgcgg caaggtcaaa tccgtcgtca cccccggaaa acttgaaaac    960

atcaatacga tcttcgacga tctgcagaat ggtcgcctcg aaggccggac agtgctcgac   1020

ttccggtcct ga                                                        1032
```

<210> SEQ ID NO 125
<211> LENGTH: 343
<212> TYPE: PRT
<213> ORGANISM: Gluconobacter oxydans DSM 17078

<400> SEQUENCE: 125

```
Met Ala Asp Thr Met Leu Ala Ala Val Val Arg Glu Phe Gly Lys Pro
1               5                   10                  15

Leu Ser Ile Glu Arg Leu Pro Ile Pro Asp Ile Lys Pro His Gln Ile
            20                  25                  30

Leu Val Lys Val Asp Thr Cys Gly Val Cys His Thr Asp Leu His Ala
        35                  40                  45

Ala Arg Gly Asp Trp Pro Ser Lys Pro Asn Pro Pro Phe Ile Pro Gly
    50                  55                  60

His Glu Gly Val Gly His Ile Val Ala Val Gly Ser Gln Val Gly Asp
65                  70                  75                  80

Phe Val Lys Thr Gly Asp Val Val Gly Val Pro Trp Leu Tyr Ser Ala
                85                  90                  95

Cys Gly His Cys Glu His Cys Leu Gly Gly Trp Glu Thr Leu Cys Glu
            100                 105                 110

Lys Gln Asp Asp Thr Gly Tyr Thr Val Asn Gly Cys Phe Ala Glu Tyr
        115                 120                 125

Val Val Ala Asp Pro Asn Tyr Val Ala His Leu Pro Ser Thr Ile Asp
    130                 135                 140

Pro Leu Gln Ala Ser Pro Val Leu Cys Ala Gly Leu Thr Val Tyr Lys
145                 150                 155                 160

Gly Leu Lys Met Thr Glu Ala Arg Pro Gly Gln Trp Val Ala Val Ser
                165                 170                 175

Gly Val Gly Gly Leu Gly Gln Met Ala Val Gln Tyr Ala Val Ala Met
            180                 185                 190

Gly Met Asn Val Val Ala Val Asp Ile Asp Asp Glu Lys Leu Ala Thr
        195                 200                 205
```

```
Ala Lys Lys Leu Gly Ala Ser Leu Thr Val Asn Ala Lys Asp Thr Asp
    210                 215                 220

Pro Ala Lys Phe Ile Gln Gln Gln Ile Gly Gly Ala His Gly Ala Leu
225                 230                 235                 240

Val Thr Ala Val Gly Arg Thr Ala Phe Ser Gln Ala Met Gly Tyr Ala
                245                 250                 255

Arg Arg Gly Gly Thr Ile Val Leu Asn Gly Leu Pro Pro Gly Asp Phe
            260                 265                 270

Pro Val Ser Ile Phe Asp Met Val Met Asn Gly Thr Thr Ile Arg Gly
        275                 280                 285

Ser Ile Val Gly Thr Arg Leu Asp Met Ile Glu Ala Met Asp Phe Phe
    290                 295                 300

Ala Arg Gly Lys Val Lys Ser Val Val Thr Pro Gly Lys Leu Glu Asn
305                 310                 315                 320

Ile Asn Thr Ile Phe Asp Asp Leu Gln Asn Gly Arg Leu Glu Gly Arg
                325                 330                 335

Thr Val Leu Asp Phe Arg Ser
            340


<210> SEQ ID NO 126
<211> LENGTH: 20
<212> TYPE: DNA
<213> ORGANISM: Artificial Sequence
<220> FEATURE:
<223> OTHER INFORMATION: primer

<400> SEQUENCE: 126

atggctgata caatgctcgc                                                   20


<210> SEQ ID NO 127
<211> LENGTH: 20
<212> TYPE: DNA
<213> ORGANISM: Artificial Sequence
<220> FEATURE:
<223> OTHER INFORMATION: primer

<400> SEQUENCE: 127

tcaggaccgg aagtcgagca                                                   20


<210> SEQ ID NO 128
<211> LENGTH: 984
<212> TYPE: DNA
<213> ORGANISM: Gluconobacter oxydans DSM 17078

<400> SEQUENCE: 128

atgttcgcca tgcagctcaa agcccatcac acacctctgg aatgggtcga actccccgat      60

cccgaacccg gccccgatga aatccgcatc cggatcggcg cctgcggcgt gtgccggacg     120

gacctgcatg tcgtggatgg cgaactcccc cacgccaccc tccccatcat ccccggccac     180

gaaatcgttg gccggatcga caagctcggc agcaatgtca ccggtctgtc ggtgggcgag     240

agggtcggcg tgccctggct cggcatacc tgcgggcact gctattactg cacgcacggg     300

atggaaaatc tctgtgacca tcccctcttc acaggcttca cccgcaatgg cggctacgcg     360

accatgacgg tcgccgatgc ccgttacgcc ttcccgatgg gcgacaaggg cgaggacaag     420

gatctggccc ctctgctctg cgccgggctg atcggctggc gctgcctgaa aaaggccggt     480

gacggcaaaa agatcgggct ctacggcttc ggcgccgccg cccatatcat cacgcaggtc     540

ctgcgctggc agggccgcga cgtctacgcc ttcacgtccc ccggcgatac gcagaaacag     600
```

```
gatttcgccc gctccctcgg cgccgtctgg gccggtggct cggacgaact cccgcctgaa    660

ccactggacg ccgtgatcct gttcgccccc gtcggcgccc tgctccccgc aggcctcaaa    720

gccatccgca agggcgggaa agtggtgtgc ggcggcatcc acatgagcga aatcccggcc    780

ttttcctacg acacattatg ggaagagcgc gaaatcgtct ccgtcgccaa cctgacccgt    840

caggacggtc tggagttcct gaaaatcgcc ccggaagtcg gcatcaaggt gaccaacacg    900

ccctatgccc tgaaggacgc caatcaggcc ctcgatgacc tccggcacgg ccgtttcgac    960

ggtgccgccg tattgctgcc ctga                                           984


<210> SEQ ID NO 129
<211> LENGTH: 327
<212> TYPE: PRT
<213> ORGANISM: Gluconobacter oxydans DSM 17078

<400> SEQUENCE: 129

Met Phe Ala Met Gln Leu Lys Ala His His Thr Pro Leu Glu Trp Val
1               5                   10                  15

Glu Leu Pro Asp Pro Glu Pro Gly Pro Asp Glu Ile Arg Ile Arg Ile
            20                  25                  30

Gly Ala Cys Gly Val Cys Arg Thr Asp Leu His Val Val Asp Gly Glu
        35                  40                  45

Leu Pro His Ala Thr Leu Pro Ile Ile Pro Gly His Glu Ile Val Gly
    50                  55                  60

Arg Ile Asp Lys Leu Gly Ser Asn Val Thr Gly Leu Ser Val Gly Glu
65                  70                  75                  80

Arg Val Gly Val Pro Trp Leu Gly His Thr Cys Gly His Cys Tyr Tyr
                85                  90                  95

Cys Thr His Gly Met Glu Asn Leu Cys Asp His Pro Leu Phe Thr Gly
            100                 105                 110

Phe Thr Arg Asn Gly Gly Tyr Ala Thr Met Thr Val Ala Asp Ala Arg
        115                 120                 125

Tyr Ala Phe Pro Met Gly Asp Lys Gly Glu Asp Lys Asp Leu Ala Pro
    130                 135                 140

Leu Leu Cys Ala Gly Leu Ile Gly Trp Arg Cys Leu Lys Lys Ala Gly
145                 150                 155                 160

Asp Gly Lys Lys Ile Gly Leu Tyr Gly Phe Gly Ala Ala Ala His Ile
                165                 170                 175

Ile Thr Gln Val Leu Arg Trp Gln Gly Arg Asp Val Tyr Ala Phe Thr
            180                 185                 190

Ser Pro Gly Asp Thr Gln Lys Gln Asp Phe Ala Arg Ser Leu Gly Ala
        195                 200                 205

Val Trp Ala Gly Gly Ser Asp Glu Leu Pro Pro Glu Pro Leu Asp Ala
    210                 215                 220

Val Ile Leu Phe Ala Pro Val Gly Ala Leu Leu Pro Ala Gly Leu Lys
225                 230                 235                 240

Ala Ile Arg Lys Gly Gly Lys Val Val Cys Gly Gly Ile His Met Ser
                245                 250                 255

Glu Ile Pro Ala Phe Ser Tyr Asp Thr Leu Trp Glu Glu Arg Glu Ile
            260                 265                 270

Val Ser Val Ala Asn Leu Thr Arg Gln Asp Gly Leu Glu Phe Leu Lys
        275                 280                 285

Ile Ala Pro Glu Val Gly Ile Lys Val Thr Asn Thr Pro Tyr Ala Leu
    290                 295                 300
```

```
Lys Asp Ala Asn Gln Ala Leu Asp Asp Leu Arg His Gly Arg Phe Asp
305                 310                 315                 320

Gly Ala Ala Val Leu Leu Pro
                325
```

<210> SEQ ID NO 130
<211> LENGTH: 20
<212> TYPE: DNA
<213> ORGANISM: Artificial Sequence
<220> FEATURE:
<223> OTHER INFORMATION: primer

<400> SEQUENCE: 130

```
atgttcgcca tgcagctcaa                                                20
```

<210> SEQ ID NO 131
<211> LENGTH: 20
<212> TYPE: DNA
<213> ORGANISM: Artificial Sequence
<220> FEATURE:
<223> OTHER INFORMATION: primer

<400> SEQUENCE: 131

```
tcagggcagc aatacggcgg                                                20
```

<210> SEQ ID NO 132
<211> LENGTH: 1458
<212> TYPE: DNA
<213> ORGANISM: Gluconobacter oxydans DSM 17078

<400> SEQUENCE: 132

```
atgattacgc gcgaaaccct caagtctctt cctgccaatg tccaggctcc tccctatgac     60

atcgacggga tcaagccggg gatcgtgcat ttcggcgtgg gtaacttctt ccgggcccat    120

gaggcgttct atgtcgagca gattcttgag catgcgccgg actgggcgat cgttggtgtt    180

ggcctgacgg gcagtgaccg ctcgaagaaa aaggccgaag aattcaaggc tcaggactgc    240

ctgtattccc tgaccgagac ggccccgtcc ggcaagagca cggtgcgtgt catgggcgca    300

ctgcgtgact acctgctggc tccggctgat ccggaagccg tgctgaagca tctcgttgat    360

ccggccattc gtattgtctc catgacgatc acggaaggcg gctacaacat caacgagacg    420

accggtgcct tcgatctgga gaatgcggcg gtgaaggctg acctccagaa cccggaaaag    480

ccgtccaccg ttttcggtta cgtcgtcgag gccctgcgcc gtcggcggga tgccggtggc    540

aaggccttta cggtcatgtc ctgtgacaac ctgcggcata acggcaatgt cgcccgcaag    600

gccttcctcg gctatgcgaa ggcgcgcgat ccggaactgg cgaagtggat tgaggaaaac    660

gcgaccttcc cgaacggcat ggtcgatcgc atcactccga ccgtctcggc ggaaatcgca    720

aagaagctga acgcagccag cgggctggac gatgatctgc cgctggtggc cgaggatttc    780

catcagtggg tgctggaaga ccagtttgcc aatggtcgtc cccgctgga aaaggcaggc    840

gtgcagttcg tcgatgacgt gacggactgg gaacacgtca agatccggat gctcaatgcc    900

ggtcacatca cgctctgctt cccgggtatt cttgtcggat acgagaacgt ggatgacgcg    960

atcgaggaca aggatctgcg gggcaacctt gagaactacc tgaacaagga cgtcatcccg   1020

accctgaagg caccgccggg catgacgctt gagggttatc gggacagcgt catcagccgc   1080

ttttcgaaca aggccatgtc tgatcagacg ctgcggatcg cgagtgacgg ctgctccaag   1140

atccaggtgt tctggacgga aaccgtgcgc cgggcgattg aaggcaaacg cgacctgtcg   1200

cggatcgcgt tcgggattgc atcttatctc gagatgctcc gcggtcgtga cgagaagggc   1260
```

-continued

```
gggacgtatg aatcgtccga gccgacttat ggcgaggccc agaagaagct ggccaaggcc   1320

gacgattttg aaagtgccct caagctgccg gcgttcgacg gctggcgtga tctggacacg   1380

tccgagctgg accagaaggt catcgcgctg cgcaaggtca tccgcgagaa aggtgtgaag   1440

gccgctattc cggcctga                                                  1458


<210> SEQ ID NO 133
<211> LENGTH: 485
<212> TYPE: PRT
<213> ORGANISM: Gluconobacter oxydans DSM 17078

<400> SEQUENCE: 133

Met Ile Thr Arg Glu Thr Leu Lys Ser Leu Pro Ala Asn Val Gln Ala
1               5                   10                  15

Pro Pro Tyr Asp Ile Asp Gly Ile Lys Pro Gly Ile Val His Phe Gly
            20                  25                  30

Val Gly Asn Phe Phe Arg Ala His Glu Ala Phe Tyr Val Glu Gln Ile
        35                  40                  45

Leu Glu His Ala Pro Asp Trp Ala Ile Val Gly Val Gly Leu Thr Gly
    50                  55                  60

Ser Asp Arg Ser Lys Lys Lys Ala Glu Glu Phe Lys Ala Gln Asp Cys
65                  70                  75                  80

Leu Tyr Ser Leu Thr Glu Thr Ala Pro Ser Gly Lys Ser Thr Val Arg
                85                  90                  95

Val Met Gly Ala Leu Arg Asp Tyr Leu Leu Ala Pro Ala Asp Pro Glu
            100                 105                 110

Ala Val Leu Lys His Leu Val Asp Pro Ala Ile Arg Ile Val Ser Met
        115                 120                 125

Thr Ile Thr Glu Gly Gly Tyr Asn Ile Asn Glu Thr Thr Gly Ala Phe
    130                 135                 140

Asp Leu Glu Asn Ala Ala Val Lys Ala Asp Leu Gln Asn Pro Glu Lys
145                 150                 155                 160

Pro Ser Thr Val Phe Gly Tyr Val Val Glu Ala Leu Arg Arg Arg Arg
                165                 170                 175

Asp Ala Gly Gly Lys Ala Phe Thr Val Met Ser Cys Asp Asn Leu Arg
            180                 185                 190

His Asn Gly Asn Val Ala Arg Lys Ala Phe Leu Gly Tyr Ala Lys Ala
        195                 200                 205

Arg Asp Pro Glu Leu Ala Lys Trp Ile Glu Glu Asn Ala Thr Phe Pro
    210                 215                 220

Asn Gly Met Val Asp Arg Ile Thr Pro Thr Val Ser Ala Glu Ile Ala
225                 230                 235                 240

Lys Lys Leu Asn Ala Ala Ser Gly Leu Asp Asp Asp Leu Pro Leu Val
                245                 250                 255

Ala Glu Asp Phe His Gln Trp Val Leu Glu Asp Gln Phe Ala Asn Gly
            260                 265                 270

Arg Pro Pro Leu Glu Lys Ala Gly Val Gln Phe Val Asp Asp Val Thr
        275                 280                 285

Asp Trp Glu His Val Lys Ile Arg Met Leu Asn Ala Gly His Ile Thr
    290                 295                 300

Leu Cys Phe Pro Gly Ile Leu Val Gly Tyr Glu Asn Val Asp Asp Ala
305                 310                 315                 320

Ile Glu Asp Lys Asp Leu Arg Gly Asn Leu Glu Asn Tyr Leu Asn Lys
                325                 330                 335
```

Asp Val Ile Pro Thr Leu Lys Ala Pro Pro Gly Met Thr Leu Glu Gly
340 345 350

Tyr Arg Asp Ser Val Ile Ser Arg Phe Ser Asn Lys Ala Met Ser Asp
355 360 365

Gln Thr Leu Arg Ile Ala Ser Asp Gly Cys Ser Lys Ile Gln Val Phe
370 375 380

Trp Thr Glu Thr Val Arg Arg Ala Ile Glu Gly Lys Arg Asp Leu Ser
385 390 395 400

Arg Ile Ala Phe Gly Ile Ala Ser Tyr Leu Glu Met Leu Arg Gly Arg
405 410 415

Asp Glu Lys Gly Gly Thr Tyr Glu Ser Ser Glu Pro Thr Tyr Gly Glu
420 425 430

Ala Gln Lys Lys Leu Ala Lys Ala Asp Asp Phe Glu Ser Ala Leu Lys
435 440 445

Leu Pro Ala Phe Asp Gly Trp Arg Asp Leu Asp Thr Ser Glu Leu Asp
450 455 460

Gln Lys Val Ile Ala Leu Arg Lys Val Ile Arg Glu Lys Gly Val Lys
465 470 475 480

Ala Ala Ile Pro Ala
485

<210> SEQ ID NO 134
<211> LENGTH: 20
<212> TYPE: DNA
<213> ORGANISM: Artificial Sequence
<220> FEATURE:
<223> OTHER INFORMATION: primer

<400> SEQUENCE: 134
atgattacgc gcgaaaccct 20

<210> SEQ ID NO 135
<211> LENGTH: 20
<212> TYPE: DNA
<213> ORGANISM: Artificial Sequence
<220> FEATURE:
<223> OTHER INFORMATION: primer

<400> SEQUENCE: 135
tcaggccgga atagcggcct 20

<210> SEQ ID NO 136
<211> LENGTH: 1596
<212> TYPE: DNA
<213> ORGANISM: Gluconobacter oxydans DSM 17078

<400> SEQUENCE: 136
atgacgagcg gttttgatta catcgttgtc ggtggcggtt cggctggctg tgttctcgca 60
gcccgccttt ccgaaaatcc ttccgtccgt gtctgcctca tcgaggcggg ccggcgggac 120
acgcatcccc tgatccatat gccggtcggt ttcgcgaaga tgaccacggg gccgcatacc 180
tgggatcttc tgacggagcc gcagaaacat gcgaacaacc gccagatccc ctatgtgcag 240
ggccggattc tgggcggcgg atcgtccatc aacgcggaag tcttcacgcg gggacaccct 300
tccgatttcg accgctgggc ggcggaaggt gcggatggct ggagcttccg ggatgtccag 360
aagtacttca tccgttccga aggcaatgcc gtgttttcgg gcacctggca tggcacgaac 420
gggccgctcg gggtgtccaa cctcgcagat ccgaacccga ccagccgtgc cttcgtgcag 480

```
agctgtcagg aaatggggct gccctacaac cctgacttca atggcgcatc gcaggaaggg    540

gctggcatct accagatgac catccggaac aaccggcgct gctcgacggc tgtggggtat    600

ctgcgtccgg ccctggggcg gaagaacctg acggttgtga cgcgggcgct ggtcctgaag    660

atcgtcttca acgggacgcg ggcgacgggc gtgcagtata tcgccaacgg caccctgaat    720

accgccgaag cgagccagga aatcgttgtg acggccggag cgatcggaac gccgaagctg    780

atgatgctgt cgggcgtcgg gcctgccgcg catcttcgcg aaaatggtat cccggtcgtg    840

caggatctgc cgggcgtggg cgagaacctt caggaccatt tcggtgtgga tatcgtagcc    900

gagctcaaga cggatgagag cttcgacaag taccggaaac tgcactggat gctgtgggca    960

ggtcttgaat acaccatgtt cagatccggc cccgtcgcgt ccaacgtggt tgagggcggc   1020

gcgttctggt actcggaccc gtcatcgggt gttcctgatc tccagttcca ttttcttgcg   1080

ggggcagggg ctgaggcagg ggtgacgtcc gttcccaagg gcgcgtcggg gattacgctg   1140

aacagctatg tgctgcgtcc gaagtctcgc ggtaccgttc ggctgcgttc ggcagatcca   1200

agggtcaatc cgatggtcga tcccaatttc cttggagacc cggccgacct tgagacgtct   1260

gcggaaggtg tgcggctgag ctacgagatg ttctcccagc cttccttgca gaagcacatc   1320

aaggaaacat gcttctttag cggtaaacag ccgacgatgc agatgtatcg ggactatgcg   1380

cgggaacatg gccggacctc ctatcatccg acatgcacct gcaagatggg gcgggatgac   1440

atgtccgtcg tcgatccgcg tctgaaggtt catggccttg agggcatcag gatctgtgac   1500

agctcggtca tgccgtcgct gctcggttcc aacaccaatg ccgcgacgat catgatcagt   1560

gagcgggcag cggatttcat tcaggggaac gcctga                             1596
```

<210> SEQ ID NO 137
<211> LENGTH: 531
<212> TYPE: PRT
<213> ORGANISM: Gluconobacter oxydans DSM 17078

<400> SEQUENCE: 137

```
Met Thr Ser Gly Phe Asp Tyr Ile Val Val Gly Gly Gly Ser Ala Gly
1               5                   10                  15

Cys Val Leu Ala Ala Arg Leu Ser Glu Asn Pro Ser Val Arg Val Cys
            20                  25                  30

Leu Ile Glu Ala Gly Arg Arg Asp Thr His Pro Leu Ile His Met Pro
        35                  40                  45

Val Gly Phe Ala Lys Met Thr Thr Gly Pro His Thr Trp Asp Leu Leu
    50                  55                  60

Thr Glu Pro Gln Lys His Ala Asn Asn Arg Gln Ile Pro Tyr Val Gln
65                  70                  75                  80

Gly Arg Ile Leu Gly Gly Gly Ser Ser Ile Asn Ala Glu Val Phe Thr
                85                  90                  95

Arg Gly His Pro Ser Asp Phe Asp Arg Trp Ala Ala Glu Gly Ala Asp
            100                 105                 110

Gly Trp Ser Phe Arg Asp Val Gln Lys Tyr Phe Ile Arg Ser Glu Gly
        115                 120                 125

Asn Ala Val Phe Ser Gly Thr Trp His Gly Thr Asn Gly Pro Leu Gly
    130                 135                 140

Val Ser Asn Leu Ala Asp Pro Asn Pro Thr Ser Arg Ala Phe Val Gln
145                 150                 155                 160

Ser Cys Gln Glu Met Gly Leu Pro Tyr Asn Pro Asp Phe Asn Gly Ala
                165                 170                 175
```

-continued

Ser Gln Glu Gly Ala Gly Ile Tyr Gln Met Thr Ile Arg Asn Asn Arg
180 185 190

Arg Cys Ser Thr Ala Val Gly Tyr Leu Arg Pro Ala Leu Gly Arg Lys
195 200 205

Asn Leu Thr Val Val Thr Arg Ala Leu Val Leu Lys Ile Val Phe Asn
210 215 220

Gly Thr Arg Ala Thr Gly Val Gln Tyr Ile Ala Asn Gly Thr Leu Asn
225 230 235 240

Thr Ala Glu Ala Ser Gln Glu Ile Val Val Thr Ala Gly Ala Ile Gly
245 250 255

Thr Pro Lys Leu Met Met Leu Ser Gly Val Gly Pro Ala Ala His Leu
260 265 270

Arg Glu Asn Gly Ile Pro Val Val Gln Asp Leu Pro Gly Val Gly Glu
275 280 285

Asn Leu Gln Asp His Phe Gly Val Asp Ile Val Ala Glu Leu Lys Thr
290 295 300

Asp Glu Ser Phe Asp Lys Tyr Arg Lys Leu His Trp Met Leu Trp Ala
305 310 315 320

Gly Leu Glu Tyr Thr Met Phe Arg Ser Gly Pro Val Ala Ser Asn Val
325 330 335

Val Glu Gly Gly Ala Phe Trp Tyr Ser Asp Pro Ser Ser Gly Val Pro
340 345 350

Asp Leu Gln Phe His Phe Leu Ala Gly Ala Gly Ala Glu Ala Gly Val
355 360 365

Thr Ser Val Pro Lys Gly Ala Ser Gly Ile Thr Leu Asn Ser Tyr Val
370 375 380

Leu Arg Pro Lys Ser Arg Gly Thr Val Arg Leu Arg Ser Ala Asp Pro
385 390 395 400

Arg Val Asn Pro Met Val Asp Pro Asn Phe Leu Gly Asp Pro Ala Asp
405 410 415

Leu Glu Thr Ser Ala Glu Gly Val Arg Leu Ser Tyr Glu Met Phe Ser
420 425 430

Gln Pro Ser Leu Gln Lys His Ile Lys Glu Thr Cys Phe Phe Ser Gly
435 440 445

Lys Gln Pro Thr Met Gln Met Tyr Arg Asp Tyr Ala Arg Glu His Gly
450 455 460

Arg Thr Ser Tyr His Pro Thr Cys Thr Cys Lys Met Gly Arg Asp Asp
465 470 475 480

Met Ser Val Val Asp Pro Arg Leu Lys Val His Gly Leu Glu Gly Ile
485 490 495

Arg Ile Cys Asp Ser Ser Val Met Pro Ser Leu Leu Gly Ser Asn Thr
500 505 510

Asn Ala Ala Thr Ile Met Ile Ser Glu Arg Ala Ala Asp Phe Ile Gln
515 520 525

Gly Asn Ala
530

<210> SEQ ID NO 138
<211> LENGTH: 20
<212> TYPE: DNA
<213> ORGANISM: Artificial Sequence
<220> FEATURE:
<223> OTHER INFORMATION: primer

<400> SEQUENCE: 138
atgacgagcg gttttgatta 20

<210> SEQ ID NO 139
<211> LENGTH: 20
<212> TYPE: DNA
<213> ORGANISM: Artificial Sequence
<220> FEATURE:
<223> OTHER INFORMATION: primer

<400> SEQUENCE: 139
tcaggcgttc ccctgaatga 20

<210> SEQ ID NO 140
<211> LENGTH: 2232
<212> TYPE: DNA
<213> ORGANISM: Gluconobacter oxydans DSM 17078

<400> SEQUENCE: 140
atgcgcagat cccatcttct cgccaccgtt gcctgtgcca cgctggcctg cgcaccgctg 60
gctgccaatg cccagttcgc ccccgcaggc agcggtggct cgccaacctc ctccgtgccg 120
ggccccggca atgccagcgg caattccttc gagccgaccg agaacacgcc ggccgcgaag 180
agccgctttt ccggcccgtc cccctatgcg ccccaggctc cgggtgtgaa tgcggccaac 240
ctgccggata tcgggtccat ggatccgaac gacgttccgc agatggcccc gcagcagagt 300
gccagccccg cctccggaga ctgggccgcc tacggccatg acgacagcca gatgcgctat 360
tcgccgctgt ccgagatcac gccgcagaac gccgatcagc tcaaggttgc tttcgtctat 420
cacaccggca gctatccgcg tccgggccag acgaacaaat gggctgccga aaccaccccg 480
atcaaggtgg gtgacggcct ctacatgtgc tcggcacaga acgacatcat gaagctcgac 540
ccggcgacgg gtaaggagat ctggcgtcac aacatcaacg agaaatacga agccatcccc 600
tacaccgcag cgtgcaaggg cgtgacgtat ttcacgtcgt cgcaggtgcc tgaaggccag 660
ccctgccata accgtatcct tgaaggcacg ctcgacatgc gcctgatcgc ggttgatgcc 720
gcgaccggca atctgtgcga gggcttcggc aatggcggcc aggtcaacct gatgcagggt 780
cttggcgagt ccgtccccgg cttcgtctcc atgacgacgc cgccgccggt cgtgaacggt 840
gtggttgtgg tcaaccacga agttctggat ggtcagcgcc gctgggctcc gtcgggcgtg 900
atccgtggtt atgacgccga gagcggcaag ttcctgtggg cctgggacgt gaaccgcccc 960
gacgatcaca gccagccgac cggcaacaac cattacagcc gtggcacgcc gaactcctgg 1020
gctgcgatga ccggcgacaa tgcgctgggc ctcgtctacg tcccgaccgg caactcggct 1080
tccgactatt acagcgccct gcgtagccct gaagaaaaca aggtctcgtc cgcagttgtc 1140
gcgcttgacg tgaagacagg ttcgccgcgc tgggtcttcc agaccgttca caaggacgtc 1200
tgggactatg acatcggctc gcaggccacg ctcatggaca tgcccggcca ggatggtcag 1260
cctgtccccg cactcatcat gccggccaag cgcggccaga ccttcgtgct cgaccgtcgt 1320
gacggcaagc cgatcctgcc ggtcgaagag cgtcccgctc cgtcgccggg cgtgatcccg 1380
ggcgatccgc gttcgccgac gcagccctgg tccacgggaa tgccggccct gcgcgtgccg 1440
gacctgaaag agacggatat gtggggcatg tcccccatcg accagctctt ctgccgtatc 1500
aagttccgcc gtgcgaacta tacgggtgag ttcacgccgc cgagcgtcga caagccctgg 1560
atcgagtatc cgggctataa cggcggcagc gactggggct ccgtgtccta tgacccgcag 1620
agcggcatcc tgattgcgaa ctggaacatc accccgatgt acgaccagct cgtaactcgc 1680
aagaaggccg acgaacttgg cctgatgccg atcgatgacc cgaactacaa gccgggtggc 1740
ggtggcgccg aaggtaacgg cgccatggac ggcacgcctt acggtatcgt cgtgaccccg 1800
ttctgggatc agtatacggg catgatgtgc aaccgtccgc cctacggcat gatcacggcc 1860
atcgacatga agcacggcca gaaggtgctg tggcagcacc cgctgggaac ggcccgcgcc 1920
aacggtccgt ggggcctgcc gaccggtctt ccctgggaaa tcggtacgcc gaacaatggt 1980
ggctcggtcg tgacggccgg tggcgtggtg ttcatcgcgg cagctacgga taaccagatc 2040
cgtgccatcg acgagcacac cggcaaggtg gtctggagcg cggtcctgcc gggcggcggt 2100
caggccaacc cgatgaccta cgaggccaat ggtcatcagt acgtcgccat tatggcgggt 2160
ggtcatcact tcatgatgac gccggtcagc gatcagctgg tggtttacgc cctgcccgat 2220
cacaagggct ga 2232

<210> SEQ ID NO 141
<211> LENGTH: 743
<212> TYPE: PRT
<213> ORGANISM: Gluconobacter oxydans DSM 17078

<400> SEQUENCE: 141

Met Arg Arg Ser His Leu Leu Ala Thr Val Ala Cys Ala Thr Leu Ala
1 5 10 15

Cys Ala Pro Leu Ala Ala Asn Ala Gln Phe Ala Pro Ala Gly Ser Gly
20 25 30

Gly Ser Pro Thr Ser Ser Val Pro Gly Pro Gly Asn Ala Ser Gly Asn
35 40 45

Ser Phe Glu Pro Thr Glu Asn Thr Pro Ala Ala Lys Ser Arg Phe Ser
50 55 60

Gly Pro Ser Pro Tyr Ala Pro Gln Ala Pro Gly Val Asn Ala Ala Asn
65 70 75 80

Leu Pro Asp Ile Gly Ser Met Asp Pro Asn Asp Val Pro Gln Met Ala
85 90 95

Pro Gln Gln Ser Ala Ser Pro Ala Ser Gly Asp Trp Ala Ala Tyr Gly
100 105 110

His Asp Asp Ser Gln Met Arg Tyr Ser Pro Leu Ser Glu Ile Thr Pro
115 120 125

Gln Asn Ala Asp Gln Leu Lys Val Ala Phe Val Tyr His Thr Gly Ser
130 135 140

Tyr Pro Arg Pro Gly Gln Thr Asn Lys Trp Ala Ala Glu Thr Thr Pro
145 150 155 160

Ile Lys Val Gly Asp Gly Leu Tyr Met Cys Ser Ala Gln Asn Asp Ile
165 170 175

Met Lys Leu Asp Pro Ala Thr Gly Lys Glu Ile Trp Arg His Asn Ile
180 185 190

Asn Glu Lys Tyr Glu Ala Ile Pro Tyr Thr Ala Ala Cys Lys Gly Val
195 200 205

Thr Tyr Phe Thr Ser Ser Gln Val Pro Glu Gly Gln Pro Cys His Asn
210 215 220

Arg Ile Leu Glu Gly Thr Leu Asp Met Arg Leu Ile Ala Val Asp Ala
225 230 235 240

Ala Thr Gly Asn Leu Cys Glu Gly Phe Gly Asn Gly Gly Gln Val Asn
245 250 255

Leu Met Gln Gly Leu Gly Glu Ser Val Pro Gly Phe Val Ser Met Thr
260 265 270

Thr Pro Pro Pro Val Val Asn Gly Val Val Val Val Asn His Glu Val

-continued

```
        275                 280                 285

Leu Asp Gly Gln Arg Arg Trp Ala Pro Ser Gly Val Ile Arg Gly Tyr
    290                 295                 300

Asp Ala Glu Ser Gly Lys Phe Leu Trp Ala Trp Asp Val Asn Arg Pro
305                 310                 315                 320

Asp Asp His Ser Gln Pro Thr Gly Asn Asn His Tyr Ser Arg Gly Thr
                325                 330                 335

Pro Asn Ser Trp Ala Ala Met Thr Gly Asp Asn Ala Leu Gly Leu Val
            340                 345                 350

Tyr Val Pro Thr Gly Asn Ser Ala Ser Asp Tyr Tyr Ser Ala Leu Arg
        355                 360                 365

Ser Pro Glu Glu Asn Lys Val Ser Ser Ala Val Val Ala Leu Asp Val
    370                 375                 380

Lys Thr Gly Ser Pro Arg Trp Val Phe Gln Thr Val His Lys Asp Val
385                 390                 395                 400

Trp Asp Tyr Asp Ile Gly Ser Gln Ala Thr Leu Met Asp Met Pro Gly
                405                 410                 415

Gln Asp Gly Gln Pro Val Pro Ala Leu Ile Met Pro Ala Lys Arg Gly
            420                 425                 430

Gln Thr Phe Val Leu Asp Arg Arg Asp Gly Lys Pro Ile Leu Pro Val
        435                 440                 445

Glu Glu Arg Pro Ala Pro Ser Pro Gly Val Ile Pro Gly Asp Pro Arg
    450                 455                 460

Ser Pro Thr Gln Pro Trp Ser Thr Gly Met Pro Ala Leu Arg Val Pro
465                 470                 475                 480

Asp Leu Lys Glu Thr Asp Met Trp Gly Met Ser Pro Ile Asp Gln Leu
                485                 490                 495

Phe Cys Arg Ile Lys Phe Arg Arg Ala Asn Tyr Thr Gly Glu Phe Thr
            500                 505                 510

Pro Pro Ser Val Asp Lys Pro Trp Ile Glu Tyr Pro Gly Tyr Asn Gly
        515                 520                 525

Gly Ser Asp Trp Gly Ser Val Ser Tyr Asp Pro Gln Ser Gly Ile Leu
    530                 535                 540

Ile Ala Asn Trp Asn Ile Thr Pro Met Tyr Asp Gln Leu Val Thr Arg
545                 550                 555                 560

Lys Lys Ala Asp Glu Leu Gly Leu Met Pro Ile Asp Asp Pro Asn Tyr
                565                 570                 575

Lys Pro Gly Gly Gly Gly Ala Glu Gly Asn Gly Ala Met Asp Gly Thr
            580                 585                 590

Pro Tyr Gly Ile Val Val Thr Pro Phe Trp Asp Gln Tyr Thr Gly Met
        595                 600                 605

Met Cys Asn Arg Pro Pro Tyr Gly Met Ile Thr Ala Ile Asp Met Lys
    610                 615                 620

His Gly Gln Lys Val Leu Trp Gln His Pro Leu Gly Thr Ala Arg Ala
625                 630                 635                 640

Asn Gly Pro Trp Gly Leu Pro Thr Gly Leu Pro Trp Glu Ile Gly Thr
                645                 650                 655

Pro Asn Asn Gly Gly Ser Val Val Thr Ala Gly Gly Val Val Phe Ile
            660                 665                 670

Ala Ala Ala Thr Asp Asn Gln Ile Arg Ala Ile Asp Glu His Thr Gly
        675                 680                 685

Lys Val Val Trp Ser Ala Val Leu Pro Gly Gly Gly Gln Ala Asn Pro
    690                 695                 700
```

Met Thr Tyr Glu Ala Asn Gly His Gln Tyr Val Ala Ile Met Ala Gly
705 710 715 720

Gly His His Phe Met Met Thr Pro Val Ser Asp Gln Leu Val Val Tyr
725 730 735

Ala Leu Pro Asp His Lys Gly
740

<210> SEQ ID NO 142
<211> LENGTH: 20
<212> TYPE: DNA
<213> ORGANISM: Artificial Sequence
<220> FEATURE:
<223> OTHER INFORMATION: primer

<400> SEQUENCE: 142
atgcgcagat cccatcttct 20

<210> SEQ ID NO 143
<211> LENGTH: 20
<212> TYPE: DNA
<213> ORGANISM: Artificial Sequence
<220> FEATURE:
<223> OTHER INFORMATION: primer

<400> SEQUENCE: 143
tcagcccttg tgatcgggca 20

<210> SEQ ID NO 144
<211> LENGTH: 381
<212> TYPE: DNA
<213> ORGANISM: Gluconobacter oxydans DSM 17078

<400> SEQUENCE: 144
atgccgaata cttatggcag cagaaccctg accgagtggc tcacactggt cctaggggtt 60
gtcatcattc tggtggggct gttcttcgtg atcgccgggg ccgacctcgc gatgctgggc 120
ggctctgtct attacgtcat ctgtggcatt ccgctggttg ccggcggtgt tttcatgctc 180
atgggacgga cgcttggcgc attcctgtat ctgggtgcgc tggcctacac ctgggtctgg 240
tccctgtggg aagtgggctt cagccccgtt gaccttctgc cgcgcgattt cggcccgacg 300
ctgctgggca tccttgtcgc cctcaccatt ccggttcttc gccggatgga aacccgccgt 360
accctgaggg gaaccgtctg a 381

<210> SEQ ID NO 145
<211> LENGTH: 126
<212> TYPE: PRT
<213> ORGANISM: Gluconobacter oxydans DSM 17078

<400> SEQUENCE: 145

Met Pro Asn Thr Tyr Gly Ser Arg Thr Leu Thr Glu Trp Leu Thr Leu
1 5 10 15

Val Leu Gly Val Val Ile Ile Leu Val Gly Leu Phe Phe Val Ile Ala
20 25 30

Gly Ala Asp Leu Ala Met Leu Gly Gly Ser Val Tyr Tyr Val Ile Cys
35 40 45

Gly Ile Pro Leu Val Ala Gly Gly Val Phe Met Leu Met Gly Arg Thr
50 55 60

Leu Gly Ala Phe Leu Tyr Leu Gly Ala Leu Ala Tyr Thr Trp Val Trp
65 70 75 80

```
Ser Leu Trp Glu Val Gly Phe Ser Pro Val Asp Leu Leu Pro Arg Asp
                85                  90                  95

Phe Gly Pro Thr Leu Leu Gly Ile Leu Val Ala Leu Thr Ile Pro Val
            100                 105                 110

Leu Arg Arg Met Glu Thr Arg Arg Thr Leu Arg Gly Thr Val
        115                 120                 125
```

```
<210> SEQ ID NO 146
<211> LENGTH: 20
<212> TYPE: DNA
<213> ORGANISM: Artificial Sequence
<220> FEATURE:
<223> OTHER INFORMATION: primer

<400> SEQUENCE: 146

atgccgaata cttatggcag                                                   20


<210> SEQ ID NO 147
<211> LENGTH: 20
<212> TYPE: DNA
<213> ORGANISM: Artificial Sequence
<220> FEATURE:
<223> OTHER INFORMATION: primer

<400> SEQUENCE: 147

tcagacggtt cccctcaggg                                                   20


<210> SEQ ID NO 148
<211> LENGTH: 516
<212> TYPE: DNA
<213> ORGANISM: Gluconobacter oxydans DSM 17078

<400> SEQUENCE: 148

atgtttggct tgtcggctct attcctggcg cgtttccagt tcgcgtttac ggtcgggttc      60

cacatcgtgt tcccggcatt ctcgatcggt ctcgcagcct atctcgcagt cctcgaaggc     120

ctgtggctca aaacgggtcg cagcgcctat ctcgaccttt tcaaatactg gctcaaagtt     180

ttctccgtcg tcttcggcat gggggtggtc tccggcctcg tcatgtccta cgaattcgga     240

acaaactggt cgtcgttctc ccagaaagcc ggtccgatcc tcggcccgat gctggcctac     300

gaggtcatga cggccttctt ccttgaagcc ggcttcctcg gcgtcatgat gttcggcctc     360

aaccgcgtcg gcaaaggcct gcacttcgca gccacctgca tggtctcgat cggcacgctg     420

atctccatga gctggatcct gtcgtccaat tcctggatgc agacgccccc gcggttatcg     480

catcgacgag gccaccggcc ggttcctgcc ggttga                                516


<210> SEQ ID NO 149
<211> LENGTH: 171
<212> TYPE: PRT
<213> ORGANISM: Gluconobacter oxydans DSM 17078

<400> SEQUENCE: 149

Met Phe Gly Leu Ser Ala Leu Phe Leu Ala Arg Phe Gln Phe Ala Phe
1               5                   10                  15

Thr Val Gly Phe His Ile Val Phe Pro Ala Phe Ser Ile Gly Leu Ala
            20                  25                  30

Ala Tyr Leu Ala Val Leu Glu Gly Leu Trp Leu Lys Thr Gly Arg Ser
        35                  40                  45

Ala Tyr Leu Asp Leu Phe Lys Tyr Trp Leu Lys Val Phe Ser Val Val
    50                  55                  60
```

```
Phe Gly Met Gly Val Val Ser Gly Leu Val Met Ser Tyr Glu Phe Gly
65                  70                  75                  80

Thr Asn Trp Ser Ser Phe Ser Gln Lys Ala Gly Pro Ile Leu Gly Pro
                85                  90                  95

Met Leu Ala Tyr Glu Val Met Thr Ala Phe Phe Leu Glu Ala Gly Phe
            100                 105                 110

Leu Gly Val Met Met Phe Gly Leu Asn Arg Val Gly Lys Gly Leu His
        115                 120                 125

Phe Ala Ala Thr Cys Met Val Ser Ile Gly Thr Leu Ile Ser Met Ser
    130                 135                 140

Trp Ile Leu Ser Ser Asn Ser Trp Met Gln Thr Pro Pro Arg Leu Ser
145                 150                 155                 160

His Arg Arg Gly His Arg Pro Val Pro Ala Gly
                165                 170


<210> SEQ ID NO 150
<211> LENGTH: 20
<212> TYPE: DNA
<213> ORGANISM: Artificial Sequence
<220> FEATURE:
<223> OTHER INFORMATION: primer

<400> SEQUENCE: 150

atgtttggct tgtcggctct                                                  20


<210> SEQ ID NO 151
<211> LENGTH: 20
<212> TYPE: DNA
<213> ORGANISM: Artificial Sequence
<220> FEATURE:
<223> OTHER INFORMATION: primer

<400> SEQUENCE: 151

tcaaccggca ggaaccggcc                                                  20


<210> SEQ ID NO 152
<211> LENGTH: 912
<212> TYPE: DNA
<213> ORGANISM: Gluconobacter oxydans DSM 17078

<400> SEQUENCE: 152

tggtggcaga tcgtcttcaa cccctccttc ccgtaccgca tcgtgcacat gggcctcgca      60

gccttcctgt gcgtggcgtt catcgtcgcg ggcgttgccg gatggcatct gctcaaggcc     120

cgtcgtgaag gccgtcaggc ctccgaacag gttcgcctga tgttctccat ggccatgtgg     180

atggccgcca tcgtctcccc gatccaggtt ctggccggcg atacgcaggg cctgaacacg     240

ctggaatacc agcccgccaa gatcgctgcc ctcgaaggcg actgggagtc cgaaagccgc     300

gctccggagc ttctgttcgg cattccggac atgaagaacg agacgacgca tttcaagatc     360

gccatcccct atctgggttc gctgatcctg acgcacagcc tcgatggcaa ggttccgggc     420

ctgaaggact atccgaagga agaccgtccc tactccccgc tgctgttctt ctctttccgc     480

atcatgatcg cactcggcat gctgatggtg ctggtcggac tgtggtcgct gtatctgcgc     540

tggaagggca agctgtacga tacgccgctt ctgcaccgta tcgcgctgtt catgtcgcct     600

gcgggcttcc tggcactgct ctgcggctgg atcacgactg aagtcggccg tcagcccttc     660

acggtctatg gcctgctgcg gacgtccgac agcgtctccc cgatcgccct gccgaacatc     720

gcgacgtcga tgatcgcttt cgtcatcgtc tatttcatcg tgttcacggg cggcatcacc     780
```

atcctgctgc ggaccttcgc cgaagagccc catccggatc agcatggtcc ggccgaagat 840
cagccccagc gcgctgcggg tacaacacag gtctcccatc agccccagcc cgacgctggc 900
atggcggagt aa 912

<210> SEQ ID NO 153
<211> LENGTH: 303
<212> TYPE: PRT
<213> ORGANISM: Gluconobacter oxydans DSM 17078

<400> SEQUENCE: 153

```
Trp Trp Gln Ile Val Phe Asn Pro Ser Phe Pro Tyr Arg Ile Val His
1               5                   10                  15

Met Gly Leu Ala Ala Phe Leu Cys Val Ala Phe Ile Val Ala Gly Val
            20                  25                  30

Ala Gly Trp His Leu Leu Lys Ala Arg Arg Glu Gly Arg Gln Ala Ser
        35                  40                  45

Glu Gln Val Arg Leu Met Phe Ser Met Ala Met Trp Met Ala Ala Ile
    50                  55                  60

Val Ser Pro Ile Gln Val Leu Ala Gly Asp Thr Gln Gly Leu Asn Thr
65                  70                  75                  80

Leu Glu Tyr Gln Pro Ala Lys Ile Ala Ala Leu Glu Gly Asp Trp Glu
                85                  90                  95

Ser Glu Ser Arg Ala Pro Glu Leu Leu Phe Gly Ile Pro Asp Met Lys
            100                 105                 110

Asn Glu Thr Thr His Phe Lys Ile Ala Ile Pro Tyr Leu Gly Ser Leu
        115                 120                 125

Ile Leu Thr His Ser Leu Asp Gly Lys Val Pro Gly Leu Lys Asp Tyr
    130                 135                 140

Pro Lys Glu Asp Arg Pro Tyr Ser Pro Leu Leu Phe Phe Ser Phe Arg
145                 150                 155                 160

Ile Met Ile Ala Leu Gly Met Leu Met Val Leu Val Gly Leu Trp Ser
                165                 170                 175

Leu Tyr Leu Arg Trp Lys Gly Lys Leu Tyr Asp Thr Pro Leu Leu His
            180                 185                 190

Arg Ile Ala Leu Phe Met Ser Pro Ala Gly Phe Leu Ala Leu Leu Cys
        195                 200                 205

Gly Trp Ile Thr Thr Glu Val Gly Arg Gln Pro Phe Thr Val Tyr Gly
    210                 215                 220

Leu Leu Arg Thr Ser Asp Ser Val Ser Pro Ile Ala Leu Pro Asn Ile
225                 230                 235                 240

Ala Thr Ser Met Ile Ala Phe Val Ile Val Tyr Phe Ile Val Phe Thr
                245                 250                 255

Gly Gly Ile Thr Ile Leu Leu Arg Thr Phe Ala Glu Glu Pro His Pro
            260                 265                 270

Asp Gln His Gly Pro Ala Glu Asp Gln Pro Gln Arg Ala Ala Gly Thr
        275                 280                 285

Thr Gln Val Ser His Gln Pro Gln Pro Asp Ala Gly Met Ala Glu
    290                 295                 300
```

<210> SEQ ID NO 154
<211> LENGTH: 20
<212> TYPE: DNA
<213> ORGANISM: Artificial Sequence
<220> FEATURE:
<223> OTHER INFORMATION: primer -continued

<400> SEQUENCE: 154
tggtggcaga tcgtcttcaa                                                  20

<210> SEQ ID NO 155
<211> LENGTH: 20
<212> TYPE: DNA
<213> ORGANISM: Artificial Sequence
<220> FEATURE:
<223> OTHER INFORMATION: primer

<400> SEQUENCE: 155
ttactccgcc atgccagcgt                                                  20

<210> SEQ ID NO 156
<211> LENGTH: 1026
<212> TYPE: DNA
<213> ORGANISM: Gluconobacter oxydans DSM 17078

<400> SEQUENCE: 156
atgacagaaa cagccggctt ctggctcccg gtggtctggg cgctgctcgc agcaaccgcc      60
atcttcctct atatctgcct cgatggcttc gacctcggga tcggcatcct ctttctcaag     120
gaaaaggacc acgatcaccg caacctcatg gtcaacaccg tcgcccctgt ctgggacggc     180
aacgagacct ggatgatctt cggtggcgcc gcgctctacg gcgtcttccc cgtggcttac     240
ggcacgatcc tcccggcgct ctacctgccg gtcctgttca tgctgctggc cctgatcctg     300
cgcggcgtgt ccttcgagtt ccgcttcaag tcggaatcgc cgatgagcca gttcttctgg     360
gacacggcct tctgcggcgg ctccttcgtg gcggccttca tgcagggcgt catcctcgga     420
acgctcgtcc agggcataaa ggtcgagaac aacgtgttcg tcgggtccag cttcgactgg     480
ttctccccgt tcgccctgtt ctgtggcctt gccgtggtca tcggctatgc gcttctcggc     540
gcaacctggc tcctgtggcg ctgcgagggt gaactgcacg acacgatgcg cagggtttcc     600
ttcggtctcg gcgcgctgat gctgatcacg atcgcactgg tttccatctg gacgcccatg     660
ctgcacacca cctacatgca gcactggctc gccatgccgc agtttgcact ggtcgctccg     720
gtgccagtcg ctgtcatcgt gctgacgggc gtcctgttca tggggctgcg caacccgcgc     780
tcgcacctgc tgccgttcgt cgcaacgctg ggcctgttct tcctgtgctt cagcggcctt     840
ggcatcaatg tgtggcccta catcgtgccc ccgaccatca ccatctggca ggcttcctct     900
ccgccggaga gccagacctt cctgctggtc ggcacgatgt tcctgctacc gctgatcctc     960
tcctacacgg cctattcgta ctacgtgttc cgcggaaaga tgtccgccgg acatcactac    1020
cactga                                                               1026

<210> SEQ ID NO 157
<211> LENGTH: 341
<212> TYPE: PRT
<213> ORGANISM: Gluconobacter oxydans DSM 17078

<400> SEQUENCE: 157

Met Thr Glu Thr Ala Gly Phe Trp Leu Pro Val Val Trp Ala Leu Leu
1               5                   10                  15

Ala Ala Thr Ala Ile Phe Leu Tyr Ile Cys Leu Asp Gly Phe Asp Leu
            20                  25                  30

Gly Ile Gly Ile Leu Phe Leu Lys Glu Lys Asp His Asp His Arg Asn
        35                  40                  45

Leu Met Val Asn Thr Val Ala Pro Val Trp Asp Gly Asn Glu Thr Trp
    50                  55                  60

```
Met Ile Phe Gly Gly Ala Ala Leu Tyr Gly Val Phe Pro Val Ala Tyr
65                  70                  75                  80

Gly Thr Ile Leu Pro Ala Leu Tyr Leu Pro Val Leu Phe Met Leu Leu
                85                  90                  95

Ala Leu Ile Leu Arg Gly Val Ser Phe Glu Phe Arg Phe Lys Ser Glu
            100                 105                 110

Ser Pro Met Ser Gln Phe Phe Trp Asp Thr Ala Phe Cys Gly Gly Ser
        115                 120                 125

Phe Val Ala Ala Phe Met Gln Gly Val Ile Leu Gly Thr Leu Val Gln
    130                 135                 140

Gly Ile Lys Val Glu Asn Asn Val Phe Val Gly Ser Ser Phe Asp Trp
145                 150                 155                 160

Phe Ser Pro Phe Ala Leu Phe Cys Gly Leu Ala Val Val Ile Gly Tyr
                165                 170                 175

Ala Leu Leu Gly Ala Thr Trp Leu Leu Trp Arg Cys Glu Gly Glu Leu
            180                 185                 190

His Asp Thr Met Arg Arg Val Ser Phe Gly Leu Gly Ala Leu Met Leu
        195                 200                 205

Ile Thr Ile Ala Leu Val Ser Ile Trp Thr Pro Met Leu His Thr Thr
    210                 215                 220

Tyr Met Gln His Trp Leu Ala Met Pro Gln Phe Ala Leu Val Ala Pro
225                 230                 235                 240

Val Pro Val Ala Val Ile Val Leu Thr Gly Val Leu Phe Met Gly Leu
                245                 250                 255

Arg Asn Pro Arg Ser His Leu Leu Pro Phe Val Ala Thr Leu Gly Leu
            260                 265                 270

Phe Phe Leu Cys Phe Ser Gly Leu Gly Ile Asn Val Trp Pro Tyr Ile
        275                 280                 285

Val Pro Pro Thr Ile Thr Ile Trp Gln Ala Ser Ser Pro Pro Glu Ser
    290                 295                 300

Gln Thr Phe Leu Leu Val Gly Thr Met Phe Leu Leu Pro Leu Ile Leu
305                 310                 315                 320

Ser Tyr Thr Ala Tyr Ser Tyr Tyr Val Phe Arg Gly Lys Met Ser Ala
                325                 330                 335

Gly His His Tyr His
            340


<210> SEQ ID NO 158
<211> LENGTH: 20
<212> TYPE: DNA
<213> ORGANISM: Artificial Sequence
<220> FEATURE:
<223> OTHER INFORMATION: primer

<400> SEQUENCE: 158

atgacagaaa cagccggctt                                                  20


<210> SEQ ID NO 159
<211> LENGTH: 20
<212> TYPE: DNA
<213> ORGANISM: Artificial Sequence
<220> FEATURE:
<223> OTHER INFORMATION: primer

<400> SEQUENCE: 159

tcagtggtag tgatgtccgg                                                  20
```

<210> SEQ ID NO 160
<211> LENGTH: 936
<212> TYPE: DNA
<213> ORGANISM: Gluconobacter oxydans DSM 17078

<400> SEQUENCE: 160
atgaaagcag gaccgatgaa aaaactctgg cgatatctcc cagcgttgcc ggcgctgatg 60
ctatcgggtt gtacggttga tctgcttcag ccgcgcggcc cggtcgcaga aatgaaccgc 120
gatgtcatgg tggcggaatt cgtcatcatg atgctggtcg tggttcccac ctgcgccgcg 180
acgctttatt ttgcgtggaa gtatcgtgct tccaacaaag aggccgaata cctcccgacc 240
tgggatcatt cgaccgcaat cgaatatgtc atctggggcg ttcccgccat tctgatcgcc 300
cttctgggtg ccatcagctg gtggagcacg catgcttatg acccgtaccg cccgcttcag 360
acggctgaca acgtcaagcc cctgaatgtc caggtggtct ctctcgactg gaagtggatg 420
ttcatctatc cggacctggg gatcgcaacg atcaaccagc tggatgttcc gacgaacacg 480
ccgctgaact tccagatcac gtctgattcc gtcatgacgt cgttcttcat cccccgtctg 540
ggttcgatga tctacgccat gccgggtgaa cagacccagc tgcatctgct tgcaagtgaa 600
tccggggatt acctgggtga ggcttcacag ttcagcggcc gtggtttctc ggatatgaag 660
ttccgtaccc tcgccatgga tccggctcag ttcaacgact gggttgagaa ggtgaagagc 720
ggaagcgaaa atctcgacga caccacatac ccgaaatatg ctgcaccgca ggaagctgca 780
ccggtacagt atttcgcgca tgtccagccg gatctcttcg acggcatcgt tgccaagtac 840
aacaacggca tgatggtgga caagaagacg ggcaaggtca tgcacatgca gtctgcttcc 900
aacgctgcac cgtccgacac tggcatgaag gaataa 936

<210> SEQ ID NO 161
<211> LENGTH: 311
<212> TYPE: PRT
<213> ORGANISM: Gluconobacter oxydans DSM 17078

<400> SEQUENCE: 161

Met Lys Ala Gly Pro Met Lys Lys Leu Trp Arg Tyr Leu Pro Ala Leu
1 5 10 15

Pro Ala Leu Met Leu Ser Gly Cys Thr Val Asp Leu Leu Gln Pro Arg
20 25 30

Gly Pro Val Ala Glu Met Asn Arg Asp Val Met Val Ala Glu Phe Val
35 40 45

Ile Met Met Leu Val Val Val Pro Thr Cys Ala Ala Thr Leu Tyr Phe
50 55 60

Ala Trp Lys Tyr Arg Ala Ser Asn Lys Glu Ala Glu Tyr Leu Pro Thr
65 70 75 80

Trp Asp His Ser Thr Ala Ile Glu Tyr Val Ile Trp Gly Val Pro Ala
85 90 95

Ile Leu Ile Ala Leu Leu Gly Ala Ile Ser Trp Trp Ser Thr His Ala
100 105 110

Tyr Asp Pro Tyr Arg Pro Leu Gln Thr Ala Asp Asn Val Lys Pro Leu
115 120 125

Asn Val Gln Val Val Ser Leu Asp Trp Lys Trp Met Phe Ile Tyr Pro
130 135 140

Asp Leu Gly Ile Ala Thr Ile Asn Gln Leu Asp Val Pro Thr Asn Thr
145 150 155 160

Pro Leu Asn Phe Gln Ile Thr Ser Asp Ser Val Met Thr Ser Phe Phe

```
                165                 170                 175

Ile Pro Arg Leu Gly Ser Met Ile Tyr Ala Met Pro Gly Glu Gln Thr
            180                 185                 190

Gln Leu His Leu Leu Ala Ser Glu Ser Gly Asp Tyr Leu Gly Glu Ala
        195                 200                 205

Ser Gln Phe Ser Gly Arg Gly Phe Ser Asp Met Lys Phe Arg Thr Leu
    210                 215                 220

Ala Met Asp Pro Ala Gln Phe Asn Asp Trp Val Glu Lys Val Lys Ser
225                 230                 235                 240

Gly Ser Glu Asn Leu Asp Asp Thr Thr Tyr Pro Lys Tyr Ala Ala Pro
                245                 250                 255

Gln Glu Ala Ala Pro Val Gln Tyr Phe Ala His Val Gln Pro Asp Leu
            260                 265                 270

Phe Asp Gly Ile Val Ala Lys Tyr Asn Asn Gly Met Met Val Asp Lys
        275                 280                 285

Lys Thr Gly Lys Val Met His Met Gln Ser Ala Ser Asn Ala Ala Pro
    290                 295                 300

Ser Asp Thr Gly Met Lys Glu
305                 310


<210> SEQ ID NO 162
<211> LENGTH: 20
<212> TYPE: DNA
<213> ORGANISM: Artificial Sequence
<220> FEATURE:
<223> OTHER INFORMATION: primer

<400> SEQUENCE: 162

atgaaagcag gaccgatgaa                                                   20


<210> SEQ ID NO 163
<211> LENGTH: 20
<212> TYPE: DNA
<213> ORGANISM: Artificial Sequence
<220> FEATURE:
<223> OTHER INFORMATION: primer

<400> SEQUENCE: 163

ttattccttc atgccagtgt                                                   20


<210> SEQ ID NO 164
<211> LENGTH: 1989
<212> TYPE: DNA
<213> ORGANISM: Gluconobacter oxydans DSM 17078

<400> SEQUENCE: 164

atgctcggaa aactctcctt atcagccata ccgttggatg tgccgattct tgtcggtacg       60

ttcattggtg ttgctgtcat cggtctcgcc gtactgggtg ctgtcaccta ttatggcaaa      120

tggggctatc tctggcgcga ctggctgacg actgtcgacc acaagcgtct tgccgtaatg      180

tacatcatcc tggcgatcgt catgctgttc cgcggttttg cggacgccat catgatgcgt      240

acccagctcg cgctggctta caagggtaat cccggttacc tgccgcctca tcactacgac      300

cagatcttct ccgctcacgg caccatcatg atcttcttca tggcgatggc gttcatgacg      360

ggcctgatga acctggttgt tccccttcag atcggtgccc gcgacgttgc gttcccgttc      420

ctgaactcgc tcagcttcta tatgacgctg gtcggtgccc tgctgatcaa catctcgctg      480

ttcatcggtg agtttgctca gtgcggctgg ctggtttacc cgcctctgtc cgaaatgcag      540
```

-continued ttcagcccgg gtgtcggcgt tgactactat atctgggccg ttcagatctc cggtgtcggt 600
acgctgctga cgggcgtgaa cttcttcacg accatcgtca agatgcgtgc gcctggcatg 660
ggctggatgc agatgccggt cttcacgtgg actgctttct gcacgaccgt tctgatcatg 720
gtgtccttcc cggttctgac ggtgacgctg gctctgctca gccttgaccg ttacctcggc 780
atgcacttct tcacgaacga tgccggcggc aacgtcatgc tttacctcag catgatctgg 840
acctggggcc atccggaagt ttacatcctt gtcattccgg cattcggtgt tttctccgaa 900
gtcactgcaa cgttctccca gaagccgctc ttcggctaca agacgatggt gtacgccacg 960
tgctccatca tggtgctctc cttcgtcgtg tgggtgcatc acttcttcac catgggtgcc 1020
ggtgccaacg tcaatacctt cttcggtatc atgacgatga tcatcgccgt cccgacgggt 1080
gtgaagatct tcaactggct gttcacgatg tataagggcc gcgtggaatt cacggctccg 1140
atgcactgga cgctcggctt catgatcacc ttctccatcg gtggtatgac cggtgtcatg 1200
atggccatgc cggccgctga ctggatcctg cataactccc tgttcctgat tgcccacttc 1260
cacaacgtca tcatcggcgg tgtgtacttc ggctacattg caggtatggg tttctggttc 1320
ccgaaggctt tcggcttcaa gctgaacgaa gcctggggca agcgcgcttt ctggtgctgg 1380
ttcgtcggtt tctacctggc cttcattccg ctttatgtcc tcggcctcga aggcatgacg 1440
cgtcgtatga accactatga caaccccgac tggtatccgt ggatgctcgt tgctgaagtt 1500
ggtgcaatcg ttatcgctct cggtatcgtc tgccagctca cgcagctcta cgtttccatc 1560
cgtgaccgta acctgcccga gaaccttgat ctgacgggtg atccgtggaa cggccgtacg 1620
ctggagtggt ccatttcttc tccgccgccg gcttataact tcgcggtcat tcctgacatt 1680
catggtctcg acacgttcca caccgagaag cagctgggtc tgaaggctca cggcaagccg 1740
ctggctccga tccacatgcc gaagaacaca tctgctggtg tcttcatcgg tctgttcagc 1800
ttcatcctcg gtttcgcttc gatctggtac atctggtggc tcgctgccat cggcctgatc 1860
ggtatcgttg caaccatgat cctgcgcagc gccaaccgcg acgtcgacta ctatgtcccg 1920
gtgagcgaaa tcgagcacaa cgaggaagtc tattctcgtc gtatcgctgc tgcgcaggca 1980
gcagagtaa 1989

<210> SEQ ID NO 165
<211> LENGTH: 662
<212> TYPE: PRT
<213> ORGANISM: Gluconobacter oxydans DSM 17078

<400> SEQUENCE: 165

Met Leu Gly Lys Leu Ser Leu Ser Ala Ile Pro Leu Asp Val Pro Ile
1 5 10 15

Leu Val Gly Thr Phe Ile Gly Val Ala Val Ile Gly Leu Ala Val Leu
20 25 30

Gly Ala Val Thr Tyr Tyr Gly Lys Trp Gly Tyr Leu Trp Arg Asp Trp
35 40 45

Leu Thr Thr Val Asp His Lys Arg Leu Ala Val Met Tyr Ile Ile Leu
50 55 60

Ala Ile Val Met Leu Phe Arg Gly Phe Ala Asp Ala Ile Met Met Arg
65 70 75 80

Thr Gln Leu Ala Leu Ala Tyr Lys Gly Asn Pro Gly Tyr Leu Pro Pro
85 90 95

His His Tyr Asp Gln Ile Phe Ser Ala His Gly Thr Ile Met Ile Phe
100 105 110

-continued

```
Phe Met Ala Met Ala Phe Met Thr Gly Leu Met Asn Leu Val Val Pro
        115                 120                 125

Leu Gln Ile Gly Ala Arg Asp Val Ala Phe Pro Phe Leu Asn Ser Leu
    130                 135                 140

Ser Phe Tyr Met Thr Leu Val Gly Ala Leu Leu Ile Asn Ile Ser Leu
145                 150                 155                 160

Phe Ile Gly Glu Phe Ala Gln Cys Gly Trp Leu Val Tyr Pro Pro Leu
                165                 170                 175

Ser Glu Met Gln Phe Ser Pro Gly Val Gly Val Asp Tyr Tyr Ile Trp
            180                 185                 190

Ala Val Gln Ile Ser Gly Val Gly Thr Leu Leu Thr Gly Val Asn Phe
        195                 200                 205

Phe Thr Thr Ile Val Lys Met Arg Ala Pro Gly Met Gly Trp Met Gln
    210                 215                 220

Met Pro Val Phe Thr Trp Thr Ala Phe Cys Thr Thr Val Leu Ile Met
225                 230                 235                 240

Val Ser Phe Pro Val Leu Thr Val Thr Leu Ala Leu Leu Ser Leu Asp
                245                 250                 255

Arg Tyr Leu Gly Met His Phe Phe Thr Asn Asp Ala Gly Gly Asn Val
            260                 265                 270

Met Leu Tyr Leu Ser Met Ile Trp Thr Trp Gly His Pro Glu Val Tyr
        275                 280                 285

Ile Leu Val Ile Pro Ala Phe Gly Val Phe Ser Glu Val Thr Ala Thr
    290                 295                 300

Phe Ser Gln Lys Pro Leu Phe Gly Tyr Lys Thr Met Val Tyr Ala Thr
305                 310                 315                 320

Cys Ser Ile Met Val Leu Ser Phe Val Val Trp Val His His Phe Phe
                325                 330                 335

Thr Met Gly Ala Gly Ala Asn Val Asn Thr Phe Phe Gly Ile Met Thr
            340                 345                 350

Met Ile Ile Ala Val Pro Thr Gly Val Lys Ile Phe Asn Trp Leu Phe
        355                 360                 365

Thr Met Tyr Lys Gly Arg Val Glu Phe Thr Ala Pro Met His Trp Thr
    370                 375                 380

Leu Gly Phe Met Ile Thr Phe Ser Ile Gly Gly Met Thr Gly Val Met
385                 390                 395                 400

Met Ala Met Pro Ala Ala Asp Trp Ile Leu His Asn Ser Leu Phe Leu
                405                 410                 415

Ile Ala His Phe His Asn Val Ile Ile Gly Gly Val Tyr Phe Gly Tyr
            420                 425                 430

Ile Ala Gly Met Gly Phe Trp Phe Pro Lys Ala Phe Gly Phe Lys Leu
        435                 440                 445

Asn Glu Ala Trp Gly Lys Arg Ala Phe Trp Cys Trp Phe Val Gly Phe
    450                 455                 460

Tyr Leu Ala Phe Ile Pro Leu Tyr Val Leu Gly Leu Glu Gly Met Thr
465                 470                 475                 480

Arg Arg Met Asn His Tyr Asp Asn Pro Asp Trp Tyr Pro Trp Met Leu
                485                 490                 495

Val Ala Glu Val Gly Ala Ile Val Ile Ala Leu Gly Ile Val Cys Gln
            500                 505                 510

Leu Thr Gln Leu Tyr Val Ser Ile Arg Asp Arg Asn Leu Pro Glu Asn
        515                 520                 525

Leu Asp Leu Thr Gly Asp Pro Trp Asn Gly Arg Thr Leu Glu Trp Ser
```

```
    530                 535                 540

Ile Ser Ser Pro Pro Pro Ala Tyr Asn Phe Ala Val Ile Pro Asp Ile
545                 550                 555                 560

His Gly Leu Asp Thr Phe His Thr Glu Lys Gln Leu Gly Leu Lys Ala
                565                 570                 575

His Gly Lys Pro Leu Ala Pro Ile His Met Pro Lys Asn Thr Ser Ala
            580                 585                 590

Gly Val Phe Ile Gly Leu Phe Ser Phe Ile Leu Gly Phe Ala Ser Ile
        595                 600                 605

Trp Tyr Ile Trp Trp Leu Ala Ala Ile Gly Leu Ile Gly Ile Val Ala
    610                 615                 620

Thr Met Ile Leu Arg Ser Ala Asn Arg Asp Val Asp Tyr Tyr Val Pro
625                 630                 635                 640

Val Ser Glu Ile Glu His Asn Glu Glu Val Tyr Ser Arg Arg Ile Ala
                645                 650                 655

Ala Ala Gln Ala Ala Glu
            660
```

<210> SEQ ID NO 166
<211> LENGTH: 20
<212> TYPE: DNA
<213> ORGANISM: Artificial Sequence
<220> FEATURE:
<223> OTHER INFORMATION: primer

<400> SEQUENCE: 166

```
atgctcggaa aactctcctt                                                20
```

<210> SEQ ID NO 167
<211> LENGTH: 20
<212> TYPE: DNA
<213> ORGANISM: Artificial Sequence
<220> FEATURE:
<223> OTHER INFORMATION: primer

<400> SEQUENCE: 167

```
ttactctgct gcctgcgcag                                                20
```

<210> SEQ ID NO 168
<211> LENGTH: 618
<212> TYPE: DNA
<213> ORGANISM: Gluconobacter oxydans DSM 17078

<400> SEQUENCE: 168

```
atggctcacg aagcaacaat gtcgcctctg gcacacgctg acgaccacca cggggaacac     60

cacgagtccc ccaacgtgtt cggcttctgg ctctacctga tgacggactg cgtcctgttc    120

gggtcgatct tcgctgcctt cgcggtcctc cggaaccagt ttgccggtgg cccgtcgggc    180

aaggaactgt tcgacctgac gaacgtgggg atcgagacgg ctatcctgct gttctcgtct    240

atcacgtacg gcttcgcctc gctgaacgcg ctggcgaaga acaagaagat ggtcctgctc    300

tggctggccg ttacgttcgt gctgggtgtt tccttcgtcg gtctggagct gaacgagttc    360

agctccatga tcgcagaagg caatggtcct gaccgctccg cattcctctc cgcgttcttc    420

acgctggttg gaacgcacgg tctgcacgtc acctgcggcc tgatctggat ggtcgttctg    480

atggtgcaga tgatgggtcc gcaggatctg tccgagcgta tgatgaacaa gctggcttgc    540

ctcagcctgt tctggcactt tcttgacatc gtctggatct gtgtcttctc gttcgtctat    600

ctcgcaggtg tgatgtaa                                                  618
```

<210> SEQ ID NO 169
<211> LENGTH: 205
<212> TYPE: PRT
<213> ORGANISM: Gluconobacter oxydans DSM 17078

<400> SEQUENCE: 169

```
Met Ala His Glu Ala Thr Met Ser Pro Leu Ala His Ala Asp Asp His
1               5                   10                  15

His Gly Glu His His Glu Ser Pro Asn Val Phe Gly Phe Trp Leu Tyr
            20                  25                  30

Leu Met Thr Asp Cys Val Leu Phe Gly Ser Ile Phe Ala Ala Phe Ala
        35                  40                  45

Val Leu Arg Asn Gln Phe Ala Gly Gly Pro Ser Gly Lys Glu Leu Phe
    50                  55                  60

Asp Leu Thr Asn Val Gly Ile Glu Thr Ala Ile Leu Leu Phe Ser Ser
65                  70                  75                  80

Ile Thr Tyr Gly Phe Ala Ser Leu Asn Ala Leu Ala Lys Asn Lys Lys
                85                  90                  95

Met Val Leu Leu Trp Leu Ala Val Thr Phe Val Leu Gly Val Ser Phe
            100                 105                 110

Val Gly Leu Glu Leu Asn Glu Phe Ser Ser Met Ile Ala Glu Gly Asn
        115                 120                 125

Gly Pro Asp Arg Ser Ala Phe Leu Ser Ala Phe Phe Thr Leu Val Gly
    130                 135                 140

Thr His Gly Leu His Val Thr Cys Gly Leu Ile Trp Met Val Val Leu
145                 150                 155                 160

Met Val Gln Met Met Gly Pro Gln Asp Leu Ser Glu Arg Met Met Asn
                165                 170                 175

Lys Leu Ala Cys Leu Ser Leu Phe Trp His Phe Leu Asp Ile Val Trp
            180                 185                 190

Ile Cys Val Phe Ser Phe Val Tyr Leu Ala Gly Val Met
        195                 200                 205
```

<210> SEQ ID NO 170
<211> LENGTH: 20
<212> TYPE: DNA
<213> ORGANISM: Artificial Sequence
<220> FEATURE:
<223> OTHER INFORMATION: primer

<400> SEQUENCE: 170

```
atggctcacg aagcaacaat                                                  20
```

<210> SEQ ID NO 171
<211> LENGTH: 20
<212> TYPE: DNA
<213> ORGANISM: Artificial Sequence
<220> FEATURE:
<223> OTHER INFORMATION: primer

<400> SEQUENCE: 171

```
ttacatcaca cctgcgagat                                                  20
```

<210> SEQ ID NO 172
<211> LENGTH: 336
<212> TYPE: DNA
<213> ORGANISM: Gluconobacter oxydans DSM 17078

<400> SEQUENCE: 172

-continued atgacccagg ctcctaccac cacgatgacg ggtgacagcc acggctctta tccgtcctat 60
ctgatcggct tcgttctggc cgtgatcctg acggtggcat cctttgccgc tgtcatgacc 120
cacgccctct ccccggggat gacgatggca gcactgacgg ttctcgccgt cgtgcagatc 180
gtcgtccatc tggtgttctt cctccacatg aacaccagca ccgagcagag ctggaacctg 240
atgtgcttca tctttgctgc ggcatcggtg atcgtcatca tcggcggtac gatcttcatc 300
atgcacgaca cggccatcaa catgatgtcc cgctaa 336

<210> SEQ ID NO 173
<211> LENGTH: 111
<212> TYPE: PRT
<213> ORGANISM: Gluconobacter oxydans DSM 17078

<400> SEQUENCE: 173

Met Thr Gln Ala Pro Thr Thr Thr Met Thr Gly Asp Ser His Gly Ser
1 5 10 15

Tyr Pro Ser Tyr Leu Ile Gly Phe Val Leu Ala Val Ile Leu Thr Val
20 25 30

Ala Ser Phe Ala Ala Val Met Thr His Ala Leu Ser Pro Gly Met Thr
35 40 45

Met Ala Ala Leu Thr Val Leu Ala Val Val Gln Ile Val Val His Leu
50 55 60

Val Phe Phe Leu His Met Asn Thr Ser Thr Glu Gln Ser Trp Asn Leu
65 70 75 80

Met Cys Phe Ile Phe Ala Ala Ala Ser Val Ile Val Ile Ile Gly Gly
85 90 95

Thr Ile Phe Ile Met His Asp Thr Ala Ile Asn Met Met Ser Arg
100 105 110

<210> SEQ ID NO 174
<211> LENGTH: 20
<212> TYPE: DNA
<213> ORGANISM: Artificial Sequence
<220> FEATURE:
<223> OTHER INFORMATION: primer

<400> SEQUENCE: 174
atgacccagg ctcctaccac 20

<210> SEQ ID NO 175
<211> LENGTH: 20
<212> TYPE: DNA
<213> ORGANISM: Artificial Sequence
<220> FEATURE:
<223> OTHER INFORMATION: primer

<400> SEQUENCE: 175
ttagcgggac atcatgttga 20

<210> SEQ ID NO 176
<211> LENGTH: 1437
<212> TYPE: DNA
<213> ORGANISM: Gluconobacter oxydans DSM 17078

<400> SEQUENCE: 176
atgctgaacg cattaactcg ggacaggctg gtatctgaga tgaaacaggg atggaaactc 60
gcggccgcta tcggcctcat ggcggtgtct ttcggcgccg cccatgccca ggacgccgat 120
gaagccctga tcaagcgtgg cgaatatgtc gcccgcctgt cggactgcat cgcctgccac 180

```
acggctcttc acggacaacc ctatgcgggc ggtctggaga tcaagagccc gatcggcacg    240

atctattcga ccaacatcac gccggacccg gaacacggta tcggcaacta caccctggag    300

gacttcacga aggccctccg caagggcatc cgcaaggatg gtgcaacggt ctatccggcc    360

atgccctatc ctgaattcgc acgtctgtcc gatgacgaca tccgtgcgat gtatgccttc    420

ttcatgcacg gcgtgaagcc ggtcgccctg cagaacaagg cgccggacat cagctggccg    480

ctctccatgc gctggccgct gggcatgtgg cgcgccatgt tcgtcccgag catgacgccg    540

ggcgtggaca agagcatcag tgatccggaa gtcgcccgcg gcgaatacct cgtcaacggc    600

ccgggccatt gcggcgaatg ccatacgccc cgcggtttcg gaatgcaggt caaggcctat    660

ggcacggctg gcggcaacgc ctacctggcc ggtggtgccc cgatcgacaa ctggatcgca    720

ccgagcctgc gcagcaacag cgacacgggt ctgggccgct ggtctgaaga tgacatcgtc    780

accttcctca agagcggccg tatcgaccac tccgccgtct tcggtggcat ggccgacgtg    840

gtggcctaca gcacgcagca ctggtccgac gacgatctgc gcgccacggc caagtacctc    900

aagagcatgc cggccgtgcc ggaaggcaag aacctcggtc aggatgacgg tcagacgacc    960

gctctgctga acaagggtgg ccagggcaac gcaggtgcgg aagtctatct gcacaactgc   1020

gccatctgcc acatgaacga tggtacgggc gtcaaccgca tgttcccgcc gctggcaggc   1080

aacccggtcg tcatcaccga cgatccgacg tcgctcgcca atgtcgtggc cttcggtggc   1140

atcctgcccc cgaccaacag cgcaccgtcc gctgttgcca tgcccgggtt caagaatcac   1200

ctctccgacc aggagatggc cgatgtcgtg aacttcatgc gcaagggctg gggcaacaac   1260

gcaccgggaa ccgtgtccgc ttccgatatc cagaagctgc gcacgacggg tgcaccggtc   1320

tccaccgcgg gctggaacgt ctccagcaag ggctggatgg cctacatgcc gcagccttat   1380

ggcgaaggct ggaccttctc cccgcagacc cacaccggcg tggacgacgc acagtaa      1437
```

```
<210> SEQ ID NO 177
<211> LENGTH: 478
<212> TYPE: PRT
<213> ORGANISM: Gluconobacter oxydans DSM 17078

<400> SEQUENCE: 177

Met Leu Asn Ala Leu Thr Arg Asp Arg Leu Val Ser Glu Met Lys Gln
1               5                   10                  15

Gly Trp Lys Leu Ala Ala Ala Ile Gly Leu Met Ala Val Ser Phe Gly
            20                  25                  30

Ala Ala His Ala Gln Asp Ala Asp Glu Ala Leu Ile Lys Arg Gly Glu
        35                  40                  45

Tyr Val Ala Arg Leu Ser Asp Cys Ile Ala Cys His Thr Ala Leu His
    50                  55                  60

Gly Gln Pro Tyr Ala Gly Gly Leu Glu Ile Lys Ser Pro Ile Gly Thr
65                  70                  75                  80

Ile Tyr Ser Thr Asn Ile Thr Pro Asp Pro Glu His Gly Ile Gly Asn
                85                  90                  95

Tyr Thr Leu Glu Asp Phe Thr Lys Ala Leu Arg Lys Gly Ile Arg Lys
            100                 105                 110

Asp Gly Ala Thr Val Tyr Pro Ala Met Pro Tyr Pro Glu Phe Ala Arg
        115                 120                 125

Leu Ser Asp Asp Asp Ile Arg Ala Met Tyr Ala Phe Phe Met His Gly
    130                 135                 140

Val Lys Pro Val Ala Leu Gln Asn Lys Ala Pro Asp Ile Ser Trp Pro
```

-continued

```
145                 150                 155                 160

Leu Ser Met Arg Trp Pro Leu Gly Met Trp Arg Ala Met Phe Val Pro
                165                 170                 175

Ser Met Thr Pro Gly Val Asp Lys Ser Ile Ser Asp Pro Glu Val Ala
            180                 185                 190

Arg Gly Glu Tyr Leu Val Asn Gly Pro Gly His Cys Gly Glu Cys His
        195                 200                 205

Thr Pro Arg Gly Phe Gly Met Gln Val Lys Ala Tyr Gly Thr Ala Gly
    210                 215                 220

Gly Asn Ala Tyr Leu Ala Gly Gly Ala Pro Ile Asp Asn Trp Ile Ala
225                 230                 235                 240

Pro Ser Leu Arg Ser Asn Ser Asp Thr Gly Leu Gly Arg Trp Ser Glu
                245                 250                 255

Asp Asp Ile Val Thr Phe Leu Lys Ser Gly Arg Ile Asp His Ser Ala
            260                 265                 270

Val Phe Gly Gly Met Ala Asp Val Val Ala Tyr Ser Thr Gln His Trp
        275                 280                 285

Ser Asp Asp Asp Leu Arg Ala Thr Ala Lys Tyr Leu Lys Ser Met Pro
    290                 295                 300

Ala Val Pro Glu Gly Lys Asn Leu Gly Gln Asp Asp Gly Gln Thr Thr
305                 310                 315                 320

Ala Leu Leu Asn Lys Gly Gly Gln Gly Asn Ala Gly Ala Glu Val Tyr
                325                 330                 335

Leu His Asn Cys Ala Ile Cys His Met Asn Asp Gly Thr Gly Val Asn
            340                 345                 350

Arg Met Phe Pro Pro Leu Ala Gly Asn Pro Val Val Ile Thr Asp Asp
        355                 360                 365

Pro Thr Ser Leu Ala Asn Val Val Ala Phe Gly Gly Ile Leu Pro Pro
    370                 375                 380

Thr Asn Ser Ala Pro Ser Ala Val Ala Met Pro Gly Phe Lys Asn His
385                 390                 395                 400

Leu Ser Asp Gln Glu Met Ala Asp Val Val Asn Phe Met Arg Lys Gly
                405                 410                 415

Trp Gly Asn Asn Ala Pro Gly Thr Val Ser Ala Ser Asp Ile Gln Lys
            420                 425                 430

Leu Arg Thr Thr Gly Ala Pro Val Ser Thr Ala Gly Trp Asn Val Ser
        435                 440                 445

Ser Lys Gly Trp Met Ala Tyr Met Pro Gln Pro Tyr Gly Glu Gly Trp
    450                 455                 460

Thr Phe Ser Pro Gln Thr His Thr Gly Val Asp Asp Ala Gln
465                 470                 475
```

<210> SEQ ID NO 178
<211> LENGTH: 20
<212> TYPE: DNA
<213> ORGANISM: Artificial Sequence
<220> FEATURE:
<223> OTHER INFORMATION: primer

<400> SEQUENCE: 178
atgctgaacg cattaactcg 20

<210> SEQ ID NO 179
<211> LENGTH: 20
<212> TYPE: DNA
<213> ORGANISM: Artificial Sequence
<220> FEATURE:
<223> OTHER INFORMATION: primer

<400> SEQUENCE: 179
ttactgtgcg tcgtccacgc 20

<210> SEQ ID NO 180
<211> LENGTH: 81
<212> TYPE: DNA
<213> ORGANISM: Gluconobacter oxydans DSM 17078

<400> SEQUENCE: 180
atggcctgga acacaccgaa agttaccgaa atcccgctgg gcgcagaaat caactcgtat 60
gtctgcggcg agaagaaata a 81

<210> SEQ ID NO 181
<211> LENGTH: 26
<212> TYPE: PRT
<213> ORGANISM: Gluconobacter oxydans DSM 17078

<400> SEQUENCE: 181

Met Ala Trp Asn Thr Pro Lys Val Thr Glu Ile Pro Leu Gly Ala Glu
1 5 10 15

Ile Asn Ser Tyr Val Cys Gly Glu Lys Lys
20 25

<210> SEQ ID NO 182
<211> LENGTH: 20
<212> TYPE: DNA
<213> ORGANISM: Artificial Sequence
<220> FEATURE:
<223> OTHER INFORMATION: primer

<400> SEQUENCE: 182
atggcctgga acacaccgaa 20

<210> SEQ ID NO 183
<211> LENGTH: 20
<212> TYPE: DNA
<213> ORGANISM: Artificial Sequence
<220> FEATURE:
<223> OTHER INFORMATION: primer

<400> SEQUENCE: 183
ttatttcttc tcgccgcaga 20

<210> SEQ ID NO 184
<211> LENGTH: 978
<212> TYPE: DNA
<213> ORGANISM: Gluconobacter oxydans DSM 17078

<400> SEQUENCE: 184
atggagcggc cgttttcgtt catgggtgcc ctgtggtgcc ccagtcagac ggtttgtgaa 60
aaaatgattg atgtcatcgt gcttggcgcg gcggcagggg gcggttttcc gcagtggaac 120
tccgcagcac ccggctgtgt ggccgcccgc acgcgacagg gcgcgaaagc ccggacccag 180
gcctccatcg ccgtcagtgc cgacggaaag cgctggttca ttctcaacgc ctcgcccgat 240
ctgcggcagc agatcatcga tacgccggcc ctgcatcatc agggcagtct gcgcggcacg 300
cccattcagg gcgtcgtcct gacctgcggc gagatcgacg ccataaccgg ccttctgacc 360
ctgcgcgagc gtgagccttt taccctgatg ggcagcgact cgaccctgca gcagcttgcg 420

-continued

```
gacaacccga ttttcggcgc gcttgatccc gcaatcgtcc cgcgtgtccc gcttattctc    480

gatgaagcca cgtccctgat gaataaggac gggattccgt ccggtcttct gctcacggcc    540

tttgccgttc cgggcaaggc gccgctttac gcggaagccg caggctcacg cccggacgag    600

acgctgggcc tgtccatcac ggatggatgt aagacgatgc tcttcattcc cggctgtgcg    660

cagatcacgc cggaaatcgt ggaacgggtg gcggcagccg atctcgtgtt ctttgacggg    720

acgttgtggc gggatgatga aatgatccgc gccgggttga gcccgaagag cggacagcgg    780

atggggcatg tgtccgtgaa tgatgccggg ggcccggtcg aatgtttcac gacatgcgaa    840

aaaccccgta aagtgttgat tcatatcaac aactctaatc caattctgtt cgaagacagc    900

cccgaacgca aagacgtcga acgcgccgga tggacggttg cggaagacgg catgactttc    960

agactggaca caccatga                                                  978


<210> SEQ ID NO 185
<211> LENGTH: 325
<212> TYPE: PRT
<213> ORGANISM: Gluconobacter oxydans DSM 17078

<400> SEQUENCE: 185

Met Glu Arg Pro Phe Ser Phe Met Gly Ala Leu Trp Cys Pro Ser Gln
1               5                   10                  15

Thr Val Cys Glu Lys Met Ile Asp Val Ile Val Leu Gly Ala Ala Ala
            20                  25                  30

Gly Gly Gly Phe Pro Gln Trp Asn Ser Ala Ala Pro Gly Cys Val Ala
        35                  40                  45

Ala Arg Thr Arg Gln Gly Ala Lys Ala Arg Thr Gln Ala Ser Ile Ala
    50                  55                  60

Val Ser Ala Asp Gly Lys Arg Trp Phe Ile Leu Asn Ala Ser Pro Asp
65                  70                  75                  80

Leu Arg Gln Gln Ile Ile Asp Thr Pro Ala Leu His His Gln Gly Ser
                85                  90                  95

Leu Arg Gly Thr Pro Ile Gln Gly Val Val Leu Thr Cys Gly Glu Ile
            100                 105                 110

Asp Ala Ile Thr Gly Leu Leu Thr Leu Arg Glu Arg Glu Pro Phe Thr
        115                 120                 125

Leu Met Gly Ser Asp Ser Thr Leu Gln Gln Leu Ala Asp Asn Pro Ile
    130                 135                 140

Phe Gly Ala Leu Asp Pro Ala Ile Val Pro Arg Val Pro Leu Ile Leu
145                 150                 155                 160

Asp Glu Ala Thr Ser Leu Met Asn Lys Asp Gly Ile Pro Ser Gly Leu
                165                 170                 175

Leu Leu Thr Ala Phe Ala Val Pro Gly Lys Ala Pro Leu Tyr Ala Glu
            180                 185                 190

Ala Ala Gly Ser Arg Pro Asp Glu Thr Leu Gly Leu Ser Ile Thr Asp
        195                 200                 205

Gly Cys Lys Thr Met Leu Phe Ile Pro Gly Cys Ala Gln Ile Thr Pro
    210                 215                 220

Glu Ile Val Glu Arg Val Ala Ala Ala Asp Leu Val Phe Phe Asp Gly
225                 230                 235                 240

Thr Leu Trp Arg Asp Asp Glu Met Ile Arg Ala Gly Leu Ser Pro Lys
                245                 250                 255

Ser Gly Gln Arg Met Gly His Val Ser Val Asn Asp Ala Gly Gly Pro
            260                 265                 270
```

```
Val Glu Cys Phe Thr Thr Cys Glu Lys Pro Arg Lys Val Leu Ile His
        275                 280                 285

Ile Asn Asn Ser Asn Pro Ile Leu Phe Glu Asp Ser Pro Glu Arg Lys
    290                 295                 300

Asp Val Glu Arg Ala Gly Trp Thr Val Ala Glu Asp Gly Met Thr Phe
305                 310                 315                 320

Arg Leu Asp Thr Pro
                325


<210> SEQ ID NO 186
<211> LENGTH: 20
<212> TYPE: DNA
<213> ORGANISM: Artificial Sequence
<220> FEATURE:
<223> OTHER INFORMATION: primer

<400> SEQUENCE: 186

atggagcggc cgttttcgtt                                                 20


<210> SEQ ID NO 187
<211> LENGTH: 20
<212> TYPE: DNA
<213> ORGANISM: Artificial Sequence
<220> FEATURE:
<223> OTHER INFORMATION: primer

<400> SEQUENCE: 187

tcatggtgtg tccagtctga                                                 20


<210> SEQ ID NO 188
<211> LENGTH: 765
<212> TYPE: DNA
<213> ORGANISM: Gluconobacter oxydans DSM 17078

<400> SEQUENCE: 188

atggacggtt gcggaagacg gcatgacttt cagactggac acaccatgac gctcctcaca     60

cctgaccagc ttgaagcaca gcttcgccag atcggggccg agcggtatca caaccggcac    120

ccgttccatc gcaagctgca tgacggcaag ctcgacaagg cacaggttca ggcctgggcg    180

ttgaaccgct attattatca ggcccgcatc ccggcgaagg atgcgacgct tctcgcacgc    240

cttccgacgg ccgagctgcg ccgcgaatgg cgtcgccgga tcgaagacca tgacggtacg    300

gaacccggaa cgggtggtgt cgcgcgctgg ctgatgctga cggatggtct ggggctggat    360

cgggattatg tggaaagcct cgatggtctg cttccggcca cgcgcttttc agttgatgcc    420

tatgtgaact tcgtgcggga ccagtcgatt ctggcggcca ttgcgtcgtc gctgacggaa    480

ctgttttcgc ccacgatcat cagcgagcgt gtctcgggga tgctgcgtca ctacgacttc    540

gtgtcggaaa agacgctggc ctatttcacg ccgcgcctga cgcaggctcc gcgggattcc    600

gatttcgcat tggcctatgt ccgcgaaaac gcccgcacgc cggagcagca gaaagaagtc    660

ctgggagcgc tggagttcaa gtgttccgtg ctgtggacga tgctggatgc gctcgactac    720

gcctatgtgg aaggccatat tccgccgggg gctttcgttc catga                    765


<210> SEQ ID NO 189
<211> LENGTH: 254
<212> TYPE: PRT
<213> ORGANISM: Gluconobacter oxydans DSM 17078

<400> SEQUENCE: 189

Met Asp Gly Cys Gly Arg Arg His Asp Phe Gln Thr Gly His Thr Met
```

-continued

```
1               5                   10                  15

Thr Leu Leu Thr Pro Asp Gln Leu Glu Ala Gln Leu Arg Gln Ile Gly
            20                  25                  30

Ala Glu Arg Tyr His Asn Arg His Pro Phe His Arg Lys Leu His Asp
        35                  40                  45

Gly Lys Leu Asp Lys Ala Gln Val Gln Ala Trp Ala Leu Asn Arg Tyr
    50                  55                  60

Tyr Tyr Gln Ala Arg Ile Pro Ala Lys Asp Ala Thr Leu Leu Ala Arg
65                  70                  75                  80

Leu Pro Thr Ala Glu Leu Arg Arg Glu Trp Arg Arg Arg Ile Glu Asp
                85                  90                  95

His Asp Gly Thr Glu Pro Gly Thr Gly Gly Val Ala Arg Trp Leu Met
            100                 105                 110

Leu Thr Asp Gly Leu Gly Leu Asp Arg Asp Tyr Val Glu Ser Leu Asp
        115                 120                 125

Gly Leu Leu Pro Ala Thr Arg Phe Ser Val Asp Ala Tyr Val Asn Phe
    130                 135                 140

Val Arg Asp Gln Ser Ile Leu Ala Ala Ile Ala Ser Ser Leu Thr Glu
145                 150                 155                 160

Leu Phe Ser Pro Thr Ile Ile Ser Glu Arg Val Ser Gly Met Leu Arg
                165                 170                 175

His Tyr Asp Phe Val Ser Glu Lys Thr Leu Ala Tyr Phe Thr Pro Arg
            180                 185                 190

Leu Thr Gln Ala Pro Arg Asp Ser Asp Phe Ala Leu Ala Tyr Val Arg
        195                 200                 205

Glu Asn Ala Arg Thr Pro Glu Gln Gln Lys Glu Val Leu Gly Ala Leu
    210                 215                 220

Glu Phe Lys Cys Ser Val Leu Trp Thr Met Leu Asp Ala Leu Asp Tyr
225                 230                 235                 240

Ala Tyr Val Glu Gly His Ile Pro Pro Gly Ala Phe Val Pro
                245                 250
```

<210> SEQ ID NO 190
<211> LENGTH: 20
<212> TYPE: DNA
<213> ORGANISM: Artificial Sequence
<220> FEATURE:
<223> OTHER INFORMATION: primer

<400> SEQUENCE: 190
atggacggtt gcggaagacg 20

<210> SEQ ID NO 191
<211> LENGTH: 20
<212> TYPE: DNA
<213> ORGANISM: Artificial Sequence
<220> FEATURE:
<223> OTHER INFORMATION: primer

<400> SEQUENCE: 191
tcatggaacg aaagcccccg 20

<210> SEQ ID NO 192
<211> LENGTH: 291
<212> TYPE: DNA
<213> ORGANISM: Gluconobacter oxydans DSM 17078

<400> SEQUENCE: 192

```
atgacggagg ccccgcatgt cgtggcggag gggacggttc tctcctttgc ccgagggcat      60

cgtctgcagc atgatcgcgt gcgggacgtg tggatcgtgc aggcgcctga aaaagcattt     120

gtagttgagg gcgccgcgcc gcatattctg cggctgctgg atgggaagcg cagcgtcggc     180

gacatcatcc agcagcttgc aatcgagttt tccgccccgc gtgaggtcat tgcgaaggat     240

gtcctcgcgc ttctttctga actgacagaa aagaacgtcc tgcacacatg a              291


<210> SEQ ID NO 193
<211> LENGTH: 96
<212> TYPE: PRT
<213> ORGANISM: Gluconobacter oxydans DSM 17078

<400> SEQUENCE: 193

Met Thr Glu Ala Pro His Val Val Ala Glu Gly Thr Val Leu Ser Phe
1               5                   10                  15

Ala Arg Gly His Arg Leu Gln His Asp Arg Val Arg Asp Val Trp Ile
            20                  25                  30

Val Gln Ala Pro Glu Lys Ala Phe Val Val Glu Gly Ala Ala Pro His
        35                  40                  45

Ile Leu Arg Leu Leu Asp Gly Lys Arg Ser Val Gly Asp Ile Ile Gln
    50                  55                  60

Gln Leu Ala Ile Glu Phe Ser Ala Pro Arg Glu Val Ile Ala Lys Asp
65                  70                  75                  80

Val Leu Ala Leu Leu Ser Glu Leu Thr Glu Lys Asn Val Leu His Thr
                85                  90                  95


<210> SEQ ID NO 194
<211> LENGTH: 20
<212> TYPE: DNA
<213> ORGANISM: Artificial Sequence
<220> FEATURE:
<223> OTHER INFORMATION: primer

<400> SEQUENCE: 194

atgacggagg ccccgcatgt                                                  20


<210> SEQ ID NO 195
<211> LENGTH: 20
<212> TYPE: DNA
<213> ORGANISM: Artificial Sequence
<220> FEATURE:
<223> OTHER INFORMATION: primer

<400> SEQUENCE: 195

tcatgtgtgc aggacgttct                                                  20


<210> SEQ ID NO 196
<211> LENGTH: 1071
<212> TYPE: DNA
<213> ORGANISM: Gluconobacter oxydans DSM 17078

<400> SEQUENCE: 196

atgacactcc cttcgccgcc gatgagcctt ctggctgaac tgacgcatcg atgcccgctt      60

tcctgcccct actgctccaa tccgcttgaa ctcgaacgca aggcggcaga actcgacacg     120

gccacctgga ctgccgtact ggagcaggcg gccgagcttg gggtgctcca ggttcacttc     180

tccggcggcg agcccatggc gcggcctgat ctggtcgaac tggtctccgt tgcgcggaga     240

ctcaacctat attccaacct gatcacgtcc ggcgtgctgc tggacgaacc gaaactggaa     300

gctctcgaca gggcggggct ggatcacatc cagctctctt tccaggacgt gacggaggcg     360
```

```
ggagccgagc gtatcggcgg tctcaagggc gcgcaggccc gcaaggttgc ggcggcgcgg    420

ctcatccgcg cgtccggcat tccgatgacg ctcaattttg tggtgcacag ggaaaatgtc    480

gcccgtatcc ccgagatgtt cgccctggcg cgggaactcg gagcggggcg ggtggagatc    540

gcgcataccc agtattatgg ctgggggctg aaaaaccgtg aggcgcttct tcccagccgg    600

gatcagctgg aggaatccac ccgggccgtt gaagctgaac gcgcgaaggg tgggctttcc    660

attgattatg tgacgccgga ctatcatgca gaccggccca agccctgcat ggggggatgg    720

ggccagcgtt tcgtgaatgt cacgccctcg ggccgggtac tgccgtgtca tgcggccgag    780

atcattcccg atgtctcgtt cccgaatgtg aaagacgtga ccctgtccga gatctggaac    840

atctcgccgc tgttcaacat gttccgcggg acggactgga tgcccgagcc ctgccggtcc    900

tgcgaacgta aggaaaggga ctggggcgga tgccgctgtc aggctctggc cctgacggga    960

aatgcggcaa acaccgatcc ggtctgtagc ctgtcaccgt ttcatgatct tgtggaacag   1020

gccgcgaccg gagtgccgga aaagccggaa cttctgtacc ggcgtttctg a            1071
```

<210> SEQ ID NO 197
<211> LENGTH: 356
<212> TYPE: PRT
<213> ORGANISM: Gluconobacter oxydans DSM 17078

<400> SEQUENCE: 197

```
Met Thr Leu Pro Ser Pro Pro Met Ser Leu Leu Ala Glu Leu Thr His
1               5                   10                  15

Arg Cys Pro Leu Ser Cys Pro Tyr Cys Ser Asn Pro Leu Glu Leu Glu
            20                  25                  30

Arg Lys Ala Ala Glu Leu Asp Thr Ala Thr Trp Thr Ala Val Leu Glu
        35                  40                  45

Gln Ala Ala Glu Leu Gly Val Leu Gln Val His Phe Ser Gly Gly Glu
    50                  55                  60

Pro Met Ala Arg Pro Asp Leu Val Glu Leu Val Ser Val Ala Arg Arg
65                  70                  75                  80

Leu Asn Leu Tyr Ser Asn Leu Ile Thr Ser Gly Val Leu Leu Asp Glu
                85                  90                  95

Pro Lys Leu Glu Ala Leu Asp Arg Ala Gly Leu Asp His Ile Gln Leu
            100                 105                 110

Ser Phe Gln Asp Val Thr Glu Ala Gly Ala Glu Arg Ile Gly Gly Leu
        115                 120                 125

Lys Gly Ala Gln Ala Arg Lys Val Ala Ala Ala Arg Leu Ile Arg Ala
    130                 135                 140

Ser Gly Ile Pro Met Thr Leu Asn Phe Val Val His Arg Glu Asn Val
145                 150                 155                 160

Ala Arg Ile Pro Glu Met Phe Ala Leu Ala Arg Glu Leu Gly Ala Gly
                165                 170                 175

Arg Val Glu Ile Ala His Thr Gln Tyr Tyr Gly Trp Gly Leu Lys Asn
            180                 185                 190

Arg Glu Ala Leu Leu Pro Ser Arg Asp Gln Leu Glu Glu Ser Thr Arg
        195                 200                 205

Ala Val Glu Ala Glu Arg Ala Lys Gly Gly Leu Ser Ile Asp Tyr Val
    210                 215                 220

Thr Pro Asp Tyr His Ala Asp Arg Pro Lys Pro Cys Met Gly Gly Trp
225                 230                 235                 240

Gly Gln Arg Phe Val Asn Val Thr Pro Ser Gly Arg Val Leu Pro Cys
```

```
                245                 250                 255

His Ala Ala Glu Ile Ile Pro Asp Val Ser Phe Pro Asn Val Lys Asp
            260                 265                 270

Val Thr Leu Ser Glu Ile Trp Asn Ile Ser Pro Leu Phe Asn Met Phe
        275                 280                 285

Arg Gly Thr Asp Trp Met Pro Glu Pro Cys Arg Ser Cys Glu Arg Lys
    290                 295                 300

Glu Arg Asp Trp Gly Gly Cys Arg Cys Gln Ala Leu Ala Leu Thr Gly
305                 310                 315                 320

Asn Ala Ala Asn Thr Asp Pro Val Cys Ser Leu Ser Pro Phe His Asp
                325                 330                 335

Leu Val Glu Gln Ala Ala Thr Gly Val Pro Glu Lys Pro Glu Leu Leu
            340                 345                 350

Tyr Arg Arg Phe
        355


<210> SEQ ID NO 198
<211> LENGTH: 20
<212> TYPE: DNA
<213> ORGANISM: Artificial Sequence
<220> FEATURE:
<223> OTHER INFORMATION: primer

<400> SEQUENCE: 198

atgacactcc cttcgccgcc                                                   20


<210> SEQ ID NO 199
<211> LENGTH: 20
<212> TYPE: DNA
<213> ORGANISM: Artificial Sequence
<220> FEATURE:
<223> OTHER INFORMATION: primer

<400> SEQUENCE: 199

tcagaaacgc cggtacagaa                                                   20


<210> SEQ ID NO 200
<211> LENGTH: 666
<212> TYPE: DNA
<213> ORGANISM: Gluconobacter oxydans DSM 17078

<400> SEQUENCE: 200

atgaccgctt ttcttgccct gatcgaccgt gacctccgtc tggccttccg cttcggcgcc      60

gacacgctgg cctcgctgct gttctttatc ttgtgtggca gcctgttccc gctggctctc     120

gggccgtcgc cggacctgct gcgacacatg ggaccaggca tcatctgggt ctgtgccctg     180

ctcgcctgcc tgctgccgct ggaccgcctg ttcggagccg aactcgaaga tggctccctt     240

gacctgctga tgctgagcgg cccggccccg gctgccgtgg cctttgccaa aatggcggca     300

cactggctaa cgaccggcct gccgctgctg atcgccagta tcccgctcgg catcatgctc     360

ggcgtcaaag gctcggaact tccgctcctg ctgctcggcc ttgcgatggg cacgatgtcc     420

ctctcgctcc tcggcggcat ggcggcttcg atcgtcctgg gtgcacggcg tggtggcgta     480

ctgctgccgc ttctggtttt gccactcgca acccctgtgc tgattttcgg cgcggcctcc     540

tcctatgccg gacagcttgc aacatccccc gccgccagtc tggatctgct gggagcgtgc     600

ctcttcgcct gcctgccgct gtgccccctc gccgccggac aggggctgaa agccgccgtg     660

ggctga                                                                666
```

<210> SEQ ID NO 201
<211> LENGTH: 221
<212> TYPE: PRT
<213> ORGANISM: Gluconobacter oxydans DSM 17078

<400> SEQUENCE: 201

```
Met Thr Ala Phe Leu Ala Leu Ile Asp Arg Asp Leu Arg Leu Ala Phe
1               5                   10                  15

Arg Phe Gly Ala Asp Thr Leu Ala Ser Leu Leu Phe Phe Ile Leu Cys
            20                  25                  30

Gly Ser Leu Phe Pro Leu Ala Leu Gly Pro Ser Pro Asp Leu Leu Arg
        35                  40                  45

His Met Gly Pro Gly Ile Ile Trp Val Cys Ala Leu Leu Ala Cys Leu
    50                  55                  60

Leu Pro Leu Asp Arg Leu Phe Gly Ala Glu Leu Glu Asp Gly Ser Leu
65                  70                  75                  80

Asp Leu Leu Met Leu Ser Gly Pro Ala Pro Ala Ala Val Ala Phe Ala
                85                  90                  95

Lys Met Ala Ala His Trp Leu Thr Thr Gly Leu Pro Leu Leu Ile Ala
            100                 105                 110

Ser Ile Pro Leu Gly Ile Met Leu Gly Val Lys Gly Ser Glu Leu Pro
        115                 120                 125

Leu Leu Leu Leu Gly Leu Ala Met Gly Thr Met Ser Leu Ser Leu Leu
    130                 135                 140

Gly Gly Met Ala Ala Ser Ile Val Leu Gly Ala Arg Arg Gly Gly Val
145                 150                 155                 160

Leu Leu Pro Leu Leu Val Leu Pro Leu Ala Thr Pro Val Leu Ile Phe
                165                 170                 175

Gly Ala Ala Ser Ser Tyr Ala Gly Gln Leu Ala Thr Ser Pro Ala Ala
            180                 185                 190

Ser Leu Asp Leu Leu Gly Ala Cys Leu Phe Ala Cys Leu Pro Leu Cys
        195                 200                 205

Pro Leu Ala Ala Gly Gln Gly Leu Lys Ala Ala Val Gly
    210                 215                 220
```

<210> SEQ ID NO 202
<211> LENGTH: 20
<212> TYPE: DNA
<213> ORGANISM: Artificial Sequence
<220> FEATURE:
<223> OTHER INFORMATION: primer

<400> SEQUENCE: 202
atgaccgctt ttcttgccct 20

<210> SEQ ID NO 203
<211> LENGTH: 20
<212> TYPE: DNA
<213> ORGANISM: Artificial Sequence
<220> FEATURE:
<223> OTHER INFORMATION: primer

<400> SEQUENCE: 203
tcagcccacg gcggctttca 20

<210> SEQ ID NO 204
<211> LENGTH: 400
<212> TYPE: DNA
<213> ORGANISM: Gluconobacter oxydans DSM 17078

<400> SEQUENCE: 204
gtggcctcag cgtccctgac acgctttttc gtagaggagg acgctctgct tttctcaagg 60
ggcatcaggg gtttgttccg ctctcagtag gggcgctctt tctgggggaa accgccccaa 120
aagaaaagcg gatcataaaa tcacacttaa agtacgaaaa aatatcaacg taacgtgatt 180
tcatgctggc gtacccctgc gatatgtgta agtaactaca tggtgcgtta cgcgttagga 240
agttggaacc cgagcgtctg tggtcaaatg caggtgaggg tcgtccgtga ttaagaattg 300
catgttgtaa tatctctcgg ggtttccagt tcataagagt aaaaccgggc tgttcatcgg 360
aaaagggatg gcagcaccat agttcgcaca ggagttcgta 400

<210> SEQ ID NO 205
<211> LENGTH: 20
<212> TYPE: DNA
<213> ORGANISM: Artificial Sequence
<220> FEATURE:
<223> OTHER INFORMATION: primer

<400> SEQUENCE: 205
gacgctgccg aaggcgaagg 20

<210> SEQ ID NO 206
<211> LENGTH: 45
<212> TYPE: DNA
<213> ORGANISM: Artificial Sequence
<220> FEATURE:
<223> OTHER INFORMATION: primer

<400> SEQUENCE: 206
cacgaggcag acctcagcgc ctataacgct ctccaaacgc tagac 45

<210> SEQ ID NO 207
<211> LENGTH: 45
<212> TYPE: DNA
<213> ORGANISM: Artificial Sequence
<220> FEATURE:
<223> OTHER INFORMATION: primer

<400> SEQUENCE: 207
cagagatttt gagacacaac gtggcggcct cagcgtccct gacac 45

<210> SEQ ID NO 208
<211> LENGTH: 44
<212> TYPE: DNA
<213> ORGANISM: Artificial Sequence
<220> FEATURE:
<223> OTHER INFORMATION: primer

<400> SEQUENCE: 208
ggggggggaa gattcggaca ttacgaactc ctgtgcgaac tatg 44

<210> SEQ ID NO 209
<211> LENGTH: 44
<212> TYPE: DNA
<213> ORGANISM: Artificial Sequence
<220> FEATURE:
<223> OTHER INFORMATION: primer

<400> SEQUENCE: 209
catagttcgc acaggagttc gtaatgtccg aatcttcccc cccc 44

<210> SEQ ID NO 210

<211> LENGTH: 22
<212> TYPE: DNA
<213> ORGANISM: Artificial Sequence
<220> FEATURE:
<223> OTHER INFORMATION: primer

<400> SEQUENCE: 210
cgtgcaaact gcgagccaag cg 22

<210> SEQ ID NO 211
<211> LENGTH: 25
<212> TYPE: DNA
<213> ORGANISM: Artificial Sequence
<220> FEATURE:
<223> OTHER INFORMATION: primer

<400> SEQUENCE: 211
gccacgttgt gtctcaaaat ctctg 25

<210> SEQ ID NO 212
<211> LENGTH: 21
<212> TYPE: DNA
<213> ORGANISM: Artificial Sequence
<220> FEATURE:
<223> OTHER INFORMATION: primer

<400> SEQUENCE: 212
ggcgctgagg tctgcctcgt g 21

<210> SEQ ID NO 213
<211> LENGTH: 22
<212> TYPE: DNA
<213> ORGANISM: Artificial Sequence
<220> FEATURE:
<223> OTHER INFORMATION: primer

<400> SEQUENCE: 213
gccatgcgtg gtgtgtgtgc tg 22

<210> SEQ ID NO 214
<211> LENGTH: 44
<212> TYPE: DNA
<213> ORGANISM: Artificial Sequence
<220> FEATURE:
<223> OTHER INFORMATION: primer

<400> SEQUENCE: 214
cacgaggcag acctcagcgc cgcgataacc gttagatgcg tcag 44

<210> SEQ ID NO 215
<211> LENGTH: 45
<212> TYPE: DNA
<213> ORGANISM: Artificial Sequence
<220> FEATURE:
<223> OTHER INFORMATION: primer

<400> SEQUENCE: 215
catagttcgc acaggagttc gtaatggcct ggaacacacc gaaag 45

<210> SEQ ID NO 216
<211> LENGTH: 21
<212> TYPE: DNA
<213> ORGANISM: Artificial Sequence
<220> FEATURE:
<223> OTHER INFORMATION: primer

<400> SEQUENCE: 216

-continued

```
ggtcgagtcg ctgcccatca g                                              21


<210> SEQ ID NO 217
<211> LENGTH: 63
<212> TYPE: DNA
<213> ORGANISM: Artificial Sequence
<220> FEATURE:
<223> OTHER INFORMATION: primer

<400> SEQUENCE: 217

ctttcggtgt gttccaggcc attacgaact cctgtgcgaa ctatggtgct gccatccctt     60

ttc                                                                  63
```